US010934284B2

(12) United States Patent
Simpson et al.

(10) Patent No.: US 10,934,284 B2
(45) Date of Patent: Mar. 2, 2021

(54) AMINOQUINAZOLINE COMPOUNDS HAVING ANTI-INFLAMMATORY, ANTIFUNGAL, ANTIPARASITIC, AND ANTICANCER ACTIVITY

(71) Applicant: Wellstat Therapeutics Corporation, Rockville, MD (US)

(72) Inventors: David M. Simpson, North Bethesda, MD (US); Dennis Bryan Zerby, Chambersburg, PA (US); Ming Lu, Bethesda, MD (US); Reid W. Von Borstel, Potomac, MD (US); Rui Li, Darnestown, MD (US); Julian Reading, Frederick, MD (US); Stephen Wolpe, Boyds, MD (US)

(73) Assignee: Wellstat Therapeutics Corporation, Rockville, MD (US)

( * ) Notice: Subject to any disclaimer, the term of this patent is extended or adjusted under 35 U.S.C. 154(b) by 0 days.

(21) Appl. No.: 16/285,460

(22) Filed: Feb. 26, 2019

(65) Prior Publication Data

US 2019/0194193 A1  Jun. 27, 2019

Related U.S. Application Data

(63) Continuation of application No. 16/015,264, filed on Jun. 22, 2018, now abandoned, which is a
(Continued)

(51) Int. Cl.
| | |
|---|---|
| *C07D 471/04* | (2006.01) |
| *A61K 31/337* | (2006.01) |
| *A61K 31/4164* | (2006.01) |
| *A61K 31/437* | (2006.01) |
| *A61K 31/44* | (2006.01) |
| *A61K 31/4425* | (2006.01) |
| *A61K 31/4709* | (2006.01) |
| *A61K 31/4745* | (2006.01) |
| *A61K 31/475* | (2006.01) |
| *A61K 31/505* | (2006.01) |
| *A61K 31/517* | (2006.01) |
| *A61K 31/555* | (2006.01) |
| *A61K 31/704* | (2006.01) |
| *A61K 31/40* | (2006.01) |
| *A61K 31/4184* | (2006.01) |
| *A61K 31/472* | (2006.01) |
| *A61K 31/4965* | (2006.01) |
| *A61K 31/498* | (2006.01) |
| *C07D 215/42* | (2006.01) |
| *C07D 215/44* | (2006.01) |
| *A61K 31/4706* | (2006.01) |
| *A61P 35/00* | (2006.01) |
| *A61P 33/02* | (2006.01) |

(Continued)

(52) U.S. Cl.
CPC ........... *C07D 471/04* (2013.01); *A01N 43/42* (2013.01); *A01N 43/50* (2013.01); *A01N 43/54* (2013.01); *A01N 43/60* (2013.01); *A01N 43/90* (2013.01); *A61K 31/337* (2013.01); *A61K 31/40* (2013.01); *A61K 31/4164* (2013.01); *A61K 31/4184* (2013.01); *A61K 31/437* (2013.01); *A61K 31/44* (2013.01); *A61K 31/4425* (2013.01); *A61K 31/472* (2013.01); *A61K 31/475* (2013.01); *A61K 31/4706* (2013.01); *A61K 31/4709* (2013.01); *A61K 31/4745* (2013.01); *A61K 31/498* (2013.01); *A61K 31/4965* (2013.01); *A61K 31/505* (2013.01); *A61K 31/517* (2013.01); *A61K 31/555* (2013.01); *A61K 31/704* (2013.01); *A61P 33/02* (2018.01); *A61P 35/00* (2018.01); *C07D 209/12* (2013.01); *C07D 213/73* (2013.01); *C07D 213/74* (2013.01); *C07D 215/38* (2013.01); *C07D 215/40* (2013.01); *C07D 215/42* (2013.01); *C07D 215/44* (2013.01); *C07D 215/46* (2013.01); *C07D 233/60* (2013.01); *C07D 235/08* (2013.01); *C07D 239/42* (2013.01); *C07D 239/94* (2013.01); *C07D 241/20* (2013.01); *C07D 241/44* (2013.01); *C07D 401/12* (2013.01); *Y02A 50/409* (2018.01); *Y02A 50/411* (2018.01); *Y02P 20/582* (2015.11)

(58) Field of Classification Search
CPC .................................................. C07D 471/04
See application file for complete search history.

(56) References Cited

U.S. PATENT DOCUMENTS

| | | |
|---|---|---|
| 3,541,094 A | 11/1970 | Lutz et al. |
| 4,213,987 A | 7/1980 | Nakagami et al. |

(Continued)

FOREIGN PATENT DOCUMENTS

| | | |
|---|---|---|
| AU | 25353/84 A | 9/1984 |
| AU | 73007/98 A | 6/1998 |

(Continued)

OTHER PUBLICATIONS

RN1305730-33-9, STN Registry, Jun. 5, 2011.
(Continued)

*Primary Examiner* — Paul V Ward
(74) *Attorney, Agent, or Firm* — Lewis J. Kreisler

(57) ABSTRACT

Amine compounds having activity against inflammation, fungi, unicellular parasitic microorganisms, and cancer are described. The compounds contain a monocyclic, bicyclic, or tricyclic aromatic ring having one, two, or three ring nitrogen atoms.

7 Claims, No Drawings

Related U.S. Application Data continuation of application No. 14/764,207, filed as application No. PCT/US2014/013992 on Jan. 31, 2014, now Pat. No. 10,300,015.

(60) Provisional application No. 61/759,512, filed on Feb. 1, 2013.

(51) Int. Cl.

| | | |
|---|---|---|
| *A01N 43/42* | (2006.01) | |
| *A01N 43/50* | (2006.01) | |
| *A01N 43/54* | (2006.01) | |
| *A01N 43/60* | (2006.01) | |
| *A01N 43/90* | (2006.01) | |
| *C07D 209/12* | (2006.01) | |
| *C07D 213/73* | (2006.01) | |
| *C07D 213/74* | (2006.01) | |
| *C07D 215/38* | (2006.01) | |
| *C07D 215/40* | (2006.01) | |
| *C07D 215/46* | (2006.01) | |
| *C07D 233/60* | (2006.01) | |
| *C07D 235/08* | (2006.01) | |
| *C07D 239/42* | (2006.01) | |
| *C07D 239/94* | (2006.01) | |
| *C07D 241/20* | (2006.01) | |
| *C07D 241/44* | (2006.01) | |
| *C07D 401/12* | (2006.01) | |

(56) References Cited

U.S. PATENT DOCUMENTS

| | | | |
|---|---|---|---|
| 4,323,680 A | 4/1982 | Nakagami et al. | |
| 4,331,667 A | 5/1982 | Schneider | |
| 4,698,348 A | 10/1987 | Gerster | |
| 5,114,939 A | 5/1992 | Dreikorn et al. | |
| 5,141,941 A * | 8/1992 | Fujii | A01N 43/54 |
| | | | 514/256 |
| 5,278,173 A | 1/1994 | Davis | |
| 5,294,622 A | 3/1994 | Dreikorn et al. | |
| 5,389,640 A | 2/1995 | Gerster et al. | |
| 5,770,599 A | 6/1998 | Gibson | |
| 6,046,206 A | 4/2000 | Pamukcu et al. | |
| 7,176,213 B2 | 2/2007 | Aranyi et al. | |
| 7,365,089 B2 | 4/2008 | Aranyi et al. | |
| 7,419,977 B2 | 9/2008 | Aranyi et al. | |
| 7,470,709 B2 | 12/2008 | Barsanti et al. | |
| 7,572,915 B2 | 8/2009 | Barker et al. | |
| 7,875,624 B2 | 1/2011 | Heise et al. | |
| 7,928,111 B2 | 4/2011 | Tachdjian et al. | |
| 7,932,272 B2 * | 4/2011 | Nakamoto | A61K 31/404 |
| | | | 514/336 |
| 8,637,532 B2 | 1/2014 | Sutton et al. | |
| 8,697,875 B2 * | 4/2014 | Feng | C07D 215/48 |
| | | | 546/159 |
| 10,030,015 B2 | 7/2018 | Simpson et al. | |
| 2005/0131020 A1 | 6/2005 | D'Amico | |
| 2005/0137399 A1 | 6/2005 | Cai et al. | |
| 2006/0247223 A1 | 11/2006 | Schwartz et al. | |
| 2007/0105943 A1 | 5/2007 | Nakamoto et al. | |
| 2009/0163545 A1 | 6/2009 | Goldfarb | |
| 2009/0221556 A1 | 9/2009 | Kshirsagar et al. | |
| 2010/0120741 A1 | 5/2010 | Borchardt et al. | |
| 2010/0190808 A1 | 7/2010 | Mjalli et al. | |
| 2010/0331293 A1 | 12/2010 | Cushing et al. | |
| 2011/0092504 A1 | 4/2011 | Bo et al. | |
| 2012/0258975 A1 | 10/2012 | Yuan et al. | |

FOREIGN PATENT DOCUMENTS

| | | |
|---|---|---|
| CN | 1034204 C | 3/1997 |
| DE | 3406992 A1 | 9/1984 |
| EP | 0520722 A1 | 12/1992 |
| EP | 0566226 B1 | 8/1995 |
| EP | 0326331 B1 | 4/2002 |
| GB | 1182507 A | 2/1970 |
| GB | 1496371 | 12/1977 |
| GB | 2068732 A | 8/1981 |
| GB | 2135887 A | 9/1984 |
| JP | 43-20294 | 8/1968 |
| JP | S53-103484 A | 9/1978 |
| JP | 54-2325 A | 1/1979 |
| JP | S55-76803 A | 6/1980 |
| JP | 01-246266 | 10/1989 |
| JP | 2011026251 A | 2/2011 |
| KR | 2011121019 * | 11/2011 |
| SU | 1111675 A | 8/1984 |
| WO | 1992015582 A1 | 9/1992 |
| WO | 1996009294 A1 | 3/1996 |
| WO | 1997048705 A1 | 12/1997 |
| WO | 9822446 A1 | 5/1998 |
| WO | 2005033079 A1 | 4/2005 |
| WO | 2006034235 A2 | 3/2006 |
| WO | 2006071095 A1 | 7/2006 |
| WO | WO20060711095 * | 7/2006 |
| WO | 2007056170 A2 | 5/2007 |
| WO | 2012079079 A1 | 6/2012 |
| WO | WO2012079079 * | 6/2012 |
| WO | 2012149186 A2 | 11/2012 |

OTHER PUBLICATIONS

RN1305730-07-7, STN Registry, Jun. 5, 2011.
RN1304938-90-6, STN Registry, Jun. 3, 2011.
Cavier et al., "Recherche sur les aminoquinoleines. XIX: Activite amoebicide in vivo d'alkylamino-4 quinoleines a longues chaines", Ann. Pharm. Fr., 36(3-4): 115-119; 1978.
Desvignes et al., "Recherche sur les aminoquinoleines. XVIII: Activite antibacterienne et antifongique in vitro d'alkylamino-4 quinoleines a longues chaines", Ann. Pharm. Fr., 35(7-8): 239-247; 1977.
Renault et al., "Aminoquinoleines secondaires a activite amoebicide potentielle: influence de la longueur et de la position de la chaine alkylaminee", C.R. Acad. Sc. Paris, Serie D, 282(5): 509-511; Feb. 1976.
Galanakis et al., "Synthesis and quantitative structure-activity relationship of a novel series of small conductance Ca2 +-activated K+ channel blockers related to dequalinium", J. Med. Chem. 39: 359-370; 1996.
Ferguson et al., "The mutagenic effects of diacridines and diquinolines in microbial systems", Mutation Res., 232: 337-343; 1990.
McFadyen et al., "Alkyl-linked diquinolines are monofunctional AT-selective DNA-intercalating agents", FEBS Letters, 228(2): 235-240; Feb. 1988.
Adams et al., "Differences between central and peripheral rat alpha-adrenoceptors revealed using binuclear ligands", Eur. J. Pharmacol., 127: 27-35; 1986.
Deshpande et al., "p-Toluenesulphonyl derivatives of N,N'-bis-(4-quinolino-4-quinaldino/4-quinazolino and 9-acridino) polymethylene diamines as hypoglycemic agents", J. Indian Chem. Soc., 52: 746-749; Aug. 1975.
Li, Ping-ling, "Synthesis and evaluation of novel dimeric acetylcholinesterase inhibitors" 148 pages (master thesis, Hong Kong University of Science and Technology; Sep. 1998) (avail. from Sel. Org. React. Database (SORD) 1998.).
Han et al., "Dual-site binding of bivalent 4-aminopyridine- and 4-aminoquinoline-based AChE inhibitors: contribution of the hydrophobic alkylene tether to monomer and dimer affinities", Bioorg. Med. Chem., 7: 2569-2575; 1999.
Miller et al., "Cell killing by lysosomotropic detergents", J. Cell. Biol., 97(6): 1841-1851; 1983.
Chen et al., "[alpha]1-Adrenoceptor and serotonin 5-HT1A receptor affinity of homobivalent 4-aminoquinoline compounds: An investigation of the effect of linker length", Biochem. Pharmacol., 85(10): 1534-1541; May 1, 2013 (available online Mar. 19, 2013).
Firestone et al., "Lysosomotropic agents. 7.1. Broad-spectrum antifungal activity of lysosomotropic detergents", J. Med. Chem., 30(8): 1519-1521; 1987.

(56) References Cited

OTHER PUBLICATIONS

Sukhai et al., "Lysosomal disruption preferentially targets acute myeloid leukemia cells and progenitors", J. Clin. Investigation, 123(1): 315-328; Jan. 2013 (available online Dec. 3, 2012).
Firestone, "Lysosomotropic agents. 1. Synthesis and cytotaxic action of lysosomotropic detergents", J. Med. Chem., 22(9): 1130-1133; 1979.
Nadanaciva et al., "A high content screening assay for identifying lysosomotropic compounds", Toxicol. In Vitro, 25(3): 715-723; 2011 (available online Dec. 22, 2010).
Yap et al., "4-Arylalkoxyquinazolines with antifungal activity", in "Synthesis and Chemistry of Agrochemicals V", Baker et al., eds. (ACS 1998) chapter 26, pp. 258-272.
Nishimura et al., "Phosphoinositide 3-kinase (PI3K)/mammalian target of rapamycin (mTOR) dual inhibitors: discovery annd structure—activity relationships of a series of quinoline and quinoxaline derivatives", J. Med. Chem., 54(13): 4735-4751; 2011.
Pedersen et al., "Phosphoramides: XVI. Mixtures of phosphorous pentoxide, amine hydrochlorides and tertiary amines as reagents in the synthesis of quinolinamines", Chemica Scripta, 18(5): 240-241; 1981.
Gerster et al., "Synthesis and structure-activity-relationships of 1H-Imidazo[4,5-c]quinolines that induce interferon production", J. Med. Chem. 48(10): 3481-3491; 2005.

Renault et al., "Recherche sur les aminoquinoleines. I. Etude des diverses methodes de syntheses des amino-4 quinoleines secondaires et tertiares a chaines hydrocarbonees", Chimica Therapeutica, 66(5-6): 339-346; 1966.
RN384374-55-4, STN Registry, Jan. 19, 2002.
RN1027641-33-3, STN Registry, Jun. 12, 2008.
RN1305730-17-9, STN Registry, Jun. 5, 2011.
RN1303776-05-7, STN Registry, Jun. 1, 2011.
RN1292730-81-4, STN Registry, May 10, 2011.
Hocart et al., "4-Aminoquinolines active against chloroquine-resistant Plasmodium falciparum: Basis of antiparasite activity and quantitative structure-activity relationship analyses", Antimicrobial Agents and Chemother., 55(5): 2233-2244; 2011.
McAfee et al., "Autophagy inhibitor Lys05 has single-agent anti-tumor activity and reproduces the phenotype of a genetic authopagy deficiency", PNAS Early Edition, 6 pages, May 2012. <www.pnas.org/cgi/doi/10.1073/pnas.1118193109>.
Pinedo et al., "Translational research: the role of VEGF in tumor angiogenesis", The Oncologist, 5(suppl):1-2; 2000.
McMahon, "VEGF receptor signaling in tumor angiogenesis", The Oncologist, 5(suppl.):3-10; 2000.
Kovalenko et al., "Synthesis and Anticancer Activity of 2-(Alkyl-, Alkaryl-, Aryl-, Hetaryl-)-[1,2,4]triazolo[1,5-c] quinazolines", Sci. Pharm., 81(2): 359-391; Jan. 1, 2013.

\* cited by examiner

AMINOQUINAZOLINE COMPOUNDS HAVING ANTI-INFLAMMATORY, ANTIFUNGAL, ANTIPARASITIC, AND ANTICANCER ACTIVITY

BACKGROUND OF THE INVENTION

Most nucleated eukaryotic cells, whether unicellular organisms or constituents of multicellular organism including humans, contain acidified vacuoles that are critical for cellular maintenance and function. In mammalian cells, these vacuoles comprise lysosomes and other endosomal vesicular organelles. The pH of the interior of lysosomes is typically about 4.5 to 5, maintained by vacuolar ATP-dependent proton pumps and also by Donnan equilibrium effects. Lysosomes contribute to cytosolic pH buffering, protecting the cell from acidic environments, and are also primary sites for degrading and recycling the constituents of aging or damaged organelles such as mitochondria, a process known as autophagy. There are several important pathological conditions where lysosomal characteristics are altered and contribute to disease pathogenesis, presenting a potential target for pharmacological therapy.

A growing body of evidence indicates that a common phenotypic change in invasive cancer cells is a redirection of lysosomes to participate in destruction of surrounding cells via exocytosis of acidic contents, including enzymes. Proteolytic enzymes normally found in lysosomes but secreted by cancer cells, such as cathepsins, can degrade extracellular matrix proteins, facilitating tumor invasion and metastasis. Furthermore, lysosomes and other acidic vacuolar organelles are often enlarged in cancer cells, which aids pH buffering; many solid tumors generate an acidic extracellular environment, favoring invasion, which requires that cancer cells adapt to both produce and tolerate a low extracellular pH. Cancer cells selected in vitro for invasive potential have larger, more acidic lysosomes than do less aggressive cells. Cancer cells exposed to ionizing radiation undergo a protective response involving enlargement and acidification of lysosomes. A related protective response through cancer cells acquire survival advantages is activation of autophagy, which involves fusion of autophagosomes containing damaged organelles or other cell debris, with lysosomes; disruption of autophagy can impair cancer cell viability. Some cancer cells also sequester chemotherapy agents in lysosomes, as a mechanism of drug resistance. Chloroquine, an antimalarial drug that accumulates in mammalian lysosomes, potentiates, or restores sensitivity to, anticancer activity of several classes of chemotherapy agents and targeted small molecule and antibody cancer treatments. Lysosomotropic fluorescent dyes such as acridine orange can be used to visually differentiate tumors in situ from surrounding tissues, indicating a potential sharp distinction for specific lysosome-targeting cytotoxic agents to selectively kill cancer cells.

Lysosomal alterations are also important features of common inflammatory diseases, especially those involving activated macrophages, where exocytosis of lysosomal enzymes, cytokines, and some inflammatory mediators such as HMBG1 that are processed and released via lysosomes can participate in tissue damage and both local and systemic inflammation. Glucocorticoid signaling is also linked to lysosomes, such that compromising lysosomal function can enhance anti-inflammatory pathways mediating glucocorticoid effects.

Most fungi have acidic vacuoles similar to lysosomes. These acidic vacuoles are critical for ion and pH homeostasis, storage of amino acids, autophagy and for processing some proteins. Vacuoles are acidified via a proton pump, the vacuolar HtATPase, or "V-ATPase", and it is known that fungi with inactivating mutations of subunits of V-ATPase that result in impaired vacuole acidification also lose virulence and grow poorly. Ergosterol, a fungal-specific steroid analogous to cholesterol in mammalian cells as a major membrane component, is critical for conformation and activity of the V-ATPase, and V-ATPase dysfunction appears to be a major mechanism of antifungal activity of ergosterol synthesis inhibitors, which includes several classes of existing antifungal agents. Antifungal agents that act via binding to specific proteins, e.g. enzyme inhibitors, are inherently vulnerable to development of drug resistance via single mutations in genes encoding target proteins. Agents that target fungi via adequately specific targeting and disruption of fungal acidic vacuoles by cation trapping may be less susceptible to development of resistance through point mutations than are drugs acting by binding to specific protein targets, due to impaired viability and virulence when vacuolar acidification, is impaired.

Clinically important antimalarial drugs are known that accumulate in acidic vacuoles and lysosomes and their biological activity is largely mediated through their concentration in acidic vacuoles, not only in malaria but in inflammatory diseases, some cancers and non-malarial infections by fungi and unicellular and protozoal parasites. Quinoline analog antimalarial drugs target malaria plasmodia via cation trapping in acidic digestive vacuoles, where they can accumulate to concentrations several orders of magnitude higher than in extracellular spaces. A large molar fraction of chloroquine, mefloquine, quinacrine and several of their congeners are uncharged at the usual extracellular pH of about 7.4 and the cytoplasmic pH of 7.1, and can thereby pass through cellular and organelle membranes. In an acidic environment such as the interior of a lysosome or fungal acidic vacuole, these antimalarials are predominantly cationic and are thereby restricted from free passage through the vacuolar membrane. Antimalarials such as chloroquine impair processing of heme from hemoglobin ingested by malaria plasmodia after accumulating in the feeding vacuoles, accounting for much of their specific toxicity to plasmodia. However, chloroquine and similar quinoline-analog antimalarials can accumulate in mammalian lysosomes and fungal acidic vacuoles and impair vacuolar function to a degree sufficient to provide some clinical benefit, if only by partially deacidifying the vacuoles. Chloroquine is used for treatment of in chronic autoimmune and inflammatory diseases such as systemic lupus erythematosis or rheumatoid arthritis, with moderate efficacy. A degree of antifungal activity has been reported for antimalarials such as chloroquine or quinacrine, both as single agents or in combination with other classes of antifungal agents, such as fluconazole, notably in animal models of systemic cryptococcosis. However, their activity is suboptimal, yielding incomplete fungal growth inhibition. Recent work has also demonstrated moderate growth inhibitory activity of chloroquine, mefloquine and other weakly cationic drugs such as siramesine in animal models of cancer. Existing lysosomotropic agents such as antimalarial quinolone compounds can thus display some therapeutically relevant activity in diseases in which acidic vacuoles contribute to pathogenesis. However, the activity and potency of antimalarials in such diseases are limited, as the target cells can tolerate accumulation of relatively high concentrations of the antimalarials; the specific lethal effect of quinoline compounds in malaria is largely attributed to disruption of heme processing within plasmodial feeding vacuoles, a mechanism of cytotoxicity not applicable in the areas of inflammatory disease, cancer or fungal infections. Despite the body of evidence indicating strong potential for targeting lysosomes for treating cancers, existing agents have not shown adequate activity or therapeutic index for effectively treating cancer in humans.

"Lyosomotropic detergents", comprising weakly cationic heterocyclic moieties bearing a single alkyl chain with approximately 10 to 14 carbon atoms, were reported be potently cytotoxic to mammalian cells and to display broad spectrum antifungal activity in vitro. This class of agents accumulate in lysosomes and acidic vacuoles via the same type of cation trapping process through which antimalarials are concentrated, and when they reach a critical micellar concentration in the vacuole, they behave as detergents, damaging vacuolar membranes. They display a characteristic sigmoid dose-response curve, as a consequence of their formation of micellar micro structures. However, there is no information about activity or safety of this class of agents in vivo in animal models of relevant diseases.

SUMMARY OF THE INVENTION

This invention provides a compound represented by Formula I or a pharmaceutically acceptable salt thereof

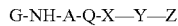

G-NH-A-Q-X—Y—Z                        I wherein

G is a monocyclic, bicyclic, or tricyclic aromatic ring having one, two, or three ring nitrogen atoms. G can be unsubstituted, or it can substituted at a ring carbon by amino, dimethylamino, hydroxy, halo, methyl, perfluoromethyl, or alkyl having from 1 to 16 carbon atoms which alkyl is either unsubstituted or substituted by hydroxy or alkoxy having 1 to 12 carbon atoms or acetoxy. Or it can be substituted at a ring nitrogen by alkyl having from 1 to 16 carbon atoms which alkyl is either unsubstituted or substituted by hydroxy or alkoxy having from 1 to 8 carbon atoms. N is nitrogen, H is hydrogen, and NH is absent or present. A is absent or present and is alkyl having from 1 to 12 carbon atoms, provided that if A has 1 carbon atom Q must be absent; Q is absent or present and is O, NHC(O), or NH, provided that if A is absent Q must be absent, and if both X and Y are absent Q cannot be O or NH. X is absent or present and is alkyl having from 1 to 5 carbon atoms, provided that if Y is absent and Z is alkoxy or phenoxy X must have more than 1 carbon atom. Y is absent or present and is phenyl unsubstituted or substituted by halo, or is a monocyclic or bicyclic aromatic ring having one or two nitrogen atoms. Z is absent or present and is hydrogen, alkyl having from 1 to 12 carbon atoms either unsubstituted or substituted by one phenyl or phenoxy group, alkoxy having from 1 to 12 carbon atoms either unsubstituted or substituted by one phenyl or phenoxy group, phenyl, phenoxy, or NHC(O)R$^6$ or C(O)NHR$^6$ or C(O)OR$^6$ where R$^6$ is alkyl having from 1 to 6 carbon atoms, provided that if all of A, Q, X, and Y are absent then Z must be alkyl having 6 to 12 carbon atoms.

This invention also provides a use or method for treating or preventing a condition in a mammalian subject; the condition being selected from the group consisting of an inflammatory disease, a fungal infection, a unicellular parasitic infection, and a neoplastic disease; comprising administering to the subject an effective amount of the compound or salt of the invention. It also provides compositions comprising these compounds or salt. And it provides a method of inhibiting a fungus ex vivo, comprising contacting a surface or the fungus with the compound or salt.

DETAILED DESCRIPTION OF THE INVENTION

Without wishing to be bound by theory, this invention provides compounds and their use for treating diseases characterized by pathogenic cells featuring lysosomes or other acidic vacuoles with disease-related alterations predisposing them to accumulation of compounds of the invention, which then selectively inactivate or eliminate such pathogenic cells. Compounds of the invention, many of which are aminoquinoline and aminoquinazoline derivatives, feature significant improvements in potency and activity over known aminoquinoline drugs such as chloroquine, as a consequence of structural moieties that potently disrupt lysosomal or vacuolar membrane integrity when the compounds accumulate in acidic vacuoles in cells. Diseases that are at least moderately responsive to antimalarial quinoline derivatives and analogs are in general more effectively treated with compounds of the invention. Such diseases broadly comprise inflammatory diseases, neoplastic diseases, including both hematologic cancers and solid tumors, and infections by eukaryotic pathogens, including fungi and several classes of protozoal or other unicellular parasites.

Definitions

As used herein the term "alkyl" means a linear or branched-chain or cyclic alkyl group. An alkyl group identified as having a certain number of carbon atoms means any alkyl group having the specified number of carbons. For example, an alkyl having three carbon atoms can be propyl or isopropyl; and alkyl having four carbon atoms can be n-butyl, 1-methylpropyl, 2-methylpropyl or t-butyl.

As used herein the term "halo" refers to one or more of fluoro, chloro, bromo, and iodo.

As used herein the term "perfluoro" as in perfluoromethyl, means that the group in question has fluorine atoms in place of all of the hydrogen atoms.

Certain chemical compounds are referred to herein by their chemical name or by the two-letter code shown below. The following are compounds of this invention.

| | |
|---|---|
| CH | N-[8-(Hexyloxy)octyl]quinolin-4-amine |
| CI | N-(8-Butoxyoctyl)quinolin-4-amine |
| CJ | N-(8-Methoxyoctyl)quinolin-4-amine |
| CK | N-[6-(Hexyloxy)hexyl]quinolin-4-amine |
| CL | N-(6-Butoxyhexyl)quinolin-4-amine |
| AL | N-[10-(Hexyloxy)decyl]quinolin-4-amine |
| AM | N-(10-Butoxydecyl)quinolin-4-amine |
| CM | N-(5-Methoxypentyl)quinolin-4-amine |
| AV | N-[8-(Hexyloxy)octyl]-2-methylquinolin-4-amine |
| AW | 7-Chloro-N-[8-(hexyloxy)octyl]quinolin-4-amine |
| AX | 8-Chloro-N-[8-(hexyloxy)octyl]quinolin-4-amine |
| AY | N-[8-(Hexyloxy)octyl]-7-(trifluoromethyl)quinolin-4-amine |
| CN | N-[8-(Hexyloxy)octyl]-8-(trifluoromethyl)quinolin-4-amine |
| BB | N-{5-[3-(Hexyloxy)propoxy]pentyl}quinolin-4-amine |
| BC | N-{3-[5-(Hexyloxy)pentyloxy]propyl}quinolin-4-amine |
| AJ | N-[8-(3-Ethoxypropoxy)octyl]quinolin-4-amine |
| BD | N-[8-(2-Propoxyethoxy)octyl]quinolin-4-amine |
| CO | N-[8-(Benzyloxy)octyl]quinolin-4-amine |
| AR | N-(6-Phenoxyhexyl)quinolin-4-amine |
| AN | N-(8-Phenoxyoctyl)quinolin-4-amine |
| CP | N-{2-[2-(Hexyloxy)phenoxy]ethyl}quinolin-4-amine |
| CQ | N-{3-[2-(Hexyloxy)phenoxy]propyl}quinolin-4-amine |
| CR | N-{4-[2-(Hexyloxy)phenoxy]butyl}quinolin-4-amine |
| CS | N-[3-(2-Ethoxyphenoxy)propyl]quinolin-4-amine |
| CT | N-[3-(2-Methoxyphenoxy)propyl]quinolin-4-amine |
| CU | N-{3-[2-(Benyloxy)phenoxy]propyl}quinolin-4-amine |
| BH | N-[8-(3-Methoxyphenoxy)octyl]quinolin-4-amine |
| CV | N-{4-[3-(Hexyloxy)phenoxy]butyl}quinolin-4-amine |
| AZ | N-{3-[3-(Hexyloxy)phenoxy]propyl}quinolin-4-amine |
| CW | N-{2-[3-(Hexyloxy)phenoxy]ethyl}quinolin-4-amine |
| AD | N-[8-(4-Methoxyphenoxy)octyl]quinolin-4-amine |

| | |
|---|---|
| CX | N-[6-(4-Methoxyphenoxy)hexyl]quinolin-4-amine |
| BA | N-{2-[4-(Hexyloxy)phenoxy]ethyl}quinolin-4-amine |
| CY | N-{3-[4-(Hexyloxy)phenoxy]propyl}quinolin-4-amine |
| CZ | N-{4-[4-(Hexyloxy)phenoxy]butyl}quinolin-4-amine |
| BE | N-[8-(m-Tolyloxy)octyl]quinolin-4-amine |
| BF | N-[8-(p-Tolyloxy)octyl]quinolin-4-amine |
| BG | N-[8-(o-Tolyloxy)octyl]quinolin-4-amine |
| DA | N-[8-(4-tert-Butylphenoxy)octyl]quinolin-4-amine |
| BJ | N-[8-(4-Fluorophenoxy)octyl]quinolin-4-amine |
| BI | N-[8-(3-Fluorophenoxy)octyl]quinolin-4-amine |
| DB | N-[8-(2-Fluorophenoxy)octyl]quinolin-4-amine |
| DC | N-(Biphenyl-4-yl)quinolin-4-amine |
| AO | N-(4-Hexylphenyl)quinolin-4-amine |
| AP | Hexyl 4-(quinolin-4-ylamino)benzoate |
| DD | N-(4-Phenoxyphenyl)quinolin-4-amine |
| DE | N-(3-Phenoxyphenyl)quinolin-4-amine |
| DF | N-(2-Phenoxyphenyl)quinolin-4-amine |
| DG | N-[4-(Quinolin-4-ylamino)phenyl]hexanamide |
| DH | N-[3-(Quinolin-4-ylamino)phenyl]hexanamide |
| AQ | N-Hexyl-4-(quinolin-4-ylamino)benzamide |
| BV | N-Hexyl-3-(quinolin-4-ylamino)benzamide |
| DI | N-(4-Methoxyphenyl)quinolin-4-amine |
| DJ | N-[4-(Benzyloxy)phenyl]quinolin-4-amine |
| DK | N-(4-Butoxyphenyl)quinolin-4-amine |
| DL | N-[4-(Hexyloxy)phenyl]quinolin-4-amine |
| DM | N-[3-(Benzyloxy)phenyl]quinolin-4-amine |
| DN | N-[3-(Hexyloxy)phenyl]quinolin-4-amine |
| DO | N-[2-(Benzyloxy)phenyl]quinolin-4-amine |
| DP | N-[2-(Hexyloxy)phenyl]quinolin-4-amine |
| BL | N-[2-Fluoro-4-(hexyloxy)phenyl]quinolin-4-amine |
| DQ | N-Benzylquinolin-4-amine |
| DR | N-Phenethylquinolin-4-amine |
| AA | N-[4-(Hexyloxy)benzyl]quinolin-4-amine |
| AC | N-[3-(Hexyloxy)benzyl]quinolin-4-amine |
| DS | N-[2-(Hexyloxy)benzyl]quinolin-4-amine |
| BK | N-[3-Fluoro-4-(hexyloxy)benzyl]quinolin-4-amine |
| DT | N-[4-(Decyloxy)benzyl]quinolin-4-amine |
| DU | N-[3-(Decyloxy)benzyl]quinolin-4-amine |
| AF | N-(3-Phenoxybenzyl)quinolin-4-amine |
| BU | N-[3-(Benzyloxy)benzyl]quinolin-4-amine |
| DV | N-(3-Phenethoxybenzyl)quinolin-4-amine |
| DW | N-[4-(Quinolin-4-ylamino)butyl]benzamide |
| DX | N-[6-(Quinolin-4-ylamino)hexyl]benzamide |
| DY | N-[8-(Quinolin-4-ylamino)octyl]benzamide |
| DZ | 3-Methoxy-N-[8-(quinolin-4-ylamino)octyl]benzamide |
| EA | 4-Methoxy-N-[8-(quinolin-4-ylamino)octyl]benzamide |
| EB | 2-(Hexyloxy)-N-[2-(quinolin-4-ylamino)ethyl]benzamide |
| EC | 2-(Hexyloxy)-N-[3-(quinolin-4-ylamino)propyl]benzamide |
| ED | 2-(Hexyloxy)-N-[4-(quinolin-4-ylamino)butyl]benzamide |
| EE | N-[8-(Quinolin-4-ylamino)octyl]picolinamide |
| EF | N-[8-(Quinolin-4-ylamino)octyl]nicotinamide |
| EG | N-[8-(Quinolin-4-ylamino)octyl]isonicotinamide |
| BZ | N-(Pyridin-4-ylmethyl)quinolin-4-amine |
| BY | N-(Pyridin-3-ylmethyl)quinolin-4-amine |
| EH | N-(Pyridin-2-ylmethyl)quinolin-4-amine |
| EI | N-Hexylquinolin-4-amine |
| AG | N-(Decyl)quinolin-4-amine |
| EJ | N-(Dodecyl)quinolin-4-amine |
| AI | $N^1,N^8$-Di(quinolin-4-yl)octane-1,8-diamine |
| EK | N-[8-(Hexyloxy)octyl]quinolin-6-amine |
| EL | N-[8-(Hexyloxy)octyl]quinolin-3-amine |
| EM | N-[8-(Hexyloxy)octyl]quinolin-8-amine |
| EN | N-[8-(Hexyloxy)octyl]-2-(trifluoromethyl)quinolin-4-amine |
| EO | 7-Chloro-N-decylquinolin-4-amine |
| EP | 7-Chloro-N-dodecylquinolin-4-amine |
| AH | N-(Decyl)quinazolin-4-amine |
| EQ | N-Dodecylquinazolin-4-amine |
| ER | N-Decyl-7-fluoroquinazolin-4-amine |
| ES | N-Dodecyl-7-fluoroquinazolin-4-amine |
| ET | 7-Chloro-N-decylquinazolin-4-amine |
| EU | 7-Chloro-N-dodecylquinazolin-4-amine |
| EV | N-(6-Butoxyhexyl)quinazolin-4-amine |
| EW | N-[8-(Hexyloxy)octyl]quinazolin-4-amine |
| AE | N-[8-(4-Methoxyphenoxy)octyl]quinazolin-4-amine |
| EX | N-{2-[2-(Hexyloxy)phenoxy]ethyl}quinazolin-4-amine |
| EY | N-{3-[2-(Hexyloxy)phenoxy]propyl}quinazolin-4-amine |
| EZ | N-{4-[2-(Hexyloxy)phenoxy]butyl}quinazolin-4-amine |
| FA | N-[8-(Quinazolin-4-ylamino)octyl]nicotinamide |
| AK | N-[3-(Hexyloxy)benzyl]quinazolin-4-amine |
| CG | N-[3-(Decyloxy)benzyl]quinazolin-4-amine |
| BM | N-(3-Phenoxybenzyl)quinazolin-4-amine |
| BN | N-[4-(Decyloxy)benzyl]quinazolin-4-amine |
| AB | N-[4-(Hexyloxy)benzyl]quinazolin-4-amine |
| FB | 1-[2-(Ethoxymethyl)-1H-imidazo[4,5-c]quinolin-1-yl]-2-methylpropan-2-ol |
| FC | 1-(4-Amino-1-isobutyl-1H-imidazo[4,5-c]quinolin-2-yl)pentyl acetate |
| FD | 1-Isobutyl-2-pentadecyl-1H-imidazo[4,5-c]quinolin-4-ol |
| BP | 1-Octyl-1H-imidazo[4,5-c]quinoline |
| FE | 1-Hexadecyl-1H-imidazo[4,5-c]quinoline |
| FF | 1-Hexadecyl-1H-imidazo[4,5-c]quinolin-4-amine |
| FG | 1-[2-(Dodecyloxy)ethyl]-1H-imidazo[4,5-c]quinoline |
| FH | 1-[2-(Dodecyloxy)ethyl]-N,N-dimethyl-1H-imidazo[4,5-c]quinolin-4-amine |
| FI | 1-[6-(Octyloxy)hexyl]-1H-imidazo[4,5-c]quinoline |
| CD | 1-(8-Ethoxyoctyl)-1H-imidazo[4,5-c]quinoline |
| CE | 1-(8-Methoxyoctyl)-1H-imidazo[4,5-c]quinoline |
| BQ | 1-(8-Butoxyoctyl)-1H-imidazo[4,5-c]quinoline |
| FJ | 1-[9-(Hexyloxy)nonyl]-1H-imidazo[4,5-c]quinoline |
| FK | 1-(10-Butoxydecyl)-1H-imidazo[4,5-c]quinoline |
| BO | 4-Amino-1-[8-(hexyloxy)octyl]pyridinium salts |
| FL | 4-(8-Methoxyoctylamino)-1-methylpyridinium iodide |
| AS | 1-[8-(Hexyloxy)octyl]-1H-imidazo[4,5-c]pyridine |
| FM | 1-Hexadecyl-1H-imidazo[4,5-c]pyridine |
| AT | 1-(10-Butoxydecyl)-1H-imidazo[4,5-c]pyridine |
| FN | N-(8-Methoxyoctyl)pyridin-4-amine |
| FO | N-[8-(Hexyloxy)octyl]pyridin-3-amine |
| FP | N-[8-(Hexyloxy)octyl]pyridin-2-amine |
| AU | N-[8-(Hexyloxy)octyl]pyrimidin-4-amine |
| FQ | N-[8-Hexyloxy)octyl]pyrimidin-2-amine |
| FR | 1-[8-(Hexyloxy)octyl]-4-phenyl-1H-imidazole |
| FS | N-[8-(Hexyloxy)octyl]isoquinolin-1-amine |
| FT | N-[8-(Hexyloxy)octyl]isoquinolin-5-amine |
| FU | N-[8-(Hexyloxy)octyl]quinoxalin-2-amine |
| CC | 1-[8-(Hexyloxy)octyl]-1H-benzimidazole |
| FV | N-[8-(Hexyloxy)octyl]pyrazin-2-amine |
| FW | 1-[8-(Hexyloxy)octyl]-1H-indole |
| FX | 3-[8-(Hexyloxy)octyl]-3H-imidazo[4,5-b]pyridine |
| FY | 1-Dodecyl-1H-imidazo[4,5-c]quinoline |
| FZ | 1-[3-(Decyloxy)propyl]-1H-imidazo[4,5-c]quinoline |
| GA | 1-[4-(Decyloxy)butyl]-1H-imidazo[4,5-c]quinoline |
| GB | 1-[8-(Hexyloxy)octyl]-1H-imidazo[4,5-c]quinoline |
| GC | 1-{5-[3-(Hexyloxy)propoxy]pentyl}-1H-imidazo[4,5-c]quinoline |
| GD | 1-{3-[3-(Hexyloxy)phenoxy]propyl}-1H-imidazo[4,5-c]quinoline |

The following compounds were less active in the biological activity example(s) in which they were tested.

| | |
|---|---|
| BR | N-(2-Methoxyethyl)quinolin-4-amine |
| BS | N-[2-(Morpholin-4-yl)ethyl]quinolin-4-amine |
| BT | N-[3-(Quinolin-4-ylamino)propyl]benzamide |
| BW | N-(2-Diethylaminoethyl)-4-(quinolin-4-ylamino)benzamide |
| BX | N-(4-Dimethylaminobenzyl)quinolin-4-amine |
| CA | N-(Pyridin-4-ylmethyl)-8-(hexyloxy)octanamide |
| CB | N-(Quinolin-6-yl)-8-(hexyloxy)octanamide |
| CF | 1-{3-[(5-(Hexyloxy)pentoxy]propyl}1H-imidazo[4,5-c]quinoline |

As used herein the transitional term "comprising" is open-ended. A claim utilizing this term can contain elements in addition to those recited in such claim.

As used in the claims the word "or" means "and/or" unless such reading does not make sense in context. So for example, when it is stated in connection with Formula I that variable G can be substituted at a ring carbon "or" at a ring nitrogen, it may be substituted at a ring carbon, at a ring nitrogen, or at both a ring carbon and a ring nitrogen.

The following abbreviations are used in the chemical synthesis examples and elsewhere in this description:
DCM dichloromethane
DIEA N,N-diisopropylethylamine
DMA N,N-dimethylacetamide
DMAP 4-(N,N-dimethylamino)pyridine DME 1,2-dimethoxyethane
DMF N,N-dimethylformamide
DMSO dimethyl sulfoxide
EA ethyl acetate
Et$_2$O diethyl ether
EtOH ethanol
FC flash chromatography
Hex hexanes
IPA 2-propanol
LAH lithium tetrahydridoaluminate
MeOH methanol
mp melting point
NMP N-methylpyrrolidinone
NMR nuclear magnetic resonance spectrometry
SPE solid phase extraction
TEA triethylamine
THF tetrahydrofuran
TLC thin layer chromatography
Compounds In an embodiment of the compound or salt of Formula I, G is selected from the group consisting of substituted or unsubstituted quinolyl, substituted or unsubstituted quinazolyl, unsubstituted isoquinolyl, unsubstituted quinoxalyl, unsubstituted benzimidazolyl, unsubstituted pyridyl, unsubstituted pyrazinyl, unsubstituted indolyl, substituted or unsubstituted imidazoquinolyl, substituted pyridinium, unsubstituted imidazopyridine, unsubstituted pyrimidyl, and substituted imidazolyl. In another embodiment of the compound or salt of Formula I A-Q-X—Y—Z is selected from the group consisting of alkoxyphenylalkyl, alkoxyphenyl, alkoxyphenoxyalkyl, alkoxyalkyl, alkoxyalkoxyalkyl, phenoxyphenyl, phenoxyphenylalkyl, phenylalkoxyphenylalkyl, phenoxyalkyl, phenylalkoxyalkyl, alkylphenoxyalkyl, alkyl, (halophenoxy)alkyl, biphenyl, alkylphenyl, alkoxycarbonylphenyl, N-alkylcarbamoylphenyl, alkoxy(halophenyl), phenylalkyl, alkoxy(halophenyl)alkyl, (alkoxybenzamido)alkyl, picolinamidoalkyl, nicotinamidoalkyl, isonicotinamidoalkyl, N-(quinolylamino)alkyl, N-(quinazolylamino)alkyl, phenylalkoxyphenoxyalkyl, alkylalkoxyphenyl, phenylalkoxyphenyl, pyridylalkyl and hydroxyalkyl.

Some of the compounds of this invention in which G is unsubstituted or substituted quinolyl can be represented by Formula IA

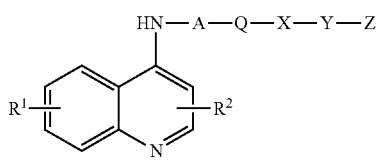

wherein A is absent or present and is alkyl having from 1 to 12 carbon atoms, provided that if A has 1 carbon atom Q must be absent. Q is absent or present and is O, NHC(O), or NH, provided that if A is absent Q must be absent, and if both X and Y are absent Q cannot be O or NH.

X is absent or present and is alkyl having from 1 to 5 carbon atoms, provided that if Y is absent and Z is alkoxy or phenoxy X must have more than 1 carbon atom. Y is absent or present and is phenyl unsubstituted or substituted by halo, or is a monocyclic or bicyclic aromatic ring having one or two nitrogen atoms. Z is absent or present and is hydrogen, alkyl having from 1 to 12 carbon atoms either unsubstituted or substituted by one phenyl or phenoxy group, alkoxy having from 1 to 12 carbon atoms either unsubstituted or substituted by one phenyl or phenoxy group, phenyl, phenoxy, or NHC(O)R$^6$ or C(O)NHR$^6$ or C(O)OR$^6$ where R$^6$ is alkyl having from 1 to 6 carbon atoms, provided that if all of A, Q, X, and Y are absent then Z must be alkyl having 6 to 12 carbon atoms. One of R$^1$ and R$^2$ is hydrogen and the other is selected from the group consisting of hydrogen, halo, methyl, and perfluoromethyl. In an embodiment of this invention both R$^1$ and R$^2$ are hydrogen. In an embodiment of Formula IA, A-Q-X—Y—Z is selected from the group consisting of alkoxyphenylalkyl, alkoxyphenyl, alkoxyphenoxyalkyl, alkoxyalkyl, alkoxyalkoxyalkyl, phenoxyphenyl, phenoxyphenylalkyl, phenylalkoxyphenylalkyl, phenoxyalkyl, phenylalkoxyalkyl, alkylphenoxyalkyl, alkyl, (halophenoxy)alkyl, biphenyl, alkylphenyl, alkoxycarbonylphenyl, N-alkylcarbamoylphenyl, alkoxy(halophenyl), phenylalkyl, alkoxy(halophenyl)alkyl, (alkoxybenzamido)alkyl, picolinamidoalkyl, nicotinamidoalkyl, isonicotinamidoalkyl, phenylalkoxyphenoxyalkyl, alkylalkoxyphenyl, phenylalkoxyphenyl, pyridylalkyl and N-(quinolylamino)alkyl.

A more specific embodiment of compounds in which G quinolyl can be represented by Formula IA1

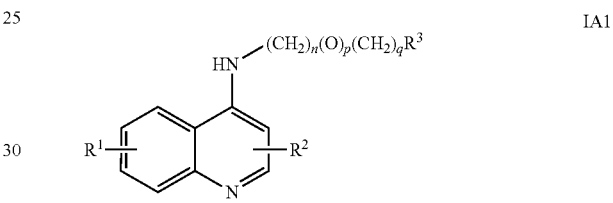

wherein n is 0, 1, 2, 3, 4, 5, 6, 7, 8, 9, 10, 11, or 12, provided that if p is 1 then n must not be 0 or 1. p is 0 or 1; and q is 0 or 1. One of R$^1$ and R$^2$ is hydrogen and the other is selected from the group consisting of hydrogen, halo, methyl, and perfluoromethyl. R$^3$ can be alkyl having from 1 to 10 carbon atoms either unsubstituted or substituted by: a) a phenyl or monocyclic or bicyclic aromatic ring having one or two nitrogen atoms or phenoxy either unsubstituted or substituted by phenoxy or alkoxy having from 1 to 6 carbon atoms, or b) alkoxy having from 1 to 6 carbon atoms, provided that if R$^3$ is alkyl substituted by alkoxy then alkyl must have more than 1 carbon atom. Alternatively R$^3$ can be phenyl unsubstituted or substituted by halo and unsubstituted or substituted by: a) alkyl having from 1 to 6 carbon atoms unsubstituted or substituted by phenyl or phenoxy, b) alkoxy having from 1 to 10 carbon atoms unsubstituted or substituted by phenyl or phenoxy, provided that when substituted by phenoxy the alkoxy must have more than one carbon atom, c) phenyl, d) phenoxy, or e) C(O)OR$^6$, C(O)NHR$^6$, or NHC(O)R$^6$, wherein R$^6$ is alkyl having from 1 to 6 carbon atoms.

In an embodiment of the compounds of Formula IA1, R$^1$ is hydrogen and R$^2$ is hydrogen. In a more specific embodiment n is 2, 3, 4, 5, 6, 7, 8, 9, or 10; p is 1; and R$^3$ is alkyl having from 1 to 6 carbon atoms. Examples of such compounds include N-[8-(Hexyloxy)octyl]quinolin-4-amine, N-(8-Butoxyoctyl)quinolin-4-amine, N-(8-Methoxyoctyl)quinolin-4-amine, N-[6-(Hexyloxy)hexyl]quinolin-4-amine, N-(6-Butoxyhexyl)quinolin-4-amine, N-[10-(Hexyloxy)decyl]quinolin-4-amine, N-(10-Butoxydecyl)quinolin-4-amine, N-(5-Methoxypentyl)quinolin-4-amine.

In another embodiment of the compounds of Formula IA1, n is 2, 3, 4, 5, 6, 7, 8, 9, or 10; p is 1; one of R$^1$ and R$^2$ is hydrogen and the other is selected from the group consisting of halo, methyl, and perfluoromethyl; and R³ is alkyl having from 1 to 6 carbon atoms. Examples of such compounds include N-[8-(Hexyloxy)octyl]-2-methylquinolin-4-amine, 7-Chloro-N-[8-(hexyloxy)octyl]quinolin-4-amine, 8-Chloro-N-[8-(hexyloxy)octyl]quinolin-4-amine, N-[8-(Hexyloxy)octyl]-7-(trifluoromethyl)quinolin-4-amine, N-[8-(Hexyloxy)octyl]-8-(trifluoromethyl)quinolin-4-amine.

In another embodiment of the compounds of Formula IA1 in which R¹ is hydrogen and R² is hydrogen: n is 2, 3, 4, 5, 6, 7, 8, 9, or 10; p is 1; R³ is alkyl having from 2 to 5 carbon atoms substituted by alkoxy having from 1 to 6 carbon atoms. Examples of such compounds include N-{5-[3-(Hexyloxy)propoxy]pent}quinolin-4-amine, N-{3-[5-(Hexyloxy)pentyloxy]propyl}quinolin-4-amine, N-[8-(3-Ethoxypropoxy)octyl]quinolin-4-amine, N-[8-(2-Propoxyethoxy)octyl]quinolin-4-amine.

A subset of compounds of Formula IA1 can be represented by Formula IA1a

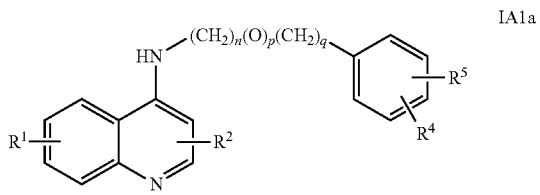

wherein n is 0, 1, 2, 3, 4, 5, 6, 7, or 8; p is 0 or 1; q is 0 or 1, provided that if p is 1 then n must not be 0 or 1. One of R¹ and R² is hydrogen and the other is selected from the group consisting of hydrogen, halo, methyl, and perfluoromethyl. R⁴ is hydrogen or halo. R⁵ is selected from the group consisting of hydrogen; halo; unbranched or branched alkyl having from 1 to 6 carbon atoms unsubstituted or substituted by phenyl or phenoxy; alkoxy having from 1 to 10 carbon atoms unsubstituted or substituted by phenyl or phenoxy, provided that when substituted by phenoxy the alkoxy must have more than one carbon atom; phenyl; phenoxy; C(O)OR⁶; C(O)NHR⁶; or NHC(O)R⁶, wherein R⁶ is alkyl having from 1 to 6 carbon atoms. In embodiment of Formula IA1a R¹ is hydrogen and R² is hydrogen. In a more specific embodiment p is 1 and R⁴ is hydrogen. In a still more specific embodiment R⁵ is hydrogen. Examples of such compounds include N-[8-(Benzyloxy)octyl]quinolin-4-amine, N-(6-Phenoxyhexyl)quinolin-4-amine, N-(8-Phenoxyoctyl)quinolin-4-amine.

In another embodiment of Formula IA1a, both R¹ and R² are hydrogen, q is 0, and R⁵ is alkoxy having from 1 to 6 carbon atoms unsubstituted or substituted by phenyl. In a more specific embodiment R⁵ is in the ortho position. Examples of such compounds include N-{2-[2-(Hexyloxy)phenoxy]ethyl}quinolin-4-amine, N-{3-[2-(Hexyloxy)phenoxy]propyl}quinolin-4-amine, N-{4-[2-(Hexyloxy)phenoxy]butyl}quinolin-4-amine, N-[3-(2-Ethoxyphenoxy)propyl]quinolin-4-amine, N-[3-(2-Methoxyphenoxy)propyl]quinolin-4-amine, N-{3-[2-(Benyloxy)phenoxy]propyl}quinolin-4-amine. Alternatively R⁵ is in the meta position. Examples of such compounds include N-[8-(3-Methoxyphenoxy)octyl]quinolin-4-amine, N-{4-[3-(Hexyloxy)phenoxy]butyl}quinolin-4-amine, N-{3-[3-(Hexyloxy)phenoxy]propyl}quinolin-4-amine, N-{2-[3-(Hexyloxy)phenoxy]ethyl}quinolin-4-amine. Alternatively R⁵ is in the para position. Examples of such compounds include N-[8-(4-Methoxyphenoxy)octyl]quinolin-4-amine, N-[6-(4-Methoxyphenoxy)hexyl]quinolin-4-amine, N-{2-[4-(Hexyloxy)phenoxy]ethyl}quinolin-4-amine, N-{3-[4-(Hexyloxy)phenoxy]propyl}quinolin-4-amine, N-{4-[4-(Hexyloxy)phenoxy]butyl}quinolin-4-amine.

In another embodiment of Formula IA1a, R¹ is hydrogen and R² is hydrogen, p is 1, R⁴ is hydrogen, and R⁵ is unbranched or branched alkyl having from 1 to 6 carbon atoms. Examples of such compounds include N-[8-(m-Tolyloxy)octyl]quinolin-4-amine, N-[8-(p-Tolyloxy)octyl]quinolin-4-amine, N-[8-(o-Tolyloxy)octyl]quinolin-4-amine, N-[8-(4-tert-Butylphenoxy)octyl]quinolin-4-amine. Alternatively R⁵ is fluoro. Examples of such compounds include N-[8-(4-Fluorophenoxy)octyl]quinolin-4-amine, N-[8-(3-Fluorophenoxy)octyl]quinolin-4-amine, N-[8-(2-Fluorophenoxy)octyl]quinolin-4-amine.

In another embodiment of Formula IA1a, R¹ is hydrogen and R² is hydrogen, and p is 0. In a more specific embodiment q is 0. In a still more specific embodiment n is 0. Examples of such compound include N-(Biphenyl-4-yl)quinolin-4-amine, N-(4-Hexylphenyl)quinolin-4-amine, Hexyl 4-(quinolin-4-ylamino)benzoate, N-(4-Phenoxyphenyl)quinolin-4-amine, N-(3-Phenoxyphenyl)quinolin-4-amine, N-(2-Phenoxyphenyl)quinolin-4-amine, N-[4-(Quinolin-4-ylamino)phenyl]hexanamide, N-[3-(Quinolin-4-ylamino)phenyl]hexanamide, N-Hexyl-4-(quinolin-4-ylamino)benzamide, N-Hexyl-3-(quinolin-4-ylamino)benzamide. Alternatively R⁵ is alkoxy having from 1 to 10 carbon atoms unsubstituted or substituted by phenyl. Examples of such compounds include N-(4-Methoxyphenyl)quinolin-4-amine, N-[4-(Benzyloxy)phenyl]quinolin-4-amine, N-(4-Butoxyphenyl)quinolin-4-amine, N-[4-(Hexyloxy)phenyl]quinolin-4-amine, N-[3-(Benzyloxy)phenyl]quinolin-4-amine, N-[3-(Hexyloxy)phenyl]quinolin-4-amine, N-[2-(Benzyloxy)phenyl]quinolin-4-amine, N-[2-(Hexyloxy)phenyl]quinolin-4-amine, N-[2-Fluoro-4-(hexyloxy)phenyl]quinolin-4-amine. In another embodiment of Formula IA1a, R¹ is hydrogen and R² is hydrogen, p is 0, q is 0, and n is 1 or 2. Examples of such compounds include N-Benzylquinolin-4-amine, and N-Phenethylquinolin-4-amine.

In another embodiment of Formula IA1a, R¹ is hydrogen and R² is hydrogen, p is 0, and q is 1. In a more specific embodiment R⁵ is alkoxy having from 1 to 10 carbon atoms. Examples of such compounds include N-[4-(Hexyloxy)benzyl]quinolin-4-amine, N-[3-(Hexyloxy)benzyl]quinolin-4-amine, N-[2-(Hexyloxy)benzyl]quinolin-4-amine, N-[3-Fluoro-4-(hexyloxy)benzyl]quinolin-4-amine, N-[4-(Decyloxy)benzyl]quinolin-4-amine, N-[3-(Decyloxy)benzyl]quinolin-4-amine. Alternatively R⁵ is phenoxy, or alkoxy having from 1 to 10 carbon atoms substituted by phenyl. Examples of such compounds include N-(3-Phenoxybenzyl)quinolin-4-amine, N-[3-(Benzyloxy)benzyl]quinolin-4-amine, N-(3-Phenethoxybenzyl)quinolin-4-amine.

Another more specific embodiment of compounds in which G quinolyl can be represented by Formula IA2

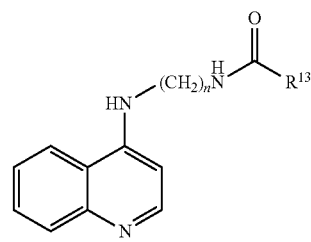

wherein n is 2, 3, 4, 5, 6, 7, or 8. $R^{13}$ is phenyl unsubstituted or substituted by alkoxy having from 1 to 6 carbon atoms; or 2-, 3-, or 4-pyridyl. In one embodiment $R^{13}$ is unsubstituted phenyl. Examples of such compounds include N-[4-(Quinolin-4-ylamino)butyl]benzamide, N-[6-(Quinolin-4-ylamino)hexyl]benzamide, N-[8-(Quinolin-4-ylamino)octyl]benzamide. In another embodiment $R^{13}$ is phenyl substituted by alkoxy having from 1 to 6 carbon atoms. Examples of such compounds include 3-Methoxy-N-[8-(quinolin-4-ylamino)octyl]benzamide, 4-Methoxy-N-[8-(quinolin-4-ylamino)octyl]benzamide, 2-(Hexyloxy)-N-[2-(quinolin-4-ylamino)ethyl]benzamide, 2-(Hexyloxy)-N-[3-(quinolin-4-ylamino)propyl]benzamide, 2-(Hexyloxy)-N-[4-(quinolin-4-ylamino)butyl]benzamide. Alternatively $R^{13}$ is 2-pyridyl, 3-pyridyl, or 4-pyridyl. Examples of such compounds include N-[8-(Quinolin-4-ylamino)octyl]picolinamide, N-[8-(Quinolin-4-ylamino)octyl]nicotinamide, N-[8-(Quinolin-4-ylamino)octyl]isonicotinamide.

Other examples of compounds of Formula IA include N-(Pyridin-4-ylmethyl)quinolin-4-amine, N-(Pyridin-3-ylmethyl)quinolin-4-amine, N-(Pyridin-2-ylmethyl)quinolin-4-amine, N-Hexylquinolin-4-amine, N-(Decyl)quinolin-4-amine, N-(Dodecyl)quinolin-4-amine, $N^1,N^8$-Di(quinolin-4-yl)octane-1,8-diamine. Other examples of compounds of Formula I in which G is quinolyl include N-[8-(Hexyloxy)octyl]quinolin-6-amine, N-[8-(Hexyloxy)octyl]quinolin-3-amine, N-[8-(Hexyloxy)octyl]quinolin-8-amine, N-[8-(Hexyloxy)octyl]-2-(trifluoromethyl)quinolin-4-amine, 7-Chloro-N-decylquinolin-4-amine, 7-Chloro-N-dodecylquinolin-4-amine.

Some of the compounds of this invention in which G is unsubstituted or substituted quinazolyl can be represented by Formula IB

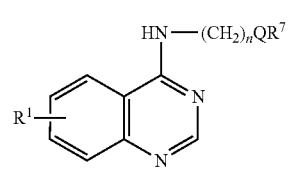

wherein A is absent or present and is alkyl having from 1 to 12 carbon atoms, provided that if A has 1 carbon atom Q must be absent. Q is absent or present and is O, NHC(O), or NH, provided that if A is absent Q must be absent, and if both X and Y are absent Q cannot be O or NH. X is absent or present and is alkyl having from 1 to 5 carbon atoms, provided that if Y is absent and Z is alkoxy or phenoxy X must have more than 1 carbon atom. Y is absent or present and is phenyl unsubstituted or substituted by halo, or is a monocyclic or bicyclic aromatic ring having one or two nitrogen atoms. Z is absent or present and is hydrogen, alkyl having from 1 to 12 carbon atoms either unsubstituted or substituted by one phenyl or phenoxy group, alkoxy having from 1 to 12 carbon atoms either unsubstituted or substituted by one phenyl or phenoxy group, phenyl, phenoxy, or NHC(O)$R^6$ or C(O)NHR$^6$ or C(O)OR$^6$ where $R^6$ is alkyl having from 1 to 6 carbon atoms, provided that if all of A, Q, X, and Y are absent then Z must be alkyl having 6 to 12 carbon atoms. $R^1$ is selected from the group consisting of hydrogen, halo, methyl, and perfluoromethyl.

In an embodiment of Formula IB, $R^1$ is hydrogen. In another embodiment, A-Q-X—Y—Z is selected from the group consisting of alkoxyphenylalkyl, alkoxyphenyl, alkoxyphenoxyalkyl, alkoxyalkyl, alkoxyalkoxyalkyl, phenoxyphenyl, phenoxyphenylalkyl, phenylalkoxyphenylalkyl, phenoxyalkyl, phenylalkoxyalkyl, alkylphenoxyalkyl, alkyl, (halophenoxy)alkyl, biphenyl, alkylphenyl, alkoxycarbonylphenyl, N-alkylcarbamoylphenyl, alkoxy(halophenyl), phenylalkyl, alkoxy(halophenyl)alkyl, (alkoxybenzamido)alkyl, picolinamidoalkyl, nicotinamidoalkyl, isonicotinamidoalkyl, phenylalkoxyphenoxyalkyl, alkylalkoxyphenyl, phenylalkoxyphenyl, pyridylalkyl, N-(quinazolylamino)alkyl, and N-(quinolylamino)alkyl.

A subset of compounds of Formula IB can be represented by Formula IB1

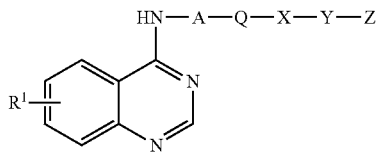

wherein n is 0, 1, 2, 3, 4, 5, 6, 7, 8, 9, 10, 11, or 12; Q is absent or present and is O or NHC(O), provided that if Q is present n cannot be 0 or 1; and provided that if Q is absent, then (CH$_2$)$_n$R$^7$ must have more than 5 carbon atoms. $R^1$ is hydrogen or halo. $R^7$ is selected from the group consisting of: hydrogen; alkyl having from 1 to 6 carbon atoms; and phenyl or monocyclic aromatic ring having one nitrogen atom, unsubstituted or substituted by alkyl having from 1 to 6 carbon atoms or alkoxy having from 1 to 10 carbon atoms or phenyl or phenoxy. In an embodiment Q is absent. Examples of such compounds include N-(Decyl)quinazolin-4-amine, N-Dodecylquinazolin-4-amine, N-Decyl-7-fluoroquinazolin-4-amine, N-Dodecyl-7-fluoroquinazolin-4-amine, 7-Chloro-N-decylquinazolin-4-amine, 7-Chloro-N-dodecylquinazolin-4-amine. In another embodiment Q is O or NHC(O). Examples of such compounds include N-(6-Butoxyhexyl)quinazolin-4-amine, N-[8-(Hexyloxy)octyl]quinazolin-4-amine, N-[8-(4-Methoxyphenoxy)octyl]quinazolin-4-amine, N-{2-[2-(Hexyloxy)phenoxy]ethyl}quinazolin-4-amine, N-{3-[2-(Hexyloxy)phenoxy]propyl}quinazolin-4-amine, N-{4-[2-(Hexyloxy)phenoxy]butyl}quinazolin-4-amine, N-[8-(Quinazolin-4-ylamino)octyl]nicotinamide. In an embodiment of Formula IB1, n is 1, Q is absent, and $R^7$ is phenyl substituted by alkoxy having from 1 to 10 carbon atoms or phenoxy. Examples of such compounds include N-[3-(Hexyloxy)benzyl]quinazolin-4-amine, N-[3-(Decyloxy)benzyl]quinazolin-4-amine, N-(3-Phenoxybenzyl)quinazolin-4-amine, N-[4-(Decyloxy)benzyl]quinazolin-4-amine, N-[4-(Hexyloxy)benzyl]quinazolin-4-amine.

Some of the compounds of this invention in which G is unsubstituted or substituted imidazoquinolyl can be represented by Formula IC

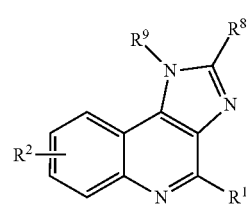

Wherein $R^1$ is hydrogen, OH, $NH_2$, or $N(CH_3)_2$; $R^2$ is selected from the group consisting of hydrogen, halo, methyl, and perfluoromethyl; $R^8$ is hydrogen, or alkyl having from 1 to 15 carbon atoms unsubstituted or substituted by alkoxy having 1 or 2 carbon atoms or acetoxy; and $R^9$ is a branched or unbranched alkyl having from 1 to 16 carbon atoms, unsubstituted or substituted by hydroxy, or alkoxy having from 1 to 12 carbon atoms, provided that if substituted by hydroxy or alkoxy $R^9$ must have more than 1 carbon atom. In an embodiment $R^2$ is hydrogen. Examples of such compounds include 1-[2-(Ethoxymethyl)-1H-imidazo[4,5-c]quinolin-1-yl]-2-methylpropan-2-ol, 1-(4-Amino-1-isobutyl-1H-imidazo[4,5-c]quinolin-2-yl)pentyl acetate, 1-Isobutyl-2-pentadecyl-1H-imidazo[4,5-c]quinolin-4-ol, 1-Octyl-1H-imidazo[4,5-c]quinoline, 1-Hexadecyl-1H-imidazo[4,5-c]quinoline, 1-Hexadecyl-1H-imidazo[4,5-c]quinolin-4-amine, 1-Dodecyl-1H-imidazo[4,5-c]quinoline, 1-{5-[3-(Hexyloxy)propoxy]pentyl}-1H-imidazo[4,5-c]quinoline, 1-{3-[3-(Hexyloxy)phenoxy]propyl}-1H-imidazo[4,5-c]quinoline. In another embodiment of Formula IC, $R^2$ is hydrogen, and $R^9$ is an unbranched alkyl having from 2 to 10 carbon atoms, substituted by alkoxy having from 1 to 12 carbon atoms. Examples of such compounds include 1-[2-(Dodecyloxy)ethyl]-1H-imidazo[4,5-c]quinoline, 1-[2-(Dodecyloxy)ethyl]-N,N-dimethyl-1H-imidazo[4,5-c]quinolin-4-amine, 1-[6-(Octyloxy)hexyl]-1H-imidazo[4,5-c]quinoline, 1-(8-Ethoxyoctyl)-1H-imidazo[4,5-c]quinoline, 1-(8-Methoxyoctyl)-1H-imidazo[4,5-c]quinoline, 1-(8-Butoxyoctyl)-1H-imidazo[4,5-c]quinoline, 1-[9-(Hexyloxy)nonyl]-1H-imidazo[4,5-c]quinoline, 1-(10-Butoxydecyl)-1H-imidazo[4,5-c]quinoline, 1-[3-(Decyloxy)propyl]-1H-imidazo[4,5-c]quinoline, 1-[4-(Decyloxy)butyl]-1H-imidazo[4,5-c]quinoline, 1-[8-(Hexyloxy)octyl]-1H-imidazo[4,5-c]quinoline.

Some of the compounds of this invention in which G is substituted pyridinium can be represented by Formula ID

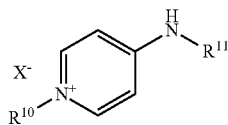

ID wherein $R^{10}$ is alkyl having from 1 to 8 carbon atoms, unsubstituted or substituted by alkoxy having from 1 to 6 carbon atoms, provided that if substituted by alkoxy $R^{10}$ must have more than 1 carbon atom. $R^{11}$ is hydrogen; or alkyl having from 1 to 8 carbon atoms, unsubstituted or substituted by alkoxy having from 1 to 3 carbon atoms, provided that if substituted by alkoxy $R^{11}$ must have more than 1 carbon atom. $X^-$ is a counterion. Examples of such compounds include a 4-Amino-1-[8-(hexyloxy)octyl]pyridinium salt, and 4-(8-Methoxyoctylamino)-1-methylpyridinium iodide.

In an embodiment of this invention G is 1H-imidazo[4,5-c]pyridine. Some of those compounds can be represented by Formula IE

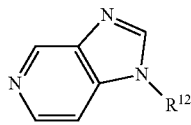

IE wherein $R^{12}$ is alkyl having from 2 to 16 carbon atoms, unsubstituted or substituted by alkoxy having from 4 to 6 carbon atoms. Examples of such compounds include 1-[8-(Hexyloxy)octyl]-1H-imidazo[4,5-c]pyridine, 1-Hexadecyl-1H-imidazo[4,5-c]pyridine, 1-(10-Butoxydecyl)-1H-imidazo[4,5-c]pyridine.

Examples of this invention in which G is pyridyl include N-(8-Methoxyoctyl)pyridine-4-amine, N-[8-(Hexyloxy)octyl]pyridin-3-amine, and N-[8-(Hexyloxy)octyl]pyridin-2-amine.

Examples of this invention in which G is pyrimidyl include N-[8-(Hexyloxy)octyl]pyrimidin-4-amine, and N-[8-Hexyloxy)octyl]pyrimidin-2-amine. In an embodiment of this invention G is 5-aryl 1H-imidazolyl. Examples of such compounds include 1-[8-(Hexyloxy)octyl]-4-phenyl-1H-imidazole. Examples of compounds of this invention in which G is isoquinolyl include N-[8-(Hexyloxy)octyl]isoquinolin-1-amine, N-[8-(Hexyloxy)octyl]isoquinolin-5-amine. Examples of compounds in which G is quinoxalyl include N-[8-(Hexyloxy)octyl]quinoxalin-2-amine. Examples of compounds in which G is benzimidazolyl include 1-[8-(Hexyloxy)octyl]-1H-benzimidazole. Examples of compounds in which G is pyrazinyl include N-[8-(Hexyloxy)octyl]pyrazin-2-amine. Examples of compounds in which G is indolyl include 1-[8-(Hexyloxy)octyl]-1H-indole. In an embodiment of this invention G is 3H-imidazo[4,5-b]pyridine. Examples of such compounds include 3-[8-(Hexyloxy)octyl]-3H-imidazo[4,5-b]pyridine.

In certain embodiments of this invention, one or more of the following compounds are excluded: imiquimod; 4-(n-decylamino)quinoline [58911-14-1]; 4-decylaminoquinazoline [22754-12-7].

In an embodiment of the compound of this invention, the compound is in substantially (at least 98%) pure form. This invention provides prodrugs of the compounds and salts described above, and their uses as described herein. Whenever a phenyl ring is substituted, the substitution may be at the ortho-, meta-, or para-position.

Reaction Schemes

The compounds of the present invention can be made in accordance with the following reaction schemes.

The compound of formula I wherein G is a monocyclic or bicyclic aromatic ring having one or two ring nitrogen atoms, either unsubstituted or substituted at a ring carbon by halo, methyl, or perfluoromethyl;

N is nitrogen, H is hydrogen;

A is absent or present and is alkyl having from 1 to 12 carbon atoms, provided that if A has 1 carbon atom Q must be absent;

Q is absent or present and is O, NHC(O), or NH, provided that if A is absent Q must be absent, and if both X and Y are absent Q cannot be O or NH;

X is absent or present and is alkyl having from 1 to 5 carbon atoms, provided that if Y is absent and Z is alkoxy or phenoxy X must have more than 1 carbon atom;

Y is absent or present and is phenyl unsubstituted or substituted by halo, or is a monocyclic or bicyclic aromatic ring having one nitrogen atom;

Z is absent or present and is: a) hydrogen, b) alkyl having from 1 to 12 carbon atoms either unsubstituted or substituted by one phenyl or phenoxy group, c) alkoxy having from 1 to 10 carbon atoms either unsubstituted or substituted by one phenyl or phenoxy group, d) phenyl, e) phenoxy, or f) $NHC(O)R^6$ or $C(O)NHR^6$ or $C(O)OR^6$ where $R^6$ is alkyl with 1 to 6 carbon atoms except if both X and Y are absent, provided that if all of A, Q, X, and Y are absent then Z must be alkyl having 6 to 12 carbon atoms, can be prepared from the reaction of the compound of formula 1 with the compound of formula 2 where LG is a leaving group such as a halogen, a sulfonyloxy, a siloxy, or a borate via the reaction scheme in Scheme 1. If LG is located in a position on the aromatic ring that is activated by a nitrogen atom, the reaction of step (a) can proceed thermally without the use of a catalyst, and LG is halo is preferred, and LG is chloro is most preferred. G is preferably selected from the group of compounds consisting of unsubstituted or substituted 4-quinolyl, 4-quinazolyl, 2-quinolyl, 2-quinazolyl, 1-isoquinolyl, 3-isoquinolyl, 2-quinoxalyl, 1-phthalazyl, 2-pyridyl, 4-pyridyl, 2-pyrimidyl, 4-pyrimidyl, and 2-pyrazinyl. The compound of formula 1 and the compound of formula 2 and a suitable base such as triethylamine, tripropylamine, N-methylmorpholine, or diisopropylethylamine are heated in a suitable solvent such as 1-pentanol, 1-butanol, 2-propanol, dimethylformamide, N-methylpyrrolidinone, or a mixture of suitable solvents. If LG is not located in a position on the aromatic ring that is activated by a nitrogen atom, the reaction can proceed with the use of a catalyst such as a transition metal complex catalyst such as a palladium complex or a nickel complex.

Scheme 1

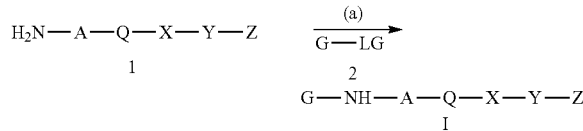

The compound of formula 7 where T is CH and $R^2$ is present or T is N and $R^2$ is absent and where either: a) n is 2-12 and p is 1; or b) n is 0 or 1 and p is 0; and where q is 0 or 1, and one of $R^1$ and $R^2$ is hydrogen and the other is selected from the group consisting of hydrogen, halo, methyl, and perfluoromethyl, and $R^3$ is alkyl having from 1 to 10 carbon atoms either unsubstituted or substituted by: a) a monocyclic or bicyclic aromatic ring having one or two nitrogen atoms or phenyl either unsubstituted or substituted by alkoxy having from 1 to 6 carbon atoms, or b) alkoxy having from 1 to 6 carbons, provided that if $R^3$ is alkyl substituted by alkoxy then alkyl cannot have 1 carbon atom; phenyl unsubstituted or substituted by halo and unsubstituted or substituted by: a) alkyl having from 1 to 6 carbon atoms, b) alkoxy having from 1 to 10 carbon atoms unsubstituted or substituted by phenyl or phenoxy provided that when substituted by phenoxy the alkoxy must have more than one carbon atom, c) phenyl, d) phenoxy, or e) C(O)OR$^6$, C(O)NHR$^6$, or NHC(O)R$^6$ wherein R$^6$ is alkyl having from 1 to 6 carbon atoms can be prepared starting from the compound of formula 3 or starting from the compound of formula 6 via the reaction scheme in Scheme 2.

Some compounds of the formula 3 and some compounds of the formula 6 are commercially available. The compound of formula 3 is reacted with the compound of formula 4 to give the compound of formula 5 via reaction of step (a): the compound of formula 3 is treated with a suitable base and then is reacted with the compound of formula 4. The selectivity of the reaction for substitution of only one of the bromides of the compound of formula 4 can be increased by using a stoichiometric excess of the compound of formula 3. If n is 1, any base that is commonly used to convert an alcohol to an alkoxide is suitable, such as sodium hydride or a hindered alkali metal alkoxide such as sodium isopropoxide. If n is 1, the base must be completely reacted with the compound of formula 3 before the addition of the compound of formula 4 is performed. If n is 0, any base that is commonly used to convert a phenol to a phenoxide is suitable, such as potassium carbonate or sodium carbonate. If n is 0, the compound of formula 4 may be present when the base is reacted with the compound of formula 3.

The compound of formula 5 is converted to the compound of formula 6 via reactions of step (b), the Gabriel synthesis of primary amines. The compound of formula 5 is reacted with potassium phthalimide under conventionally used conditions to give the phthalimide intermediate, which is converted to the compound of formula 6 under conventionally used conditions such as hydrazine monohydrate in ethanol at reflux. Any method for the cleavage of phthalimides may be used.

The compound of formula 6 is converted to the compound of formula 7 via step (c): the compound of formula 6 reacts with the compound of formula 7 in the presence of a tertiary amine base such as triethylamine, diisopropylethylamine, or tripropylamine at elevated temperature in a suitable solvent, such as 2-propanol heated at reflux if T is N or 1-pentanol heated at reflux or dimethylformamide or N-methylpyrrolidinone at 130-150° C. if T is CH.

Scheme 2.

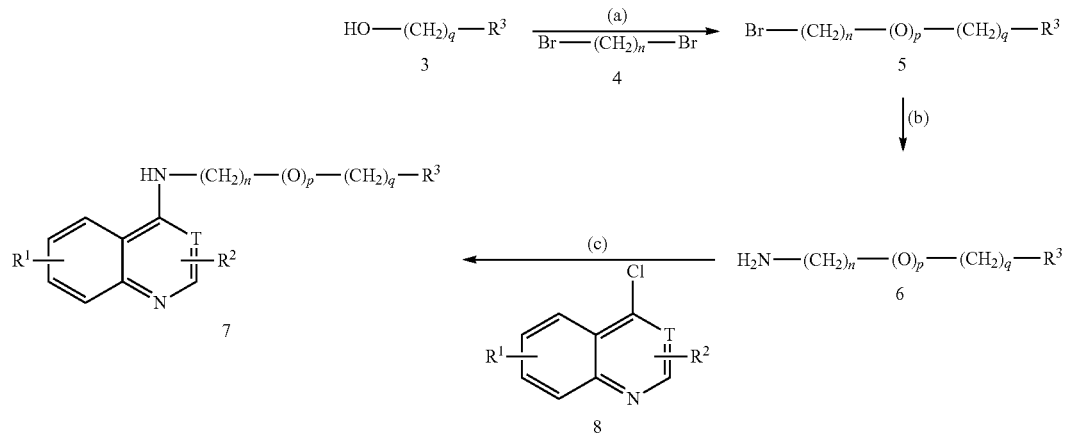

The compound of formula 3 where q is 0 or 1 and $R^3$ is alkyl having from 1 to 10 carbon atoms substituted by alkoxy having from 1 to 12 carbon atoms, provided that if $R^3$ is alkyl substituted by alkoxy then alkyl cannot have one carbon, can be prepared via the reaction scheme in Scheme 3. In step (a), the compound of formula 9 where n is 2-11 is treated with any base that is commonly used to convert an alcohol to an alkoxide, such as sodium hydride or a hindered alkali metal alkoxide such as sodium isopropoxide. Then, the compound of formula 10 where $R^6$ is alkyl having from 1 to 12 carbon atoms is added. The selectivity of the reaction for alkylation of only one of the hydroxyls of the compound of formula 9 can be increased by using a stoichiometric excess of the compound of formula 9.

Scheme 3.

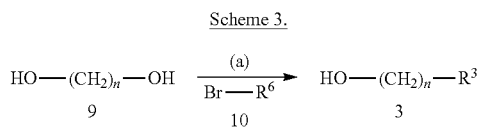

The compound of formula 3 where q is 0 or 1 and $R^3$ is phenyl substituted by halo, alkoxy having from 1 to 10 carbon atoms unsubstituted or substituted by phenyl or phenoxy, can be prepared from the compound of formula 11 where q is 0 or 1 and $R^4$ is hydrogen or halo via the reaction scheme in Scheme 4. The compound of formula 11 is treated with a suitable base such as potassium carbonate or sodium carbonate and reacted with the compound of formula 10, where $R^6$ is alkyl having from 1 to 10 carbon atoms unsubstituted or substituted by phenyl or phenoxy. When using carbonate bases with the compound of formula 11 wherein q is 1, the aromatic hydroxyl will react selectively with the compound of formula 10, despite the presence of the aliphatic hydroxyl. If n is 0, the use of a stoichiometric excess of the compound of formula 11 will minimize the quantity of the dialkylated side product.

Scheme 4.

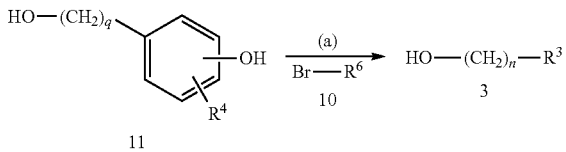

The compound of formula 6 where n is 0, p is 0, q is 0, and $R^3$ is phenyl unsubstituted or substituted by halo, $C(O)OR^6$ wherein $R^6$ is alkyl having from 1 to 6 carbon atoms can be prepared starting from the compound of formula 12 where $R^4$ is hydrogen or halo and the compound of formula 13 where $R^6$ is alkyl having from 1 to 6 carbon atoms via the reaction scheme in Scheme 5. The compound of formula 12 may be commercially available or can be prepared from the carboxylic acid using conventional methods. The compound of formula 14 where $R^4$ is hydrogen or halo and $R^5$ is $C(O)OR^6$ wherein $R^6$ is alkyl having from 1 to 6 carbon atoms is prepared from the reaction of the compound of formula 12 with the compound of formula 13 in the presence of a base such as pyridine or triethylamine via step (a). Any of the conventional methods for the preparation of carboxylic esters from carboxylic acids or their derivatives and alcohols may be used to prepare the compound of formula 14. If the compound of formula 13 is replaced by the amine analog, the reaction scheme will produce the compound of formula 6 where $R^3$ is substituted by $C(O)NHR^6$. The compound of formula 14 is reduced to form the compound of formula 6 by catalytic reduction using hydrogen and a palladium on charcoal catalyst via step (b). Any of the conventional methods for selective reduction of nitro groups to amino groups in the presence of carboxylic ester groups can be used in step (b).

Scheme 5.

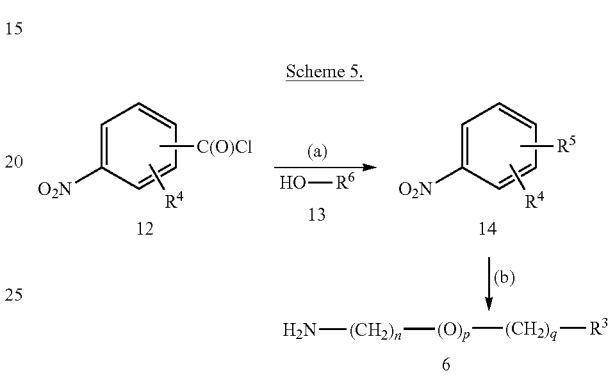

The compound of formula 6 where n is 0, p is 0, q is 0, and $R^3$ is phenyl unsubstituted or substituted by halo, $NHC(O)R^6$ wherein $R^6$ is alkyl having from 1 to 6 carbon atoms can be prepared starting from the compound of formula 15 where $R^4$ is hydrogen or halo and the compound of formula 16 where $R^6$ is alkyl having from 1 to 6 carbon atoms via the reaction scheme in Scheme 5. The compound of formula 15 and the compound of formula 16 can react to produce the compound of formula 14 where $R^4$ is hydrogen or halo and $R^5$ is $NHC(O)R^6$ wherein $R^6$ is alkyl having from 1 to 6 carbon atoms via the reaction of step (a) under any conventional conditions for preparing carboxamides from the reaction of amines with carboxylic acid chlorides. The compound of formula 14 is reduced to form the compound of formula 6 by catalytic reduction using hydrogen and a palladium on charcoal catalyst via step (b). Any of the conventional methods for reduction of nitro groups to amino groups can be used in step (b).

Scheme 6.

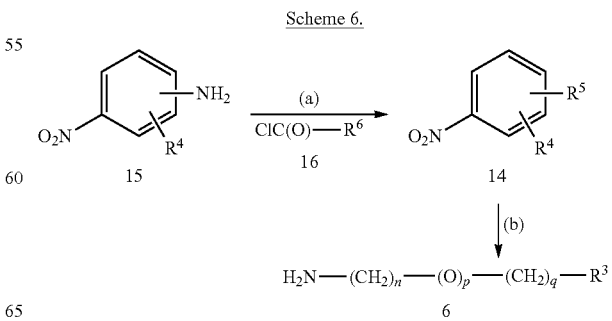

The compound of formula 6 where n is 0, p is 0, q is 0, and $R^3$ is phenyl unsubstituted or substituted by halo, alkoxy having from 1 to 12 carbon atoms either unsubstituted or substituted by one phenyl or phenoxy group, can be prepared starting from the compound of formula 17 where $R^4$ is hydrogen or halo and the compound of formula 10 where $R^6$ is alkyl having from 1 to 12 carbon atoms either unsubstituted or substituted by phenyl or phenoxy via the reaction scheme in Scheme 7. A mixture of compound of formula 17 and compound of formula 10 is reacted in the presence of a suitable base such as potassium carbonate or sodium carbonate and a suitable solvent such as dimethylformamide to give compound of formula 14 where $R^4$ is hydrogen or halo and $R^5$ is alkoxy having from 1 to 12 carbon atoms either unsubstituted or substituted by one phenyl or phenoxy group. The compound of formula 14 is reduced to form the compound of formula 6 by catalytic reduction using hydrogen and a palladium on charcoal catalyst via step (b). Any of the conventional methods for reduction of nitro groups to amino groups can be used in step (b).

Scheme 7.

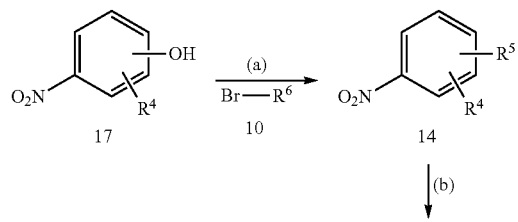

The compound of formula 6 where n is 0, p is 0, q is 1 and $R^3$ is either phenyl or a monocyclic or bicyclic aromatic ring having one or two nitrogen atoms, that is unsubstituted or substituted by halo and by: a) alkyl having from 1 to 12 carbon atoms, b) alkoxy having from 1 to 10 carbon atoms either unsubstituted or substituted by one phenyl or phenoxy group, c) phenyl, d) phenoxy, or e) $NHC(O)R^6$ or $C(O)NHR^6$ or $C(O)OR^6$ where $R^6$ is alkyl having from 1 to 6 carbon atoms can be prepared starting from the compound of formula 3 where q is 1 and $R^3$ is either phenyl or a monocyclic or bicyclic aromatic ring having one or two nitrogen atoms, that is unsubstituted or substituted by halo and by: a) alkyl having from 1 to 12 carbon atoms, b) alkoxy having from 1 to 10 carbon atoms either unsubstituted or substituted by one phenyl or phenoxy group, c) phenyl, d) phenoxy, or e) $NHC(O)R^6$ or $C(O)NHR^6$ or $C(O)OR^6$ where $R^6$ is alkyl having from 1 to 6 carbon atoms via the reaction scheme in Scheme 8. The compound of formula 3 is converted to the compound of formula 18 via the reaction of step (a) by treatment with thionyl chloride. Any of the reagents and reactions that are used conventionally to convert an alcohol and particularly a benzylic alcohol to a halide and particularly a benzylic halide can be used in step (a). Alternatively, the compound of formula 3 is converted to the compound of formula 19 via the reaction of step (b) by treatment with methanesulfonyl chloride and triethylamine. In step (b), any sulfonylation reagent that is conventionally used to convert a hydroxyl to a leaving group can be substituted for methanesulfonyl chloride, and any suitable base can be used in place of triethylamine. The compound of formula 18 or the compound of formula 19 is converted to the compound of formula 6 via reactions of step (c), the Gabriel synthesis of primary amines. The compound of formula 18 or the compound of formula 19 is reacted with potassium phthalimide under conventionally used conditions to give the phthalimide intermediate, which is converted to the compound of formula 6 under conventionally used conditions such as hydrazine monohydrate in ethanol at reflux. Any method for the cleavage of phthalimides may be used.

Scheme 8.

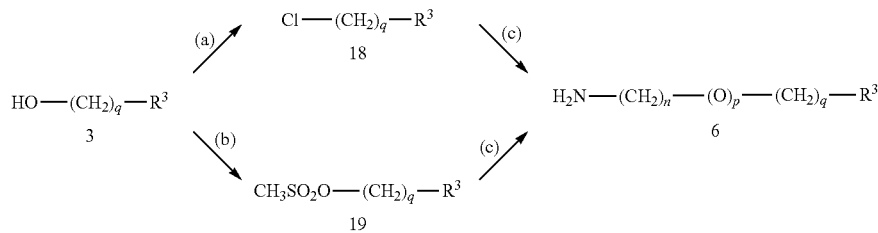

-continued

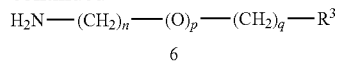

The compound of formula 24 where T is CH and $R^2$ is present or T is N and $R^2$ is absent and wherein n is 2, 3, 4, 5, 6, 7, or 8; $R^1$ and $R^2$ are hydrogen; and $R^{13}$ is phenyl, 2-, 3-, or 4-pyridyl unsubstituted or substituted by: a) alkyl having from 1 to 12 carbon atoms either unsubstituted or substituted by one phenyl or phenoxy group, b) alkoxy having from 1 to 12 carbon atoms either unsubstituted or substituted by one phenyl or phenoxy group, c) phenyl, or d) phenoxy can be prepared starting from the compound of formula 20 where $R^6$ is alkyl of 1 to 6 carbon atoms or, if commercially available, starting from the compound of formula 21 where $R^6$ is alkyl of 1 to 6 carbon atoms and $R^{13}$ is phenyl, 2-, 3-, or 4-pyridyl unsubstituted or substituted by: a) alkyl having from 1 to 12 carbon atoms either unsubstituted or substituted by one phenyl or phenoxy group, b) alkoxy having from 1 to 12 carbon atoms either unsubstituted or substituted by one phenyl or phenoxy group, c) phenyl, or d) phenoxy via the reaction scheme in Scheme 9. The compound of formula 20 is reacted with the compound of formula 10 where $R^6$ is alkyl having from 1 to 6 carbon atoms in the presence of a suitable base such as potassium carbonate via the reaction of step (a). The benzoic acid derivative of the compound of formula 20 can be used as the starting material, as well, if two equivalents of the compound of formula 10 and two equivalents of a suitable base are used. The compound of formula 21 can be reacted with the compound of formula 22 where n is 2-8 to produce the compound of formula 23 via the reaction of step (b). Step (b) can be carried out in the absence of solvent at a temperature of 100-130° C. The selectivity of acylation of only one of the amino groups of the compound of formula 22 can be increased by using a stoichiometric excess of the compound of formula 22. The compound of formula 23 can be reacted with the compound of formula 8 to give the compound of formula 24 via the reaction of step (c). A mixture of the compound of formula 23 and the compound of formula 7 where T is CH and $R^1$ and $R^2$ are hydrogen is heated in 1-pentanol at reflux or dimethylformamide or N-methylpyrrolidinone or a mixture thereof at 130-160° C. in the presence of a suitable base such as triethylamine, tripropylamine, N-methylmorpholine, or diisopropylethylamine base such as triethylamine or diisopropylethylamine to give the compound of formula 24 where T is N. As an alternative preparation of the compound of formula 24, compound of formula 8 where T is CH and $R^2$ is present or T is N and $R^2$ is absent can be reacted with the compound of formula 22 to give the compound of formula 25 where T is CH and $R^2$ is present or T is N and $R^2$ is absent via the reaction of step (d). Step (d) is performed using the same solvent, temperature, and base as described for step (c). The compound of formula 21 can be converted to the compound of formula 26 via the reactions of step (e). Any conventional method for the conversion of a carboxylic ester to a carboxylic acid chloride can be used for step (e); e.g., basic saponification and then reaction with thionyl chloride, oxalyl chloride, phosphoryl chloride, or phosphorus(V) chloride. The compound of formula 25 where T is CH or N and where $R^1$ and $R^2$ are hydrogen and the compound of formula 26 can be reacted to give the compound of formula 24 where T is CH or N via the reaction of step (f) using any of the conventional methods for the formation of carboxamides from carboxylic acid chlorides and amines.

Scheme 9.

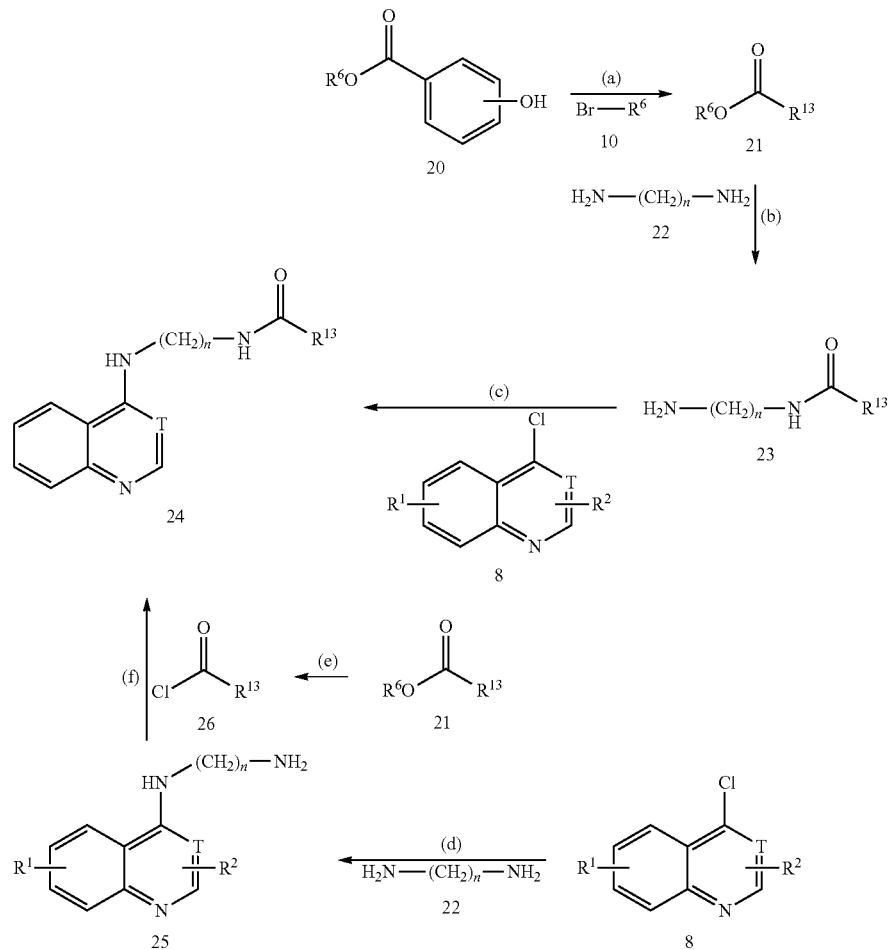

to give the compound of formula 24 where T is CH. A mixture of the compound of formula 23 and the compound of formula 7 where T is N and $R^1$ and $R^2$ are hydrogen is heated in 2-propanol at reflux in the presence of a suitable The compound of formula I wherein G is imidazoquinolyl unsubstituted or substituted at a ring carbon by halo, methyl, or perfluoromethyl; NH is absent; $R^1$ is hydrogen, OH, $NH_2$, or $N(CH_3)_2$; and either: a) AQXYZ is represented by $R^8$, and $R^9$ is a branched or unbranched alkyl having from 1 to 16 carbon atoms, unsubstituted or substituted by hydroxy or alkoxy having from 1 to 12 carbon atoms, provided that if substituted by hydroxy or alkoxy $R^9$ cannot have 1 carbon atom, or b) AQXYZ is represented by $R^9$, and $R^8$ is hydrogen or alkyl having from 1 to 15 carbon atoms unsubstituted or substituted by alkoxy having 1 or 2 carbon atoms or acetoxy can be prepared starting from the compound of formula 27 where $R^1$ is hydrogen or hydroxy and $R^2$ is hydrogen, halo, methyl, or perfluoromethyl via the reaction scheme in Scheme 10. In step (a), compound of the formula 27 where $R^1$ is hydrogen or hydroxy is nitrated to produce the compound of the formula 28 using nitric acid in hot acetic acid or propionic acid. In step (b), the compound of formula 28 is treated with a chlorinating agent such as phosphoryl chloride, alone or in combination with phosphorus(V) chloride, or with phenylphosphonic dichloride to produce the compound of formula 29, where $R^1$ is chloro if the compound of formula 28 had hydroxy as $R^1$. In step (c), the compound of formula 29 is reacted with the compound of formula 30 in the presence of a tertiary amine base such as triethylamine in an inert solvent such as dichloromethane, aided by gentle warming to produce the compound of formula 31. It is well-established in the literature that the 4-chloro of the compound of formula 29 where $R^1$ is chloro is the more reactive with amines. Any of the amines described in the invention can be used in step (c). It was discovered that if compound of formula 29 where $R^1$ is chloro is stirred with the compound of formula 30 in a mixture of dimethylformamide and dichloromethane initially, and then the dichloromethane is replaced with toluene and the mixture is heated at reflux, the compound of formula 31 where $R^1$ is $N(CH_3)_2$ is produced. In step (d), the nitro group of the compound of formula 31 is reduced by any of a number of methods. If $R^1$ is hydrogen or chloro, hydrogenation using 5% or 10% Pd—C or reduction using zinc dust and hydrochloric acid will produce the compound of formula 32 where $R^1$ is hydrogen. If $R^1$ is chloro, hydrogenation using 10% Pt—C will produce the compound of formula 32 where $R^1$ is chloro. If $R^1$ is dimethylamino, all these methods leave $R^1$ unchanged. In step (e), the ortho-diamine of the compound of formula 32 is heated with the carboxylic acid compound of formula 33 or the compound of formula 34, the ortho ester of the compound of 33, to produce the compound of formula 35. Any ortho ester analog of the compound of formula 33 may be used. In step (f), if the compound of formula 35 where $R^1$ is chloro is treated with hydrolytic conditions, the compound of formula 36 where $R^1$ is hydroxy is produced. In step (f), if the compound of formula 35 where $R^1$ is chloro is treated with ammonia or a primary amine, the $R^1$-amino derivative of the compound of formula 36 is produced. In step (f), if the compound of formula 35 where $R^1$ is chloro is treated with zinc dust and hydrochloric acid, the compound of formula 36 where $R^1$ is hydrogen is produced. The compound of formula 35 where $R^1$ and $R^2$ and $R^8$ are hydrogen and $R^9$ is stable to organolithium bases can be reacted with an organolithium base and then alkylated by an organohalide or aldehyde to give the compound of formula 36 where $R^8$ contains the derivative of the alkylation reagent.

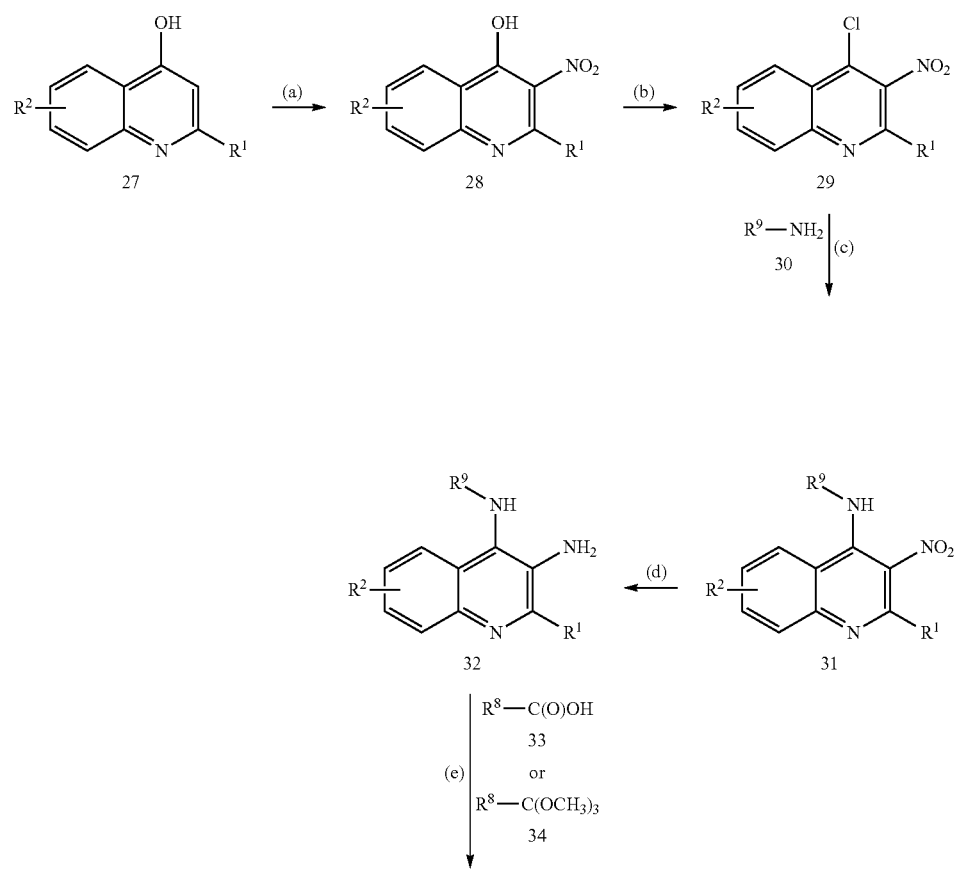

Scheme 10.

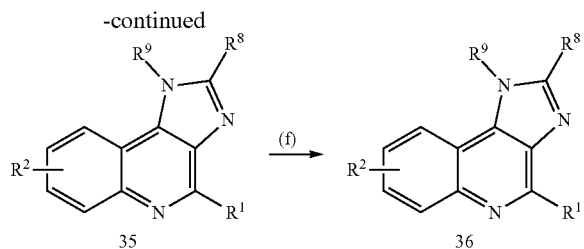

If the compound of formula 33, or the compound of formula 34, or the compound of formula 37 wherein n is 0-12, provided that if p is 1 then n must not be 0 or 1; p is 0 or 1; q is 0 or 1; $R^3$ is selected from the group consisting of: alkyl having from 1 to 10 carbon atoms either unsubstituted or substituted by: a) a monocyclic or bicyclic aromatic ring having one or two nitrogen atoms either unsubstituted or substituted by alkoxy having from 1 to 6 carbon atoms, or b) alkoxy having from 1 to 6 carbon atoms, provided that if $R^3$ is alkyl substituted by alkoxy then alkyl must have more than 1 carbon atom; and phenyl unsubstituted or carboxylic acid compound of the formula 33 via the reaction of step (b) using any of the numerous suitable methods for the oxidation of alcohols to acids, such as the Jones oxidation. Alternatively, the compound of formula 5 is reacted with an alkali metal cyanide such as sodium cyanide or potassium cyanide in a suitable solvent such as dimethylformamide to produce the compound of formula 38 via the reaction of step (c). In step (d), the compound of formula 38 is treated with an alcohol such as methanol and an acid catalyst such as hydrochloric acid to form the compound of formula 34.

Scheme 11.

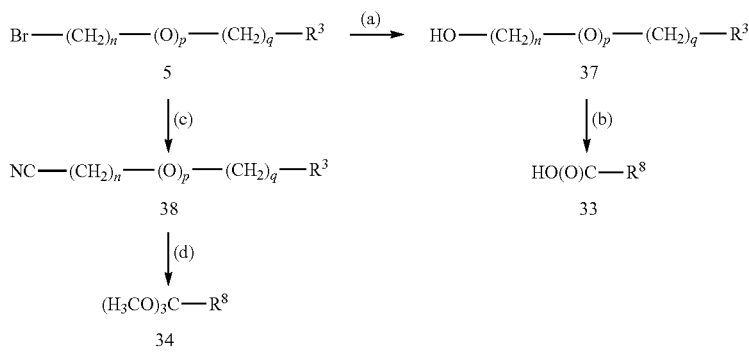

substituted by halo and unsubstituted or substituted by: a) alkyl having from 1 to 6 carbon atoms, b) alkoxy having from 1 to 10 carbon atoms unsubstituted or substituted by phenyl or phenoxy, provided that when substituted by phenoxy the alkoxy must have more than one carbon atom, c) phenyl, d) phenoxy, or e) $C(O)OR^6$, $C(O)NHR^6$, or $NHC(O)R^6$, wherein $R^6$ is alkyl having from 1 to 6 carbon atoms is not available commercially or as a synthetic intermediate, the compound of formula 5 can be converted to the compound of formula 37 and hence to the compound of formula 33, or the compound of formula 5 can be converted to the compound of formula 34 via the Pinner reaction by the scheme shown in Scheme 11. In step (a), the compound of formula 5 is reacted with the alkali metal salt of acetic acid, such as potassium acetate or sodium acetate or lithium acetate, in a suitable solvent such as dimethylformamide. Then, the acetate ester is hydrolyzed at moderately basic pH to produce the compound of formula 37. The compound of formula 37, a primary alcohol, can be oxidized to the The compound of formula ID wherein $R^{10}$ is alkyl having from 1 to 8 carbon atoms, unsubstituted or substituted by alkoxy having from 1 to 6 carbon atoms, provided that if substituted by alkoxy $R^{10}$ must have more than 1 carbon atom; $R^{11}$ is hydrogen, or alkyl having from 1 to 8 carbon atoms, unsubstituted or substituted by alkoxy having from 1 to 3 carbon atoms, provided that if substituted by alkoxy $R^{11}$ must have more than 1 carbon atom; and $X^-$ is a counterion can be prepared by the scheme shown in Scheme 12. If the compound of formula 41 is not commercially available, compound 39, 4-chloropyridine hydrochloride, can be used to prepare it via the reaction of step (a). Compound 39 is heated at 130-140° C. in a hindered alcohol such as 2-propanol in the presence of a tertiary amine base such as triethylamine with the compound of formula 40 to give the compound of formula 41. Via the reaction of step (b), the compound of formula 41 is reacted with an alkyl sulfonate such as the compound of formula 42 in a suitable solvent such as acetone to give the compound of formula ID, where $X^-$ is a counterion such as methanesulfonate, iodide, bromide, or chloride. Any alkyl iodide or alkyl bromide or alkyl sulfonate derivative of $R^{10}$ can be used in the reaction of step (b).

Scheme 12.

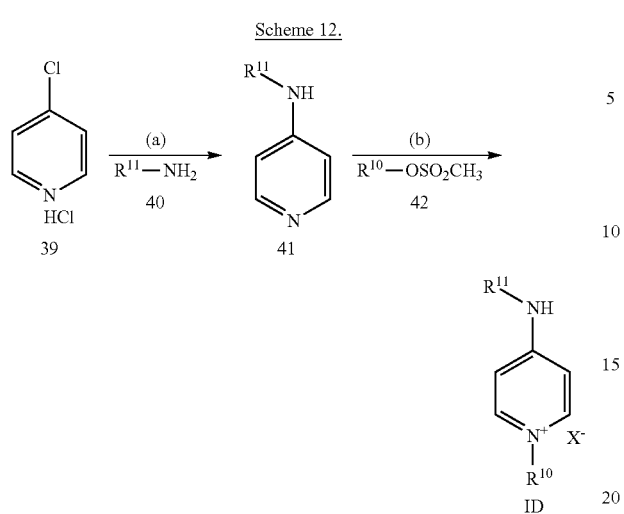

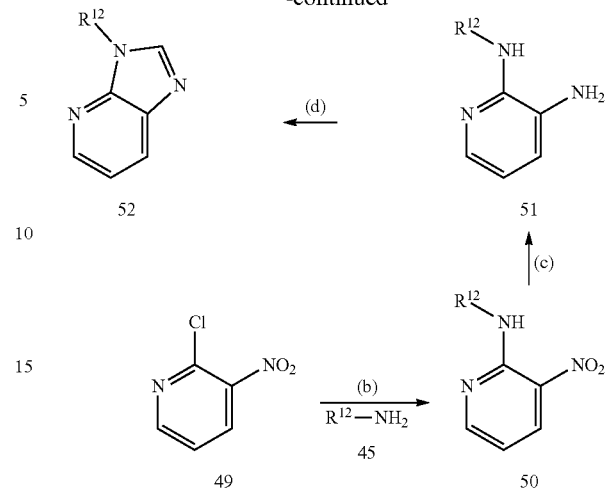

The compound of formula 48, where $R^{12}$ is alkyl having from 2 to 16 carbon atoms, unsubstituted or substituted by alkoxy having from 4 to 6 carbons, can be prepared starting from compound 43, 4-hydroxy-3-nitropyridine, by the scheme shown in Scheme 13. Compound 43 is reacted with a suitable halogenating agent such as phenylphosphonic dichloride to give compound 44, 4-chloro-3-nitropyridine via the reaction of step (a). Compound 44 is reacted with the compound of formula 45 in the presence of a suitable base such as triethylamine in a suitable solvent such as pyridine to produce the compound of formula 46 via the reaction of step (b). Any of the amines described in the invention can be used in step (b). The nitro group of the compound of formula 46 is reduced to the amino group of the compound of formula 47 by catalytic hydrogenation via the reaction of step (c). The compound of formula 47 is heated in triethyl orthoformate to produce the compound of formula 48 via the reaction of step (d). Using the same steps (b), (c), and (d), but starting from commercially available compound 49, 2-chloro-3-nitropyridine, the compound of formula 52 is prepared.

Scheme 13.

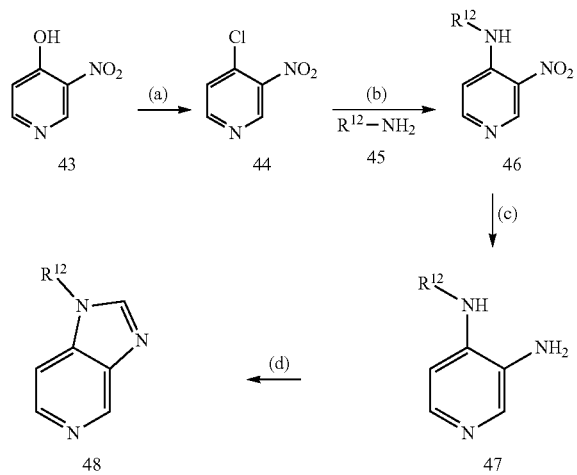

Any compound of formula 53 where G is a monocyclic, bicyclic, or tricyclic aromatic ring having one, two, or three ring nitrogen atoms where a ring nitrogen atom is bonded to hydrogen can react with the compound of formula 55 where Br-AQXYZ is a primary alkyl bromide to produce the compound of the formula 54, where AQXYZ is given by claim 1 for the compound of formula I, by the scheme shown in Scheme 14. The compound of the formula 53 is treated with a strong base such as sodium tert-butoxide in a suitable solvent such as dimethylformamide, and the resulting amide anion is treated with the compound of formula 55 to produce the compound of formula 54 via the reaction of step (a). If the amide anion is in resonance with a neighboring nitrogen, the alkylation by the compound of formula 55 occurs at the less hindered nitrogen selectively. The primary alkyl iodide, chloride, alkanesulfonate, or arylsulfonate of AQXYZ can be used in place of the compound of formula 55 for the reaction of step (a).

Scheme 14.

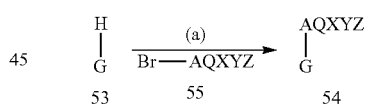

Any compound of formula 58 where G is a monocyclic, bicyclic, or tricyclic aromatic ring having one, two, or three ring nitrogen atoms as defined in claim 1, where a ring carbon atom is bonded to an $NH_2$ group, can undergo an alkylation procedure to produce a compound with the formula 59, where A, Q, X, Y, and Z are as defined in claim 1, starting from the compound of formula 56, where (AQXYZ) is a radical that is terminated by a primary alcohol group, by the scheme shown in Scheme 15. Many compounds of the formula 58 are available commercially. The compound of the formula 56, where the radical (AQXYZ) is terminated by a primary alcohol function and where (AQXYZ) does not contain another alcohol group or an amino group, can undergo oxidation by any of a variety of conventional methods such as the Swern oxidation or oxidation by tetrapropylammonium perruthenate/N-methylmorpholine N-oxide to produce the compound of formula 57 via the reaction of step (a). The compound of formula 58 can undergo reductive alkylation by the compound of formula 57 via the reaction of step (b) using any conventional method for amine reductive alkylation such as by sodium cyanoborohydride in tetrahydrofuran. Alternatively, the compound of formula 58 can undergo acylation by the carboxylic acid radical of (AQXYZ) via the reaction of step (d) using any conventional method for amide formation such as a carbodiimide condensation or a mixed anhydride acylation using isopropyl chloroformate. Also, step (d) can be carried out using the acid chloride derivative of the compound of formula 60, which can be produced using any conventional reagent for the preparation of acid chlorides such as thionyl chloride or oxalyl chloride. The compound of formula 60 can be produced from the compound of formula 56 via the reaction of step (c) using any suitable conventional reagent for the oxidation of alcohols such as the Jones reagent. The amide group of the compound of formula 61, where (AQXYZ) does not contain an ester or another amide group, can be reduced to the amino group of the compound of formula 59 via the reaction of step (e) using a suitable reducing agent such as lithium aluminum hydride.

Scheme 15.

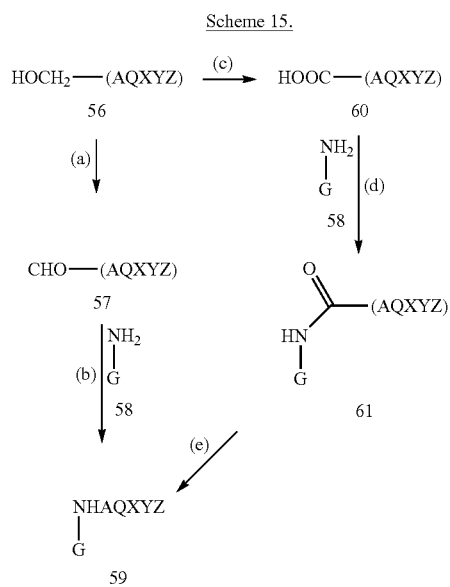

Any compound of formula 58 where G is a monocyclic, bicyclic, or tricyclic aromatic ring having one, two, or three ring nitrogen atoms as defined in claim 1, where a ring carbon atom is bonded to an $NH_2$ group, can undergo an alkylation procedure to produce a compound with the formula 59, where A, Q, X, Y, and Z are as defined in claim 1, starting from the compound of formula 56, where (AQXYZ) is a radical that is terminated by a primary alcohol group, by the scheme shown in Scheme 16. Many compounds of the formula 58 are available commercially. The compound of the formula 56, where the radical (AQXYZ) is terminated by a primary alcohol function and where (AQXYZ) does not contain another alcohol or amino group, can undergo a sulfonylation reaction using methanesulfonyl chloride and an amine base such as pyridine or triethylamine to produce the compound of formula 62 via the reaction of step (a). The compound of formula 58 can undergo substitutive alkylation by the compound of formula 62 to produce the compound of formula 59 via the reaction of step (b) using any conventional method for amine alkylation, such as heating the mixture in tetrahydrofuran or dimethylformamide in the absence or presence of a base such as triethylamine, diisopropylamine, or N-methylmorpholine. Analogs of the compound of formula 62 where the methanesulfonate group is replaced by a conventional good leaving group such as iodide, bromide, chloride, or a different sulfonate group can be used in step (b).

Scheme 16.

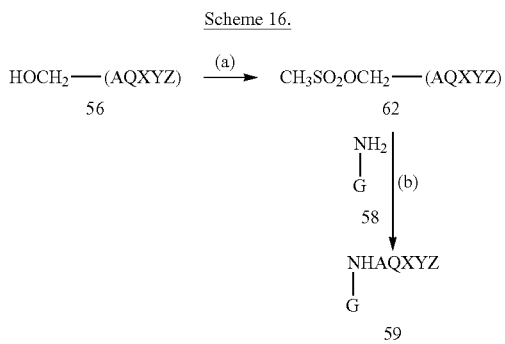

Uses and Methods of Treatment

This invention provides certain compounds, described below, for treating diseases characterized by pathogenic cells featuring lysosomes or other acidic vacuoles with disease-related alterations predisposing them to accumulation of compounds of the invention, which then selectively inactivate or eliminate such pathogenic cells. Compounds of the invention, many of which are aminoquinoline and aminoquinazoline derivatives, feature significant improvements in potency and activity over known aminoquinoline drugs such as chloroquine, as a consequence of structural moieties that potently disrupt lysosomal or vacuolar membrane integrity when the compounds accumulate in acidic vacuoles in cells. Diseases that are at least moderately responsive to antimalarial quinoline derivatives and analogs are in general more effectively treated with compounds of the invention. Such diseases broadly comprise inflammatory diseases, neoplastic diseases, including both hematologic cancers and solid tumors, and infections by eukaryotic pathogens, including fungi and several classes of protozoal or other unicellular parasites.

Anti-Inflammatory Use

An important action of compounds of the invention is anti-inflammatory activity, providing utility for treating or preventing diseases or symptoms related to excessive tissue inflammation. This invention also provides compositions containing a compound of this invention as well as the use of a compound of this invention for the manufacture of a medicament for treatment or prevention of inflammatory diseases. Compounds of the invention display selectivity for suppressing or inactivating macrophages that have been stimulated into a pro-inflammatory state, with less of an effect on non-stimulated macrophages. Activated pro-inflammatory macrophages contribute to pathogenesis of a large variety of inflammatory and autoimmune diseases. Macrophages are both antigen presenting cells and effectors for tissue damage directed by autoreactive T cells, and participate in tissue damage and dysfunction in diseases including but not limited to rheumatoid arthritis, systemic lupus erythematosis, psoriasis, inflammatory bowel disease, and atopic dermatitis Inflammatory macrophages participate in many systemic diseases, including autoimmune diseases, cardiovascular and metabolic diseases, and neurodegenerative conditions. Activated macrophages play a primary role in tissue damage in instability of atherosclerotic plaques, with consequent risk of rupture and thrombotic vessel occlusion. Activated macrophages in adipose tissue contribute to metabolic abnormalities including insulin resistance, type 2 diabetes and other consequences of obesity. Osteoclasts are macrophage-like cells that mediate bone degeneration in osteoporosis and in participate in bone destruction and "bone pain" in cancers arising in or metastasized to bones. Compositions of the invention are useful for treating these and other disorders in which activated macrophages contribute to inflammatory disease pathogenesis.

Several classes of topical agents are used for treatment of inflammatory diseases of the skin, such as atopic dermatitis, eczema or psoriasis. Corticosteroids are widely used, but have the potential for both local and systemic toxicities, particularly with prolonged use. They can cause local skin atrophy or thinning, which may lead to disruption of the skin, as well as telangiectasia. Furthermore, topical corticosteroids can be absorbed systemically in amounts sufficient to cause systemic side effects. A second class of agents for treatment of atopic dermatitis is T cell immunosuppressants, such as the calcineurin inhibitors tacrolimus and pimecrolimus. Their local and systemic immunosuppressive effects have led to concerns about depressing immunosurveillance of cancers, including melanomas and lymphomas.

Vitamin D analogs, notably calcipotriene, are known for topical treatment of psoriasis. Calcipotoriene acts by inhibiting excessive proliferation of keratinocytes. Application to normal skin is contra-indicated due to a bleaching effect and there is also a possibility of adverse events from systemic absorption. Dermal irritation or itching is known as a side effect of calcipotriene. Compounds of the invention are particularly active against macrophage precursors that have been activated by exposure to vitamin D3. It is possible that psoriasis treatment with calcipotriene, while providing some improvements by inhibiting keratinocyte proliferation, may also direct local macrophages toward a pro-inflammatory state, contributing to known side effects such as irritation, and limiting the net therapeutic effect. The ability of compounds of the invention to inactivate pro-inflammatory vitamin D3-primed macrophage precursors as shown in several Examples below indicates that combination topical treatment with compounds of the invention and vitamin D analogs may provide unexpected benefits in psoriasis and psoriatic dermatitis, both in treating the inflammatory epidermal hyperproliferation and in reducing irritation or itching as side effects of vitamin D analogs.

Compounds of the invention are useful for treating ocular inflammation, including keratitis, whether caused by infection (fungal, bacterial, amoebic) or by non-infectious triggers such as corneal injury or contact lenses. Compounds of the invention are especially suitable for fungal keratitis, counteracting both infectious fungi and concurrent inflammatory damage. Compounds of the invention inhibit corneal angiogenesis and other inflammatory changes in response to mechanical or chemical injury.

Compounds of the invention are useful for treating a variety of inflammatory or hyperproliferative skin conditions or lesions, including but not limited to eczema, atopic dermatitis, psoriasis, and impetigo. Impetigo is a superficial bacterial skin infection with inflammatory damage to the epidermia; compounds of the invention both suppress inflammation and have direct inhibitory or bactericidal effects on gram positive bacteria, including but not limited to *Staphylococcus aureus* and *Staphylococcus pyogenes*, the primary organisms responsible for impetigo. Compounds of the invention also inhibit pre-neoplastic and neoplastic skin alterations, which often exhibit characteristics of both inflammation and neoplasia, including but not limited to actinic keratosis, seborrheic keratoses and warts.

Examples E and F demonstrate efficacy of compounds of the invention for treating skin inflammation and psoriatic dermatitis in established mouse models of human skin disorders.

Macrophages and related cells types contribute to pathogenesis of autoimmune diseases involving the adaptive immune system both as antigen presenting cells and as effectors damaging tissues after inappropriate stimulation by T cells, which secrete interferon gamma and other inflammatory mediators that recruit and activate macrophages. Compounds of the invention disrupt antigen presentation by macrophages and dendritic cells, and also inactivate pro-inflammatory effector macrophages that damage tissues. A general guidance is that compounds of the invention are useful for treating chronic or episodic autoimmune diseases where chloroquine, hydroxychloroquine or other antimalarial quinoline analogs display activity in humans or relevant animal models, and are generally more potent and active than the antimalarials in inflammatory and non-malaria infectious diseases. Such diseases include but are not limited to rheumatoid arthritis, systemic and discoid lupus erythematosis, psoriatic arthritis, vasculitis, Sjogrens syndrome, scleroderma, autoimmune hepatitis, and multiple sclerosis.

Macrophage activation syndrome (MAS) is an acute complication of several autoimmune diseases, especially in childhood-onset conditions such as idiopathic juvenile arthritis where it affects more than 10% of patients, and also in inflammatory bowel diseases. In MAS, macrophages are over-activated, causing damage to the hematopoietic system and systemic inflammation; MAS is sometimes lethal. Compounds of the invention are useful for treatment of MAS, and are optionally delivered orally or by intravenous injection or infusion.

Example G shows beneficial activity of compounds of the invention when administered orally to mice in a model of multiple sclerosis, an autoimmune disease.

For treatment of chronic autoimmune disorders, compounds of the invention are administered systemically, preferably orally. For treatment of acute inflammatory conditions, or flares of autoimmune diseases, intravenous treatment with compounds of the invention is an optional suitable delivery route.

For oral or intravenous treatment of autoimmune or inflammatory diseases, compounds of the invention are typically administered in doses ranging from 1 to 1000 milligrams per day, advantageously 100 to 600 milligrams per day, in single doses or divided into two or three doses per day.

Antifungal and Antiparasitic Uses

The compounds of this invention are useful in inhibiting fungal growth, both in vivo and ex vivo. Accordingly this invention also provides methods and uses for inhibiting the growth of a fungus in a mammalian subject, for example a human. These methods can be used to treat and to prevent fungal infection. Ex vivo, it is useful to treat surfaces with a compound of this invention to inhibit or prevent fungal growth, or in agriculture or horticulture to prevent or treat fungi that affect valuable plants. This invention also provides compositions containing a compound of this invention as well as the use of a compound of this invention for the manufacture of a medicament for inhibiting the growth of a fungus.

This invention is based, in part, on the finding that the compounds of this invention are effective in inhibiting the growth of a variety of fungal species, as shown in the biological activity examples below. Without wishing to be bound by theory, it is believed that compounds of this disclosure exploit the vulnerability of the fungal acidic vacuole. They are believed to accumulate in acidic vacuoles via cation trapping, and furthermore exert antifungal activity by disrupting the structure and function of the acidic vacuoles.

In accordance with this invention, the growth of fungi generally is inhibited. Examples of fungi that can be inhibited include but are not limited to *Candida, Saccharomyces, Trichophyton, Cryptococcus, Aspergillus*, and *Rhizopus*. In more specific embodiments of this invention the fungus is *Candida albicans; Candida glabrata; Saccharomyces cerevisiae; Trichophyton rubrum; Cryptococcus neoformans*, for example *Cryptococcus neoformans* serotypes D and A; and *Aspergillus fumigatus*.

This invention also provides methods of treating and preventing parasitic infections. Due to the capability of compounds of the invention to enter and accumulate within acidic vacuoles in cells, they are useful for treating infections due to parasitic microorganisms that reside within acidic vacuoles in macrophages and other cell types. Tuberculosis (mycobacteria), listeria or staphylococcus (gram positive bacteria), cryptococcus (fungus), and leishmania and trypanosomes (amoebae), *Coxiella burnetii* (gram negative bacteria), and *Plasmodium* (some of which cause malaria) are nonlimiting examples of important such infectious organisms, in which residence within macrophages can protect the organisms from cellular or humoral immunity, or reduce the efficacy of drug treatments.

Compounds of the invention, which bear lipophilic moieties and are generally partially neutral physiological pH (7.3), can pass freely into acidic vacuoles harboring parasites, and are concentrated and trapped there due to ionization in the acidic environment (pH 4-6.5). These compounds disrupt the structure and function of acidic vacuoles as hospitable sites for parasites and also have direct antiparasitic activity, due to acidic vacuoles within many parasitic organisms.

Parasites whose viability or virulence is dependent on integrity and function of an acidic vacuole are also vulnerable to compounds of the invention, similar to the basis for their antifungal activity. The acidic vacuole of malaria plasmodia provides an environment for concentration of compounds of the invention. Similarly, trypanosomes have a large acidic vacuole which is necessary for utilization of environmental nutrients. Compounds of the invention are useful for treatment or prevention of malaria and trypanosome infections. More broadly, protozoal parasites in general use acidified digestive vacuoles for acquisition and digestion of food, and are therefore susceptible to antiparasitic actions of compounds of the invention.

The antimalarial drug chloroquine is reported to have antiparasitic activity against a variety of organisms harbored in acidic vacuoles in host cells, or which have acidic vacuoles themselves, including but not limited to tuberculosis mycobacteria, cryptosporidium, leishmania and cryptococcus. In general, chloroquine acts by accumulating in acidic vacuoles via cation trapping. Activity of chloroquine is thus an indicator of likely activity of compounds of the inventions (many of which comprise an aminoquinoline or other heterocycle similar to that of chloroquine for the purpose of targeting acidic vacuoles), with the difference that compounds of the invention are substantially more potent and active than is chloroquine, as demonstrated in *Cryptococcus neoformans* in Example K, where chloroquine produced less than 50% growth inhibition at a concentration of 100 micromolar, whereas many compounds of the invention produced 100% growth inhibition at much lower concentrations. Chloroquine, despite published reports showing that it can improve survival in animal models of cryptococcosis, displays a ceiling of about 40% inhibition of *C. neoformans* growth in vitro, whereas compounds of the invention are substantially more potent than chloroquine and can cause 100% inhibition of *Cryptococcus* growth, due to superior disruption of the membranes of acidic vacuoles in which the respective drugs are accumulated.

For treatment of fungal or parasitic infections, compounds of the invention are administered in vehicles and by routes of administration appropriate for the nature and location of the infection. For dermal or nail infections, compound of the invention are applied in a topical formulation which is optionally a lotion, ointment, solution, suspension, or spray. For ocular fungal infections, compounds of the invention are formulated in eyedrops. For systemic infections, compounds of the invention are administered orally in tablets, capsules, dragees, solutions or suspensions, or administered systemically by injection in saline, lipid emulsions, liposomes or other standard parenteral vehicles. Lung infections, especially involving organisms residing in alveolar macrophages, are optionally treated via inhalational delivery of compounds of the invention and suitable excipients known to be acceptable for inhalational drug delivery. For intravenous or oral administration to treat systemic infections, compounds of the invention are administered in doses ranging from 10 to 2000 milligrams per day, advantageously 200 to 1000 milligrams per day.

Other classes of antifungal agents in clinical use include inhibitors of ergosterol synthesis ("azole" antifungals including but not limited to fluconazole, ketoconazole, voriconazole, and allylamines including but not limited to terbinafine), polyene antifungals which act by binding to fungal membrane constituents, especially ergosterol (including but not limited to amphotericin B or nystatin), echinocandin inhibitors of glucan synthesis (including but not limited to caspofungin), and other agents known as active antifungals in medical practice. Compounds of the invention act via a distinct mechanism of action versus existing clinically important antifungals and are optionally coadministered with one or more other antifungal agent to improve overall antifungal treatment. Compounds of the invention are coadministered as separate pharmaceutical formulations, or are optionally formulated into a single combined-drug product. A combination of compounds of the inventions with azole antifungals is particularly advantageous as a completely oral regimen for use against cyptoccoccosis, which otherwise generally requires amphotericin B injections or infusions for initial induction. Compounds of the invention are also optionally coadministered with amphotericin B. One formulation of amphotericin B involves its incorporation into lipids comprising the membranes of liposomes. Because many of the compounds of the invention bear lipophilic moieties that insert into lipid membranes, they are advantageously incorporated into liposomes, either as single agents or in combination with amphotericin B or other known polyene antifungal agents.

Anticancer Uses

This invention provides compounds that are useful for systemic treatment of cancer, based on consistent lysosomal changes characterizing invasive cancers. Lysosomal changes in cancer, including their enlargement and acidification, facilitates survival of cancer cells in acidic extracellular environments and also increase the ability of cancer cells to invade surrounding tissues, through exocytosis of lysosomal contents, including proteases and polysaccharidases which can degrade extracellular matrix components. However, these stereotyped changes in lysosomal properties can render cancer cells vulnerable to lysosome-disrupting agents with appropriate physicochemical properties for selectively accumulating in and damaging lysosomes in cancer cells versus normal tissues.

Compounds of the invention accumulate in lysosomes in cancer cells and disrupt their integrity, thereby displaying potent selective cytotoxic activity against cancer cells in vivo and in vitro.

Because one major mechanism for cancer cell resistance to a variety of chemotherapy agents is to sequester them in lysosomes and other acidic vesicular compartments, compounds of the invention are able to restore or enhance sensitivity of cancer cells to a variety of classes of anticancer agents, including antimetabolites, tyrosine kinase inhibitors, anticancer antibodies against growth factor receptors, anthracyclines, platinum compounds, alkylating agents, and antibodies. Compounds of the invention typically do not display toxicities overlapping dose limiting toxicities of most anticancer agents, permitting combination of compounds of the invention with other classes of antineoplastic drugs with a net improvement in efficacy and therapeutic index.

Cancer cells exposed to sublethal doses of ionizing radiation undergo a protective response that increases their resistance to subsequent irradiation. A component of this protective response is formation of enlarged lysosomes or other acidified vacuolar organelles; inhibition of the vacuolar ATPase responsible for acidifying lysosomes with bafilomycin A prevents the protective response in sublethally irradiated cells and sensitizes cancer cells to ionizing radiation Lysosomal damage is a significant mediator of radiation-induced death in cancer cells. By disrupting the integrity of lysosomal membranes, compounds of the invention are useful for reducing resistance of cancer cells to therapeutic ionizing radiation and for potentiating anticancer effectiveness of ionizing radiation therapy. Compounds of the invention are optionally administered prior to ionizing radiation therapy of cancer (whether with external irradiation or administration of antibody-targeted radioisotopes) as radiosensitizers, or they may be given after irradiation to attack surviving cancer cells undergoing protective responses to nonlethal irradiation involving production or enlargement of acidic vacuoles.

One mechanism imparting selective survival and proliferation advantages in some cancers is upregulation of autophagy, a process through which damaged organelles or other cell debris are engulfed by autophagosomes, which fuse with lysosomes to digest and recycle constituent molecules. By concentrating in and disrupting lysosomes, compounds of the invention impair autophagy in cancer cells, thereby reducing their viability and resistance to other anticancer treatments.

For treatment of cancer, compounds of the invention are administered by oral or intravenous administration in doses of 10 to 2000 milligrams per day. Compounds of the invention are administered as single agents or in combination with other cancer treatments appropriate for a particular type of cancer, and generally in doses when such agents are used alone, as compounds of the invention will generally not have overlapping toxicities with other classes of anticancer agents that would necessitate substantial dose reduction.

Pharmaceutical Compositions

This invention provides a pharmaceutical composition comprising a biologically active agent as described herein and a pharmaceutically acceptable carrier. Further embodiments of the pharmaceutical composition of this invention comprise any one of the embodiments of the biologically active agents described above. In the interest of avoiding unnecessary redundancy, each such agent and group of agents is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise from 10 to 1000 mg of the compound of this invention. It is convenient for the subject to swallow one or two tablets, coated tablets, dragees, or gelatin capsules per day. However the composition can also be adapted for administration by any other conventional means of systemic administration including rectally, e.g. in the form of suppositories, parenterally, e.g. in the form of injection solutions, or nasally.

The biologically active compounds can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances, particularly anti-inflammatory or antifungal agents (depending on whether an inflammatory disease or a fungal infection or cancer are being addressed in a patient) that act through mechanisms other than those underlying the effects of the compounds of the invention.

For treatment of cancer, preferred additional drugs that can advantageously be coadministered or coformulated with a compound of the invention comprise orally active anticancer agents. Because compounds of the invention act through a unique mechanism not shared by other anticancer drugs, they are compatible with a large variety of concurrent therapies, including antimetabolites, anthracyclines, tyrosine kinase inhibitors, platinum drugs, or alkylating agents. Such agents, when orally active, are administered or coformulated to deliver quantities of drugs determined in previous clinical trials to be effective and adequately tolerated.

For systemic treatment of diseases, including some cancers, inflammatory conditions and fungal or protozoal infections, compounds of the invention are optionally administered by intravenous injection or infusion. For intravenous administration, compounds of the invention are dissolved in suitable intravenous formulations as solutions or in lipid emulsions, using standard excipients known in the art as well-tolerated intravenous formulation ingredients and compositions.

Suitable volumes and concentrations are selected for delivery of 10 to 2000 milligrams of compounds of the invention per day, depending on the specific requirements for a compound, and a disease condition as determined in clinical trials.

Compounds of the invention are optionally incorporated into liposomal formulations. The lipophilic moieties of compounds of the invention permit their direct incorporation into lipid layers of liposomes. Liposomes are advantageous in some conditions for intravenous administration due to improved efficacy and milder infusion reactions versus nonliposomal formulations. Liposomes are also suitable for inhalational delivery to treat fungal or parasitic infections of the lungs, or inflammation of the lungs and airways. In some embodiments, compounds of the invention are incorporated into liposomal delivery formulations with other drugs, including but not limited to antifungal agents such as liposomal amphotericin B, or anticancer agents such as liposomal doxorubicin.

For treatment of inflammatory skin conditions or fungal infections of the skin or nails, or of nasal passages, compounds of the invention are applied topically in a pharmaceutically acceptable formulation. The topical composition can be in various forms, including, but not limited to, a solution, spray, gel, hydrogel, lotion, cream, ointment, paste, or an emulsion in the form of liquid suspension, lotion, or cream. The composition can also be applied via a dermal patch, or bandage which can be applied on the affected area as needed, to provide an extended exposure of the skin to the medication; in such formulations, appropriate standard topical medicament excipients and vehicles are suitable for delivering compounds of the invention. Standard constituents for topical formulations are known in the art and are suitable as vehicles for compounds of the invention. Ointment bases can comprise one or more of hydrocarbons (paraffin wax, soft paraffin, microcrystalline wax, or ceresine), absorption bases (wool fat or beeswax), macrogol (polyethylene glycol), or vegetable oils. Lotions and creams are water in oil or oil in water emulsions; the oil components can comprise long chain fatty acids, alcohols or esters, and optional contain biocompatible nonionic surfactants. Compounds of the invention are incorporated into topical vehicles in concentrations ranging from 0.01% to 5%, preferably 0.02 to 1%. Compounds of the invention are applied to skin lesions once to three times per day for durations dependent on the rate of resolution of the condition.

For treatment of some lung infections, including fungal infections or parasites residing in alveolar macrophages, inhalational formulas of the compounds of the invention are suitable. Excipients and inhalational drug delivery devices are known in the art and are useful for delivering compounds of the invention to treat lung infections, including cryptococcus and tuberculosis.

Compounds of the invention are advantageously coformulated with other antifungal or anti-inflammatory agents for topical or systemic administration, particularly when both drugs are appropriately administered via the same route and schedule. Compounds of the invention are compatible with standard formulations and excipients used for other topical or systemic antifungal or anti-inflammatory agents, including but not limited to ointments and tablets or capsules. Advantageous drug categories for combination in topical anti-inflammatory formulations include corticosteroids, calcineurin inhibitors and vitamin D analogues, and other agents known to have independent therapeutic activity in inflammatory skin conditions.

The invention will be better understood by reference to the following examples, which illustrate but do not limit the invention described herein.

EXAMPLES

Chemical Synthesis Examples

Example 1

N-[8-(Hexyloxy)octyl]quinolin-4-amine

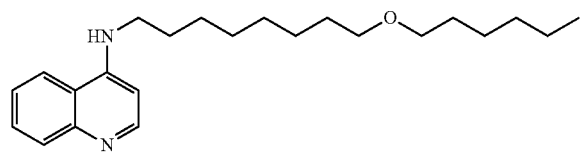

A mixture of 4-chloroquinoline (300 mg, 1.84 mmol), 8-(hexyloxy)octan-1-amine (558 mg, 2.44 mmol), and DMAP (260 mg, 2.13 mmol) was heated at 135° C. for 3 hr. The mixture was cooled and partitioned between DCM and 5% Na$_2$CO$_3$. The organic phase was dried over Na$_2$SO$_4$ and concentrated. FC (10%, 12%, 14% MeOH/DCM step gradient) gave 279 mg of product as a solid. Rf 0.26 (10% MeOH/DCM); mp 64.0-65.5° C. (from EA/Hex); $^1$H NMR (CDCl$_3$) δ 8.51 (d, 1H, J=5.2 Hz), 7.94 (d, 1H, J=8.4 Hz), 7.74 (d, 1H, J=8.4 Hz), 7.57 (m, 1H), 7.37 (m, 1H), 6.37 (d, 1H, J=5.5 Hz), 5.24 (br s, 1H, NH), 3.39-3.34 (m, 4H), 3.25 (m, 2H), 1.73-1.26 (m, 20H), 0.84 (m, 3H).

Example 2

N-(8-Butoxyoctyl)quinolin-4-amine

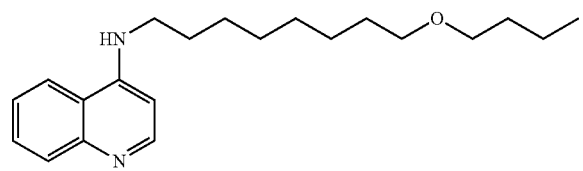 [SMILES: CCCCOCCCCCCCCNc1ccnc2ccccc12]

8-Butoxyoctan-1-ol 60% Sodium hydride in mineral oil (3.5 g, 87.5 mmol) was washed twice with 20 mL of hexanes. Anhydrous DMF (300 mL) was added, the mixture was cooled with an ice bath, and 1,8-octanediol (51.2 g, 351 mmol) was added. After 1.5 hr, 1-bromobutane (6 g, 43.8 mmol) was added slowly. The mixture was warmed to room temperature. After 24 hr, the mixture was concentrated. The residue was taken up in Et$_2$O (500 mL) and washed with saturated NaHCO$_3$ and H$_2$O (400 mL each). The aqueous phases were extracted with Et$_2$O (3×400 mL). The combined organic phases were dried over Na$_2$SO$_4$, filtered, and concentrated to give 3.9 g colorless oil. Rf 0.4 (30% EA/Hex); $^1$H NMR (CDCl$_3$) δ 3.6 (t, 2H), 3.4-3.3 (m, 4H), 1.6-1.4 (m, 6H), 1.4-1.2 (m, 10H), 0.9 (t, 3H).

8-Butoxyoctyl methanesulfonate A mixture of 8-butoxyoctan-1-ol (3.99 g, 20.2 mmol) and TEA (3.4 mL, 24.2 mmol) in 70 mL of DCM was cooled using an ice bath. Then, methanesulfonyl chloride (1.87 mL, 24.1 mmol) was added. After 2 hr, the mixture was washed with H$_2$O, saturated NaHCO$_3$, H$_2$O, 1M HCl, and H$_2$O (50 mL each). The organic phase was dried over Na$_2$SO$_4$, filtered through a pad of silica gel, and concentrated to give 1.3 g of colorless oil.

1-Butoxy-8-iodooctane A mixture of 8-butoxyoctyl methanesulfonate (1.3 g, 6.6 mmol) and sodium iodide (1.0 g, 6.7 mmol) in 100 ml of acetone was heated at reflux for 2 hr. The mixture was cooled, filtered, and concentrated. The residue was taken up in EA (400 mL) and washed with saturated NaHCO$_3$ and brine (100 mL each). The organic phase was dried over Na$_2$SO$_4$, filtered, and concentrated to give 1.3 g of yellow liquid.

N-(8-Butoxyoctyl)phthalimide 1-Butoxy-8-iodooctane (6.2 g, 20.2 mmol) and potassium phthalimide (3.73 g, 20.2 mmol) in 50 mL of DMF were mixed at 60-80° C. for 12 hr. The cooled mixture was concentrated, and the residue was partitioned between EA (3×300 mL) and 5% Na$_2$S$_2$O$_3$, H$_2$O, and brine (100 mL each). The combined organic phases were dried over Na$_2$SO$_4$, filtered, and concentrated to give 5.2 g of solid. $^1$H NMR (CDCl$_3$) δ 7.8 and 7.7 (m, 4H, AA'BB'), 3.6 (t, 2H), 3.4-3.3 (m, 4H), 1.7-1.2 (m, 16H), 0.9 (t, 3H).

8-Butoxyoctan-1-amine Hydrazine monohydrate (0.92 mL, 19 mmol) was added to a mixture of N-(8-butoxyoctyl) phthalimide (5.2 g, 15.9 mmol) and 80 mL of EtOH. The mixture was heated at reflux for 2 hr. Then, the mixture was cooled with an ice bath and stirred vigorously while 200 mL of Et$_2$O were added. The precipitate was filtered and washed with Et$_2$O, and the organic phases were concentrated to give 3.9 g of amber oil. $^1$H NMR (CD$_3$OD) 3.5-3.4 (m, 4H), 2.9 (t, 2H), 1.7-1.3 (m, 16H), 0.9 (t, 3H).

N-(8-Butoxyoctyl)quinolin-4-amine A mixture of 8-butoxyoctan-1-amine (0.569 mg, 2.89 mmol), 4-chloroquinoline (710 mg, 4.33 mmol), TEA (5 mL, 36 mmol), and 0.5 mL of NMP was sealed in a heavy walled glass tube and mixed at 130° C. for 4 days. The mixture was cooled and partitioned between EA and 5% Na$_2$CO$_3$ and brine, dried over Na$_2$SO$_4$, filtered, and concentrated. Purification by FC (60% EA/Hex+2% TEA) gave 244 mg of oil. $^1$H NMR (CDCl$_3$) δ 8.9 (m, 1H, NH), 8.7 (d, 1H), 8.2-8.1 (m, 2H), 7.6 (m, 1H), 7.4 (m, 1H), 6.4 (d, 1H), 3.5 (m, 2H), 3.4-3.3 (m, 4H), 1.8 (m, 2H), 1.7-1.3 (m, 14H), 0.9 (t, 3H).

Example 3

N-(8-Methoxyoctyl)quinolin-4-amine

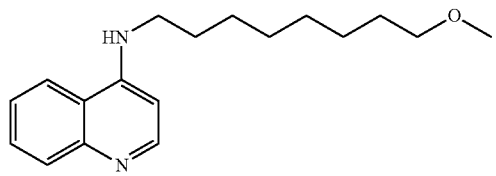 [SMILES: COCCCCCCCCNc1ccnc2ccccc12]

8-(Benzyloxy)octan-1-ol A 60% dispersion of sodium hydride in mineral oil (5.38 g, 134 mmol) was washed with hexanes to remove the oil. While cooling with an ice bath, a mixture of 1,8-octanediol (24.49 g, 168 mmol) in 300 mL of DMF was added slowly. The mixture was allowed to warm to room temperature. After 1 hr, a mixture of benzyl chloride (7.70 mL, 66.7 mmol) in 30 mL of DME was added dropwise. After 2 hr, additional benzyl chloride (1.00 mL, 8.7 mmol) was added, and the mixture was stirred overnight. Then, 2 mL of concentrated NH$_4$OH was added. After 1 hr, the volatile components were evaporated. The residue was taken up in Et$_2$O and thrice washed with 1M HCl and once with brine. The organic phase was dried over anhydrous MgSO$_4$ and evaporated onto silica gel. SPE, washing with 5% EA/Hex and then eluting with 20% EA/Hex gave 12.19 g of the product as a colorless oil. (Eluting with EA gave 12.19 g of recovered 1,8-octanediol after recrystallization from EA/Hex.) Rf 0.55 (20% EA/Hex).

[(8-Methoxyoctyloxy)methyl]benzene A 60% dispersion of sodium hydride in mineral oil (2.1 g, 52 mmol) was washed with hexanes to remove the oil. While cooling with an ice bath, a mixture of 8-(benzyloxy)octan-1-ol (9.9 g, 42 mmol) in 25 mL of DMF was added slowly. The mixture was allowed to warm to room temperature. After 1 hr, dimethyl sulfate (4.0 mL, 42 mmol) was added, and the mixture was stirred overnight. The mixture was diluted with Et$_2$O, washed with 1 M HCl, twice with 0.1 M HCl, and brine, dried over MgSO$_4$, and concentrated. SPE, washing with 1% EA/Hex and then eluting with 10% Et$_2$O/Hex gave 8.63 g of the product as an oil. Rf 0.62 (20% EA/Hex); $^1$H NMR (CDCl$_3$) δ 7.36-7.24 (m, 5H), 4.49 (s, 2H), 3.45 (t, 2H, J=6.7 Hz), 3.35 (t, 2H, J=6.7 Hz), 3.32 (s, 3H), 1.62-1.50 (m, 4H), 1.40-1.25 (m, 8H).

8-Methoxyoctan-1-ol A mixture of [(8-methoxyoctyloxy) methyl]benzene (8.60 g, 34.4 mmol) and 860 mg of 5% Pd—C in 80 mL of THF was stirred under an atmosphere of hydrogen for 40 hr. The mixture was placed under an atmosphere of argon and filtered through a pad of Celite, washing with additional THF. An aliquot was evaporated to dryness for spectroscopy. Rf 0.26 (30% EA/Hex); $^1$H NMR (CDCl$_3$) δ 3.59 (t, 2H, J=6.7 Hz), 3.33 (t, 2H, J=6.4 Hz), 3.29 (s, 3H), 1.84 (s, 1H, OH), 1.60-1.45 (m, 4H), 1.40-1.25 (m, 8H).

8-Methoxyoctyl methanesulfonate A mixture of 8-methoxyoctan-1-ol (34.3 mmol) in 100 mL of THF was cooled by an ice bath. Methanesulfonyl chloride (4.50 mL, 57.5 mmol) and TEA (8.30 mL, 59.2 mmol) were added, and a white precipitate formed quickly. After 2 hr, the mixture was diluted with EA and washed with H$_2$O, saturated NaHCO$_3$, brine, 1M HCl, and brine, and the organic phase was dried over MgSO$_4$ and concentrated. SPE, washing with 10% EA/Hex and then eluting with 30% EA/Hex gave 7.34 g of oil containing 8-methoxyoctyl methanesulfonate and 8-methoxyoctan-1-ol in a 9:1 mole ratio, as determined by NMR. 8-Methoxyoctyl methanesulfonate had Rf 0.31 (30% EA/Hex); $^1$H NMR (CDCl$_3$) δ 4.19 (t, 2H, J=6.7 Hz), 3.34 (t, 2H, J=6.5 Hz), 3.30 (s, 3H), 2.98 (s, 3H), 1.72 (m, 2H), 1.52 (m, 2H), 1.40-1.25 (m, 8H).

N-(8-Methoxyoctyl)phthalimide A 9:1 mixture of 8-methoxyoctyl methanesulfonate and 8-methoxyoctan-1-ol (4.10 g) was taken up in 80 mL of DMF and potassium phthalimide (4.4 g, 24 mmol) was added. The mixture was heated at 80-100° C. for 4 hr. Then, the mixture was cooled, diluted with EA, and washed with H$_2$O, twice with 0.1M HCl, and brine. The organic phase was dried over MgSO$_4$ and concentrated onto silica gel. SPE, eluting with 30% EA/Hex, gave 4.32 g of the product as a solid. Rf 0.50 (30% EA/Hex); $^1$H NMR (CDCl$_3$) δ 7.81 and 7.67 (m, 4H, AA'BB'), 3.64 (t, 2H, J=7.3 Hz), 3.32 (t, 2H, J=6.7 Hz), 3.29 (s, 3H), 1.62 (m, 2H), 1.50 (m, 2H), 1.40-1.20 (m, 8H).

8-Methoxyoctan-1-amine Hydrazine monohydrate (1.00 mL, 20.6 mmol) was added to a mixture of N-(8-methoxyoctyl)phthalimide (4.32 g, 14.9 mmol) in 100 mL of EtOH, and the mixture was heated at reflux for 6 hr, during which a white precipitate formed. Then, the mixture was cooled, 4 mL of 6M HCl were added, most of the volatile components were evaporated, 100 mL of 0.1M HCl were added, and the mixture was allowed to stand for 30 min. The precipitate was filtered and washed twice with 50 mL of 0.1M HCl. The combined filtrate was washed thrice with 50 mL of Et$_2$O. The pH of the filtrate was adjusted to greater than 10 by adding solid NaOH while cooling with an ice bath. The filtrate was extracted with DCM (150 mL, 2×100 mL). The organic phases were dried over anhydrous Na$_2$SO$_4$ and concentrated to give 2.17 g of oil. $^1$H NMR (CDCl$_3$) δ 3.30 (t, 2H, J=6.6 Hz), 3.27 (s, 3H), 2.62 (m, 2H), 1.53-1.24 (m, 12H), 1.41 (s, 2H, NH$_2$).

N-(8-Methoxyoctyl)quinolin-4-amine A mixture of 4-chloroquinoline (3.00 mmol), 8-methoxyoctan-1-amine (233 mg, 1.46 mmol), DIEA (0.52 mL, 3.00), and 4 mL of IPA was heated at 135° C. for 16 hr in a sealed tube. The mixture was treated with additional 8-methoxyoctan-1-amine (343 mg, 2.16 mmol) and heated for an additional 64 hr. Then, the mixture was treated with additional 8-methoxyoctan-1-amine (140 mg, 0.88 mmol) and heated for an additional 48 hr. The mixture was cooled and the volatile components were evaporated. The residue was partitioned between EA and 5% Na$_2$CO$_3$, and the organic phases were washed with brine, dried over anhydrous Na$_2$SO$_4$, and concentrated. The product was purified using FC, eluting with 10% and then 15% MeOH/DCM. The product-containing fractions were concentrated, and the residue was taken up in DCM, washed with 5% Na$_2$CO$_3$, dried over anhydrous Na$_2$SO$_4$ and evaporated to give 694 mg of the product as a solid. Rf 0.26 (10% MeOH/DCM); $^1$H NMR (CDCl$_3$) δ 8.41 (d, 1H, J=5.7 Hz), 7.93 (m, 1H), 7.52 (m, 1H), 7.30 (m, 1H), 6.33 (d, 1H, J=5.7 Hz), 6.09 (br s, 1H, NH), 3.31-3.23 (m, 7H), 1.65, (m, 2H), 1.48 (m, 2H), 1.33-1.25 (m, 8H).

Example 4

N-[6-(Hexyloxy)hexyl]quinolin-4-amine

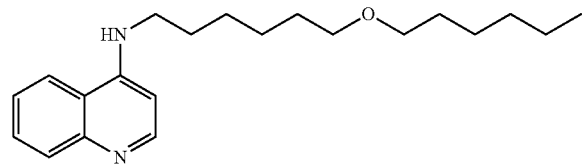 [SMILES: CCCCCCOCCCCCCNc1ccnc2ccccc12]

6-(Hexyloxy)hexan-1-amine was made starting from 1,6-hexanediol following the method for the preparation of 10-(hexyloxy)decan-1-amine.

6-(Hexyloxy)hexan-1-ol Rf 0.16 (10% EA/Hex); $^1$H NMR (CDCl$_3$) δ 3.59 (m, 2H), 3.36 (t, 2H, J=6.7 Hz), 3.35 (t, 2H, J=6.8 Hz), 1.87 (s, 1H, OH), 1.56-1.47 (m, 6H), 1.36-1.25 (m, 10H), 0.85 (m, 3H).

6-(Hexyloxy)hexyl methanesulfonate Rf 0.16 (20% EA/Hex); $^1$H NMR (CDCl$_3$) δ 4.21 (t, 2H, J=6.6 Hz), 3.38 (t, 2H, 6.4 Hz), 3.37 (t, 2H, J=6.7 Hz), 2.98 (s, 3H), 1.74 (m, 2H), 1.61-1.46 (m, 4H), 1.40-1.37 (m, 4H), 1.35-1.24 (m, 6H), 0.87 (t, 3H, J=6.8 Hz).

N-[6-(Hexyloxy)hexyl]phthalimide Rf 0.40 (20% EA/Hex).

6-(Hexyloxy)hexan-1-amine $^1$H NMR (CDCl$_3$) δ 3.36 (m, 2H), 3.35 (t, 2H, J=6.8 Hz), 2.67 (m, 2H), 2.10 (br s, 2H, NH$_2$), 1.78-1.19 (m, 16H), 0.85 (t, 3H, J=6.8 Hz).

A mixture of 6-(hexyloxy)hexan-1-amine (234 mg, 1.16 mmol), 4-chloroquinoline (235 mg, 1.44 mmol) and TEA (0.50 mL, 3.56 mmol) in 1 mL of NMP was heated at 160° C. for 16 hr. The mixture was cooled and partitioned between EA and 5% Na$_2$CO$_3$. The organic phases were washed with brine, dried over Na$_2$SO$_4$, and concentrated. SPE, washing with 40% EA/Hex and 4% MeOH/DCM and eluting with 8% MeOH/DCM, gave 137 mg of product as a solid. Rf 0.42 (7.5% MeOH/DCM); mp 41-44° C. (from EA/Hex); $^1$H NMR (CDCl$_3$) δ 8.45 (d, 1H, J=5.5 Hz), 7.92 (d, 1H, J=8.4 Hz), 7.86 (d, 1H, J=8.4 Hz), 7.55 (ddd, 1H, J=1.2, 6.9, 8.4 Hz), 7.33 (ddd, 1H, J=1.2, 6.9, 8.4 Hz), 6.35 (br s, 1H, NH), 3.37-3.22 (m, 6H), 1.72-1.19 (m, 16H), 0.83 (m, 3H).

Example 5

N-(6-Butoxyhexyl)quinolin-4-amine

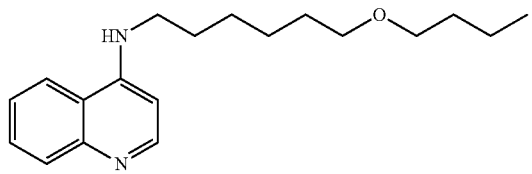 [SMILES: CCCCOCCCCCCNc1ccnc2ccccc12]

6-Butoxyhexan-1-ol 60% Sodium hydride in mineral oil (3.56 g, 89 mmol) was washed twice with 20 mL of hexanes. Anhydrous DMF (250 mL) was added, the mixture was cooled with an ice bath, and 1,6-hexanediol (41.4 g, 351 mmol) was added. After 1.5 hr, 1-bromobutane (4.71 mL, 43.7 mmol) was added slowly. The mixture was warmed to room temperature. After 24 hr, the mixture was concentrated. The residue was taken up in Et$_2$O (500 mL) and washed with saturated NaHCO$_3$ and H$_2$O (400 mL each). The aqueous phases were extracted with Et$_2$O (3×400 mL). The combined organic phases were dried over Na$_2$SO$_4$, filtered, and concentrated to give 6.55 g colorless oil. Rf 0.4 (30% EA/Hex); $^1$H NMR (CDCl$_3$) δ 3.6 (t, 2H), 3.4-3.3 (m, 4H), 1.6-1.4 (m, 6H), 1.4-1.2 (m, 6H), 0.8 (t, 3H).

6-Butoxyhexyl methanesulfonate A mixture of 6-butoxyhexan-1-ol (6.55 g, 37.6 mmol) and TEA (5.51 mL, 39.5 mmol) in 100 mL of DCM was cooled using an ice bath. Then, methanesulfonyl chloride (3.06 mL, 39.5 mmol) was added. After 1.5 hr, the mixture was washed with H$_2$O, saturated NaHCO$_3$, H$_2$O, 1M HCl, and H$_2$O (50 mL each). The organic phase was dried over Na$_2$SO$_4$, filtered through a pad of silica gel, and concentrated to give 9.24 g of colorless oil. $^1$H NMR (CDCl$_3$) δ 4.2 (t, 2H), 3.4-3.3 (m, 4H), 2.9 (s, 3H), 1.7 (m, 2H), 1.6-1.2 (m, 10H), 0.8 (t, 3H).

1-Butoxy-6-iodohexane A mixture of 6-butoxyhexyl methanesulfonate (9.23 g, 36.6 mmol) and sodium iodide (5.5 g, 36.6 mmol) in 300 ml of acetone was heated at reflux for 3 hr. The mixture was cooled, filtered, and concentrated. The residue was taken up in EA (400 mL) and washed with saturated NaHCO$_3$ and brine (100 mL each). The organic phase was dried over Na$_2$SO$_4$, filtered, and concentrated to give 10.4 g of yellow liquid.

N-(6-Butoxyhexyl)phthalimide 1-Butoxy-6-iodohexane (10.4 g, 36.6 mmol) and potassium phthalimide (6.78 g, 36.6 mmol) in 300 mL of DMF were mixed at 60-80° C. for 12 hr. The cooled mixture was concentrated, and the residue was partitioned between EA (3×300 mL) and 5% Na$_2$S$_2$O$_3$, H$_2$O, and brine (100 mL each). The combined organic phases were dried over Na$_2$SO$_4$, filtered, and concentrated to give 7.2 g of solid. $^1$H NMR (CDCl$_3$) δ 7.8 and 7.7 (m, 4H, AA'BB'), 3.6 (t, 2H), 3.4-3.3 (m, 4H), 1.7-1.2 (m, 12H), 0.8 (t, 3H).

6-Butoxyhexan-1-amine Hydrazine monohydrate (1.3 mL, 27 mmol) was added to a mixture of N-(6-butoxyhexyl)phthalimide (6.72 g, 22.2 mmol) and 100 mL of EtOH. The mixture was heated at reflux for 16 hr. Then, the mixture was cooled with an ice bath and stirred vigorously while 200 mL of Et$_2$O were added. The precipitate was filtered and washed with Et$_2$O, and the organic phases were concentrated to give 4.2 g of amber oil. $^1$H NMR (CD$_3$OD) 3.5-3.4 (m, 4H), 2.9 (t, 2H), 1.7-1.3 (m, 12H), 0.9 (t, 3H).

N-(6-Butoxyhexyl)quinolin-4-amine A mixture of 6-butoxyhexan-1-amine (0.5 g, 2.9 mmol), 4-chloroquinoline (711 mg, 4.4 mmol), TEA (5 mL, 36 mmol), and 0.5 mL of NMP was sealed in a heavy walled glass tube and mixed at 130° C. for 4 days. The mixture was cooled and partitioned between EA and 5% Na$_2$CO$_3$ and brine, dried over Na$_2$SO$_4$, filtered, and concentrated. Purification by FC (60% EA/Hex+2% TEA) gave 220 mg of amber oil. $^1$H NMR (CDCl$_3$) δ 8.4 (d, 1H), 8.3-8.1 (m, 3H), 7.6 (m, 1H), 7.4 (m, 1H), 6.4 (d, 1H), 3.5 (m, 2H), 3.4-3.3 (m, 4H), 1.8 (m, 2H), 1.7-1.3 (m, 10H), 0.9 (t, 3H).

Alternative Synthesis

6-Butoxyhexan-1-ol 60% Dispersion of sodium hydride in mineral oil (14 g, 350 mmol) was washed with two 50 mL portions of Hex, and then dried in vacuo. While cooling with an ice bath, IPA (50 mL) and 1,6-hexanediol (200 g, 1700 mmol) were added cautiously, with gas evolution observable. The mixture was allowed to warm to room temperature, and 1-bromobutane (25.0 mL, 234 mmol) was added. The mixture was warmed at 45° C. for 3 days. Then, 6.6 mL of acetic acid were added, and distillation of volatile components was carried out until bp 90° C. was attained. The residue was loaded onto silica gel. Two rounds of SPE (50% EA/Hex) gave 36.7 g of pale yellow liquid. Rf 0.40 (50% EA/Hex).

6-Butoxyhexyl methanesulfonate 6-Butoxyhexan-1-ol (36.7 g, 211 mmol) was taken up in 600 mL of Et$_2$O cooled by an ice bath. Methanesulfonyl chloride (19.8 mL, 253 mmol) and TEA (35.5 mL, 253 mmol) were added, accompanied by immediate precipitate formation. After 1.5 hr, 100 mL of H$_2$O were added, and the phases were separated. The aqueous phase was extracted with EA (2×150 mL), and the organic phases were washed with saturated NaHCO$_3$, H$_2$O, 1M HCl, H$_2$O, and brine (100 mL each). The organic phases were dried over anhydrous Na$_2$SO$_4$, filtered through a pad of silica gel, and concentrated to 52.2 g of pale yellow liquid. Rf 0.55; $^1$H NMR (CDCl$_3$) δ 4.19 (m, 2H), 3.65-3.34 (m, 4H), 2.97 (s, 3H), 1.72 (m, 2H), 1.56-1.50 (m, 4H), 1.50-1.30 (m, 6H), 0.88 (t, 3H); $^{13}$C NMR (CDCl$_3$) δ 70.8, 70.7, 70.2, 37.4, 32.0, 29.7, 29.2, 25.8, 25.4, 19.5, 14.0.

1-Butoxy-6-iodohexane A mixture of 6-butoxyhexyl methanesulfonate (52.2 g, 207 mmol) and sodium iodide (40 g, 267 mmol) in 400 ml of acetone was heated at reflux for 1 hr. The mixture was cooled, concentrated, and partitioned between EA (3×300 mL) and H$_2$O, 5% Na$_2$S$_2$O$_3$, H$_2$O, and brine (150 mL each). The organic phases were dried over Na$_2$SO$_4$ and concentrated to give the product as a yellow liquid that contained 13 mol % of the starting material. $^1$H NMR (CDCl$_3$) δ 3.38-3.35 (m, 4H), 3.16 (t, 2H, J=7.0 Hz), 1.80 (m, 2H), 1.58-1.48 (m, 4H), 1.40-1.30 (m, 6H), 0.88 (t, 3H, J=7.3 Hz); $^{13}$C NMR (CDCl$_3$) δ 70.8, 70.7, 33.6, 32.0, 30.5, 29.7, 25.3, 19.5, 14.1, 7.2.

N-(6-Butoxyhexyl)phthalimide Crude 1-butoxy-6-iodohexane and potassium phthalimide (46 g, 249 mmol) in 300 mL of DMF were mixed at room temperature for 41 hr and at 60-80° C. for 24 hr. The cooled mixture was concentrated, and the residue was partitioned between EA (3×350 mL) and H$_2$O, 5% Na$_2$S$_2$O$_3$, H$_2$O, and brine (100 mL each). The combined organic phases were dried over Na$_2$SO$_4$, filtered through a pad of silica gel, and concentrated. SPE (10% EA/Hex) gave 51.6 g of colorless liquid. Rf 0.38 (20% EA/Hex); $^1$H NMR (CDCl$_3$) δ 7.77 and 7.65 (m, 4H, AA'BB'), 3.62 (t, 2H, J=7.3 Hz), 3.34-3.31 (m, 4H), 1.63 (m, 2H), 1.52-1.44 (m, 4H), 1.35-1.25 (m, 6H), 0.85 (m, 3H); $^{13}$C NMR (CDCl$_3$) δ 168.5, 133.9, 132.3, 123.2, 70.8, 70.7, 38.0, 31.9, 29.7, 28.7, 26.8, 25.9, 19.4, 14.0.

6-Butoxyhexan-1-amine Hydrazine monohydrate (9.1 mL, 187 mmol) was added to a mixture of N-(6-butoxyhexyl)phthalimide (51.6 g, 170 mmol) and 900 mL of EtOH. The mixture was heated at reflux for 12 hr, and allowed to stand at room temperature for 3 days. Then, 250 mL of volatile material was removed by distillation. 1M HCl (200 mL) was added to the still-warm pot residue. After cooling to room temperature, the precipitate was removed by filtration, washing with three 200 mL portions of 50% aqueous EtOH. The filtrate was adjusted to pH 10 by adding NaOH pellets, concentrated, and taken up in 800 mL of DCM. The aqueous phase was separated, and the organic phase was dried over anhydrous Na$_2$SO$_4$ and concentrated. SPE, washing with DCM and 5% MeOH/DCM and eluting with 8% MeOH/DCM+3% NH$_4$OH, gave ninhydrin (+) product fractions. The product fractions were concentrated and taken up in DCM. The organic phase was separated, dried over anhydrous Na$_2$SO$_4$, and concentrated to give 29.1 g of yellow liquid. Rf 0.09 (10% MeOH/DCM); $^1$H NMR (CDCl$_3$) δ 3.26 (t, 2H, J=6.6 Hz), 3.25 (t, 2H, J=6.6 Hz), 2.55 (t, 2H, J=6.9 Hz), 1.46-1.38 (m, 4H), 1.32 (m, 2H), 1.34 (br s, 2H, NH$_2$), 1.26-1.20 (m, 6H), 0.78 (t, 3H, J=7.4 Hz); $^{13}$C NMR (CDCl$_3$) δ 70.7, 70.6, 42.1, 33.6, 31.8, 29.7, 26.7, 26.0, 19.3, 13.8.

N-(6-Butoxyhexyl)quinolin-4-amine 6-Butoxyhexan-1-amine (6.05 g, 34.6 mmol) was taken up in 150 mL of 1-pentanol, and 15 mL was removed by distillation. Tripropylamine (15.8 mL, 82.9 mmol) and 4-chloroquinoline (8.20 g, 50.3 mmol) were added, and the mixture was heated at reflux for 25 hr and allowed to stand at room temperature for 2 days. Then, most of the volatile components were evaporated, and 30 mL of 1N NaOH and 60 mL of 5% Na$_2$CO$_3$ were added. The mixture was extracted with DCM (3×150 mL), and the organic phases were dried over Na$_2$SO$_4$ and evaporated onto silica gel. SPE, washing with 50% EA/Hex and eluting with 5% MeOH/DCM+2% TEA, gave a brown oil. Upon cooling below 0° C., the oil solidified. The solid was washed with cold 10% EA/Hex and dried in vacuo to give 6.62 g of colorless solid. Rf 0.07 (50% EA/Hex) 0.35 (10% MeOH/DCM); mp 62.5-65.0° C.; $^1$H NMR (CDCl$_3$) δ 8.52 (d, 1H, J=5.5 Hz), 7.99 (dd, 1H, J=0.7, 8.4 Hz), 7.77 (dd, 1H, J=0.7, 8.4 Hz), 7.62 (ddd, 1H, J=1.5, 7.0, 8.4 Hz), 7.42 (ddd, 1H, J=1.4, 6.9, 8.4 Hz), 6.42 (d, 1H, J=5.5 Hz), 5.26 (br s, 1H, NH), 3.41 (t, 2H, J=6.6 Hz), 3.40 (t, 2H, J=6.6 Hz), 3.33 (m, 2H), 1.78 (m, 2H), 1.64-1.31 (m, 10H), 0.91 (t, 3H, J=7.3 Hz); $^{13}$C NMR (CDCl$_3$) δ 150.5, 150.3, 147.8, 129.5, 129.4, 124.9, 119.6, 118.8, 98.9, 70.9, 70.8, 43.4, 32.0, 29.9, 29.1, 27.2, 26.2, 19.6, 14.1.

Example 6

N-[10-(Hexyloxy)decyl]quinolin-4-amine

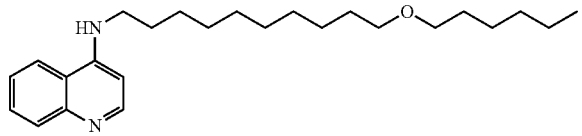 [SMILES: CCCCCCOCCCCCCCCCCNc1ccnc2ccccc12]

10-(Hexyloxy)decan-1-ol 60% Sodium hydride dispersion in mineral oil (1.08 g, 27 mmol) was washed with hexane. 2-Propanol (150 mL) was added, slowly at first. Then, 1,10-decanediol (31.3 g, 180 mmol) was added, and the mixture was warmed slightly to attain homogeneity. 1-Bromohexane (2.50 mL, 17.9 mmol) was added dropwise. After being stirred at room temperature overnight, the mixture was heated at reflux for 2 hr and then 100 mL of volatile components were removed by distillation. 1M HCl (10 mL) was added, and then the remainder of the solvent was removed by distillation. Purification by solid phase extraction, eluting with 12% EA/Hex, gave 1.20 g of 10-(hexyloxy)decan-1-ol as a colorless liquid. Rf 0.22 (20% EA/Hex); $^1$H NMR (CDCl$_3$) δ 3.63 (m, 2H), 3.40-3.35 (m, 4H), 1.65-1.55 (m, 6H), 1.40-1.20 (m, 18H), 0.87 (m, 3H).

10-(Hexyloxy)decan-1-amine Methanesulfonyl chloride (0.50 mL, 6.39 mmol) was added to a mixture of 10-(hexyloxy)decan-1-ol (1.20 g, 4.65 mmol) and triethylamine (0.98 mL, 6.99 mmol) in 100 mL of DME cooled by an ice bath. After 1 hr, the mixture was partitioned between EA (3×100 mL) and H$_2$O, saturated NaHCO$_3$, H$_2$O, 0.1M HCl, and brine (50 mL each), and the organic phases were dried over Na$_2$SO$_4$, filtered through a pad of silica gel, and concentrated. The residue was taken up in 150 mL of acetone, sodium iodide (1.27 g, 8.47 mmol) was added, and the mixture was heated at reflux for 3 hr. Then, the mixture was cooled, the solvent was evaporated, and the residue was partitioned between EA (3×100 mL) and 5% Na$_2$S$_2$O$_3$ and H$_2$O (50 mL of each), and the organic phases were dried over Na$_2$SO$_4$, filtered through a pad of silica gel, and concentrated. The residue was taken up in 20 mL of NMP and potassium phthalimide (1.66 g, 8.97 mmol) was added. After the iodide was consumed, as observed by TLC, the mixture was partitioned between EA (3×100 mL) and 0.1M HCl and brine (50 mL of each), and the organic phases were dried over Na$_2$SO$_4$, filtered through a pad of silica gel, and concentrated. The residue was taken up in 30 mL of ethanol, hydrazine monohydrate (0.60 mL, 12.5 mmol) was added, and the mixture was heated at reflux for 8 hr. Then, the volatile components were evaporated, the residue was partitioned between DCM (3×60 mL) and 5% Na$_2$CO$_3$ (50 mL), and the organic phases were dried over Na$_2$SO$_4$ and concentrated to give 964 mg of 10-(hexyloxy)decan-1-amine as an oil that solidified upon standing. $^1$H NMR (CD$_3$OD) δ 3.45-3.36 (m, 4H), 2.72 (m, 2H), 1.65-1.45 (m, 6H), 1.45-1.25 (m, 18H), 0.89 (m, 3H).

N-[10-(Hexyloxy)decyl]quinolin-4-amine A mixture of 10-(hexyloxy)decan-1-amine (256 mg, 1.00 mmol), 4-chloroquinoline (240 mg, 1.47 mmol), and a particle of prilled DMAP in 1.5 mL of DIEA were heated at 150° C. in a sealed tube for 24 hr. The cooled mixture was partitioned between DCM (3×60 mL) and 5% Na$_2$CO$_3$ (50 mL), and the organic phases were dried over Na$_2$SO$_4$ and concentrated. Purification by solid phase extraction, washing with 50% EA/Hex and then eluting the product with 50% EA/Hex+2% TEA, gave 175 mg of the product as a solid. Rf 0.42 (50% EA/Hex+0.5% TEA); $^1$H NMR (CDCl$_3$) δ 8.51 (d, 1H, J=5.2 Hz), 7.94 (dd, 1H, J=1.0, 8.4 Hz), 7.74 (d, 1H, J=8.2 Hz), 7.57 (ddd, 1H, J=1.5, 6.9, 8.4 Hz), 7.36 (ddd, 1H, J=1.2, 6.9, 8.1 Hz), 6.37 (d, 1H, J=5.4 Hz), 5.23 (br s, 1H, N$\underline{H}$), 3.36 (t, 4H, J=6.7 Hz), 3.25 (m, 2H), 1.70 (m, 2H), 1.56-1.26 (m, 22H), 0.85 (m, 3H).

Example 7

N-(10-Butoxydecyl)quinolin-4-amine

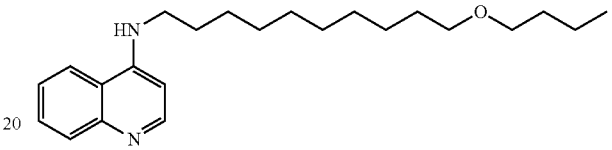

1-Bromo-10-butoxydecane 60% Sodium hydride dispersion in mineral oil (1.7 g, 42 mmol) was washed with hexane. While cooling with an ice bath, a mixture of 1-butanol (10 mL, 109 mmol) and DMF (40 mL) was added, slowly at first. After gas evolution ceased, a mixture of 1,10-dibromodecane (47.1 g, 157 mmol) and 100 mL of DCM and 40 mL of DMF were added in one portion. The mixture was allowed to come to room temperature overnight. Then, the DCM was evaporated, and the residue was partitioned between EA (3×250 mL) and 0.1M HCl and brine (100 mL each), and the organic phases were dried over Na$_2$SO$_4$ and concentrated. Purification by SPE, washing with Hex to recover excess dibromide and then eluting with 10% EA/Hex gave 10.7 g of 1-bromo-10-butoxydecane contaminated with 1,10-dibutoxydecane. Rf 0.39 (10% EA/Hex); $^1$H NMR (CDCl$_3$) δ 3.40-3.36 (m, 6H), 1.82 (m, 2H), 1.57-1.47 (m, 4H), 1.41-1.26 (m, 14H), 0.89 (m, 3H).

10-Butoxydecan-1-amine A mixture of 1-bromo-10-butoxydecane (21.1 g, 72 mmol) and sodium azide (5.1 g, 78 mmol) in 30 mL of DMF was stirred at room temperature until the bromide was consumed, as observed by TLC. The mixture was partitioned between EA (3×350 mL) and H$_2$O (3×100 mL) and brine (100 mL), and the organic phases were dried over Na$_2$SO$_4$ and concentrated. Purification by SPE using 10% EA/Hex gave 19.6 g of the azide product. The azide was taken up in 40 mL of EA and 40 mL of MeOH under a blanket of argon, 2.0 g of 5% Pd/C were added, and the mixture was stirred under an atmosphere of hydrogen until the azide was consumed, as observed by TLC. The catalyst was removed by filtration and the volatile components were evaporated. Purification by SPE, washing with 50% EA/Hex and then eluting with 15% MeOH/DCM+2% TEA, gave 7.0 g of 10-butoxydecan-1-amine as a colorless solid.

$^1$H NMR (CDCl$_3$) δ 3.40-3.34 (m, 4H), 2.55 (m, 2H), 2.1 (br s, 2H, N$\underline{H}_2$), 1.58-1.26 (m, 20H), 0.90 (m, 3H).

N-(10-Butoxydecyl)quinolin-4-amine A mixture of 10-butoxydecan-1-amine (312 mg, 1.36 mmol), 4-chloroquinoline (375 mg, 2.30 mmol) and DIEA (0.50 mL, 2.87 mmol) in 3 mL of 2-propanol was heated at 130° C. for 3 days and the 160° C. for 1 day. The volatile components were evaporated. The mixture was partitioned between DCM (3×60 mL) and 5% Na$_2$CO$_3$ (50 mL), and the organic phases were dried over Na$_2$SO$_4$ and concentrated. Purification by long-column FC (10% MeOH/DCM) gave N-(10- butoxydecyl)quinolin-4-amine. Rf 0.34 (10% MeOH/DCM); $^1$H NMR (CDCl$_3$) δ 8.52 (d, 1H, J=5.4 Hz), 7.96 (d, 1H, J=8.4 Hz), 7.75 (d, 1H, J=8.4 Hz), 7.60 (dd, 1H, J=7.0, 8.2 Hz), 7.39 (dd, 1H, J=6.9, 8.4 Hz), 6.39 (d, 1H, J=5.2 Hz), 5.20 (br s, 1H, N$\underline{H}$), 3.41-3.35 (m, 4H), 3.28 (m, 2H), 1.73 (m, 2H), 1.59-1.28 (m, 18H), 0.89 (m, 3H).

Example 8

N-(5-Methoxypentyl)quinolin-4-amine

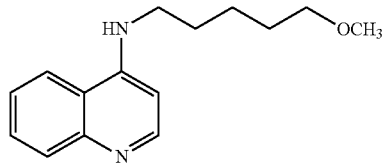 [SMILES: COCCCCCNc1ccnc2ccccc12]

1-Bromo-5-methoxypentane MeOH (20 mL) was added drop-wise to hexane-washed sodium hydride (61.8 mmol) while cooling with an ice bath. The mixture was added drop-wise to a mixture of 1,5-dibromopentane (99.44 g, 0.432 mol) and 100 mL of 1:1 MeOH and THF. After 42 hr, most of the solvent was removed by distillation at room pressure. Then, gentle vacuum distillation gave approximately 20 mL of liquid, which was comprised of a 1:1 mixture of 1,5-dibromopentane and 1-bromo-5-methoxypentane. The pot was partitioned between DCM and H$_2$O, and the organic phase was dried over MgSO$_4$ and concentrated by distillation at room pressure to leave 96 g of a 2.1:1 mixture of 1,5-dibromopentane and DCM. The dibromide was retreated with sodium methoxide. The crude 1-bromo-5-methoxypentane mixtures were combined and separated by SPE, washing with pentane to recover 1,5-dibromopentane and eluting with 10% Et$_2$O/pentane to get 8.40 g of colorless liquid after concentration by distillation. Rf 0.53 (5% EA/Hex) 0.44 (10% Et$_2$O/Hex); $^1$H NMR (CDCl$_3$) δ 3.4-3.3 (m, 4H), 3.31 (s, 3H), 1.86 (m, 2H), 1.6 (m, 2H), 1.3 (m, 2H).

1-Azido-5-methoxypentane A mixture of 1-bromo-5-methoxypentane 2.76 g, 15.2 mmol) and sodium azide (1.14 g, 17.5 mmol) in 10 mL of DMF was stirred at room temperature for 16 hr. Then, the mixture was partitioned between Et$_2$O (3×70 mL) and H$_2$O (3×50 mL) and brine. The organic phases were dried over Na$_2$SO$_4$ and the mixture was carried on. Rf 0.36 (10% Et$_2$O/Hex).

5-Methoxypentan-1-amine A mixture of 1-azido-5-methoxypentane in Et$_2$O and 286 mg of 5% Pd—C was stirred under a blanket of hydrogen for 24 hr. The mixture was blanketed with argon and filtered through a pad of Celite. Most of the Et$_2$O was removed by distillation at atmospheric pressure. $^1$H NMR (CDCl$_3$) δ 3.35 (t, 2H), 3.3 (s, 3H), 2.6 (m, 2H), 1.6-1.3 (m, 6H).

N-(5-Methoxypentyl)quinolin-4-amine A mixture of 5-methoxypentan-1-amine, 4-chloroquinoline (900 mg, 5.52 mmol), and DIEA (0.50 mL, 2.87 mmol) was heated at 130° C. in a sealed tube for 24 hr. The mixture was cooled and partitioned between EA and 5% Na$_2$CO$_3$ and brine. The organic phases were dried over anhydrous Na$_2$SO$_4$ and concentrated. SPE, washing with 40% EA/Hex+2% TEA and eluting with 80% EA/Hex+2% TEA, gave a solid. Rf 0.20 (80% EA/Hex+2% TEA); $^1$H NMR (CDCl$_3$) δ 8.46 (d, 1H, J=5.2 Hz), 7.90 (dd, 1H, J=1.0, 8.4 Hz), 7.77 (m, 1H), 7.51 (ddd, 1H, J=1.5, 6.9, 8.4 Hz), 7.28 (ddd, 1H, J=1.2, 6.9, 8.1 Hz), 6.31 (d, 1H, J=5.4 Hz), 5.55 (m, 1H, N$\underline{H}$), 3.30 (t, 2H, J=6.2 Hz), 3.25 (s, 3H), 3.20 (m, 2H), 1.65 (p, 2H, J=7 Hz), 1.57-1.42 (m, 4H).

Example 9

N-[8-(Hexyloxy)octyl]-2-methylquinolin-4-amine

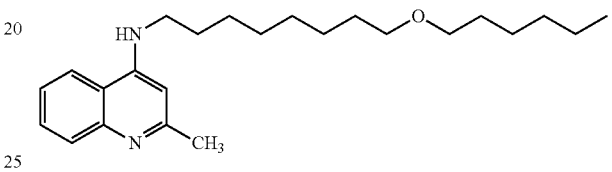

N-[8-(Hexyloxy)octyl]-2-methylquinolin-4-amine A mixture of 8-(hexyloxy)octan-1-amine (479 mg, 2.09 mmol), 4-chloroquinaldine (575 mg, 3.25 mmol), and DIEA (1.00 mL, 5.74 mmol) was heated at 140° C. in a sealed tube for 4 days. Then, the volatile material was evaporated, and the residue was purified by FC (7% MeOH/DCM) to give 217 mg of N-[8-(hexyloxy)octyl]-2-methylquinolin-4-amine. $^1$H NMR (CDCl$_3$) δ 7.87 (d, 1H, J=8.4 Hz), 7.67 (d, 1H, J=8.0 Hz), 7.53 (m, 1H), 7.29 (m, 1H), 6.26 (s, 1H), 5.10 (m, 1H, N$\underline{H}$), 3.35 (t, 4H, J=6.5 Hz), 3.21 (m, 2H), 2.57 (s, 3H), 1.73-1.21 (m, 20H), 0.85 (m, 3H).

Example 10

7-Chloro-N-[8-(hexyloxy)octyl]quinolin-4-amine

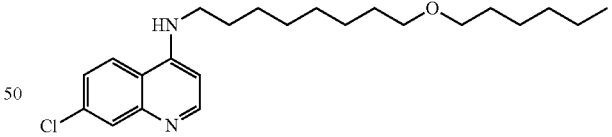

7-Chloro-N-[8-(hexyloxy)octyl]quinolin-4-amine A mixture of 8-(hexyloxy)octan-1-amine (537 mg, 2.34 mmol), 4,7-dichloroquinoline (565 mg, 2.85 mmol), DIEA (0.50 mL, 2.87 mmol), and 1 mL of NMP was heated at 140° C. in a sealed tube for 24 hr. Then, the volatile material was evaporated, and the residue was purified by SPE (5% MeOH/DCM and then 30% EA/Hex+2% TEA) to give 358 mg of 7-chloro-N-[8-(hexyloxy)octyl]quinolin-4-amine. Rf 0.20 (5% MeOH/DCM), 0.31 (30% EA/Hex+2% TEA); $^1$H NMR (CDCl$_3$) δ 8.43 (d, 1H, J=5.4 Hz), 7.87 (d, 1H, J=2.0 Hz), 7.68 (d, 1H, J=8.9 Hz), 7.22 (dd, 1H, J=2.2, 8.9 Hz), 6.30 d, 1H, J=5.4 Hz), 5.46 (t, 1H, J=4.8 Hz, N$\underline{H}$), 3.33 (t, 4H, J=6.7 Hz), 3.19 (m, 2H), 1.70-1.23 (m, 20H), 0.82 (m, 3H).

Example 11

8-Chloro-N-[8-(hexyloxy)octyl]quinolin-4-amine

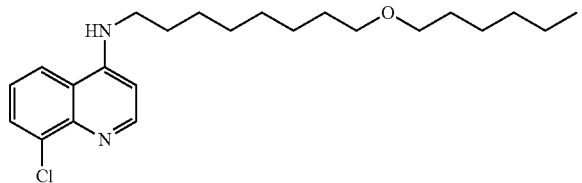 [SMILES: CCCCCCOCCCCCCCCNc1ccnc2c(Cl)cccc12]

8-Chloro-N-[8-(hexyloxy)octyl]quinolin-4-amine A mixture of 8-(hexyloxy)octan-1-amine (456 mg, 1.99 mmol), 4,8-dichloroquinoline (480 mg, 2.42 mmol), DIEA (0.43 mL, 2.47 mmol), and 1 mL of NMP was heated at 140° C. in a sealed tube for 24 hr. Then, the volatile material was evaporated, and the residue was purified by SPE (5% MeOH/DCM and then 30% EA/Hex+2% TEA) to give 338 mg of 8-chloro-N-[8-(hexyloxy)octyl]quinolin-4-amine. Rf 0.28 (5% MeOH/DCM), 0.38 (30% EA/Hex+2% TEA); $^1$H NMR (CDCl$_3$) δ 8.61 (d, 1H, J=5.5 Hz), 7.72-7.64 (m, 2H), 7.26 (m, 1H), 6.41 (d, 1H, J=5.4 Hz), 5.19 (t, 2H, J=4.7 Hz, N<u>H</u>), 3.38-3.33 (m, 4H), 3.26 (m, 2H), 1.76 (m, 20H), 0.85 (m, 3H).

Example 12

N-[8-(Hexyloxy)octyl]-7-(trifluoromethyl)quinolin-4-amine

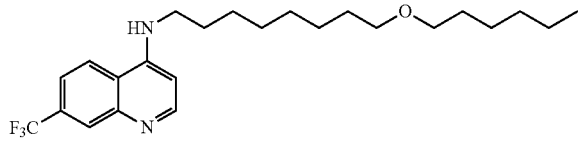 [SMILES: CCCCCCOCCCCCCCCNc1ccnc2cc(C(F)(F)F)ccc12]

A mixture of 8-(hexyloxy)octan-1-amine (546 mg, 2.38 mmol), 4-chloro-7-trifluoromethylquinoline (711 mg, 3.06 mmol), DIEA (0.50 mL, 2.87 mmol), and 1 mL of NMP was heated at 140-150° C. in a sealed tube for 24 hr. Then, the residue was partitioned between EA and 5% Na$_2$CO$_3$ and brine, and the organic phases were dried over Na$_2$SO$_4$ and concentrated. Purification by SPE failed, but FC (25% EA/Hex) gave 626 mg of a yellow oil that solidified upon standing. Rf 0.10 (20% EA/Hex); $^1$H NMR (CDCl$_3$) δ 8.53 (d, 1, J=5.4 Hz), 8.19 (s, 1), 7.87 (d, 1, J=8.9 Hz), 7.47 (dd, 1, J=1.7, 8.9 Hz), 6.42 (d, 1, J=5.5 Hz), 5.47 (m, 1), 3.36-3.32 (m, 4), 3.25 (m, 2), 1.81-1.17 (m, 20), 0.83 (m, 3).

Example 13

N-[8-(Hexyloxy)octyl]-8-(trifluoromethyl)quinolin-4-amine

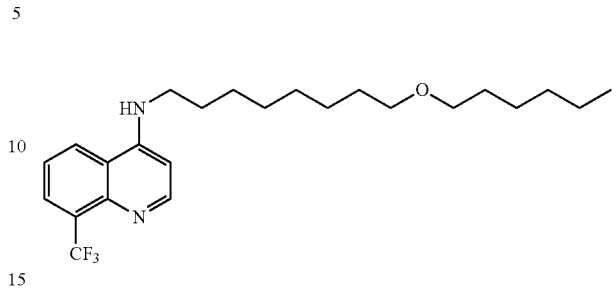

N-[8-(Hexyloxy)octyl]-8-(trifluoromethyl)quinolin-4-amine A mixture of 8-(hexyloxy)octan-1-amine (590 mg, 2.58 mmol), 4-chloro-8-(trifluoromethyl)quinoline (780 mg, 3.36 mmol), and DIEA (0.50 mL, 2.86 mmol) in 1 mL of NMP was heated in a heavy walled sealed tube at 140-150° C. for 48 hr. Then, the residue was partitioned between EA and 5% Na$_2$CO$_3$ and brine, and the organic phases were dried over Na$_2$SO$_4$ and concentrated. FC (20% EA/Hex) gave 793 mg of yellow oil. Rf 0.28 (20% EA/Hex); $^1$H NMR (CDCl$_3$) δ 8.60 (d, 1, J=5.4 Hz), 7.94 (d, 1, J=8.6 Hz), 7.91 (d, 1, J=7.4 Hz), 7.35 (m, 1), 6.42 (d, 1, J=5.4 Hz), 5.23 (m, 1, N<u>H</u>), 3.36 (t, 4, J=6.6 Hz), 3.23 (m, 2), 1.74-1.25 (m, 20), 0.85 (m, 3).

Example 14

N-{5-[3-(Hexyloxy)propoxy]pentyl}quinolin-4-amine

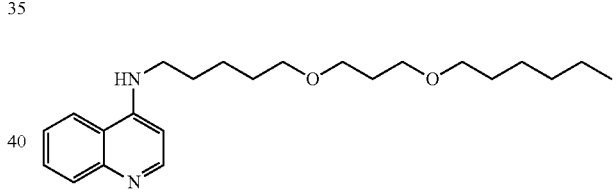

3-(Hexyloxy)propan-1-ol One mole of sodium metal was added in portions to 250 g of 1,3-propanediol cooled by an ice bath and blanketed with argon. After the metal had dissolved, 0.466 mole of 1-iodohexane mixed in 100 mL of DMF was added dropwise. The mixture was allowed to warm to room temperature overnight. Then, the mixture was warmed to 60° C. for 2 hr. Then, the mixture was cooled to room temperature and treated with 10 mL of concentrated NH$_4$OH for 1 hr. Then, the mixture was partitioned between EA (3×250 mL) and 1.5 L H$_2$O+H$_3$PO$_4$ (pH-10), H$_2$O, 1M HCl, 2×0.1M HCl, and brine. The organic phases were dried over MgSO$_4$ and concentrated. Purification by SPE, washing with 10% EA/Hex and eluting with 30% EA/Hex, gave 44.2 g of 3-(hexyloxy)propan-1-ol as a pale yellow liquid. Rf 0.28 (30% EA/Hex);

$^1$H NMR (CDCl$_3$) δ 3.74 (t, 2H), 3.60 (t, 2H, J=5.7 Hz), 3.39 (t, 2H), 2.66 (s, 1H, O<u>H</u>), 1.80 (m, 2H), 1.53 (m, 2H), 1.56-1.20 (m, 6H), 0.85 (m, 3H).

3-(Hexyloxy)propyl methanesulfonate was prepared by the method used for the preparation of 3-phenoxybenzyl methanesulfonate, using 44.2 g of 3-(hexyloxy)propan-1-ol, 43 mL of TEA, and 24 mL of methanesulfonyl chloride in 540 mL of DCM. The crude material was taken up in 450 mL of acetone and reacted with 55.7 g of sodium iodide at reflux for 4 hr. Then, the mixture was cooled and diluted with 1 volume of hexanes. The solid was filtered, and the filtrate was concentrated. The residue was taken up in 350 mL of DCM and washed with 5% $Na_2S_2O_3$ (to remove color) and $H_2O$. The organic phase was dried over $Na_2SO_4$ and concentrated to give crude 1-(3-iodopropoxy)hexane.

1,5-Pentanediol (230 mL) was blanketed with argon, and 22.6 g of potassium metal was added in portions. The exothermic evolution of gas was moderated by cooling with an ice bath. Then, at room temperature, a mixture of the crude 1-(3-iodopropoxy)hexane and 100 mL of DMA was added dropwise. After being stirred overnight, unreacted iodide was observed by TLC. Sodium hydride (7.4 g) was added in 2-gram portions with cooling by an ice bath. The mixture was allowed to stir at room temperature for 60 hr. Then, the mixture was cooled with an ice bath and neutralized by the addition of concentrated HCl. The mixture was partitioned between EA and $H_2O$, and the organic phases were washed with 5% $Na_2S_2O_3$ (to remove color) and brine, dried over $Na_2SO_4$, and concentrated. Purification by SPE, washing with 5% EA/Hex and then eluting with 30% EA/Hex, gave 39.0 g of 5-[3-(hexyloxy)propoxy]pentan-1-ol as a colorless oil. Rf 0.19 (30% EA/Hex), 0.31 (40% EA/Hex); $^1$H NMR ($CDCl_3$) δ 3.60 (t, 2H, J=6.6 Hz), 3.48-3.34 (m, 8H), 1.8 (m, 2H), 1.6-1.5 (m, 4H), 1.5-1.2 (m, 10H), 0.85 (t, 3H, J=6.7 Hz).

5-[3-(Hexyloxy)propoxy]pentyl methanesulfonate (51.0 g) was prepared by the method used for 3-(hexyloxy)propyl methanesulfonate, using 39.0 g of 5-[3-(hexyloxy)propoxy] pentan-1-ol, 24.4 mL of TEA, 13.6 mL of methanesulfonyl chloride, and 420 mL of DCM. Rf 0.38 (40% EA/Hex); $^1$H NMR ($CDCl_3$) δ 4.23 (t, 2H, J=6.4 Hz), 3.5-3.3 (m, 8H), 2.98 (s, 3H), 1.8-1.7 (m, 4H), 1.7-1.4 (m, 6H), 1.4-1.2 (m, 6H), 0.9 (t, 3H).

5-Azidopentyl 3-(hexyloxy)propyl ether (29.3 g) was produced from the reaction of 5-[3-(hexyloxy)propoxy]pentyl methanesulfonate (51 g) and sodium azide (11.3 g) in 80 mL of DMF at room temperature following the method used for 8-(3-ethoxypropoxy)octan-1-amine. Rf 0.20 (5% EA/Hex); $^1$H NMR ($CDCl_3$) δ 3.4-3.3 (m, 8H), 3.22 (t, 2H), 1.7 (m, 2H), 1.6-1.2 (m, 14H), 0.84 (t, 3H).

5-[3-(Hexyloxy)propoxy]pentan-1-amine (26.4 g) was prepared from 5-azidopentyl 3-(hexyloxy)propyl ether using LAH by the method used to prepare [4-(hexyloxy)phenyl] methanamine. $^1$H NMR ($CDCl_3$) δ 3.5-3.3 (m, 8H), 2.65 (t, 2H, J=6.4 Hz), 1.8 (m, 2H), 1.7-1.2 (m, 14H), 0.84 (t, 3, J=6.8 Hz).

N-{5-[3-(Hexyloxy)propoxy]pentyl}quinolin-4-amine A mixture of 5-[3-(hexyloxy)propoxy]pentan-1-amine (482 mg, 1.97 mmol), 4-chloroquinoline (345 mg, 2.12 mmol), DIEA (0.80 mL, 4.59 mmol), and 2 mL of NMP were heated at 160° C. for 3 days in a sealed tube. Then, the mixture was cooled, the volatile material was evaporated, the residue was partitioned between DCM and 5% $Na_2CO_3$, and the organic phase was dried over $Na_2SO_4$ and concentrated. SPE, washing with 50% EA/Hex and then eluting with 60% EA/Hex+ 2% TEA, gave 502 mg of N-{5-[3-(hexyloxy)propoxy] pentyl}quinolin-4-amine as an amber oil. Rf 0.20 (60% EA/Hex+2% TEA); $^1$H NMR ($CDCl_3$) δ 8.48 (d, 1H, J=5.4 Hz), 7.91 (dd, 1H, J=1.2, 8.4 Hz), 7.76 (m, 1H), 7.54 (ddd, 1H, J=1.2, 6.9, 8.4 Hz), 7.32 (ddd, 1H, J=1.2, 6.9, 8.2 Hz), 6.34 (d, 1H, J=5.4 Hz), 5.42 (t, 1H, J=5.0 Hz), 3.46-3.20 (m, 10H), 1.83-1.39 (m, 10H), 1.31-1.15 (m, 6H), 0.81 (m, 3H).

Example 15

N-{3-[5-(Hexyloxy)pentyloxy]propyl}quinolin-4-amine

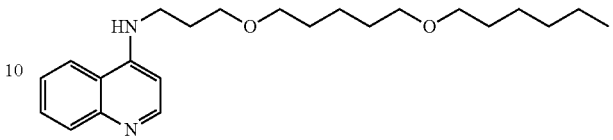

N-{3-[5-(Hexyloxy)pentyloxy]propyl}quinolin-4-amine (426 mg) was made by a method analogous to that used for the preparation of N-{5-[3-(hexyloxy)propoxy] pentyl}quinolin-4-amine, but the two diols were reacted in the reverse sequence. Rf 0.18 (60% EA/Hex+2% TEA); $^1$H NMR ($CDCl_3$) δ 8.47 (d, 1H, J=5.5 Hz), 7.90 (dd, 1H, J=0.7, 8.4 Hz), 7.70 (m, 1H), 7.54 (ddd, 1H, J=1.5, 6.9, 8.4 Hz), 7.32 (ddd, 1H, J=1.2, 6.9, 8.4 Hz), 6.30 (d, 1H, J=5.4 Hz), 6.19 (m, 1H), 3.57 (m, 2H), 3.44-3.24 (m, 8H), 1.96 (m, 2H), 1.86-1.16 (m, 14H), 0.81 (m, 3H).

Example 16

N-[8-(3-Ethoxypropoxy)octyl]quinolin-4-amine

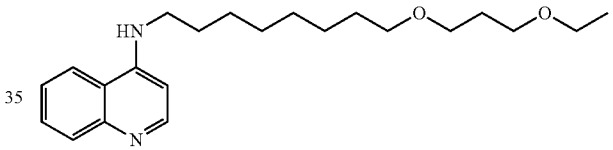

1-Bromo-8-(3-ethoxypropoxy)octane 60% Dispersion of sodium hydride in mineral oil (1.4 g, 35 mmol) was washed twice with 20 mL of hexane. Anhydrous NMP (50 mL) and DME (50 mL) were added, the mixture was cooled with an ice bath, and 3-ethoxy-1-propanol (2.00 mL, 17.4 mmol) was added. After evolution of gas ceased, 1,8-dibromooctane (25.7 mL, 139 mmol) was added in one portion. After 16 hr at room temperature, the mixture was heated at reflux for 1.5 hr. Then, the volatile components were evaporated, and the residue was diluted with 150 mL of $H_2O$ and extracted with DCM (2×25 mL). The combined organic phases were washed with 0.05M HCl, dried over anhydrous $MgSO_4$, and concentrated. SPE, washing with hexane to recover 1,8-dibromooctane and then eluting with 10% EA/Hex, gave 4.15 g of 1-bromo-8-(3-ethoxypropoxy)octane. Rf 0.28 (10% EA/Hex); $^1$H NMR ($CDCl_3$) δ 3.50-3.31 (m, 10H), 1.88-1.77 (m, 4H), 1.56-1.38 (m, 10H), 1.17 (t, 3H, J=6.9 Hz).

1-Azido-8-(3-ethoxypropoxy)octane 1-Bromo-8-(3-ethoxypropoxy)octane (4.15 g, 14.1 mmol) was taken up in 50 mL of DMF, and sodium azide (1.09 g, 16.8 mmol) and catalytic sodium iodide were added. After 88 hr, the mixture was partitioned between EA (150 mL) and $H_2O$ (50 mL), and the organic phase was washed with brine (50 mL), dried over $Na_2SO_4$, and concentrated. FC (5% EA/Hex) gave 2.55 g of colorless liquid. Rf 0.37 (10% EA/Hex); $^1$H NMR ($CDCl_3$) δ 3.50-3.42 (m, 6H), 3.38 (t, 2H, J=6.7 Hz), 3.24 (t, 2H, J=6.9 Hz), 1.82 (m, 2H), 1.64-1.49 (m, 4H), 1.31 (br m, 8H), 1.18 (t, 3H, J=6.9 Hz).

8-(3-Ethoxypropoxy)octan-1-amine 1-Azido-8-(3-ethoxypropoxy)octane (2.55 g, 9.84 mmol) was taken up in 100 mL of EA. The mixture was placed under an atmosphere of argon, 10% Pd/C (200 mg) was added, and the argon was replaced by hydrogen. When the starting material was consumed, as observed by TLC, the hydrogen was replaced by argon, and the mixture was filtered through Celite, washing with EA. The filtrate was concentrated to give 1.0 g of yellow oil. $^1$H NMR (CDCl$_3$) δ 3.6-3.3 (m, 8H), 2.6 (m, 1H), 2.4 (m, 1H), 1.8 (m, 2H), 1.7-1.1 (m, 15H).

N-[8-(3-Ethoxypropoxy)octyl]quinolin-4-amine A mixture of 8-(3-ethoxypropoxy)octan-1-amine (1.0 g, 4.4 mmol), 4-chloroquinoline (1.46 g, 9.0 mmol), TEA (4.0 mL, 28 mmol), and 0.2 mL of NMP was sealed in a heavy walled glass tube and mixed at 130° C. for 4 days. The mixture was cooled and partitioned between EA and 5% Na$_2$CO$_3$ and brine, dried over Na$_2$SO$_4$, filtered, and concentrated. Purification by FC (60% EA/Hex+2% TEA) gave 147 mg of amber oil. $^1$H NMR (CDCl$_3$) δ 8.4 (d, 1H), 8.1-7.9 (m, 2H), 7.6 (m, 1H), 7.4 (m, 1H), 6.4 (d, 1H), 6.2 (br s, 1H, N$\underline{H}$), 3.6-3.3 (m, 10H), 1.9-1.7 (m, 6H), 1.6-1.2 (m, 8H), 1.2 (m, 3H).

Example 17

N-[8-(2-Propoxyethoxy)octyl]quinolin-4-amine

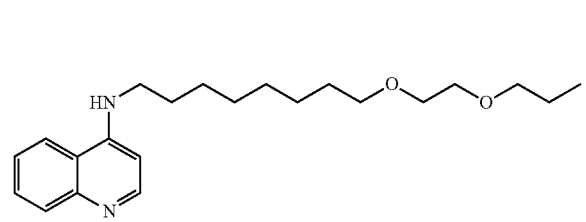 [SMILES: CCCOCCOCCCCCCCCNc1ccnc2ccccc12]

N-[8-(2-Propoxyethoxy)octyl]quinolin-4-amine (550 mg) was made using ethylene glycol monopropyl ether (2.00 mL, 17.5 mmol), 1,8-dibromooctane (25.7 mL, 139 mmol), and 4-chloroquinoline (1.42 g) using the method for the preparation of N-[8-(3-ethoxypropoxy)octyl]quinolin-4-amine.

1-Bromo-8-(2-propoxyethoxy)octane: Rf 0.29 (10% EA/Hex); 3.55 (br s, 4H, A$_2$B$_2$), 3.46-3.34 (m, 6H), 1.81 (m, 2H), 1.65-1.52 (m, 4H), 1.42-1.30 (m, 8H), 0.88 (t, 3H, J=7.4 Hz).

1-Azido-8-(2-propoxyethoxy)octane: Rf 0.37 (10% EA/Hex); 3.55 (br s, 4H, A$_2$B$_2$), 3.43 (t, 2H, J=6.7 Hz), 3.40 (t, 2H, J=6.8 Hz), 3.22 (m, 2H, J=6.9 Hz), 1.65-1.52 (m, 6H), 1.29-1.20 (m, 8H), 0.88 (t, 3H, J=7.4 Hz).

N-[8-(2-Propoxyethoxy)octyl]quinolin-4-amine: $^1$H NMR (CDCl$_3$) δ 8.3 (m, 2H), 8.1 (d, 1H), 7.6 (m, 1H), 7.4 (m, 2H), 6.4 (d, 1H), 3.55 (br s, 4H, A$_2$B$_2$), 3.45-3.35 (m, 6H), 1.8 (m, 2H), 1.6-1.2 (m, 12H), 0.9 (t, 3H).

Example 18

N-[8-(Benzyloxy)octyl]quinolin-4-amine

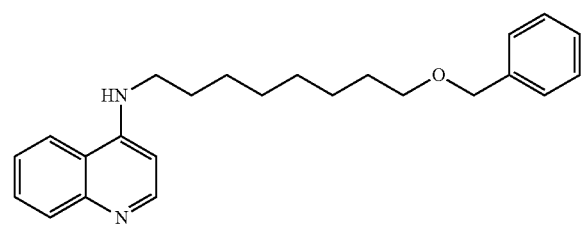 [SMILES: c1ccc(COCCCCCCCCNc2ccnc3ccccc23)cc1]

8-(Benzyloxy)octan-1-amine (880 mg) was prepared from 8-(benzyloxy)octan-1-ol (4.23 g) following the method used in the preparation of 10-(hexyloxy)decan-1-amine.

A mixture of 8-(benzyloxy)octan-1-amine (235 mg, 1.00 mmol), 4-chloroquinoline (201 mg, 1.23 mmol), DIEA (0.50 mL, 2.87 mmol), and 2 mL of IPA was heated in a heavy walled glass tube at 150° C. for 4 days. The mixture was cooled and partitioned between DCM and 5% Na$_2$CO$_3$, and the organic phase was dried over Na$_2$SO$_4$, and concentrated. SPE, washing with 3% MeOH/DCM and eluting with 8% MeOH/DCM, gave 150 mg of the product as a yellow oil. Rf 0.13 (5% MeOH/DCM); $^1$H NMR (CDCl$_3$) δ 8.49 (d, 1H, J=5.4 Hz), 7.97 (d, 1H, J=8.4 Hz), 7.86 (d, 1H, J=8.4 Hz), 7.58 (ddd, 1H, J=1.2, 7.0, 8.5 Hz), 7.40-7.21 (m, 6H), 6.38 (d, 1H, J=5.4 Hz), 5.68 (m, 1H), 4.48 (s, 2H), 3.44 (t, 2H, J=6 Hz), 3.27 (m, 2H), 1.75-1.52 (m, 4H), 1.37-1.32 (m, 8H).

Example 19

N-(6-Phenoxyhexyl)quinolin-4-amine

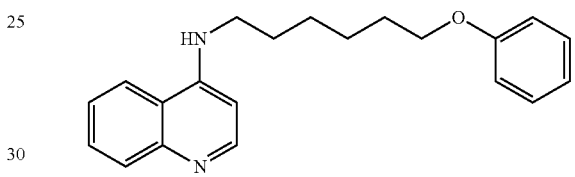

N-(6-Phenoxyhexyl)quinolin-4-amine (188 mg) was prepared starting from 1,6-dibromohexane (4.25 mL) and phenol (326 mg) following the method used for the preparation of N-(8-phenoxyoctyl)quinolin-4-amine.

(6-Bromohexyloxy)benzene (409 mg): Rf 0.46 (5% EA/Hex); $^1$H NMR (CDCl$_3$) δ 7.3 (m, 2H), 6.9 (m, 3H), 4.0 (m, 2H), 3.4 (m, 2H), 2.0-1.7 (m, 4H), 1.6-1.4 (m, 4H).

(6-Azidohexyloxy)benzene (344 mg): $^1$H NMR (CDCl$_3$) δ 7.3 (m, 2H), 6.9 (m, 3H), 4.0 (m, 2H), 3.28 (t, 2H, J=6.8 Hz), 1.8 (m, 2H), 1.7-1.4 (m, 6H).

6-Phenoxyhexan-1-amine (224 mg): $^1$H NMR (CDCl$_3$) δ 7.3 (m, 2H), 6.9 (m, 3H), 3.91 (t, 2H, J=6.4 Hz), 2.6 (m, 2H), 1.8-1.3 (m, 8H).

N-(6-Phenoxyhexyl)quinolin-4-amine: Rf 0.15 (50% EA/Hex+2% TEA); $^1$H NMR (CDCl$_3$) δ 8.53 (d, 1H, J=5.2 Hz), 7.97 (m, 1H), 7.75 (m, 1H), 7.60 (ddd, 1H, J=1.2, 6.9, 8.2 Hz), 7.38 (ddd, 1H, J=1.2, 6.9, 8.1 Hz), 7.30-7.22 (m, 2H), 6.95-6.86 (m, 3H), 6.39 (d, 1H, J=5.5 Hz), 5.22 (t, 1H, J=4.7 Hz), 3.94 (t, 2H, J=6 Hz), 3.29 (m, 2H), 1.81-1.44 (m, 8H).

Example 20

N-(8-Phenoxyoctyl)quinolin-4-amine

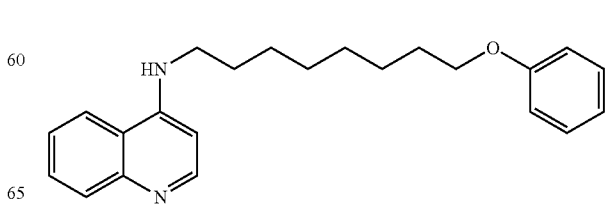

(8-Bromooctyloxy)benzene A mixture of phenol (321 mg, 3.41 mmol), 1,8-dibromooctane (5.00 mL, 27.0 mmol), and $K_2CO_3$ (1.41 g, 10.2 mmol) in 6 mL of DMF and 6 mL of 1,2-dimethoxyethane was heated at 90° C. for 24 hr. The mixture was cooled and partitioned between ether (3×175 mL) and 0.1N NaOH (75 mL) and 1:1 0.1M HCl/brine (75 mL). The organic phases were dried over $MgSO_4$ and concentrated. Purification by FC (5% EA/Hex) gave 533 mg of (8-bromooctyloxy)benzene as a colorless oil. Rf 0.50 (5% EA/Hex); $^1$H NMR ($CDCl_3$) δ 7.31-7.24 (m, 2H), 6.95-6.88 (m, 3H), 3.95 (t, 2H, J=6.5 Hz), 3.41 (t, 2H, J=6.8 Hz), 1.91-1.73 (m, 4H), 1.47-1.27 (m, 8H).

(8-Azidooctyloxy)benzene (460 mg of a colorless oil) and then 8-phenoxyoctan-1-amine (339 mg of a colorless solid) were prepared following the method for 10-butoxydecan-1-amine using 533 mg of (8-bromooctyloxy)benzene and 170 mg of sodium azide.

(8-Azidooctyloxy)benzene: $^1$H NMR ($CDCl_3$) δ 7.33-7.25 (m, 2H), 6.97-6.88 (m, 3H), 3.96 (m, 2H), 3.26 (t, 2H, J=7.0 Hz), 1.80 (m, 2H), 1.60 (m, 2H), 1.50-1.38 (m, 8H).

8-Phenoxyoctan-1-amine: $^1$H NMR ($CDCl_3$) δ 7.26-7.20 (m, 2H), 6.91-6.84 (m, 3H), 3.90 (t, 2H, J=6.4 Hz), 2.63 (m, 2H), 1.74 (m, 2H), 1.5-1.2 (m, 10H).

N-(8-Phenoxyoctyl)quinolin-4-amine A mixture of 8-phenoxyoctan-1-amine (339 mg, 1.53 mmol), 4-chloroquinoline (328 mg, 2.01 mmol) and TEA (0.50 mL, 3.56 mmol) in 1 mL of NMP was heated at 160° C. for 24 hr. The mixture was cooled and partitioned between EA and 5% $Na_2CO_3$. The organic phases were washed with brine, dried over $Na_2SO_4$, and concentrated. Purification by FC (50% EA/Hex+2% TEA) gave 431 mg of N-(8-phenoxyoctyl) quinolin-4-amine. Rf 0.18 (50% EA/Hex+2% TEA); $^1$H NMR ($CDCl_3$) δ 8.53 (d, 1H, J=5.4 Hz), 7.97 (dd, 1H, J=1.0, 8.4 Hz), 7.74 (m, 1H), 7.60 (ddd, 1H, J=1.5, 6.9, 8.4 Hz), 7.39 (ddd, 1H, J=1.5, 6.9, 8.4 Hz), 7.30-7.22 (m, 2H), 6.95-6.86 (m, 3H), 6.39 (d, 1H, J=5.4 Hz), 5.17 (br s, 1H, NH), 3.93 (t, 2H, J=6.5 Hz), 3.27 (m, 2H), 1.82-1.68 (m, 4H), 1.47-1.40 (m, 8H).

Example 21

N-{2-[2-(Hexyloxy)phenoxy]ethyl}quinolin-4-amine

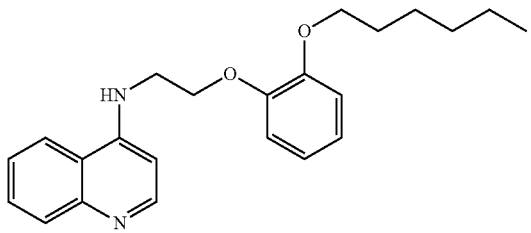 [SMILES: CCCCCCOc1ccccc1OCCNc1ccnc2ccccc12]

2-[2-(Hexyloxy)phenoxy]ethanol A mixture of 2-(hexyloxy)phenol (9.10 g, 46.9 mmol), ethylene carbonate (6.4 g, 72.7 mmol), and $K_2CO_3$ (10.0 g, 72.5 mmol) in 50 mL of DMF was heated at 70-75° C. for 17 hr and then 90° C. for 6 hr. The mixture was cooled, partly neutralized with 1M HCl, and partitioned between EA and 1M HCl, $H_2O$ (2×), and brine. The organic phases were dried over $MgSO_4$, filtered through a pad of silica gel, and concentrated to a brown oil. SPE, washing with 10% EA/Hex and then eluting with 37% EA/Hex, gave 10.73 g of pale yellow liquid. Rf 0.15 (20% EA/Hex); $^1$H NMR ($CDCl_3$) δ 6.99-6.94 (m, 2H), 6.92-6.87 (m, 2H), 4.12 (m, 2H), 4.00 (t, 2H, 2H), 3.88 (m, 2H), 2.80 (s, 1H, OH), 1.82 (m, 2H), 1.46 (m, 2H), 1.38-1.31 (m, 4H), 0.90 (m, 3H); $^{13}$C NMR ($CDCl_3$) δ 150.2, 148.6, 122.8, 121.3, 117.2, 113.9, 72.5, 69.3, 61.5, 31.8, 29.4, 25.9, 22.8, 14.2.

2-[2-(Hexyloxy)phenoxy]ethyl methanesulfonate The crude 2-[2-(hexyloxy)phenoxy]ethanol (10.73 g, 45.1 mmol) was taken up in 170 mL of 1,2-dimethoxyethane and cooled by an ice bath. Methanesulfonyl chloride (4.90 mL, 62.6 mmol) and then TEA (9.40 mL 67.0 mmol) were added. After 2 hr, 5 mL of $H_2O$ were added, and the volatile components were evaporated. The residue was partitioned between EA and $H_2O$, saturated $NaHCO_3$, $H_2O$, 1M HCl, $H_2O$ (2×), and brine. The organic phases were dried over $MgSO_4$ and concentrated to give 13.67 g of colorless solid. Rf 0.37 (30% EA/Hex); $^1$H NMR ($CDCl_3$) δ 6.99-6.86 (m, 4H), 4.60 (m, 2H), 4.25 (m, 2H), 3.98 (m, 2H), 3.16 (s, 3H), 1.78 (m, 2H), 1.46 (m, 2H), 1.38-1.30 (m, 4H), 0.90 (m, 3H); $^{13}$C NMR ($CDCl_3$) δ 149.7, 147.9, 122.8, 121.1, 115.5, 113.7, 69.1, 69.0, 67.6, 38.1, 31.8, 29.5, 25.9, 22.8, 14.2.

-[2-(Hexyloxy)ethyl]phthalimide A mixture of 2-[2-(hexyloxy)phenoxy]ethyl methanesulfonate (13.67 g, 43.2 mmol), potassium phthalimide (15.5 g, 84 mmol), and sodium iodide (610 mg) in 50 mL of DMF was heated at 90° C. for 24 hr. The cooled mixture was partitioned between EA and 5% $Na_2CO_3$ and brine. The organic phases were dried over $Na_2SO_4$ and concentrated, and the residue was filtered through a pad of silica gel in 30% EA/Hex and evaporated to give a solid. Recrystallization from EtOH gave 10.4 g of colorless solid. $^1$H NMR ($CDCl_3$) δ 7.85 and 7.72 (m, 4H, AA'BB'), 6.94-6.82 (m, 4H), 4.26 and 4.12 (m, 4H, $A_2B_2$), 3.88 (t, 2H), 1.71 (m, 2H), 1.42-1.27 (m, 6H), 0.90 (m, 3H); $^{13}$C NMR ($CDCl_3$) δ 168.3, 149.8, 148.6, 134.1, 132.4, 123.5, 122.3, 121.1, 115.6, 114.3, 69.3, 66.4, 37.7, 31.8, 29.4, 25.8, 22.8, 14.2.

2-[2-(Hexyloxy)phenoxy]ethanamine N-[2-(Hexyloxy) ethyl]phthalimide (10.4 g, 28.3 mmol) was taken up in 130 mL of EtOH, and hydrazine monohydrate (2.0 mL, 41 mmol) was added. The mixture was heated at reflux for 16 hr. After heating was halted, 140 mL of 1M HCl was added to the still-warm mixture, and the mixture was stirred vigorously during cooling. The precipitate was filtered and washed with EtOH. The filtrate was concentrated. SPE, washing with 7% MeOH/DCM and then 7% MeOH/DCM+ 2% TEA gave fractions containing 6.80 g of oily-solid ninhydrin (+) product. Rf 0.40 (5% MeOH/DCM+2% TEA); $^1$H NMR ($CDCl_3$) δ 6.94-6.82 (m, 4H), 4.00 (t, 2H, J=5.2 Hz), 3.97 (t, 2H, J=6.7 Hz), 3.05 (t, 2H, J=5.2 Hz), 1.80 (m, 2H), 1.54 (br s, 2H, $NH_2$), 1.50-1.28 (m, 6H), 0.89 (m, 3H).

N-{2-[2-(Hexyloxy)phenoxy]ethyl}quinolin-4-amine Crude 2-[2-(hexyloxy)phenoxy]ethanamine (6.8 g, 28.7 mmol) was taken up in 30 mL of DMA, and 25 mL was evaporated in vacuo. The residue was diluted with 5 mL of NMP, and 4-chloroquinoline (4.20 g, 25.8 mmol) and DIEA (10.0 mL, mmol) were added. The mixture was heated in a sealed tube at 160° C. for 24 hr. Then, the mixture was cooled, partitioned between EA and 5% $Na_2CO_3$ (3×) and brine. The organic phase was dried over $Na_2SO_4$ and concentrated to give a solid. Trituration with $Et_2O$ and drying gave 3.11 g of colorless solid. Rf 0.31 (10% MeOH/DCM); mp 104.5-106.0° C.; $^1$H NMR ($CDCl_3$) δ 8.55 (d, 1H, J=5.5 Hz), 8.04 (m, 1H), 7.85 (d, 1H, J=8.4 Hz), 7.66 (ddd, 1H, J=1.4, 6.9, 8.4 Hz), 7.44 (m, 1H), 7.02-6.97 (m, 2H), 6.95-6.89 (m, 2H), 6.50 (d, 1H, J=5.5 Hz), 6.00 (br s, 1H, NH), 4.37 (t, 2H, J=5.1 Hz), 4.02 (t, 2H, J=6.9 Hz), 3.71 (m, 2H), 1.79 (m, 2H), 1.40 (m, 2H), 1.28-1.20 (m, 4H), 0.83 (m, 3H).

Example 22

N-{3-[2-(Hexyloxy)phenoxy]propyl}quinolin-4-amine

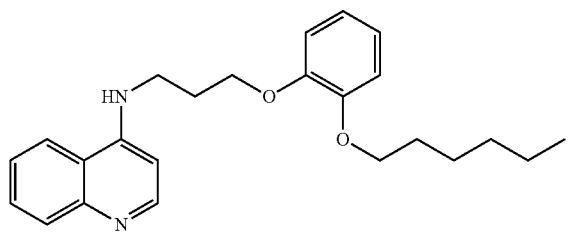 [SMILES: CCCCCCOc1ccccc1OCCCNc1ccnc2ccccc12]

2-(Hexyloxy)phenol A mixture of catechol (28.9 g, 263 mmol), $K_2CO_3$ (37 g, 268 mmol), and 1-bromohexane (29.0 mL, 207 mmol) in 130 mL of DMA reacted at room temperature for 20 hr with the aid of mechanical stirring. TLC of an aliquot showed the presence of a substantial amount of catechol. The mixture was heated at 80° C., and TLC of an aliquot showed good reaction progress. 1-Bromohexane (5.9 mL, 42 mmol) and $K_2CO_3$ (6 g, 43 mmol) were added, and heating continued for 10 hr. Then, the mixture was cooled, and most of the volatile components were evaporated. The residue was partitioned between EA (3×250 mL) and $H_2O$, 5% $Na_2CO_3$ (2×), $H_2O$, 0.1M HCl, and brine (200 mL each). The combined organic phases were dried over $MgSO_4$ and concentrated. SPE (5% EA/Hex) gave 34.8 g of a 4:1 mixture of 2-(hexyloxy)phenol and 1,2-bis(hexyloxy)benzene as determined by $^1H$ NMR. A sample was purified by SPE, washing with Hex to obtain the diether, and then eluting 2-(hexyloxy)phenol using 5% EA/Hex. Rf 0.38 (5% EA/Hex); $^1H$ NMR ($CDCl_3$) δ 7.0-6.8 (m, 4H), 5.7 (s, 1H), 4.0 (t, 2H), 1.9 (m, 2H), 1.5 (m, 2H), 1.4-1.3 (m, 4H), 1.9 (t, 3H).

N-{3-[2-(Hexyloxy)phenoxy]propyl}phthalimide A mixture of 2-(hexyloxy)phenol that contained 1,2-bis(hexyloxy) benzene (90 mol % pure, 61.8 g), $K_2CO_3$ (43.6 g, 316 mmol), and N-(3-bromopropyl)phthalimide (76.9 g, 287 mmol) in 150 mL of DMF was heated at 60° C. for 24 hr with the aid of mechanical stirring. TLC (5% EA, 45% toluene, 50% Hex) of an aliquot showed that substantial bromide starting material remained, so the temperature was raised to 100° C. After 16 hr, the reaction was completed, as shown by TLC. Then, the mixture was cooled, and most of the volatile components were evaporated. The residue was partitioned between EA (3×250 mL) and $H_2O$ neutralized using $H_3PO_4$, 0.1M HCl, $H_2O$, and brine (200 mL each). The combined organic phases were dried over $MgSO_4$ and concentrated to give 83 g of the product as a light tan solid that contained 2-(hexyloxy)phenol and 1,2-bis(hexyloxy)benzene, as shown by $^1H$ NMR. Rf 0.21 (1:9:10 EA/toluene/Hex) 0.19 (10% EA/Hex); $^1H$ NMR ($CDCl_3$) δ 7.82 and 7.71 (m, 4H, AA'BB'), 6.93-6.82 (m, 4H), 4.06 (t, 2H), 3.96-3.88 (m, 4H), 2.19 (m, 2H), 1.76 (m, 2H), 1.46-1.24 (m, 6H), 0.87 (m, 3H).

3-[2-(Hexyloxy)phenoxy]propan-1-amine Crude N-{3-[2-(hexyloxy)phenoxy]propyl}phthalimide was dissolved in 450 mL of warm IPA, and hydrazine monohydrate (24.8 mL, 327 mmol) was added. The mixture was heated at 80° C. for 12 hr with the aid of mechanical stirring, and then the mixture was allowed to stand at room temperature for 48 hr. The solid was broken up, diluted with 400 mL of $Et_2O$, and stirred for 1 hr. The precipitate was filtered and washed with 50% MeOH/$Et_2O$ (2×200 mL). The combined filtrates were concentrated to give 73 g of amber liquid. The liquid was taken up in 400 mL of DCM and washed with 1N NaOH and $H_2O$ (100 mL each). The organic phase was concentrated. The mixture was separated by SPE. Elution with 1% MeOH/DCM gave 20 g of a mixture of 2-(hexyloxy)phenol and 1,2-bis(hexyloxy)benzene. Then, elution with 7% MeOH/DCM+2% $NH_4OH$ gave the product. The partially concentrated fractions were washed with 200 mL of $H_2O$, the water phase was extracted with 150 mL of DCM, and the combined organic phases were dried over $Na_2SO_4$, filtered, and concentrated to give 33.6 g of an amber liquid. Rf 0.06 (5% MeOH/DCM, ninhydrin (+)); $^1H$ NMR ($CDCl_3$) δ 6.91-6.87 (m, 4H), 4.09 (t, 2H), 3.98 (t, 2H, J=6.6 Hz), 2.93 (t, 2H), 1.95 (q, 2H), 1.80 (m, 2H), 1.50-1.31 (m, 6H), 0.90 (m, 3H); $^{13}C$ NMR ($CDCl_3$) δ 121.5, 121.2, 114.4, 114.1, 69.3, 67.9, 40.0, 33.4, 31.8, 29.5, 25.9, 22.8, 14.2.

N-{3-[2-(Hexyloxy)phenoxy]propyl}quinolin-4-amine 3-[2-(Hexyloxy)phenoxy]propan-1-amine (28.4 g, 113 mmol) was taken up in 230 mL of 1-pentanol, and 70 mL of volatile material was removed by distillation in order to ensure anhydrous conditions. The mixture was allowed to cool below reflux temperature, and tripropylamine (43 mL, 226 mmol) and 4-chloroquinoline (23.9 g, 147 mmol) were added. Heating at reflux was resumed. After 15 hr, TLC of an aliquot indicated no ninhydrin (+) starting material remained. After stirring at room temperature for 48 hr, 120 mL of volatile material was removed by distillation. The cooled mixture was diluted with 350 mL of DCM and washed with 2N NaOH, $H_2O$, and 5% $Na_2CO_3$ (100 mL each). The aqueous phases were extracted in turn with 350 mL of DCM. The combined organic phases were dried over $Na_2SO_4$, filtered, and concentrated. Purification by FC, eluting with a step gradient of 40, 50, and 60% EA/Hex+2% TEA, gave pure product fractions, as shown by TLC and NMR. The product mixture was concentrated, taken up in EA, washed with 5% $Na_2CO_3$ and brine, dried over $Na_2SO_4$, filtered, and concentrated to give a yellow oil. Standing under $Et_2O$ and cooling using an ice bath gave a colorless precipitate. The precipitate was collected by filtration and washed with ice-cold $Et_2O$ to give 33.9 g of the product after drying in vacuo. mp 61.0-62.0° C.;

$^1H$ NMR ($CDCl_3$) δ 8.55 (d, 1H, J=5.1 Hz), 7.95 (dd, 1H, J=0.8, 8.5 Hz), 7.84 (dd, 1H, J=1.1, 8.4 Hz), 7.60 (m, 1H), 7.35 (m, 1H), 6.98-6.87 (m, 4H), 6.44 (d, 1H, J=5.5 Hz), 5.98 (t, 1H, J=4.4 Hz, N$\underline{H}$), 4.21 (t, 1H, J=5.5 Hz), 4.02 (t, 2H), 3.58 (m, 2H), 2.27 (m, 2H), 1.75 (m, 2H), 1.40 (m, 2H), 1.27-1.21 (m, 4H), 0.84 (m, 3H); $^{13}C$ NMR ($CDCl_3$) δ 151.2, 150.1, 149.6, 148.7, 148.6, 130.0, 129.0, 124.5, 122.3, 121.1, 120.2, 119.2, 115.2, 113.8, 98.7, 69.2, 69.2, 42.1, 31.6, 29.3, 28.5, 25.8, 22.7, 14.1.

Example 23

N-{4-[2-(Hexyloxy)phenoxy]butyl}quinolin-4-amine

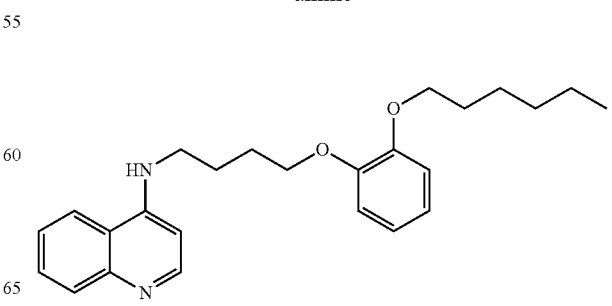

N-(4-Bromobutyl)phthalimide A mixture of 1,4-dibromobutane (22 mL, 185 mmol) and potassium phthalimide (11.35 g, 61.4 mmol) in 60 mL of DMF was mixed at room temperature for 1 day. Then, the reaction mixture was extracted with hexane (3×150 mL). The hexane fractions were dried over $MgSO_4$, filtered, and concentrated to give 30 g of a 1:2.2 molar mixture of recovered 1,4-dibromobutane and DMF. This mixture was diluted with 30 mL of DMF and retreated with potassium phthalimide (4.80 g, 26 mmol) at room temperature for 1 day. The two reaction mixtures in DMF were partitioned between 1:1 EA/Hex (3×150 mL) and $H_2O$ (2×100 mL), 0.1M HCl (100 mL), and brine (100 mL). The organic phases were dried over $MgSO_4$ and concentrated. SPE, eluting with 0% and 10% EA/Hex, gave 17.3 g of colorless solid. Rf 0.55 (40% EA/Hex); $^1$H NMR ($CDCl_3$) δ 7.86-7.81 (m, 2H), 7.73-7.69 (m, 2H), 3.71 (t, 2H), 3.43 (t, 2H), 1.94-1.80 (m, 4H); $^{13}$C NMR ($CDCl_3$) δ 168.5, 134.2, 132.3, 123.5, 37.2, 32.9, 30.1, 27.4.

N-{4-[2-(Hexyloxy)phenoxy]butyl}phthalimide A mixture of N-(4-bromobutyl)phthalimide (17.3 g, 61.3 mmol), 2-(hexyloxy)phenol (14.9 g, 61 mmol), and $K_2CO_3$ (9.5 g, 69 mmol) in 80 mL of DMF was heated at 80° C. for 20 hr. Then, the mixture was cooled, partitioned between 40% EA/Hex (3×300 mL) and 0.25M HCl (340 mL), $H_2O$, 0.1M HCl, and brine (150 mL each), dried over $MgSO_4$, concentrated, filtered through a pad of silica gel with 40% EA/Hex, and concentrated to give 25.7 g of pale yellow solid.

4-[2-(Hexyloxy)phenoxy]butan-1-amine Crude N-{4-[2-(hexyloxy)phenoxy]butyl}phthalimide was taken up in 400 mL of IPA, and hydrazine monohydrate (4.40 mL, 91 mmol) was added. The mixture was heated at 80° C. for 12 hr. Then, the mixture was cooled, resulting in precipitation. $Et_2O$ (400 mL) was added, and the heterogeneous mixture was stirred vigorously. The precipitate was removed by filtration through Celite, and the precipitate was washed with $Et_2O$ (4×150 mL). The volatile components were evaporated to leave 14.2 g of colorless solid. $^1$H NMR ($CDCl_3$) δ 6.88-6.83 (m, 4H), 3.98 (t, 2H, J=6.2 Hz), 3.96 (t, 2H, J=6.7 Hz), 2.77 (t, 2H, J=6.9 Hz), 2.17 (br s, 2H), 1.89-1.74 (m, 4H), 1.64 (m, 2H), 1.50-1.23 (m, 6H), 0.89 (m, 3H).

N-{4-[2-(Hexyloxy)phenoxy]butyl}quinolin-4-amine
Crude 4-[2-(hexyloxy)phenoxy]butan-1-amine (14.2 g, 53.6 mmol) was taken up in 400 mL of 1-pentanol, and 100 mL was removed by distillation. The mixture was cooled below boiling, and tripropylamine (15 mL, 78.7 mmol) and 4-chloroquinoline (8.75 g, 53.7 mmol) were added. Heating at reflux was resumed for 18 hr. Then, the mixture was concentrated by distillation. SPE, washing with 50% EA/Hex and then eluting with 10% MeOH/DCM gave a brown oil after concentration. The oil was taken up in DCM and washed with 5% $Na_2CO_3$, dried over $Na_2SO_4$, and concentrated. Purification by FC (60% EA/Hex+2% TEA), evaporation of solvents from the product fractions, and then evaporation of MeOH and drying gave 3.7 g of the product as a colorless solid. $^1$H NMR ($CDCl_3$) δ 8.53 (d, 1H, J=5.5 Hz), 7.95 (dd, 1H, J=0.7, 8.4 Hz), 7.74 (m, 1H), 7.59 (ddd, 1H, J=1.1, 7.0, 8.1 Hz), 7.33 (m, 1H), 6.97-6.88 (m, 4H), 6.43 (d, 1H, J=5.2 Hz), 5.63 (t, 1H, N$\underline{H}$), 4.11 (t, 1H), 4.00 (t, 2H), 3.49 (m, 2H), 2.01-1.94 (m, 4H), 1.74 (m, 2H), 1.39 (m, 2H), 1.23-1.16 (m, 4H), 0.80 (m, 3H); $^{13}$C NMR ($CDCl_3$) δ 151.3, 150.0, 149.5, 148.8, 148.8, 130.1, 129.1, 124.6, 121.8, 121.1, 119.8, 119.1, 114.4, 113.7, 98.8, 69.2, 69.2, 42.8, 31.7, 29.4, 26.8, 25.9, 25.8, 22.8, 14.1.

Example 24

N-[3-(2-Ethoxyphenoxy)propyl]quinolin-4-amine

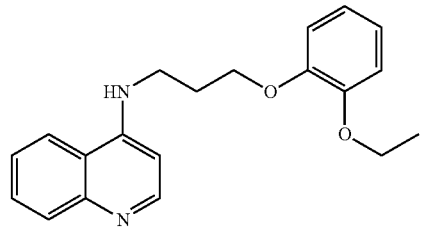 [SMILES: CCOc1ccccc1OCCCNc1ccnc2ccccc12]

N-[3-(2-Ethoxyphenoxy)propyl]quinolin-4-amine (217 mg) was prepared following the method for the preparation of N-{3-[4-(hexyloxy)phenoxy]propyl}quinolin-4-amine, starting with 2-ethoxyphenol (1.5 g) and N-(3-bromopropyl)phthalimide (2.91 g).

N-[3-(2-Ethoxyphenoxy)propyl]phthalimide (2.57 g): $^1$H NMR ($CDCl_3$) δ 7.85 and 7.75 (m, 4H, AA'BB'), 6.95-6.80 (m, 4H), 4.1-4.0 (m, 4H), 3.9 (t, 2H), 2.2 (m, 2H), 1.4 (t, 3H).

3-(2-Ethoxyphenoxy)propan-1-amine (0.76 g): $^1$H NMR ($CDCl_3$) δ 6.9 (m, 4H), 4.1-4.0 (m, 4H), 2.95 (t, 2H), 1.95 (m, 2H), 1.5 (br s, 2H, N$\underline{H}_2$), 1.4 (t, 3H).

N-[3-(2-Ethoxyphenoxy)propyl]quinolin-4-amine: $^1$H NMR ($CDCl_3$) δ 8.8 (br s, 1H, NH), 8.5 (m, 1H), 8.4 (m, 1H), 8.2 (d, 1H), 7.7 (m, 1H), 7.5 (m, 1H), 7.0-6.8 (m, 4H), 6.6 (d, 1H), 4.2 (m, 2H), 4.1 (m, 2H), 3.8 (q, 2H), 2.4 (m, 2H), 1.4 (t, 3H).

Example 25

N-[3-(2-Methoxyphenoxy)propyl]quinolin-4-amine

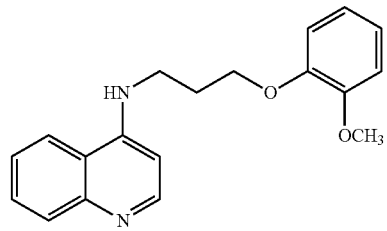 [SMILES: COc1ccccc1OCCCNc1ccnc2ccccc12]

3-(2-Methoxyphenoxy)propan-1-amine was prepared following the method for the preparation of 3-[4-(Hexyloxy)phenoxy]propan-1-amine, starting with 2-methoxyphenol (1.5 g) and N-(3-bromopropyl)phthalimide (3.2 g).

N-[3-(2-Methoxyphenoxy)propyl]phthalimide (3.19 g): $^1$H NMR ($CDCl_3$) δ 7.8 and 7.7 (m, 4H, AA'BB'), 6.9-6.8 (m, 4H), 4.1 (t, 2H), 3.9 (t, 2H), 3.7 (s, 3H), 2.2 (m, 2H).

3-(2-Methoxyphenoxy)propan-1-amine (770 mg): $^1$H NMR ($CDCl_3$) δ 6.9-6.8 (m, 4H), 4.1 (t, 2H), 3.8 (s, 3H), 2.9 (t, 2H), 2.0 (m, 2H), 1.5 (br s, 2H, N$\underline{H}_2$).

N-[3-(2-Methoxyphenoxy)propyl]quinolin-4-amine A mixture of 3-(2-methoxyphenoxy)propan-1-amine (770 mg, 3.95 mmol), 4-chloroquinoline (777 mg, 4.77 mmol), 0.15 mL of NMP and 2 mL of TEA were heated at 130° C. in a sealed tube for 5 days. Then, the mixture was cooled and concentrated in vacuo. Purification by preparative TLC (5% MeOH/DCM) gave the product. $^1$H NMR ($CDCl_3$) δ 8.4 (d, 1H), 8.2 (d, 1H), 8.1 (d, 1H), 7.7 (m, 1H), 7.4 (m, 1H), 7.1 (br s, 1H, N<u>H</u>), 7.0-6.9 (m, 4H), 6.5 (d, 1H), 4.3 (t, 2H), 3.9 (s, 3H), 3.7 (m, 2H), 2.3 (m, 2H).

Example 26

N-{3-[2-(B enyloxy)phenoxy]propyl}quinolin-4-amine

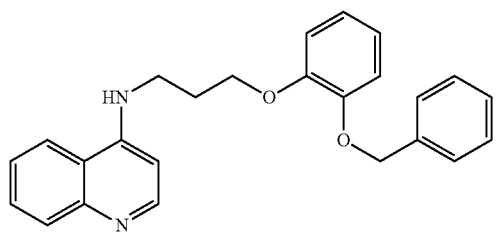 [SMILES: c1ccc(COc2ccccc2OCCCNc2ccnc3ccccc23)cc1]

N-{3-[2-(Benyloxy)phenoxy]propyl}quinolin-4-amine was prepared following the method for the preparation of N-{3-[4-(hexyloxy)phenoxy]propyl}quinolin-4-amine, starting with 2-(benzyloxy)phenol (2.0 g) and N-(3-bromopropyl)phthalimide (2.68 g).

N-{3-[2-(Benzyloxy)phenoxy]propyl}phthalimide (3.6 g): $^1$H NMR (CDCl$_3$) δ 7.8 and 7.7 (m, 4H, AA'BB'), 7.5-7.3 (m, 4H), 7.0-6.8 (m, 5H), 5.1 (s, 2H), 4.1 (t, 2H), 3.9 (t, 2H), 2.2 (m, 2H).

3-[2-(Benzyloxy)phenoxy]propan-1-amine (1.92 g): $^1$H NMR (CDCl$_3$) δ 7.5-7.3 (m, 5H), 6.9-6.8 (m, 4H), 5.1 (s, 2H), 4.1 (t, 2H), 2.9 (t, 2H), 2.0 (m, 2H).

N-{3-[2-(Benzyloxy)phenoxy]propyl}quinolin-4-amine: $^1$H NMR (CDCl$_3$) δ 8.5 (d, 1H), 7.9 (d, 1H), 7.8 (d, 1H), 7.5 (m, 1H), 7.4-7.2 (m, 6H), 7.0-6.9 (m, 4H), 6.4 (d, 1H), 6.0 (br s, 1H, N<u>H</u>), 5.1 (s, 2H), 4.2 (t, 2H), 3.6 (m, 2H), 2.3 (m, 2H).

Example 27

N-[8-(3-Methoxyphenoxy)octyl]quinolin-4-amine

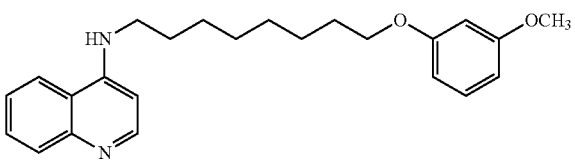 [SMILES: COc1cccc(OCCCCCCCCNc2ccnc3ccccc23)c1]

1-(8-Bromooctyloxy)-3-methoxybenzene (1.28 g) was prepared by the same method used for 1-(8-bromooctyloxy)-3-methylbenzene using 3-methoxyphenol (638 mg, 5.14 mmol), 1,8-dibromooctane (14.3 g, 53 mmol), and K$_2$CO$_3$ (852 mg, 6.17 mmol) in 14 mL of NMP and 7 mL of DME heated for 24 hr. $^1$H NMR (CDCl$_3$) δ 7.2 (m, 1H), 6.46 (m, 3H), 3.9 (t, 2H), 3.4 (t, 2H, J=6.9 Hz), 1.9-1.7 (m, 4H), 1.6-1.2 (m, 8H).

1-(8-Iodooctyloxy)-3-methoxybenzene (1.47 g) was prepared from 1-(8-bromooctyloxy)-3-methoxybenzene (1.28 g, 6.78 mmol) and sodium iodide (601 mg) in 50 mL of acetone following the method used in the preparation of 10-(hexyloxy)decan-1-amine.

N-[8-(3-Methoxyphenoxy)octyl]phthalimide (1.0 g) was prepared from 1-(8-iodooctyloxy)-3-methoxybenzene (1.47 g, 4.06 mmol) and potassium phthalimide (1.13 g) in 50 mL of DMF at 60-80° C. for 12 hr following the method for N-[8-(hexyloxy)octyl]phthalimide. $^1$H NMR (CDCl$_3$) δ 7.85 (m, 2H), 7.7 (m, 2H), 7.2 (m, 1H), 6.7-6.5 (m, 3H), 3.9 (m, 2H), 3.8 (s, 3H), 3.65 (m, 2H), 1.8-1.6 (m, 4H), 1.5-1.3 (m, 8H).

8-(3-Methoxyphenoxy)octan-1-amine (438 mg, 1.74 mmol) was prepared from N-[8-(3-methoxyphenoxy)octyl] phthalimide (1.0 g, 2.6 mmol) using hydrazine monohydrate (0.20 mL) in EtOH (50 mL) following the method for [3-(hexyloxy)phenyl]methanamine. $^1$H NMR (CD$_3$OD) δ 7.1 (m, 1H), 6.5-6.4 (m, 3H), 3.9 (t, 2H), 3.7 (s, 3H), 2.7 (t, 2H), 1.8 (m, 2H), 1.6-1.4 (m, 10H).

N-[8-(3-Methoxyphenoxy)octyl]quinolin-4-amine (200 mg) was prepared from 8-(3-methoxyphenoxy)octan-1-amine (438 mg, 1.74 mmol), 4-chloroquinoline (572 mg), TEA (2 mL), and NMP (0.2 mL) following the method for N-[8-(3-ethoxypropoxy)octyl]quinolin-4-amine.

$^1$H NMR (CDCl$_3$) δ 8.5 (d, 1H), 8.0 (d, 1H), 7.75 (d, 1H), 7.6 (m, 1H), 7.4 (m, 1H), 7.15 (m, 1H), 6.5-6.4 (m, 4H), 5.1 (br s, 1H, N<u>H</u>), 3.9 (t, 2H), 3.3 (m, 2H), 1.8 (m, 4H), 1.6-1.3 (m, 8H).

Example 28

N-{4-[3-(Hexyloxy)phenoxy]butyl}quinolin-4-amine

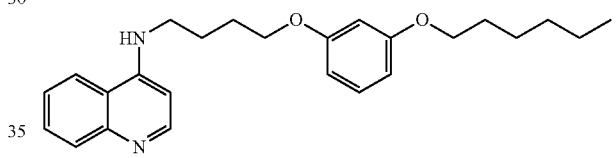

1-(4-Bromobutoxy)-3-(hexyloxy)benzene A mixture of 3-(hexyloxy)phenol (1.21 g, 6.26 mmol), 1,4-dibromobutane (7.00 mL, 59 mmol), and K$_2$CO$_3$ (950 mg, 6.88 mmol) in 14 mL of 1:1 NMP/1,2-dimethoxyethane was heated at gentle reflux for 40 hr. The mixture was cooled and partitioned between DCM and 1M HCl. The organic phase was dried over MgSO$_4$ and concentrated in vacuo with warming to remove excess dibromide. The residue was separated by SPE, washing with Hex and then eluting the product with 5% EA/Hex to give 1-(4-bromobutoxy)-3-(hexyloxy)benzene (1.42 g). Rf 0.40 (5% EA/Hex); $^1$H NMR (CDCl$_3$) δ 7.15 (m, 1H), 6.51-6.43 (m, 3H), 3.99-3.90 (m, 4H), 3.48 (t, 2H, J=6.6 Hz), 2.11 (m, 2H), 1.93 (m, 2H), 1.81 (m, 2H), 1.50-1.29 (m, 6H), 0.92 (m, 3H).

N-{4-[3-(Hexyloxy)phenoxy]butyl}phthalimide 1-(4-Bromobutoxy)-3-(hexyloxy)benzene (1.40 g, 4.26 mmol), potassium phthalimide (1.18 g, 6.38 mmol), and DMF (5 mL) were mixed at room temperature until the bromide was consumed, as observed by TLC of an aliquot. The mixture was partitioned between EA and H$_2$O and brine, and the organic phase was dried over MgSO$_4$ and concentrated. SPE (15% EA/Hex) gave 1.60 g of the product. Rf 0.40 (20% EA/Hex); $^1$H NMR (CDCl$_3$) δ 7.83 and 7.70 (m, 4H, AA'BB'), 7.12 (m, 1H), 6.48-6.42 (m, 3H), 3.98-3.88 (m, 4H), 3.76 (t, 2H, J=6.8 Hz), 1.92-1.70 (m, 6H), 1.49-1.25 (m, 6H), 0.89 (m, 3H).

4-[3-(Hexyloxy)phenoxy]butan-1-amine A mixture of the N-{4-[3-(hexyloxy)phenoxy]butyl}phthalimide (1.60 g, 4.05 mmol), hydrazine monohydrate (0.30 mL, 6.3 mmol), and 15 mL of EtOH were heated at reflux for 8 hr. The mixture was cooled and partitioned between EA and 5% K₂CO₃ and brine, and the organic phases were dried over Na₂SO₄ and concentrated. SPE, washing with 5% MeOH/DCM and eluting with 10% MeOH/DCM+2% TEA gave 1.05 g of the amine as a colorless solid. ¹H NMR (CD₃OD+ CDCl₃) δ 7.01 (t, 1H, J=7.8 Hz), 6.37-6.32 (m, 3H), 3.83-3.76 (m, 4H), 2.66 (t, 2H), 1.74-1.50 (m, 6H), 1.34-1.17 (m, 6H), 0.77 (m, 3H).

N-{4-[3-(Hexyloxy)phenoxy]butyl}quinolin-4-amine A mixture of the 4-[3-(hexyloxy)phenoxy]butan-1-amine (300 mg, 1.20 mmol), 4-chloroquinoline (283 mg, 1.74 mmol), DIEA (0.50 mL, 2.87 mmol), and 1.5 mL of IPA was sealed in a heavy walled glass tube and mixed at 180° C. for 3 days. The mixture was cooled and partitioned between EA and 5% Na₂CO₃ and brine, dried over Na₂SO₄, and concentrated. SPE, washing with 3% MeOH/DCM and eluting with 10% MeOH/DCM, gave 293 mg of the product as a solid. Rf 0.26 (10% MeOH/DCM); ¹H NMR (CDCl₃) δ 8.52 (d, 1, J=5.2 Hz), 7.97 (d, 1, J=8.4 Hz), 7.72 (d, 1, J=8.4 Hz), 7.61 (m, 1H), 7.37 (m, 1H), 7.17 (t, 1, J=8 Hz), 6.53-6.47 (m, 3), 6.42 (d, 1, J=5.5 Hz), 5.35 (br s, 1H, NH), 4.03 (m, 2H), 3.91 (m, 2H), 3.40 (m, 2H), 1.96-1.95 (m, 4), 1.75 (m, 2H), 1.46-1.31 (m, 6), 0.89 (m, 3).

Example 29

N-{3-[3-(Hexyloxy)phenoxy]propyl}quinolin-4-amine

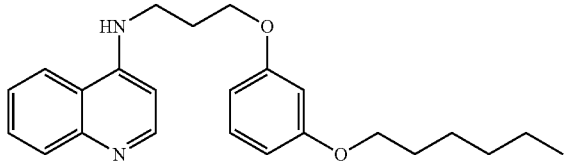 [SMILES: CCCCCCOc1cccc(OCCCNc2ccnc3ccccc23)c1]

3-(Hexyloxy)phenol A mixture of resorcinol (7.1 g), K₂CO₃ (1.13 g), and 1-bromohexane (1.0 mL) in 60 mL of NMP reacted at 50-60° C. for 20 hr with the aid of mechanical stirring. Then, the mixture was cooled, and most of the volatile components were evaporated. The residue was partitioned between EA (3×250 mL) and H₂O, 5% Na₂CO₃ (2×), H₂O, 0.1M HCl, and brine (200 mL each). The combined organic phases were dried over MgSO₄ and concentrated. SPE (5% EA/Hex) gave 1.29 g of 3-(hexyloxy)phenol. ¹H NMR (CDCl₃) δ 7.10 (m, 1H), 6.48 (m, 1H), 6.42-6.38 (m, 2H), 3.91 (t, 2H, J=6.7 Hz), 1.75 (m, 2H), 1.48-1.31 (m, 6H), 0.89 (m, 3H).

N-{3-[3-(Hexyloxy)phenoxy]propyl}phthalimide A mixture of 3-(hexyloxy)phenol (9.8 g), K₂CO₃ (9.8 g), and N-(3-bromopropyl)phthalimide (15.5 g) in 150 mL of 2-butanone was heated at reflux for 24 hr with the aid of mechanical stirring. Then, the mixture was cooled, and most of the volatile components were evaporated. The residue was partitioned between EA (3×250 mL) and H₂O neutralized using H₃PO₄, 0.1M HCl, H₂O, and brine (200 mL each). The combined organic phases were dried over MgSO₄ and concentrated to give 7.58 g of the product. ¹H NMR (CDCl₃) δ 7.81 and 7.68 (m, 4H, AA'BB'), 7.09 (t, 1H, J=8.2 Hz), 6.45 (ddd, 1H, J=1.0, 2.5, 8.4 Hz), 6.39-6.32 (m, 2H), 3.99 (t, 2H, J=6.0 Hz), 3.91-3.83 (m, 4H), 2.16 (m, 2H), 1.73 (m, 2H), 1.45-1.21 (m, 6H), 0.90 (m, 3H).

3-[3-(Hexyloxy)phenoxy]propan-1-amine Crude N-{3-[3-(hexyloxy)phenoxy]propyl}phthalimide (1.20 g) was dissolved in 50 mL of EtOH, and hydrazine monohydrate (0.22 mL) was added. The mixture was heated at reflux for 12 hr, and then the mixture was allowed to stand at room temperature for 48 hr. The solid was broken up, diluted with 50 mL of ether, and stirred for 1 hr. The precipitate was filtered and washed with 50% MeOH/ether (2×40 mL). The combined filtrates were concentrated. The liquid was taken up in 100 mL of DCM and washed with 1N NaOH and H₂O (10 mL each). The organic phase was concentrated. SPE, washing with 1% MeOH/DCM and then eluting with 7% MeOH/DCM+2% NH₄OH, gave the product. The partially concentrated fractions were washed with 20 mL of H₂O, the water phase was extracted with 40 mL of DCM, and the combined organic phases were dried over Na₂SO₄ and concentrated to give 763 mg of an amber liquid. ¹H NMR (CDCl₃) δ 7.13 (m, 1H), 6.49-6.43 (m, 3H), 4.00 (t, 2H, J=6.1 Hz), 3.90 (t, 2H), 2.89 (t, 2H, J=6.7 Hz), 1.96-1.84 (m, 4H), 1.74 (m, 2H), 1.48-1.28 (m, 6H), 0.89 (m, 3H).

N-{3-[3-(Hexyloxy)phenoxy]propyl}quinolin-4-amine A mixture of 3-[3-(hexyloxy)phenoxy]propan-1-amine (763 mg, 3.04 mmol), 4-chloroquinoline (746 mg, 4.58 mmol), DIEA (1.0 mL, 5.74 mmol), and 0.1 mL of DMF was sealed in a heavy walled glass tube and heated at 130° C. for 4 days. The mixture was cooled. SPE, washing with 50% EA/Hex and eluting with 10% MeOH/DCM, gave the product contaminated by ninhydrin (+) material. FC (8% to 9% MeOH/DCM) resulted in partial purification. SPE (60% EA/Hex+1% TEA) gave 389 mg of product as an oil that solidified upon standing. Rf 0.25 (10% MeOH/DCM); ¹H NMR (CDCl₃) δ 8.52 (d, 1H, J=5.2 Hz), 7.96 (dd, 1H, J=0.8, 8.4 Hz), 7.77 (dd, 1H, J=1.0, 8.4 Hz), 7.61 (ddd, 1H, J=1.5, 6.9, 8.4 Hz), 7.40 (ddd, 1H, J=1.2, 6.9, 8.4 Hz), 7.17 (m, 1H), 6.53-6.48 (m, 3), 6.42 (d, 1H, J=5.4 Hz), 5.74 (br s, 1H, NH), 4.14 (m, 2H), 3.90 (m, 2H), 3.54 (m, 2H), 2.23 (m, 2H), 1.76 (m, 2H), 1.49-1.24 (m, 6), 0.89 (m, 3).

Example 30

N-{2-[3-(Hexyloxy)phenoxy]ethyl}quinolin-4-amine

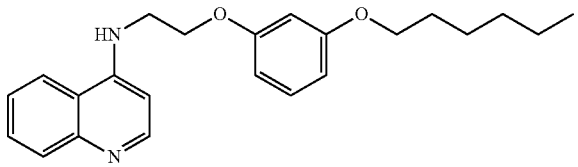 [SMILES: CCCCCCOc1cccc(OCCNc2ccnc3ccccc23)c1]

3-(Hexyloxy)phenol (2.5 g), N-(2-bromoethyl)phthalimide (3.27 g), and K₂CO₃ (1.95 g) in acetone (50 mL) at reflux and subsequent treatment with hydrazine monohydrate (3.5 mL) in EtOH (24 mL) at reflux gave 226 mg of ninhydrin (+) 2-[3-(hexyloxy)phenoxy]ethan-1-amine.

¹H NMR (CDCl₃) δ 7.10 (m, 1H), 6.55-6.40 (m, 3H), 4.00-3.80 (m, 4H), 3.00 (br s, 2H), 1.90-1.70 (m, 4H), 1.50-1.30 (m, 6H), 0.90 (m, 3H).

N-{2-[3-(Hexyloxy)phenoxy]ethyl}quinolin-4-amine A mixture of 2-[3-(hexyloxy)phenoxy]ethan-1-amine (226 mg, 0.95 mmol), 4-chloroquinoline (233 mg, 1.43 mmol), DIEA (1.0 mL, 5.74 mmol), and 0.15 mL of DMF was sealed in a heavy walled glass tube and stirred at 140° C. and mixed for 5 days. The cooled mixture was concentrated and separated by FC (7% MeOH/DCM) to give 150 mg of product as a pink solid. Rf 0.32 (10% MeOH/DCM); $^1$H NMR (CDCl$_3$) δ 8.50 (d, 1H, J=5.5 Hz), 7.99 (d, 1H, J=8.2 Hz), 7.93 (d, 1H, J=8.1 Hz), 7.62 (m, 1H), 7.42 (m, 1H), 7.16 (m, 1H), 6.54-6.47 (m, 4), 6.21 (br s, 1H, NH), 4.28 (t, 2H, J=5.2 Hz), 3.92 (m, 2H), 3.75 (m, 2H), 1.75 (m, 2H), 1.48-1.24 (m, 6), 0.88 (t, 3, J=6.7 Hz).

Example 31

N-[8-(4-Methoxyphenoxy)octyl]quinolin-4-amine

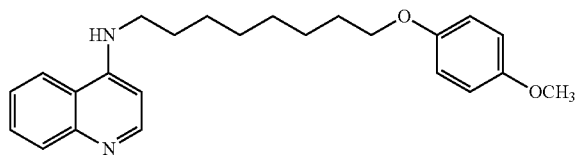

1-(8-Bromooctyloxy)-4-methoxybenzene A mixture of 4-methoxyphenol (5.08 g, 41.0 mmol) and K$_2$CO$_3$ (6.12 g, 44.3 mmol) in 40 mL of DMF was stirred for 1.25 hr. Then, a mixture of 1,8-dibromooctane (86.0 g, 316 mmol) in 40 mL of DMF was added. The mixture was stirred for 24 hr and then it was allowed to stand for 6 days. The mixture was partitioned between 1:1 EA/Hex and H$_2$O (3×), 0.1M HCl, and brine, and the organic phases were dried over Na$_2$SO$_4$, filtered, and concentrated. The residue in 10% EA/Hex was filtered through a pad of silica gel, and then most of the solvents were evaporated. Vacuum distillation was performed to remove most of the excess dibromide, and the pot residue consisted of almost colorless solid and a small amount of liquid. The pot was rinsed twice with Hex and the solid was dried in vacuo. Rf 0.42 (10% EA/Hex); $^1$H NMR (CDCl$_3$) δ 6.82 (s, 4H), 3.89 (t, 2H), 3.76 (s, 3H), 3.40 (t, 2H, J=6.8 Hz), 1.90-1.70 (m, 4H), 1.48-1.33 (m, 8H).

N-[8-(4-Methoxyphenoxy)octyl]phthalimide A mixture of crude 1-(8-bromooctyloxy)-4-methoxybenzene and potassium phthalimide (7.59 g, 41.0 mmol) in 60 mL of NMP was stirred at room temperature until the bromide was consumed, as shown by TLC analysis of an aliquot. Then, 30 mL of H$_2$O was added, and much of the volatile material was evaporated in vacuo. The residue was partitioned between 1:1 EA/Hex and H$_2$O and brine. The organic phases were dried over Na$_2$SO$_4$, filtered, and concentrated to give 14.88 g of a colorless solid. Rf 0.11 (10% EA/Hex).

8-(4-Methoxyphenoxy)octan-1-amine Hydrazine monohydrate (4.00 mL, 84 mmol) was added to a mixture of N-[8-(4-methoxyphenoxy)octyl]phthalimide (14.8 g, 38.8 mmol) and 125 mL of denatured EtOH using mechanical stirring. The mixture was heated at reflux for 15 hr, during which time a colorless precipitate formed. The mixture was concentrated by evaporation, and the residue was partitioned between isopropyl acetate (300, 2×125 mL) and 5% Na$_2$CO$_3$ (200, 3×100 mL) and brine (100 mL). The combined organic phases were dried over Na$_2$SO$_4$, filtered, and concentrated to give 8.63 g of white solid after drying in vacuo. $^1$H NMR (CDCl$_3$) δ 6.79 (s, 4H), 4.66 (s, 3H), 3.86 (t, 2H, J=6.4 Hz), 3.72 (s, 3H), 2.72 (t, 2H, J=7.4 Hz), 1.71 (m, 2H), 1.55-1.33 (m, 10H).

N-[8-(4-Methoxyphenoxy)octyl]quinolin-4-amine 8-(4-Methoxyphenoxy)octan-1-amine (4.60 g, 18.3 mmol) was taken up in 100 mL of 1-pentanol, and 30 mL of volatile material was removed by distillation. The mixture was cooled below boiling, and tripropylamine (7.00 mL, 36.7 mmol) and 4-chloroquinoline (3.28 g, 20.1 mmol) were added. Heating at reflux was resumed. After 26.25 hr, the mixture was cooled, and 20 mL of 1N NaOH was added. Volatile material was removed by evaporation. The mixture was diluted with DCM (350 mL) and washed with 5% Na$_2$CO$_3$ (50 mL). The aqueous phase was extracted with DCM (100 mL). The combined organic phases were dried over Na$_2$SO$_4$, filtered, and concentrated. SPE, washing with 50% EA/Hex and then eluting with 50% EA/Hex+2% TEA, gave product fractions that were combined and concentrated. The residue was partitioned between DCM and 5% Na$_2$CO$_3$. The combined organic phases were dried over Na$_2$SO$_4$, filtered, and concentrated to afford a yellow solid. The solid was triturated with ice-cold 20% Et$_2$O/Hex and dried in vacuo. The solid had mp 141.0-144.0° C. The solid was dissolved in minimal hot butanone and then the mixture was allowed to cool to room temperature. After chilling in an ice bath for 2 hr, the precipitate was collected and washed with ice-cold butanone to give 3.98 g of a tan solid. Rf 0.23 (5% MeOH/DCM+2% TEA); mp 143.0-145.5° C.; $^1$H NMR (CDCl$_3$) δ 8.56 (d, 1H, J=5.1 Hz), 7.98 (dd, 1H, J=0.7, 8.5 Hz), 7.72 (m, 1H), 7.62 (m, 1H), 7.42 (m, 1H), 6.85-6.80 (m, 4H, AA'BB'), 6.42 (d, 1H, J=5.5 Hz), 4.97 (br s, 1H, NH), 3.90 (t, 2H, J=6.6 Hz), 3.76 (s, 3H), 3.31 (m, 2H), 1.80-1.73 (m, 4H), 1.48-1.39 (m, 8H); $^{13}$C NMR (CDCl$_3$) δ 153.9, 153.5, 151.3, 149.8, 148.7, 130.3, 129.1, 124.8, 119.3, 118.9, 115.6, 114.8, 99.0, 68.8, 56.0, 43.4, 29.6, 29.5, 29.5, 29.2, 27.3, 26.2.

Example 32

N-[6-(4-Methoxyphenoxy)hexyl]quinolin-4-amine

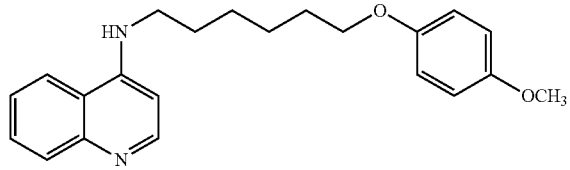 [SMILES: COc1ccc(OCCCCCCNc2ccnc3ccccc23)cc1]

1-(6-Bromohexyloxy)-4-methoxybenzene A mixture of 1,6-dibromohexane (2.4 mL, 15.7 mmol), 4-methoxyphenol (243 mg, 1.96 mmol), and K$_2$CO$_3$ (550 mg, 3.99 mmol) in 4 mL of DMF and 3 mL of DME was stirred 16 hr at room temperature, 4 hr at 80° C., and 64 hr at room temperature. The mixture was diluted with EA and washed with H$_2$O, 5% Na$_2$CO$_3$, H$_2$O, 0.1M HCl, and brine. The organic phase was dried over anhydrous Na$_2$SO$_4$, filtered through a pad of silica gel, and concentrated. SPE, washing with Hex and then eluting with 15% EA/Hex, gave 623 mg of the product as a colorless solid. Rf 0.29 (5% EA/Hex); $^1$H NMR (CDCl$_3$) δ 6.82 (s, 4H, AA'BB'), 3.90 (t, 2H, J=6.3 Hz), 3.76 (s, 3H), 3.41 (m, 2H, AB), 1.88 (m, 2H), 1.76 (m, 2H), 1.56-1.39 (m, 4H).

1-(6-Azidohexyloxy)-4-methoxybenzene A mixture of 1-(6-bromohexyloxy)-4-methoxybenzene 623 mg, 2.17 mmol) and sodium azide (210 mg, 3.23 mmol) in 5 mL of DMF was stirred at room temperature for 48 hr. Then, the mixture was diluted with EA and washed with H$_2$O and brine. The organic phase was dried over MgSO$_4$ and concentrated to give 500 mg of oily solid. Rf 0.50 (15% Et$_2$O/Hex); $^1$H NMR (CDCl$_3$) δ 6.82 (s, 4H, AA'BB'), 3.89

(t, 2H, J=6.5 Hz), 3.74 (s, 3H), 3.25 (t, 2H, J=6.9 Hz), 1.76 (m, 2H), 1.62 (m, 2H), 1.55-1.36 (m, 4H).

6-(4-Methoxyphenoxy)hexan-1-amine A mixture of 1-(6-azidohexyloxy)-4-methoxybenzene (500 mg) and 65 mg of 5% Pd—C in 25 mL of MeOH was stirred under a blanket of hydrogen for 16 hr. The mixture was blanketed with argon and filtered through a pad of Celite. The filtrate was concentrated to give 448 mg of oil. $^1$H NMR (CDCl$_3$) δ 6.77 (s, 4H, AA'BB'), 3.84 (m, 2H), 3.70 (s, 3H), 2.64 and 2.56 (m, 2H, AB), 1.71 (m, 2H), 1.51-1.31 (m, 6H).

N-[6-(4-Methoxyphenoxy)hexyl]quinolin-4-amine Four mL of pyridine was evaporated from 6-(4-methoxyphenoxy)hexan-1-amine (448 mg, 2.01 mmol). Then, a mixture of the amine, 4-chloroquinoline (424 mg, 2.60 mmol), DIEA (0.80 mL, 4.59 mmol), and 1.5 mL of NMP was heated at 160° C. in a sealed tube for 24 hr. The mixture was cooled and partitioned between DCM and 5% Na$_2$CO$_3$. The organic phase was dried over anhydrous Na$_2$SO$_4$ and concentrated. FC (50% EA/Hex+2% TEA) gave an oil that contained residual NMP, as observed by NMR. Dilution with EtOH and evaporation under high vacuum was repeated until NMP was undetectable by NMR. Rf 0.12 (50% EA/Hex+2% TEA); $^1$H NMR (CDCl$_3$) δ 8.52 (d, 1H, J=5.2 Hz), 7.96 (d, 1H, J=8.4 Hz), 7.74 (d, 1H, J=8.4 Hz), 7.59 (ddd, 1H, J=1.2, 6.9, 8.4 Hz), 7.37 (ddd, 1H, J=1.2, 6.9, 8.2 Hz), 6.82-6.80 (m, 4H), 6.39 (d, 1H, J=5.4 Hz), 5.20 (m, 1H, NH), 3.89 (t, 2H, J=6.3 Hz), 3.74 (s, 3H), 3.31 (m, 2H), 1.78-1.75 (m, 4H), 1.52-1.49 (m, 4H).

Example 33

N-{2-[4-(Hexyloxy)phenoxy]ethyl}quinolin-4-amine

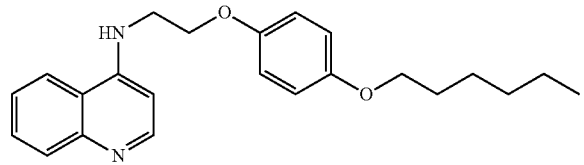 [SMILES: CCCCCCOc1ccc(OCCNc2ccnc3ccccc23)cc1]

4-(Hexyloxy)phenol was prepared by methods similar to that used for the preparation of 3-(hexyloxy)phenol. 4-(Benzyloxy)phenol (11.45 g), K$_2$CO$_3$ (8.68 g), 1-bromohexane (10.4 mL), and DMF (50 mL) at 80-100° C. gave 1-(benzyloxy)-4-(hexyloxy)benzene (12.97 g). Rf 0.68 (20% EA/Hex); $^1$H NMR (CDCl$_3$) δ 7.44-7.28 (m, 5H), 6.91-6.76 (m, 4H), 5.00 (s, 2H), 3.89 (t, 2H, J=6.6 Hz), 1.74 (m, 2H), 1.49-1.24 (m, 6H), 0.89 (m, 3H).

4-(Hexyloxy)phenol A mixture of 1-(benzyloxy)-4-(hexyloxy)benzene (12.97 g) and 5% Pd/C (1.2 g) in 200 mL of 1:1 MeOH/EA was stirred under hydrogen for 16 hr. Starting material was consumed, as seen by TLC analysis. The reaction mixture was filtered through Celite, the solvents were exchanged to 12% EA/Hex, and the mixture was filtered through a pad of silica gel and concentrated to give 8.84 g of 4-(hexyloxy)phenol. Rf 0.21 (10% EA/Hex); $^1$H NMR (CDCl$_3$) δ 6.80-6.72 (m, 4H), 3.88 (t, 2H, J=6.7 Hz), 1.79-1.68 (m, 2H), 1.48-1.30 (m, 6H), 0.91-0.86 (m, 3H).

2-[4-(Hexyloxy)phenoxy]ethanol A mixture of 4-(hexyloxy)phenol (11.0 g, 56.7 mmol), ethylene carbonate (7.5 g, 85 mmol), and K$_2$CO$_3$ (11.7 g, 85 mmol) in 60 mL of DMF was heated at 60° C. for 16 hr. The mixture was partitioned between EA and H$_2$O, 0.1M HCl, H$_2$O, and brine. The organic phases were dried over MgSO$_4$ and concentrated. SPE, washing with 10% EA/Hex (which gave 5.8 g of recovered starting phenol) and eluting with 37% EA/Hex, gave the product as colorless solid. The recovered starting material was retreated with the reagents. The combined product yield was 11.4 g of colorless solid. Rf 0.20 (20% EA/Hex); $^1$H NMR (CDCl$_3$) δ 6.83-6.81 (m, 4H, AA'BB'), 4.03 and 3.93 (m, 4H, A$_2$B$_2$), 3.90 (t, 2H, J=6.6 Hz), 1.79-1.72 (m, 2H), 1.45 (m, 2H), 1.36-1.30 (m, 4H), 0.90 (m, 3H); $^{13}$C NMR (CDCl$_3$) δ 153.9, 152.9, 115.8, 115.7, 70.2, 68.9, 61.8, 31.8, 29.6, 25.9, 22.8, 14.2.

2-[4-(Hexyloxy)phenoxy]ethanamine was prepared by the method used for the preparation of [3-(hexyloxy)phenyl]methanamine.

2-[4-(Hexyloxy)phenoxy]ethanol (11.4 g), methanesulfonyl chloride (5.60 mL), TEA (11.0 mL), and DCM (150 mL) at 0° C. gave 2-[4-(hexyloxy)phenoxy]ethyl methanesulfonate (13.9 g). $^1$H NMR (CDCl$_3$) δ 6.85-6.81 (m, 4H, AA'BB'), 4.54 and 4.19 (m, 4H, A$_2$B$_2$), 3.90 (t, 2H, J=6.6 Hz), 3.08 (s, 3H), 1.76 (m, 2H), 1.44 (m, 2H), 1.36-1.30 (m, 4H), 0.90 (m, 3H); $^{13}$C NMR (CDCl$_3$) δ 154.3, 152.2, 116.0, 115.8, 68.9, 68.4, 66.9, 38.0, 31.8, 29.5, 25.9, 22.8, 14.2.

2-[4-(Hexyloxy)phenoxy]ethyl methanesulfonate (13.9 g), potassium phthalimide (8.57 g), and DMF (40 mL) at 60° C. gave N-{2-[4-(hexyloxy)phenoxy]ethyl}phthalimide (11.58 g after recrystallization from EtOH/H$_2$O). Rf 0.40 (30% EA/Hex); $^1$H NMR (CDCl$_3$) δ 7.85 and 7.71 (m, 4H, AA'BB'), 6.79 (m, 4H, AA'BB'), 4.18 and 4.08 (m, 4H, A$_2$B$_2$), 3.86 (t, 2H, J=6.6 Hz), 1.73 (m, 2H), 1.42 (m, 2H), 1.34-1.28 (m, 4H), 0.89 (m, 3H); $^{13}$C NMR (CDCl$_3$) δ 168.4, 153.9, 152.6, 134.2, 132.3, 123.5, 115.9, 115.6, 68.8, 65.7, 37.7, 31.8, 29.5 25.9, 22.8, 14.2.

2-[4-(Hexyloxy)phenoxy]ethanamine N-{2-[4-(Hexyloxy)phenoxy]ethyl}phthalimide (11.6 g), hydrazine monohydrate (2.25 mL), IPA (125 mL), and EtOH (50 mL) at reflux gave a colorless solid (7.50 g). $^1$H NMR (CDCl$_3$) δ 6.73 (s, 4H, AA'BB'), 3.80 (t, 2H, J=5.2 Hz), 3.79 (t, 2H, J=6.7 Hz), 2.93 (t, 2H), 1.66 (m, 2H), 1.41-1.21 (m, 6H), 0.85-0.80 (m, 3H).

N-{2-[4-(Hexyloxy)phenoxy]ethyl}quinolin-4-amine Crude 2-[4-(hexyloxy)phenoxy]ethanamine (7.40 g, 31.2 mmol) was taken up in 30 mL of DMA, and then 25 mL was evaporated. The residue was transferred to a heavy-walled sealed tube, and 5 mL of NMP, 4-chloroquinoline (5.09 g, 31.2 mmol), and DIEA (10.8 mL, 62 mmol) were added. The mixture was heated at 160° C. for 16 hr. After cooling, dilution of the mixture with 5% Na$_2$CO$_3$ resulted in the formation of a precipitate. The precipitate was filtered and washed with H$_2$O. The precipitate was recrystallized from MeOH/H$_2$O and then from MeOH to give 7.50 g of colorless solid. Rf 0.20 (5% MeOH/DCM); mp 131.5-132.0° C.; $^1$H NMR (CDCl$_3$) δ 8.58 (d, 1H, J=5.2 Hz), 8.00 (dd, 1H, J=0.8, 8.4 Hz), 7.79 (dd, 1H, J=0.8, 8.4 Hz), 7.66-7.62 (m, 1H), 7.44 (ddd, 1H, J=1.5, 7.0, 8.5 Hz), 6.86 (m, 4H, AA'BB'), 6.49 (d, 1H, J=5.5 Hz), 5.60 (br s, 1H, NH), 4.25 (t, 2H), 3.90 (t, 2H, J=6.6 Hz), 3.70 (m, 2H), 1.74 (m, 2H), 1.45 (m, 2H), 1.36-1.30 (m, 4H), 0.90 (m, 3H); $^{13}$C NMR (CDCl$_3$) δ 154.2, 152.6, 151.0, 149.9, 148.5, 130.0, 129.4, 125.1, 119.7, 119.1, 115.9, 115.8, 99.2, 68.9, 66.9, 42.9, 31.8, 29.5, 25.9, 22.8, 14.2.

Example 34

N-{3-[4-(Hexyloxy)phenoxy]propyl}quinolin-4-amine

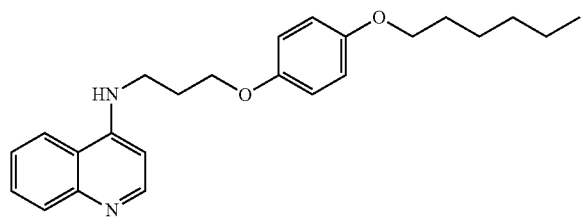 [SMILES: CCCCCCOc1ccc(OCCCNc2ccnc3ccccc23)cc1]

N-{3-[4-(Hexyloxy)phenoxy]propyl}phthalimide A mixture of 4-(hexyloxy)phenol (1.04 g, 5.36 mmol), N-(3-bromopropyl)phthalimide (1.44 g, 5.37 mmol), $K_2CO_3$ (1.12 g, 8.12 mmol), and 10 mL of DMF was reacted for 26 hr. Then, the mixture was diluted with EA and washed with $H_2O$, 0.1M HCl, and brine, dried over anhydrous $Na_2SO_4$, and concentrated. The residue was filtered through a pad of silica gel using 20% EA/Hex, and the filtrate was concentrated to give 1.96 g of a pale yellow solid. Rf 0.20 (15% EA/Hex), 0.38 20% EA/Hex+2% DIEA); $^1$H NMR ($CDCl_3$) δ 7.83 and 7.69 (m, 4H, AA'BB'), 6.79-6.71 (m, 4H, AA'BB'), 3.96 (t, 2H, J=6.2 Hz), 3.91-3.81 (m, 4H), 2.14 (m, 2H), 1.73 (m, 2H), 1.48-1.28 (m, 6H), 0.89 (m, 3H).

3-[4-(Hexyloxy)phenoxy]propan-1-amine A mixture of N-{3-[4-(hexyloxy)phenoxy]propyl}phthalimide (1.96 g) and hydrazine monohydrate (0.40 mL, 8.24 mmol) in 40 mL of EtOH was heated at reflux for 20 hr. Then, the volatile components were evaporated. SPE, washing with 5% MeOH/DCM and then eluting with 5% MeOH/DCM+2% TEA, gave 632 mg of colorless solid. Rf 0.21 (5% MeOH/DCM+25 DIEA); $^1$H NMR ($CDCl_3$) δ 6.75 (br s, 4H), 3.92 (t, 2H, J=6.0 Hz), 3.83 (t, 2H, J=6.7 Hz), 3.00 (br m, 2H, N$\underline{H}_2$), 2.82 (t, 2H, J=6.8 Hz), 1.87 (m, 2H), 1.68 (m, 2H), 1.43-1.23 (m, 6H), 0.83 (m, 3H).

N-{3-[4-(Hexyloxy)phenoxy]propyl}quinolin-4-amine A mixture of 3-[4-(hexyloxy)phenoxy]propan-1-amine (476 mg, 1.90 mmol), 4-chloroquinoline (416 mg, 2.55 mmol), and DIEA (0.50 mL, 2.86 mmol) in 1 mL of NMP was heated at 150° C. in a sealed tube for 18 hr. Then, the mixture was cooled and partitioned between EA and 5% $Na_2CO_3$ and brine. The organic phase was dried over $Na_2SO_4$ and concentrated. SPE, washing with 2.5% MeOH/DCM and then eluting with 7% MeOH/DCM, gave 633 mg of solid. Rf 0.28 (10% MeOH/DCM); mp 84.5-86.0° C. (from EA/Hex); $^1$H NMR ($CDCl_3$) δ 8.51 (d, 1H, J=5.4 Hz), 7.95 (dd, 1H, J=1.0, 8.5 Hz), 7.79 (m, 1H), 7.57 (ddd, 1H, J=1.5, 6.9, 8.4 Hz), 7.35 (ddd, 1H, J=1.2, 6.9, 8.1 Hz), 6.82 (br s, 4H, AA'BB'), 6.38 (d, 1H, J=5.4 Hz), 5.97 (m, 1H, N$\underline{H}$), 4.03 (t, 2H, J=5.4 Hz), 3.86 (t, 2H, J=6.4 Hz), 3.47 (m, 2H), 2.15 (m, 2H), 1.73 (m, 2H), 1.47-1.25 (m, 6H), 0.88 (m, 3H).

Example 35

N-{4-[4-(Hexyloxy)phenoxy]butyl}quinolin-4-amine

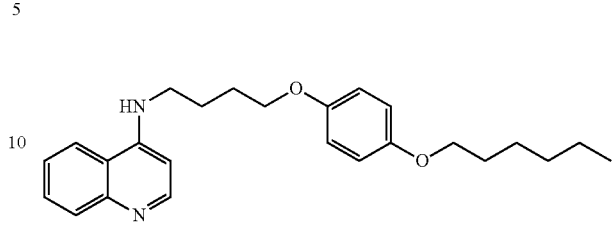

1-(4-Bromobutoxy)-4-(hexyloxy)benzene 4-(Hexyloxy)phenol (1.52 g, 7.84 mmol), 1,4-dibromobutane (7.4 mL, 62 mmol), and $K_2CO_3$ (1.22 g, 8.84 mmol) in 8 mL of DMF was mixed for 16 hr. The mixture was partitioned between EA and 0.1M HCl and brine, and the organic phases were dried over $MgSO_4$, filtered, and concentrated. SPE, washing with 1% EA/Hex and then eluting with 5% EA/Hex gave 2.36 g of colorless solid. Rf 0.59 (15% EA/Hex); $^1$H NMR ($CDCl_3$) δ 6.80 (br s, 4H, AA'BB'), 3.93 (t, 2H, J=6.0 Hz), 3.88 (t, 2H, J=6.7 Hz), 3.48 (m, 2H), 2.05 (m, 2H), 1.90 (m, 2H), 1.74 (m, 2H), 1.48-1.28 (m, 6H), 0.89 (m, 3H).

N-{4-[4-(Hexyloxy)phenoxy]butyl}phthalimide 1-(4-Bromobutoxy)-4-(hexyloxy)benzene (2.36 g, 7.17 mmol) and potassium phthalimide (2.0 g, 10.8 mmol) in 12 mL of DMF was mixed for 60 hr. The mixture was partitioned between EA and 0.1M HCl and brine, and the organic phases were dried over $MgSO_4$, filtered, and concentrated. SPE, washing with 5% EA/Hex and then eluting with 15% EA/Hex gave 2.64 g of colorless solid. Rf 0.31 (15% EA/Hex); $^1$H NMR ($CDCl_3$) δ 7.83 and 7.70 (m, 4H, AA'BB'), 6.78 (br s, 4H, AA'BB'), 3.92 (t, 2H, J=6.1 Hz), 3.87 (t, 2H, J=6.7 Hz), 3.75 (t, 2H, J=7.0 Hz), 1.92-1.68 (m, 6H), 1.48-1.22 (m, 6H), 0.89 (m, 3H).

4-[4-(Hexyloxy)phenoxy]butan-1-amine A mixture of N-{4-[4-(hexyloxy)phenoxy]butyl}phthalimide (2.64 g, 6.68 mmol) and hydrazine monohydrate (0.65 mL, 13.4 mmol) in 60 mL of EtOH was heated at reflux for 20 hr. The mixture was cooled, concentrated, and partitioned between EA and 5% $Na_2CO_3$ and brine. The organic phases were dried over $Na_2SO_4$, filtered, and concentrated. SPE, washing with 4% MeOH/DM and then eluting with 6% MeOH/DCM+2% DIEA gave product-containing fractions. These fractions were concentrated, taken up in DCM and washed with 5% $Na_2CO_3$, dried over $Na_2SO_4$, filtered, and concentrated to give 1.69 g of colorless solid. Rf 0.20 (5% MeOH/DCM+2% DIEA, ninhydrin (+)); $^1$H NMR ($CDCl_3$) δ 6.80 (br s, 4H, AA'BB'), 3.93-3.85 (m, 4H), 2.75 (t, 2H, J=7 Hz), 1.87-1.26 (m, 14H), 0.89 (m, 3H).

N-{4-[4-(Hexyloxy)phenoxy]butyl}quinolin-4-amine A mixture of 4-[4-(hexyloxy)phenoxy]butan-1-amine (499 mg, 1.88 mmol), 4-chloroquinoline (3999 mg, 2.45 mmol), and DIEA (0.50 mL, 2.86 mmol) in 1 mL of NMP was heated at 150° C. in a sealed tube for 18 hr. Then, the mixture was cooled and partitioned between EA and 5% $Na_2CO_3$ and brine. The organic phase was dried over $Na_2SO_4$ and concentrated. SPE, washing with 2.5% MeOH/DCM and then eluting with 7% MeOH/DCM, gave 633 mg of solid. Rf 0.25 (10% MeOH/DCM); mp 113.0-114.0° C. (from EA/Hex); $^1$H NMR ($CDCl_3$) δ 8.53 (d, 1H, J=5.2 Hz), 7.95 (m, 1H), 7.70 (d, 1H, J=7.6 Hz), 7.58 (ddd, 1H, J=1.5, 6.9, 8.4 Hz), 7.34 (ddd, 1H, J=1.2, 6.9, 8.2 Hz), 6.82 (br s, 4H, AA'BB'), 6.40 (d, 1H, J=5.4 Hz), 5.38 (br t, 1H, N$\underline{H}$), 3.96 (t, 2H, J=5.6 Hz), 3.88 (t, 2H, J=6.5 Hz), 3.36 (br m, 2H), 1.92-1.90 (m, 4H), 1.74 (m, 2H), 1.48-1.28 (m, 6H), 0.89 (m, 3H).

Example 36

N-[8-(m-Tolyloxy)octyl]quinolin-4-amine

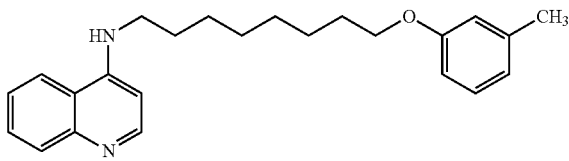 [SMILES: Cc1cccc(OCCCCCCCCNc2ccnc3ccccc23)c1]

1-(8-Bromooctyloxy)-3-methylbenzene A mixture of m-cresol (1.00 mL, 9.54 mmol), 1,8-dibromooctane (15.0 mL, 81 mmol), and $K_2CO_3$ (2.6 g, 18.8 mmol) in 20 mL of NMP and 10 mL of DME was heated at reflux for 66 hr. Then, the mixture was cooled, diluted with DCM (20 mL), and extracted with 0.05N NaOH (150, 100 mL) and 1M HCl (100 mL). The aqueous phases were extracted with DCM (20 mL), and the combined organic phases were dried over $MgSO_4$ and concentrated. SPE, washing with Hex to recover dibromide and then eluting with 3% EA/Hex, gave 1.7 g of 1-(8-bromooctyloxy)-3-methylbenzene. Rf 0.39 (5% EA/Hex); $^1$H NMR (CDCl$_3$) δ 7.15 (t, 1H), 6.8-6.65 (m, 3H), 3.95 (t, 2H), 3.4 (t, 2H), 3.3 (s, 3H), 1.9-1.7 (m, 4H), 1.5-1.2 (m, 8H).

1-(8-Azidoocyloxy)-3-methylbenzene (1.7 g) was prepared from 1-(8-bromooctyloxy)-3-methylbenzene (1.7 g, 5.69 mmol) and sodium azide (740 mg, 11.4 mmol) in 50 mL of DMF following the method for the preparation of 10-butoxydecan-1-amine.

8-(m-Tolyloxy)octan-1-amine (0.6 g) was prepared from 1-(8-azidoocyloxy)-3-methylbenzene (1.7 g) by the method used for the preparation of 10-butoxydecan-1-amine. $^1$H NMR (CDCl$_3$) δ 7.1 (m, 1H), 6.6 (m, 3H), 3.9 (m, 2H), 2.7 (t, 1H), 2.3 (m, 4H), 1.8-1.6 (m, 4H), 1.5-1.3 (m, 8H).

N-[8-(m-Tolyloxy)octyl]quinolin-4-amine (166 mg) was prepared from 8-(m-tolyloxy)octan-1-amine (0.6 g) and 4-chloroquinoline (840 mg), TEA (2 mL), and NMP (0.2 mL) following the method for N-[8-(3-ethoxypropoxy)octyl]quinolin-4-amine. $^1$H NMR (CDCl$_3$) δ 8.6 (m, 2H), 8.05 (m, 2H), 7.6 (t, 1H), 7.4 (t, 1H), 7.1 (t, 1H), 6.8-6.6 (m, 3H), 6.4 (d, 1H), 3.9 (t, 2H), 3.5 (m, 2H), 2.3 (s, 3H), 1.9-1.7 (m, 4H), 1.5-1.3 (m, 8H).

Example 37

N-[8-(p-Tolyloxy)octyl]quinolin-4-amine

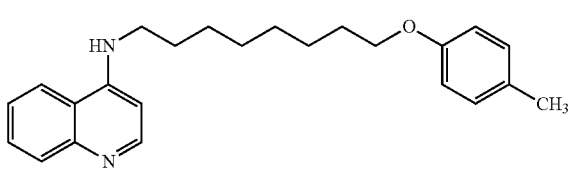 [SMILES: Cc1ccc(OCCCCCCCCNc2ccnc3ccccc23)cc1]

1-(8-Bromooctyloxy)-4-methylbenzene (1.9 g) was prepared by the same method used for 1-(8-bromooctyloxy)-3-methylbenzene using p-cresol (1.00 mL, 9.54 mmol), 1,8-dibromooctane (15.0 mL, 51 mmol), and $K_2CO_3$ (2.6 g, 18.8 mmol) in 20 mL of NMP and 10 mL of DME heated for 66 hr. $^1$H NMR (CDCl$_3$) δ 7.0 (d, 2H), 6.8 (d, 2H), 3.9 (t, 2H), 3.4 (t, 2H), 2.3 (s, 3H), 1.9-1.7 (m, 4H), 1.5-1.2 (m, 8H).

1-(8-Azidooctyloxy)-4-methylbenzene (1.9 g) was prepared from 1-(8-bromooctyloxy)-4-methylbenzene (1.9 g, 6.36 mmol) and sodium azide (830 mg, 12.7 mmol) in 50 mL of DMF following the method for the preparation of 10-butoxydecan-1-amine.

8-(p-Tolyloxy)octan-1-amine (0.6 g) was prepared 1-(8-azidooctyloxy)-4-methylbenzene (1.9 g) by the method used for the preparation of 10-butoxydecan-1-amine. $^1$H NMR (CDCl$_3$) δ 7.05 (d, 2H), 6.75 (d, 2H), 3.9 (m, 2H), 2.7 (m, 1H), 2.35 (t, 1H), 2.3 (s, 3H), 1.8-1.2 (m, 12H).

N-[8-(p-Tolyloxy)octyl]quinolin-4-amine (161 mg) was prepared from 8-(p-tolyloxy)octan-1-amine (0.6 g), 4-chloroquinoline (840 mg), TEA (2 mL), and NMP (0.2 mL) following the method for N-[8-(3-ethoxypropoxy)octyl]quinolin-4-amine. $^1$H NMR (CDCl$_3$) δ 8.5 (d, 1H), 8.0 (d, 1H), 7.85 (d, 1H), 7.6 (t, 1H), 7.4 (t, 1H), 7.1 (m, 3H), 6.8 (m, 3H), 6.4 (d, 1H), 3.9 (t, 2H), 3.4 (m, 2H), 2.3 (s, 3H), 1.9-1.7 (m, 4H), 1.5-1.3 (m, 8H).

Example 38

N-[8-(o-Tolyloxy)octyl]quinolin-4-amine

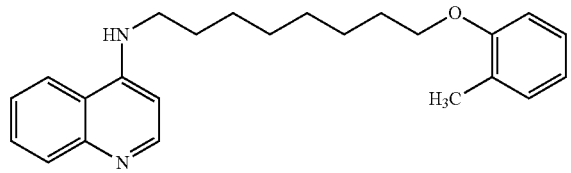 [SMILES: Cc1ccccc1OCCCCCCCCNc1ccnc2ccccc12]

1-(8-Bromooctyloxy)-2-methylbenzene (1.3 g) was prepared by the same method used for 1-(8-bromooctyloxy)-3-methylbenzene using o-cresol (696 mg, 6.44 mmol), 1,8-dibromooctane (14 g, 81 mmol), and $K_2CO_3$ (1.00 g, 7.25 mmol) in 12 mL of NMP and 12 mL of DME heated for 16 hr.

1-(8-Iodooctyloxy)-2-methylbenzene (1.3 g) was prepared from 1-(8-bromooctyloxy)-2-methylbenzene (1.3 g, 4.35 mmol) and sodium iodide (652 mg, 4.35 mmol) in 50 mL of acetone following the method used in the preparation of 10-(hexyloxy)decan-1-amine.

N-[8-(o-Tolyloxy)octyl]phthalimide (1.3 g) was prepared from 1-(8-iodooctyloxy)-2-methylbenzene (1.3 g) and potassium phthalimide (1.0 g, 5.4 mmol) in 50 mL of DMF following the method for N-[8-(hexyloxy)octyl]phthalimide. $^1$H NMR (CDCl$_3$) δ 7.85 (m, 2H), 7.7 (m, 2H), 7.15 (m, 2H), 6.8 (m, 2H), 3.95 (m, 2H), 3.7 (m, 2H), 2.2 (m, 3H), 1.9-1.6 (m, 4H), 1.6-1.25 (m, 8H).

8-(o-Tolyloxy)octan-1-amine (390 mg) was prepared from N-[8-(o-tolyloxy)octyl]phthalimide (1.0 g, 2.74 mmol) using hydrazine monohydrate (0.2 mL) in EtOH (50 mL) following the method for [3-(hexyloxy)phenyl]methanamine. $^1$H NMR (DMSO-d$_6$) δ 7.1 (m, 2H), 6.9-6.75 (m, 2H), 3.9 (t, 2H), 2.5 (m, 2H), 2.15 (s, 3H), 1.75 (m, 2H), 1.5-1.2 (m, 10H).

N-[8-(o-Tolyloxy)octyl]quinolin-4-amine (300 mg) was prepared from 8-(o-tolyloxy)octan-1-amine (390 mg), 4-chloroquinoline (544 mg), TEA (2 mL), and NMP (0.2 mL) following the method for N-[8-(3-ethoxypropoxy)octyl]quinolin-4-amine. $^1$H NMR (CDCl$_3$) δ 8.55 (d, 1H), 8.0

(d, 1H), 7.75 (d, 1H), 7.65 (m, 1H), 7.45 (m, 1H), 7.15 (m, 2H), 6.8 (m, 2H), 6.4 (d, 1H), 3.95 (t, 2H), 3.35 (m, 2H), 2.3 (s, 3H), 1.8 (m, 4H), 1.6-1.3 (m, 8H).

Example 39

N-[8-(4-tert-Butylphenoxy)octyl]quinolin-4-amine

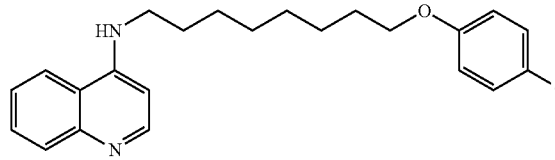

1-(8-Bromooctyloxy)-4-tert-butylbenzene (900 mg) was prepared by the same method used for 1-(8-bromooctyloxy)-3-methylbenzene using 4-tert-butylphenol (647 mg, 4.31 mmol), 1,8-dibromooctane (11.7 g, 43 mmol), and K$_2$CO$_3$ (714 mg, 5.17 mmol) in 12 mL of NMP and 6 mL of DME heated for 24 hr. $^1$H NMR (CDCl$_3$) δ 7.28 and 6.82 (m, 4H, AA'BB'), 3.93 (m, 2H), 3.40 (t, 2H, J=6.8 Hz), 1.90-1.71 (m, 4H), 1.46-1.22 (m, 8H), 1.29 (s, 9H).

1-tert-Butyl-4-(8-iodooctyloxy)benzene (900 mg) was prepared from 1-(8-bromooctyloxy)-4-tert-butylbenzene (900 mg) and sodium iodide (400 mg) in 50 mL of acetone following the method for the preparation of 10-(hexyloxy)decan-1-amine.

N-[8-(4-tert-Butylphenoxy)octyl]phthalimide (1.3 g) was prepared from 1-tert-butyl-4-(8-iodooctyloxy)benzene (900 mg) and potassium phthalimide (860 mg) in 50 mL of DMF following the method for the preparation of N-[8-(hexyloxy)octyl]phthalimide. $^1$H NMR (CDCl$_3$) δ 7.85 and 7.70 (m, 4H, AA'BB'), 7.3 and 6.8 (m, 4H, AA'BB'), 3.9 (t, 2H), 3.65 (m, 2H), 1.8-1.6 (m, 4H), 1.6-1.3 (m, 17H).

8-(4-tert-Butylphenoxy)octan-1-amine (590 mg) was prepared from N-[8-(4-tert-butylphenoxy)octyl]phthalimide (900 mg) and hydrazine monohydrate (0.17 mL) in 50 mL of EtOH following the method for the preparation of [3-(hexyloxy)phenyl]methanamine. $^1$H NMR (DMSO-d$_6$) δ 7.25 and 6.80 (m, 4H, AA'BB'), 3.9 (t, 2H), 2.5 (m, 2H), 1.68 (m, 2H), 1.5-1.2 (m, 19H).

N-[8-(4-tert-Butylphenoxy)octyl]quinolin-4-amine A mixture of 8-(4-tert-butylphenoxy)octan-1-amine (510 mg, 1.84 mmol), 4-chloroquinoline (604 mg, 3.70 mmol), TEA (4.0 mL, 28 mmol), and 0.4 mL of NMP was heated in a heavy walled glass tube at 130° C. for 4 days. The mixture was cooled and partitioned between EA and 5% Na$_2$CO$_3$ and brine, dried over Na$_2$SO$_4$, filtered, and concentrated. Purification by FC (60% EA/Hex+2% TEA) gave 320 mg of solid. Mp 108-110° C. (from MeOH); $^1$H NMR (CDCl$_3$) δ 8.4 (d, 1H), 8.0 (d, 1H), 7.8 (d, 1H), 7.6 (m, 1H), 7.4 (m, 1H), 7.3 and 6.8 (m, 4H, AA'BB'), 6.4 (d, 1H), 5.2 (br s, 1H, NH), 3.9 (m, 2H), 3.3 (m, 2H), 1.8-1.6 (m, 4H), 1.6-1.3 (m, 8H), 1.3 (s, 9H).

Example 40

N-[8-(4-Fluorophenoxy)octyl]quinolin-4-amine

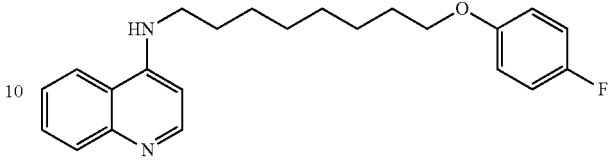

1-(8-Bromooctyloxy)-4-fluorobenzene (2.75 g) was prepared by the same method used for 1-(8-bromooctyloxy)-3-methylbenzene using 4-fluorophenol (1.33 g, 12.1 mmol), 1,8-dibromooctane (20 mL, 108 mmol), and K$_2$CO$_3$ (1.77 g, 14.3 mmol) in 20 mL of NMP and 10 mL of DME heated for 24 hr. $^1$H NMR (CDCl$_3$) δ 7.0-6.9 (m, 2H), 6.8 (m, 2H), 3.89 (t, 2H, J=6.4 Hz), 3.40 (t, 2H, J=6.8 Hz), 1.9-1.7 (m, 4H), 1.6-1.2 (m, 8H).

1-Fluoro-4-(8-iodooctyloxy)benzene was prepared from 1(8-bromooctyloxy)-4-fluorobenzene (2.75 g, 9.08 mmol) and sodium iodide (1.63 g, 10.9 mmol) in 70 mL of acetone following the method used in the preparation of 10-(hexyloxy)decan-1-amine.

N-[8-(4-Fluorophenoxy)octyl]phthalimide (2.19 g) was prepared from 1-fluoro-4-(8-iodooctyloxy)benzene and potassium phthalimide (2.52 g, 13.6 mmol) in 50 mL of DMF at 60-80° C. for 12 hr following the method for N-[8-(hexyloxy)octyl]phthalimide. $^1$H NMR (CDCl$_3$) δ 7.85 (m, 2H), 7.7 (m, 2H), 6.9 (m, 2H), 6.8 (m, 2H), 3.9 (t, 2H), 3.7 (t, 2H), 1.8-1.6 (m, 4H), 1.5-1.3 (m, 8H).

8-(4-Fluorophenoxy)octan-1-amine (657 mg, 2.75 mmol) was prepared from N-[8-(4-fluorophenoxy)octyl]phthalimide (2.19 g, 5.94 mmol) using hydrazine monohydrate (0.43 mL) in EtOH (50 mL) following the method for [3-(hexyloxy)phenyl]methanamine. $^1$H NMR (CD$_3$OD) δ 7.0-6.8 (m, 4H), 3.9 (t, 2H), 2.7 (t, 2H), 1.75 (m, 2H), 1.6-1.3 (m, 10H).

N-[8-(4-Fluorophenoxy)octyl]quinolin-4-amine was prepared from 8-(4-fluorophenoxy)octan-1-amine (657 mg, 2.75 mmol), 4-chloroquinoline (676 mg), TEA (2 mL), and NMP (0.2 mL) at 130° C. in a sealed tube for 5 days following the method for N-[8-(3-ethoxypropoxy)octyl]quinolin-4-amine. $^1$H NMR (CDCl$_3$) δ 8.5 (d, 1H), 8.0 (d, 1H), 7.9 (d, 1H), 7.65 (m, 1H), 7.4 (m, 1H), 7.1-6.8 (m, 4H), 6.4 (d, 1H), 5.6 (br s, 1H, NH), 4.0 (t, 2H), 3.35 (m, 2H), 1.8 (m, 2H), 1.7-1.2 (m, 10H).

Example 41

N-[8-(3-Fluorophenoxy)octyl]quinolin-4-amine

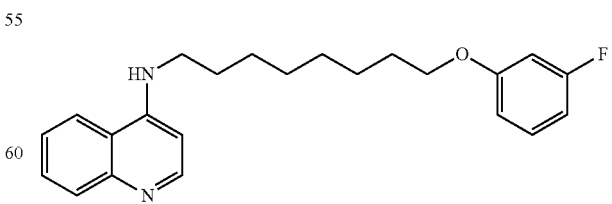

1-(8-Bromooctyloxy)-3-fluorobenzene (2.06 g) was prepared by the same method used for 1-(8-bromooctyloxy)-3-methylbenzene using 3-fluorophenol (1.60 g, 14.3 mmol), 1,8-dibromooctane (25 mL, 135 mmol), and K$_2$CO$_3$ (2.56 g, 18.5 mmol) in 25 mL of NMP and 12 mL of DME heated for 24 hr. Rf 0.42 (5% EA/Hex); ¹H NMR (CDCl₃) δ 7.2 (m, 1H), 6.7-6.6 (m, 3H), 3.9 (t, 2H), 3.4 (t, 2H), 1.9-1.7 (m, 4H), 1.6-1.2 (m, 8H).

1-Fluoro-3-(8-iodooctyloxy)benzene was prepared from 1-(8-bromooctyloxy)-3-fluorobenzene (2.06 g, 6.78 mmol) and sodium iodide (1.22 g, 8.13 mmol) in 60 mL of acetone following the method used in the preparation of 10-(hexyloxy)decan-1-amine.

N-[8-(3-Fluorophenoxy)octyl]phthalimide (1.85 g) was prepared from 1-fluoro-3-(8-iodooctyloxy)benzene and potassium phthalimide (1.9 g, 10.3 mmol) in 50 mL of DMF at 60-80° C. for 12 hr following the method for N-[8-(hexyloxy)octyl]phthalimide. ¹H NMR (CDCl₃) δ 7.85 (m, 2H), 7.7 (m, 2H), 7.2 (m, 1H), 6.7-6.5 (m, 3H), 3.9 (t, 2H), 3.7 (t, 2H), 1.8-1.6 (m, 4H), 1.5-1.3 (m, 8H).

8-(3-Fluorophenoxy)octan-1-amine (874 mg, 3.66 mmol) was prepared from N-[8-(3-fluorophenoxy)octyl]phthalimide (1.85 g, 5.01 mmol) using hydrazine monohydrate (0.36 mL) in EtOH (50 mL) following the method for [3-(hexyloxy)phenyl]methanamine. ¹H NMR (CD₃OD) δ 7.25 (m, 1H), 6.8-6.6 (m, 3H), 3.9 (t, 2H), 2.7 (t, 2H), 1.8 (m, 2H), 1.6-1.3 (m, 10H).

N-[8-(3-Fluorophenoxy)octyl]quinolin-4-amine was prepared from 8-(3-fluorophenoxy)octan-1-amine (874 mg, 3.66 mmol), 4-chloroquinoline (900 mg), TEA (2 mL), and NMP (1 mL) at 130° C. in a sealed tube for 5 days following the method for N-[8-(3-ethoxypropoxy)octyl]quinolin-4-amine.

¹H NMR (CDCl₃) δ 8.5 (d, 1H), 8.0 (d, 1H), 7.85 (d, 1H), 7.65 (m, 1H), 7.4 (m, 1H), 7.15 (m, 1H), 6.7-6.5 (m, 3H), 6.5 (d, 1H), 5.6 (br s, 1H, N$\underline{H}$), 3.9 (t, 2H), 3.35 (m, 2H), 1.8 (m, 4H), 1.6-1.3 (m, 8H).

Example 42

N-[8-(2-Fluorophenoxy)octyl]quinolin-4-amine

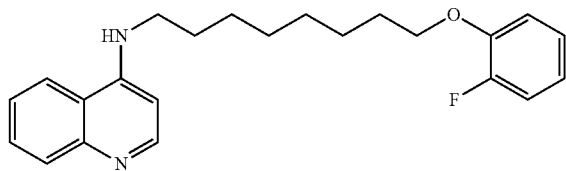 [SMILES: Fc1ccccc1OCCCCCCCCNc1ccnc2ccccc12]

1-(8-Bromooctyloxy)-2-fluorobenzene (2.97 g) was prepared by the same method used for 1-(8-bromooctyloxy)-3-methylbenzene using 2-fluorophenol (1.69 g, 15.1 mmol), 1,8-dibromooctane (38.3 g, 141 mmol), and K₂CO₃ (2.76 g, 20 mmol) in 25 mL of NMP and 20 mL of DME heated for 24 hr. Rf 0.33 (5% EA/Hex); ¹H NMR (CDCl₃) δ 7.10-6.83 (m, 4H), 4.0 (m, 2H), 3.38 (t, 2H, J=6.9 Hz), 1.91-1.76 (m, 4H), 1.47-1.32 (m, 8H).

1-Fluoro-2-(8-iodooctyloxy)benzene (3.43 g) was prepared from 1-(8-bromooctyloxy)-2-fluorobenzene (2.97 g, 9.80 mmol) and sodium iodide (1.76 g, 11.7 mmol) in 70 mL of acetone following the method used in the preparation of 10-(hexyloxy)decan-1-amine.

N-[8-(2-Fluorophenoxy)octyl]phthalimide (2.84 g) was prepared from 1-fluoro-2-(8-iodooctyloxy)benzene (3.43 g) and potassium phthalimide (2.72 g, 14.7 mmol) in DMF at 60-80° C. for 12 hr following the method for N-[8-(hexyloxy)octyl]phthalimide. ¹H NMR (CDCl₃) δ 7.85 and 7.70 (m, 4H, AA'BB'), 7.10-6.80 (m, 4H), 4.00 (t, 2H), 3.70 (t, 2H), 1.90-1.60 (m, 4H), 1.55-1.25 (m, 8H).

8-(2-Fluorophenoxy)octan-1-amine (1.27 g, 5.32 mmol) was prepared from N-[8-(2-fluorophenoxy)octyl]phthalimide (2.84 g, 7.70 mmol) using hydrazine monohydrate (0.50 mL) in EtOH (50 mL) following the method for [3-(hexyloxy)phenyl]methanamine.

N-[8-(2-Fluorophenoxy)octyl]quinolin-4-amine (100 mg) was prepared from 8-(2-fluorophenoxy)octan-1-amine (1.27 g, 5.32 mmol), 4-chloroquinoline (1.3 g, 7.98 mmol), TEA (2 mL), and NMP (1 mL) at 130° C. in a sealed tube for 5 days following the method for N-[8-(3-ethoxypropoxy)octyl]quinolin-4-amine. ¹H NMR (CDCl₃) δ 8.4 (d, 1H), 8.0 (d, 1H), 7.9 (d, 1H), 7.6 (m, 1H), 7.4 (m, 1H), 7.0-6.7 (m, 4H), 6.4 (d, 1H), 5.9 (br s, 1H, N$\underline{H}$), 3.9 (t, 2H), 3.3 (m, 2H), 1.9-1.2 (m, 12H).

Example 43

N-(Biphenyl-4-yl)quinolin-4-amine

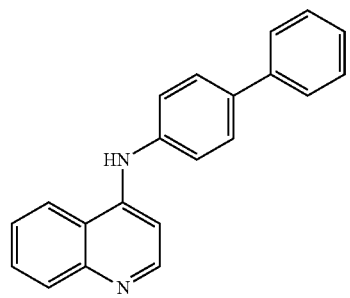 [SMILES: c1ccc(-c2ccc(Nc3ccnc4ccccc34)cc2)cc1]

A mixture of 4-biphenylamine (200 mg, 1.18 mmol), 4-chloroquinoline (228 mg,), and DIEA (0.25 mL, 1.43 mmol) in 1 mL of NMP was heated at 150° C. in a sealed tube for 24 hr. The cooled mixture was diluted with EA, washed with 5% Na₂CO₃ (2×) and brine, dried over anhydrous Na₂SO₄, and concentrated. SPE, eluting with a step gradient of 1%, 3%, and 5% MeOH/DCM, gave fractions that were concentrated to give a brown solid. The solid was washed with MeOH and dried in vacuo. Rf 0.21 (5% MeOH/DCM); mp 222-226° C.; ¹H NMR (20% CD₃OD/CDCl₃) δ 8.38 (d, 1H, J=5.7 Hz), 8.06 (m, 1H), 7.91 (m, 1H), 7.67-7.26 (m, 11H), 6.98 (d, 1H, J=5.5 Hz).

Example 44

N-(4-Hexylphenyl)quinolin-4-amine

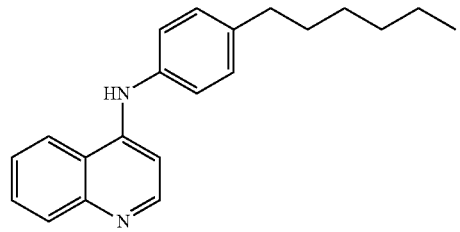 [SMILES: CCCCCCc1ccc(Nc2ccnc3ccccc23)cc1]

A mixture of 4-hexylaniline (197 mg, 1.11 mmol), 4-chloroquinoline (210 mg) and DIEA (0.24 mL) in 1 mL of NMP was heated at 150° C. in a sealed tube for 24 hr. The mixture was cooled and partitioned between EA and 5% Na₂CO₃. The organic phases were washed with brine, dried over Na₂SO₄, and concentrated. Purification by SPE (step gradient 1, 2, 3, 5, 6% MeOH/DCM) gave fractions yielding a yellow solid. Recrystallization from MeOH gave 229 mg of a colorless solid. Rf 0.14 (5% MeOH/DCM); mp 132.5-133.0° C.; ¹H NMR (CDCl₃) δ 8.52 (d, 1H, J=5.7 Hz), 8.03 (dd, 1H, J=0.7, 8.4 Hz), 7.85 (d, 1H, J=7.6 Hz), 7.64 (ddd, 1H, J=1.5, 6.9, 8.4 Hz), 7.44 (ddd, 1H, J=1.2, 6.9, 8.1 Hz), 6.88-6.81 (m, 4H), 6.50 (d, 1H, J=5.7 Hz), 5.92 (br s, 1H, NH), 4.26 (t, 2H, J=5 Hz), 3.89 (t, 2H, J=6 Hz), 3.73 (q, 2H, J=5.2 Hz), 1.74 (m, 2H), 1.48-1.28 (m, 6H), 0.89 (m, 3H).

Example 45

Hexyl 4-(quinolin-4-ylamino)benzoate

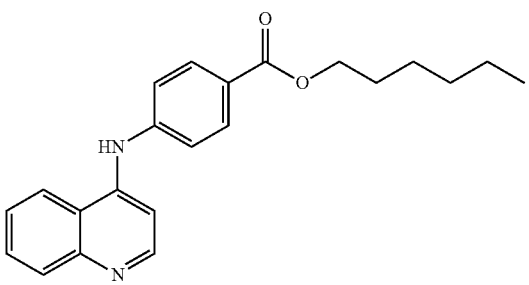 [SMILES: CCCCCCOC(=O)c1ccc(Nc2ccnc3ccccc23)cc1]

Hexyl 4-aminobenzoate (282 mg), prepared from 1-hexanol and 4-nitrobenzoyl chloride in two unremarkable steps, was reacted with 4-chloroquinoline (322 mg) and DIEA (0.50 mL) in 2 mL of NMP heated at 160° C. in a sealed tube for 16 hr. The mixture was cooled and partitioned between EA and 5% Na₂CO₃. The organic phases were washed with brine, dried over Na₂SO₄, and concentrated. Purification by SPE, washing with 20% EA/Hex and then eluting with 55% EA/Hex, gave a yellow solid. Recrystallization from EA/Hex gave a colorless solid. Rf 0.14 (50% EA/Hex); ¹H NMR (CDCl₃) δ 8.61 (d, 1H, J=5.2 Hz), 8.09-8.03 (m, 4H), 7.70 (ddd, 1H, J=1.2, 6.9, 8.4 Hz), 7.52 (ddd, 1H, J=1.2, 6.9, 8.4 Hz), 7.34-7.31 (m, 2H), 7.19 (d, 1H, J=5.2 Hz), 4.30 (t, 2H, J=6.6 Hz), 1.76 (m, 2H), 1.47-1.24 (m, 6H), 0.89 (m, 3H).

Example 46

N-(4-Phenoxyphenyl)quinolin-4-amine

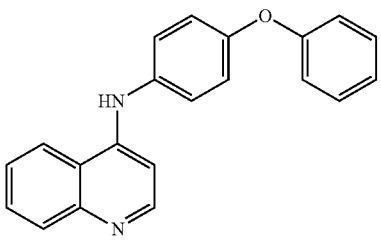 [SMILES: c1ccc(Oc2ccc(Nc3ccnc4ccccc34)cc2)cc1]

A mixture of 4-phenoxyaniline (182 mg, 0.98 mmol), 4-chloroquinoline (175 mg, 1.07 mmol), and DIEA (0.50 mL, 2.87 mmol) in 1 mL of NMP was heated at 140-150° C. in a sealed tube for 24 hr. Then, the mixture was cooled and partitioned between DCM and 5% Na₂CO₃. The organic phase was dried over Na₂SO₄ and concentrated. SPE, washing with 50% EA/Hex and eluting with 5% MeOH/DCM, gave a solid. Recrystallization from EA/Hex gave 111 mg of tan solid. A second crop of 111 mg light tan solid was obtained from MeOH. The two crops had comparable NMR spectra. Rf 0.19 (5% MeOH/DCM); mp 170-172° C. (from MeOH); ¹H NMR (CDCl₃) δ 8.51 (d, 1H, J=5.5 Hz), 8.05 (d, 1H, J=8.7 Hz), 7.99 (d, 1H, J=8.4 Hz), 7.68 (ddd, 1H, J=1.3, 6.9, 8.2 Hz), 7.50 (ddd, 1H, J=1.3, 6.9, 8.2 Hz), 7.40-7.25 (m, 5H), 7.22-6.99 (m, 5H), 6.83 (d, 1H, J=5.4 Hz).

Example 47

N-(3-Phenoxyphenyl)quinolin-4-amine

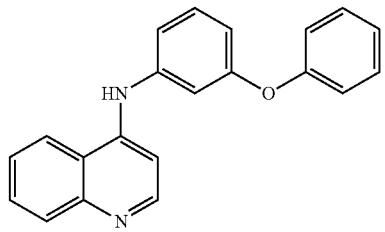 [SMILES: c1ccc(Oc2cccc(Nc3ccnc4ccccc34)c2)cc1]

A mixture of 3-phenoxyaniline (307 mg, 1.66 mmol), 4-chloroquinoline (296 mg, 1.82 mmol), and DIEA (0.32 mL, 1.84 mmol) in 1 mL of NMP was heated at 140-150° C. in a sealed tube for 24 hr. Then, the mixture was cooled and partitioned between DCM and 5% Na₂CO₃. The organic phase was dried over Na₂SO₄ and concentrated. SPE, washing with 20% EA/Hex, 20% EA/Hex+2% TEA, and 35% EA/Hex+2% TEA, then eluting with 50% EA/Hex+2% TEA, gave 208 mg of yellow solid. Rf 0.26 (7.5% MeOH/DCM); mp 189-192° C. (from MeOH); ¹H NMR (CDCl₃) δ 8.40 (d, 1H, J=5.2 Hz), 7.98-7.91 (m, 2H), 7.62 (m, 1H), 7.45 (m, 1H), 7.34-7.26 (m, 3H), 7.10-6.98 (m, 6H), 6.90 (t, 1H, J=2.2 Hz), 6.75 (dd, 1H, J=2.5, 8.1 Hz).

Example 48

N-(2-Phenoxyphenyl)quinolin-4-amine

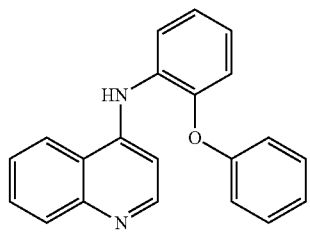 [SMILES: c1ccc(Oc2ccccc2Nc2ccnc3ccccc23)cc1]

A mixture of 2-phenoxyaniline (286 mg, 1.54 mmol), 4-chloroquinoline (278 mg, 1.70 mmol), and 4-methylmorpholine (0.19 mL, 1.73 mmol) in 0.5 mL of NMP was heated in a heavy walled sealed tube at 130° C. for 20 hr. The mixture was cooled and partitioned between EA and 5% Na₂CO₃ and brine. The organic phases were dried over Na₂SO₄ and concentrated. FC (7.5% MeOH/DCM) gave a dark oil that contained residual 4-methylmorpholine. The oil was filtered through a pad of silica gel using 30% EA/Hex+ 2% TEA to give 402 mg of solid. Rf 0.10 (5% MeOH/DCM); $^1$H NMR (CDCl$_3$) δ 8.61 (d, 1H, J=5.2 Hz), 8.03 (dd, 1H, J=0.7, 8.4 Hz), 7.85-7.81 (m, 1H), 7.64 (ddd, 1H, J=1.5, 6.9, 8.4 Hz), 7.59 (m, 1H), 7.43 (m, 1H), 7.34-7.24 (m, 2H), 7.19-6.98 (m, 8H).

Example 49

N-[4-(Quinolin-4-ylamino)phenyl]hexanamide

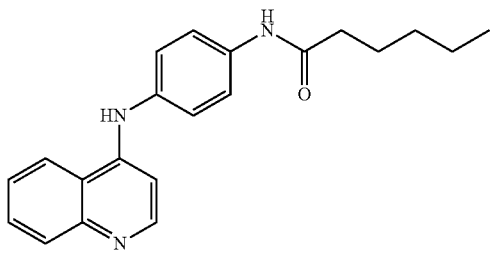 [SMILES: CCCCCC(=O)Nc1ccc(Nc2ccnc3ccccc23)cc1]

N-(4-Nitrophenyl)hexanamide Hexanoyl chloride ((0.81 mL, 5.8 mmol) was added slowly to a mixture of 4-nitroaniline ((800 mg, 5.79 mmol) in 5 mL of pyridine and 15 mL of DMF cooled by an ice bath. After 30 min, the mixture was warmed to room temperature. After an additional 2 hr, the volatile components were evaporated. The residue was taken up in EA (100 mL) and washed with saturated NaHCO$_3$ (2×75 mL), H$_2$O (2×50 mL), 0.1N HCl (2×25 mL), and H$_2$O. The organic phase was concentrated in vacuo to give 1.50 g product. $^1$H NMR (CDCl$_3$) δ 8.2 (m, 2H), 7.7 (m, 2H), 7.4 (br s, 1H, NH), 2.4 (m, 2H), 1.8 (m, 2H), 1.4-1.3 (m, 4H), 0.9 (m, 3H).

N-(4-Aminophenyl)hexanamide A mixture of N-(4-nitrophenyl)hexanamide (1.50 g), 10% Pd—C (200 mg), and 75 mL of MeOH was stirred under a blanket of hydrogen until the starting material was consumed, as observed by analytical TLC. Then, the atmosphere was purged with argon, and the mixture was filtered through a pad of Celite. Evaporation of the solvent gave 1.22 g of product. $^1$H NMR (CDCl$_3$) δ 7.2 (m, 3H), 7.0 (br s, 1H, NH), 6.6 (m, 2H), 3.6 (br s, 2H, NH$_2$), 2.3 (m, 2H), 1.7 (m, 2H), 1.4-1.2 (m, 4H), 0.9 (m, 3H).

N-[4-(Quinolin-4-ylamino)phenyl]hexanamide A mixture of 4-chloroquinoline (358 mg, 2.20 mmol), N-(4-aminophenyl)hexanamide (300 mg, 1.46 mmol), and TEA (1 mL) was heated at 130° C. in a sealed tube for 5 days. Then the volatile components were evaporated. The residue was purified by preparative TLC (10% MeOH/DCM) to give 329 mg of product. Rf 0.3 (10% MeOH/DCM); $^1$H NMR (CDCl$_3$) δ 8.56 (d, 1H, J=5.5 Hz), 8.04 (d, 2H, J=8.9 Hz), 8.05-7.99 (m, 2H), 7.69 (ddd, 1H, J=1.2, 6.9, 8.2 Hz), 7.51 (ddd, 1H, J=1.5, 6.9, 8.4 Hz), 7.30 (d, 2H, J=8.9 Hz), 7.18 (d, 1H, J=5.4 Hz), 4.35 (q, 2H, J=7 Hz), 1.38 (t, 3H, J=7 Hz).

Example 50

N-[3-(Quinolin-4-ylamino)phenyl]hexanamide

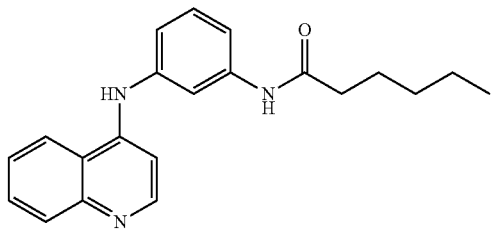 [SMILES: CCCCCC(=O)Nc1cccc(Nc2ccnc3ccccc23)c1]

N-[3-(Quinolin-4-ylamino)phenyl]hexanamide was prepared following the method for N-[4-(quinolin-4-ylamino)phenyl]hexanamide, starting with 3-nitroaniline (800 mg) and hexanoyl chloride (0.81 mL) and using 4-chloroquinoline (358 mg).

N-(4-Nitrophenyl)hexanamide (1.50 g): $^1$H NMR (CDCl$_3$) δ 8.4 (m, 1H), 8.0-7.9 (m, 2H), 7.8 (br s, 1H, NH), 7.5 (m, 1H), 2.4 (m, 2H), 1.8 (m, 2H), 1.4-1.2 (m, 4H), 0.9 (m, 3H).

N-(4-Aminophenyl)hexanamide (1.34 g): $^1$H NMR (CDCl$_3$) δ 7.4 (br s, 1H, NH), 7.2 (br s, 1H), 7.0 (t, 1H), 6.7 (d, 1H), 6.4 (d, 1H), 3.5 (br s, 2H, NH$_2$), 2.3 (t, 2H), 1.7 (m, 2H), 1.4-1.2 (m, 4H), 0.9 (m, 3H).

N-[3-(Quinolin-4-ylamino)phenyl]hexanamide: Rf 0.2 (10% MeOH/DCM); $^1$H NMR (CD$_3$OD) δ 8.5 (d, 1H), 8.4 (d, 1H), 8.0-7.8 (m, 3H), 7.7 (m, 1H), 7.5-7.3 (m, 2H), 7.1 (m, 1H), 7.0 (d, 1H), 2.4 (t, 2H), 1.7 (m, 2H), 1.4-1.2 (m, 4H), 0.9 (m, 3H).

Example 51

N-Hexyl-4-(quinolin-4-ylamino)benzamide

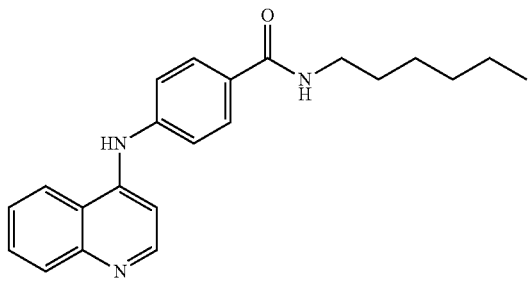 [SMILES: CCCCCCNC(=O)c1ccc(Nc2ccnc3ccccc23)cc1]

N-Hexyl-4-(quinolin-4-ylamino)benzamide 4-Amino-N-hexylbenzamide (220 mg), prepared from 1-aminohexane (0.70 mL) and 4-nitrobenzoyl chloride (450 mg) in two unremarkable steps, was reacted with 4-chloroquinoline (239 mg) and DIEA (0.50 mL) in 1 mL of IPA heated at 130-180° C. in a sealed tube for 8 days. The mixture was cooled and partitioned between DCM and 5% Na$_2$CO$_3$. The organic phases were dried over Na$_2$SO$_4$, and concentrated. Purification by SPE, washing with 3% MeOH/DCM and then eluting with 15% MeOH/DCM, gave 105 mg of a solid. Rf 0.08 (5% MeOH/DCM); $^1$H NMR (20% CD$_3$OD/CDCl$_3$) δ 8.39 (d, 1H, J=5.4 Hz), 8.15 (dd, 1H, J=0.7, 8.4 Hz), 7.89 (dd, 1H, J=0.7, 8.4 Hz), 7.80-7.75 (m, 2H), 7.65 (ddd, 1H, J=1.5, 6.9, 8.4 Hz), 7.47 (ddd, 1H, J=1.2, 6.9, 8.4 Hz), 7.36-7.30 (m, 2H), 7.07 (d, 1H, J=5.5 Hz), 3.35 (m, 2H, AB), 1.57 (m, 2H), 1.32-1.21 (m, 6H), 0.84 (t, 3H, J=6 Hz).

N-Hexyl-4-nitrobenzamide (467 mg): $^1$H NMR (CDCl$_3$) δ 8.17 (d, 2H, J=8.7 Hz), 7.91 (d, 2H, J=8.7 Hz), 7.00 (br s, 1H, NH), 3.39 (m, 2H), 1.56 (m, 2H), 1.4-1.1 (m, 6H), 0.81 (m, 3H).

4-Amino-N-hexylbenzamide: Rf 0.22 (5% MeOH/DCM); $^1$H NMR (CDCl$_3$) δ 7.56 (m, 2H), 6.58 (m, 2H), 6.56 (br s, 1H, NH), 4.12 (br s, 2H, NH$_2$), 3.57 (m, 2H), 1.53 (m, 2H), 1.47-1.22 (m, 6H), 0.84 (m, 3H).

Example 52

N-Hexyl-3-(quinolin-4-ylamino)benzamide

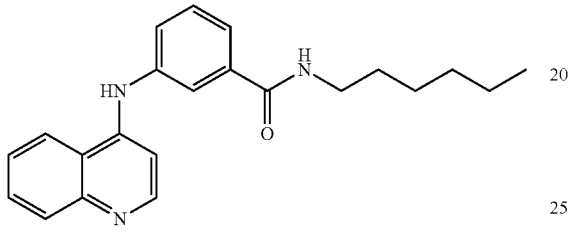

N-Hexyl-3-(quinolin-4-ylamino)benzamide (117 mg) was prepared following the method for N-hexyl-4-(quinolin-4-ylamino)benzamide, starting from 3-nitrobenzoic acid (1.17 g) and 1-hexylamine (1.02 mL) and using 4-chloroquinoline (225 mg).

N-Hexyl-3-nitrobenzamide: $^1$H NMR (CDCl$_3$) δ 8.56 (m, 1H), 8.28 (m, 1H), 8.13 (ddd, 1H, J=1.2, 1.7, 7.7 Hz), 7.58 (t, 1H, J=7.9 Hz), 6.84 (br s, 1H, NH), 3.44 (m, 2H), 1.60 (m, 2H), 1.39-1.23 (m, 6H), 0.84 (t, 3H, J=7.0 Hz).

3-Amino-N-hexylbenzamide (1.47 g): Rf 0.25 (5% MeOH/DCM); $^1$H NMR (CDCl$_3$) δ 7.14-7.00 (m, 3H), 6.71 (m, 1H), 6.42 (br s, 1H, NH), 3.80 (br s, 2H, NH$_2$), 3.34 (m, 2H), 1.53 (m, 2H), 1.48-1.21 (m, 6H), 0.84 (m, 3H).

N-Hexyl-3-(quinolin-4-ylamino)benzamide: Rf 0.05 (5% MeOH/DCM); $^1$H NMR (20% CD$_3$OD/CDCl$_3$) δ 8.34 (d, 1H, J=5.6 Hz), 8.18 (dd, 1H, J=0.7, 8.4 Hz), 7.91-7.88 (m, 1H), 7.70-7.64 (m, 2H), 7.53-7.38 (m, 4H), 6.93 (d, 1H, J=5.7 Hz), 3.35 (m, 2H), 1.57 (m, 2H), 1.32-1.20 (m, 6H), 0.84 (m, 3H).

Example 53

N-(4-Methoxyphenyl)quinolin-4-amine

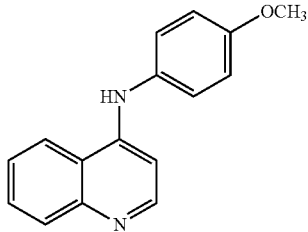 [SMILES: COc1ccc(Nc2ccnc3ccccc23)cc1]

A mixture of p-anisidine (138 mg, 1.12 mmol), 4-chloroquinoline (235 mg, 1.44 mmol), and DIEA (0.50 mL, mmol) was heated at 130° C. in a sealed tube for 40 hr. The cooled mixture was partitioned between EA (3×) and 5% Na$_2$CO$_3$ (3×) and brine, and the organic phases were dried over anhydrous Na$_2$SO$_4$ and concentrated to give 385 mg of brown oil. Purification by preparative TLC (10% MeOH/DCM) gave 294 mg of brown oil that solidified upon standing. $^1$H NMR (CDCl$_3$) δ 8.48 (d, 1H, J=5.4 Hz), 7.99 (d, 1H, J=8.4 Hz), 7.96 (d, 1H, J=8.4 Hz), 7.64 (ddd, 1H, J=1.3, 7.0, 8.5 Hz), 7.45 (m, 1H), 7.21 (m, 2H), 6.93 (m, 2H), 6.68 (d, 1H, J=5.2 Hz), 3.82 (s, 3H).

Example 54

N-[4-(Benzyloxy)phenyl]quinolin-4-amine

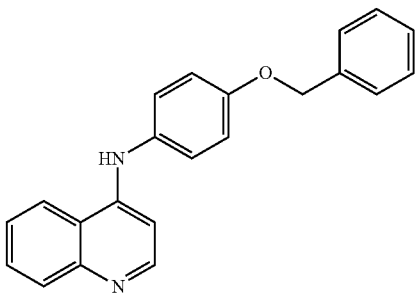 [SMILES: c1ccc(COc2ccc(Nc3ccnc4ccccc34)cc2)cc1]

A mixture of 4-(benzyloxy)aniline (197 mg, 0.99 mmol), 4-chloroquinoline (169 mg, 1.04 mmol), and DIEA (0.18 mL, 1.03 mmol) in 1 mL of NMP was heated at 150° C. in a sealed tube for 24 hr. Then, the mixture was cooled and partitioned between EA (2×) and 5% Na$_2$CO$_3$ (2×) and brine. The organic phase was dried over Na$_2$SO$_4$ and concentrated. SPE, washing with 1% MeOH/DCM and eluting with 5% MeOH/DCM while cutting fractions, gave 152 mg of colorless solid. Rf 0.18 (5% MeOH/DCM); mp 201-202° C. (from MeOH); $^1$H NMR (CDCl$_3$) δ 8.49 (d, 1H, J=5.4 Hz), 8.02 (dd, 1H, J=1.0, 8.6 Hz), 7.91 (dd, 1H, J=0.7, 8.4 Hz), 7.66 (ddd, 1H, J=1.2, 6.9, 8.4 Hz), 7.51-7.31 (m, 6H), 7.26-7.20 (m, 2H), 7.06-6.98 (m, 2H), 6.71 (d, 2H, J=5.2 Hz), 5.09 (s, 2H).

Example 55

N-(4-Butoxyphenyl)quinolin-4-amine

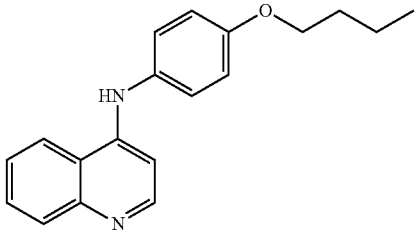 [SMILES: CCCCOc1ccc(Nc2ccnc3ccccc23)cc1]

A mixture of 4-butoxyaniline (236 mg, 1.43 mmol), 4-chloroquinoline (236 mg, 1.45 mmol), and DIEA (0.26 mL, 1.49 mmol) in 1 mL of NMP was heated at 150° C. in a sealed tube for 24 hr. The cooled mixture was partitioned between EA (2×) and 5% Na$_2$CO$_3$ (2×) and brine, and the organic phases were dried over anhydrous Na$_2$SO$_4$ and concentrated to give a solid. SPE, washing with 1% MeOH/DCM and eluting with 5% MeOH/DCM, gave fractions affording a solid after concentration. Recrystallization from MeOH gave 177 mg. Rf 0.18 (5% MeOH/DCM); mp 181-185° C.; $^1$H NMR (CDCl$_3$) δ 8.45 (d, 1H, J=5.4 Hz), 8.03 (dd, 1H, J=1.0, 8.7 Hz), 7.97 (d, 1H, J=8.4 Hz), 7.67 (ddd, 1H, J=1.2, 6.9, 8.1 Hz), 7.48 (ddd, 1H, J=1.5, 6.9, 8.4 Hz), 7.22 and 6.95 (m, 4H, AA'BB'), 6.67 (d, 1H, J=5.4 Hz), 3.98 (t, 2H, J=6.5 Hz), 1.79 (m, 2H), 1.51 (m, 2H), 0.99 (t, 3H, J=7.3 Hz).

Example 56

N-[4-(Hexyloxy)phenyl]quinolin-4-amine

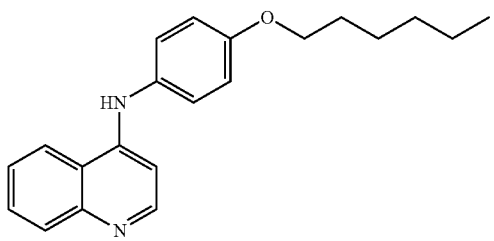 [SMILES: CCCCCCOc1ccc(Nc2ccnc3ccccc23)cc1]

1-(Hexyloxy)-4-nitrobenzene A mixture of 4-nitrophenol (480 mg, 3.45 mmol), 1-bromohexane (0.43 mL, 3.08 mmol), K$_2$CO$_3$ (481 mg, 3.57 mmol), and 20 mg sodium iodide in 5 mL of DMF was heated at 60° C. for 18 hr. The cooled mixture was diluted with Et$_2$O and washed with 5% Na$_2$CO$_3$ and brine, repetitively, until the aqueous phase was colorless. The organic phase was dried over MgSO$_4$ and concentrated to obtain 532 mg of yellow oil. Rf 0.21 (5% EA/Hex); $^1$H NMR (CDCl$_3$) δ 8.19-8.13 (m, 2H, AA'BB'), 6.94-6.88 (m, 2H, AA'BB'), 4.02 (t, 2H), 1.80 (m, 2H), 1.50-1.29 (m, 6H), 0.89 (m, 3H).

4-(Hexyloxy)aniline A mixture of 1-(hexyloxy)-4-nitrobenzene (532 mg, 2.38 mmol) and 5% Pd/C (60 mg) in 20 mL of MeOH was stirred under a hydrogen atmosphere for 3 hr. Then, the mixture was filtered through a pad of Celite and concentrated to give 458 mg of oil. $^1$H NMR (CDCl$_3$) δ 6.78-6.72 (m, 2H, AA'BB'), 6.65-6.59 (m, 2H, AA'BB'), 3.88 (t, 2H), 3.44 (br s, 2H, NH$_2$), 1.75 (m, 2H), 1.50-1.28 (m, 6H), 0.92 (m, 3H).

N-[4-(Hexyloxy)phenyl]quinolin-4-amine A mixture of 4-(hexyloxy)aniline (430 mg, 2.23 mmol), 4-chloroquinoline (431 mg, 2.64 mmol), and DIEA (1.0 mL, 5.74 mmol) in 1 mL of NMP was heated in a heavy walled sealed tube at 160° C. for 24 hr. The mixture was cooled and partitioned between EA and 5% Na$_2$CO$_3$ and brine. The organic phases were dried over Na$_2$SO$_4$ and concentrated to give a solid that was recrystallized from EtOH to give a colorless solid. $^1$H NMR (CDCl$_3$) δ 8.49 (d, 1, J=5.2 Hz), 8.02 (dd, 1, J=0.7, 8.4 Hz), 7.91 (d, 1, J=8.4 Hz), 7.67 (ddd, 1, J=1.5, 6.9, 8.4 Hz), 7.48 (ddd, 1, J=1.5, 6.9, 8.4 Hz), 7.25-7.18 (m, 2H), 6.98-6.92 (m, 2H), 6.69 (d, 1, J=5.5 Hz), 6.64 (br s, 1H), 3.97 (t, 2H, J=6 Hz), 1.80 (m, 2H), 1.50-1.30 (m, 6), 0.92 (m, 3).

Example 57

N-[3-(Benzyloxy)phenyl]quinolin-4-amine

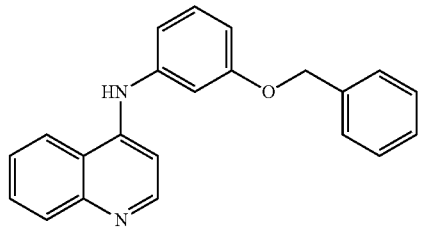 [SMILES: c1ccc(COc2cccc(Nc3ccnc4ccccc34)c2)cc1]

A mixture of 3-(benzyloxy)aniline (312 mg, 1.57 mmol), 4-chloroquinoline (280 mg, 1.72 mmol), and DIEA (0.30 mL, 1.72 mmol) in 1 mL of NMP was heated at 150° C. in a sealed tube for 24 hr. Then, the mixture was cooled and partitioned between DCM and 5% Na$_2$CO$_3$. The organic phase was dried over Na$_2$SO$_4$ and concentrated. SPE, washing with 20% EA/Hex, 20% EA/Hex+2% TEA, and 35% EA/Hex+2% TEA, then eluting with 50% EA/Hex+2% TEA, gave 528 mg of yellow solid. Recrystallization from MeOH gave 390 mg of pale yellow solid. Rf 0.26 (7.5% MeOH/DCM); mp 77-80° C. (from MeOH); $^1$H NMR (CDCl$_3$) δ 8.45 (d, 1H, J=5.5 Hz), 8.04 (d, 1H, J=8.4 Hz), 7.98 (d, 1H, J=8.4 Hz), 7.67 (m, 1H), 7.53-7.24 (m, 8H), 6.94-6.79 (m, 4H), 5.08 (s, 2H).

Example 58

N-[3-(Hexyloxy)phenyl]quinolin-4-amine

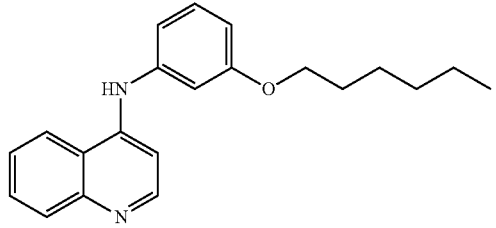 [SMILES: CCCCCCOc1cccc(Nc2ccnc3ccccc23)c1]

1-(Hexyloxy)-3-nitrobenzene A mixture of 3-nitrophenol (553 mg, 3.98 mmol), 1-bromohexane (0.50 mL, 3.58 mmol), and K$_2$CO$_3$ (618 mg, 4.48 mmol) in 5 mL of DMF was heated at 60-80° C. for 12 hr. The cooled mixture was diluted with Et$_2$O and washed with 5% Na$_2$CO$_3$ and brine, repetitively, until the aqueous phase was colorless, and then with 0.1M HCl and brine. The organic phase was dried over MgSO$_4$ and concentrated to obtain 756 mg of oil. $^1$H NMR (CDCl$_3$) δ 7.78 (ddd, 1H, J=1.0, 2.0, 7.9 Hz), 7.70 (m, 1H), 7.39 (m, 1H), 7.19 (ddd, 1H, J=1.0, 2.4, 8.1 Hz), 4.01 (t, 2H, J=6.6 Hz), 1.80 (m, 2H), 1.58-1.30 (m, 6H), 0.89 (m, 3H).

3-(Hexyloxy)aniline A mixture of 1-(hexyloxy)-3-nitrobenzene (756 mg, 3.39 mmol) and 5% Pd/C (90 mg) in 20 mL of MeOH was stirred under a hydrogen atmosphere for 3 hr. Then, the mixture was filtered through a pad of Celite and concentrated to give 660 mg of light orange oil.

$^1$H NMR (CDCl$_3$) δ 7.04 (m, 1H), 6.34-6.23 (m, 3H), 3.90 (t, 2H), 3.62 (br s, 2H, NH$_2$), 1.75 (m, 2H), 1.49-1.26 (m, 6H), 0.90 (m, 3H).

N-[3-(Hexyloxy)phenyl]quinolin-4-amine Anhydrous pyridine (4 mL) was evaporated from the crude 3-(hexyloxy)aniline (406 mg, 2.10 mmol), then 4-chloroquinoline (420 mg, 2.58 mmol), DIEA (0.80 mL, 4.59 mmol), and 1.5 mL of NMP were added, and the mixture was heated at 160° C. in a heavy walled sealed tube for 24 hr. The mixture was cooled and partitioned between EA and 5% $Na_2CO_3$ and brine. The organic phases were dried over $Na_2SO_4$ and concentrated. SPE, washing with 20% EA/Hex and then eluting with 50% EA/Hex+2% TEA, gave the product as a brown oil that contained residual NMP. Crystallization from EA/Hex gave 410 mg of light tan solid. Rf 0.32 (50% 50% EA/Hex+2% TEA); $^1$H NMR ($CDCl_3$) δ 8.55 (d, 1, J=5.2 Hz), 8.03-7.96 (m, 2H), 7.63 (ddd, 1, J=1.2, 6.9, 8.4 Hz), 7.43 (ddd, 1, J=1.2, 6.7, 8.2 Hz), 7.26 (m, 1H), 7.14 (br s, 1H), 7.04 (d, 1, J=5.5 Hz), 6.87-6.83 (m, 2H), 6.69 (m, 1H), 3.90 (t, 2H, J=6 Hz), 1.75 (m, 2H), 1.45-1.30 (m, 6), 0.89 (m, 3).

Example 59

N-[2-(Benzyloxy)phenyl]quinolin-4-amine

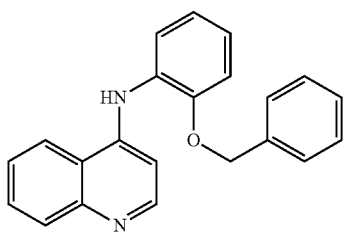 [SMILES: c1ccc(COc2ccccc2Nc2ccnc3ccccc23)cc1]

A mixture of 2-(benzyloxy)aniline (301 mg, 1.51 mmol), 4-chloroquinoline (268 mg, 1.64 mmol), and 4-methylmorpholine (0.18 mL, 1.64 mmol) in 0.5 mL of NMP was heated in a heavy walled sealed tube at 130° C. for 20 hr. The mixture was cooled and partitioned between EA and 5% $Na_2CO_3$ and brine. The organic phases were dried over $Na_2SO_4$ and concentrated. FC (7.5% MeOH/DCM) gave a dark oil that contained residual 4-methylmorpholine. The oil was filtered through a pad of silica gel using 30% EA/Hex+2% TEA to give 268 mg of tan solid. Rf 0.12 (5% MeOH/DCM); $^1$H NMR ($CDCl_3$) δ 8.60 (d, 1H, J=5.4 Hz), 8.05 (dd, 1H, 1.0, 8.4 Hz), 7.88 (dd, 1H, J=0.8, 8.4 Hz), 7.66 (ddd, 1H, J=1.2, 6.9, 8.4 Hz), 7.53-7.40 (m, 2H), 7.37-7.29 (m, 5H), 7.15 (d, 1H, J=5.2 Hz), 7.07-6.98 (m, 3H), 5.17-5.10 (m, 2H, AB).

Example 60

N-[2-(Hexyloxy)phenyl]quinolin-4-amine

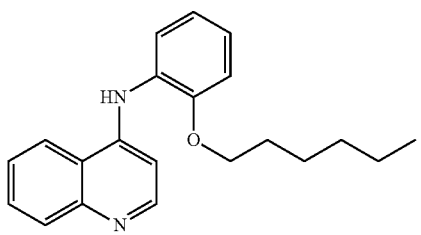 [SMILES: CCCCCCOc1ccccc1Nc1ccnc2ccccc12]

1-(Hexyloxy)-2-nitrobenzene 2-Nitrophenol (1.38 g, 9.93 mmol), 1-bromohexane (1.30 mL, 9.30 mmol), and $K_2CO_3$ (1.38 g, 10.0 mmol) in 6 mL of DMF was mixed at room temperature for 3 days. The mixture was diluted with $Et_2O$ and washed with 0.25N NaOH until the aqueous phase was colorless, and then with brine. The organic phase was dried over $MgSO_4$ and concentrated. Rf 0.39 (5% EA/Hex); $^1$H NMR ($CDCl_3$) δ 7.78 (dd, 1H, J=1.7, 8.2 Hz), 7.48 (ddd, 1H, J=1.8, 7.3, 8.9 Hz), 7.04 (dd, 1H, J=1.0, 8.5 Hz), 6.97 (ddd, 1H, 1.2, 7.4, 8.2 Hz), 4.07 (t, 2H, J=6.4 Hz), 1.80 (m, 2H), 1.51-1.28 (m, 6H), 0.90 (m, 3H).

2-(Hexyloxy)aniline A mixture of the 1-(hexyloxy)-2-nitrobenzene and 5% Pd/C (94 mg) in 15 mL of MeOH and 15 mL of EA was stirred under a hydrogen atmosphere for 5 hr. Then, the mixture was filtered through a pad of Celite and concentrated. The residue was filtered through silica gel using 30% EA/Hex to give 1.51 g of brown oil that contained residual 1-bromohexane, as shown by NMR analysis. SPE, washing with hexane and eluting with 30% EA/Hex gave 1.38 g of red-brown oil. Rf 0.26 (5% EA/Hex); $^1$H NMR ($CDCl_3$) δ 6.81-6.68 (m, 4H), 3.98 (t, 2H, J=6.4 Hz), 3.76 (br s, 2H, N$\underline{H}_2$), 1.81 (m, 2H), 1.53-1.23 (m, 6H), 0.91 (m, 3H).

N-[2-(Hexyloxy)phenyl]quinolin-4-amine A mixture of 2-(hexyloxy)aniline (282 mg, 1.46 mmol), 4-chloroquinoline (258 mg, 1.58 mmol), and 4-methylmorpholine (0.18 mL, 1.64 mmol) in 0.5 mL of NMP was heated in a heavy walled sealed tube at 130° C. for 20 hr. The mixture was cooled and partitioned between EA and 5% $Na_2CO_3$ and brine. The organic phases were dried over $Na_2SO_4$ and concentrated. FC (7.5% MeOH/DCM) gave a dark oil that contained residual 4-methylmorpholine. The oil was filtered through a pad of silica gel using 30% EA/Hex+2% TEA to give 416 mg of tan solid. Rf 0.13 (5% MeOH/DCM) 0.50 (10% MeOH/DCM); $^1$H NMR ($CDCl_3$) δ 8.59 (dd, 1H, J=6.3, 11.5 Hz), 8.05 (m, 1H), 7.95 (m, 1H), 7.65 (ddd, 1H, J=1.3, 6.7, 9.7 Hz), 7.50-7.44 (m, 2H), 7.19-7.13 (m, 2H), 7.06-6.91 (m, 3H), 3.99 (t, 2H, J=6.4 Hz), 1.75 (m, 2H), 1.45-1.17 (m, 6H), 0.83 (m, 3H).

Example 61

N-[2-Fluoro-4-(hexyloxy)phenyl]quinolin-4-amine

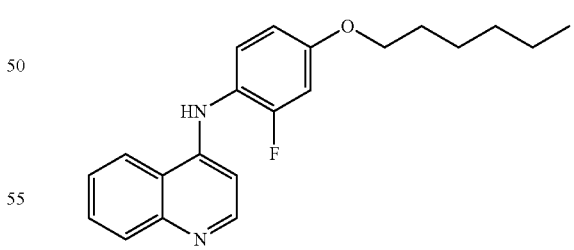

2-Fluoro-4-(hexyloxy)-1-nitrobenzene (2.6 g) was prepared from 3-fluoro-4-nitrophenol (5.0 g, 31.5 mmol), 60% sodium hydride (1.9 g), 1-bromohexane (4.75 mL), and 30 mL of DMF following the method for 1-(8-bromooctyloxy)-3-methylbenzene. $^1$H NMR ($CDCl_3$) δ 8.05 (t, 1H), 6.7 (m, 2H), 4.0 (t, 2H), 1.8 (m, 2H), 1.6-1.3 (m, 6H), 0.9 (m, 3H).

2-Fluoro-4-(hexyloxy)aniline (1.6 g) was prepared from 2-fluoro-4-(hexyloxy)-1-nitrobenzene (2.6 g) following the method for 8-(3-ethoxypropoxy)octan-1-amine. $^1$H NMR (CDCl₃) δ 6.75-6.5 (m, 3H), 3.85 (t, 2H), 3.4 (br s, 2H, NH₂), 1.75 (m, 2H), 1.5-1.2 (m, 6H), 0.9 (m, 3H).

N-[2-Fluoro-4-(hexyloxy)phenyl]quinolin-4-amine (114 mg) was prepared from 2-fluoro-4-(hexyloxy)aniline (1.6 g), 4-chloroquinoline (1.33 g), TEA (5 mL), and NMP (0.5 mL) at 130° C. in a sealed tube for 5 days following the method for N-[8-(3-ethoxypropoxy)octyl]quinolin-4-amine.

¹H NMR (CDCl₃) δ 8.55 (d, 1H), 8.05 (d, 1H), 7.95 (d, 1H), 7.7 (m, 1H), 7.5 (m, 1H), 7.3 (m, 1H), 6.75 (m, 2H), 6.65 (d, 1H), 6.4 (br s, 1H, NH), 3.95 (t, 2H), 1.8 (m, 2H), 1.6-1.3 (m, 6H), 0.9 (m, 3H).

Example 62

N-Benzylquinolin-4-amine

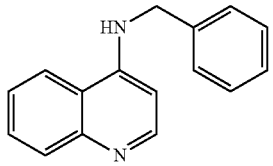 [SMILES: c1ccc(CNc2ccnc3ccccc23)cc1]

A mixture of benzylamine (166 mg, 1.55 mmol), 4-chloroquinoline (268 mg, 1.64 mmol), and DIEA (0.50 mL, 2.87 mmol) was heated in a heavy walled sealed tube at 130° C. for 40 hr. The mixture was cooled, a mixture of EtOH and H₂O was added, and the sealed mixture was heated for 16 hr. Then, the mixture was cooled and partitioned between EA (3×) and 5% Na₂CO₃ (3×) and brine. The organic phases were dried over Na₂SO₄ and concentrated to give 385 mg of oil. Purification by preparative TLC (10% MeOH/DCM) gave 294 mg of brown oil. Rf 0.33 (10% MeOH/DCM); ¹H NMR (CDCl₃) δ 8.49 (d, 1H, J=5.2 Hz), 7.98 (dd, 1H, J=0.8, 8.4 Hz), 7.82 (d, 1H, J=8.4 Hz), 7.61 (ddd, 1H, J=1.2, 6.9, 8.4 Hz), 7.42-7.27 (m, 6H), 6.41 (d, 1H, J=5.4 Hz), 5.76 (br s, 1H), 4.51 (m, 2H, AB).

Example 63

N-Phenethylquinolin-4-amine

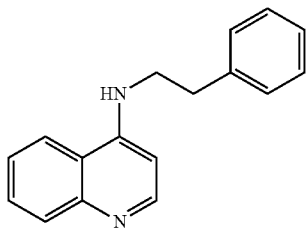 [SMILES: c1ccc(CCNc2ccnc3ccccc23)cc1]

A mixture of 2-phenethylamine (177 mg, 1.46 mmol), 4-chloroquinoline (258 mg, 1.58 mmol), and DIEA (0.50 mL, 2.87 mmol) was heated at 130° C. in a sealed tube for 40 hr. The cooled mixture was partitioned between EA (3×) and 5% Na₂CO₃ (3×) and brine, and the organic phases were dried over anhydrous Na₂SO₄ and concentrated to give a solid. Washing with Et₂O gave 230 mg of red solid. ¹H NMR (CDCl₃) δ 8.55 (d, 1H, J=5.4 Hz), 7.98 (m, 1H), 7.64-7.58 (m, 2H), 7.42-7.24 (m, 6H), 6.48 (d, 1H, J=5.4 Hz), 5.17 (br s, 1H, NH), 3.60 (m, 2H), 3.06 (t, 2H, J=6.9 Hz).

Example 64

N-[4-(Hexyloxy)benzyl]quinolin-4-amine

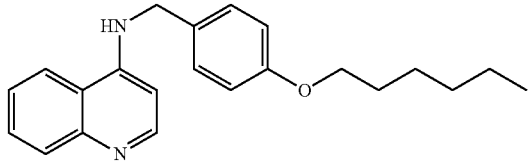 [SMILES: CCCCCCOc1ccc(CNc2ccnc3ccccc23)cc1]

4-(Hexyloxy)benzonitrile A mixture of 4-cyanophenol (25.2 g, 212 mmol), K₂CO₃ (24.7 g, 233 mmol), and 1-bromohexane (29.6 mL, 212 mmol) in 150 mL of DMF was stirred at room temperature for 24 hr and then at 55° C. for 24 hr. 4-Cyanophenol remained, as shown by TLC. Na₂CO₃ (7.0 g, 66 mmol), and 1-bromohexane (3.0 mL, 21 mmol) were added, and, after 24 hr, the temperature was lowered to 40° C. and additional Na₂CO₃ (12.4 g, 117 mmol) and 1-bromohexane (10.0 mL, 72 mmol) were added. However, after 24 hr, no consumption of the remaining 4-cyanophenol was apparent. The mixture was cooled to room temperature and 6 mL of concentrated NH₄OH was added. After standing for 3 days, the mixture was partitioned between EA (3×250 mL) and H₂O (300 and 200 mL), 1M HCl (100 mL), and brine (150 mL). The combined organic phases were dried over MgSO₄ and concentrated. SPE (10% EA/Hex) gave 35.8 g of colorless oil that solidified upon standing. Rf 0.63 (20% EA/Hex); ¹H NMR (CDCl₃) δ 7.55 and 6.92 (m, 4H, AA'BB'), 3.98 (t, 2H, J=6.6 Hz), 1.78 (m, 2H), 1.43 (m, 2H), 1.35-1.30 (m, 4H), 0.89 (m, 3H); ¹³C NMR (CDCl₃) δ 162.6, 134.1, 119.5, 115.4, 103.8, 68.6, 31.7, 29.1, 25.8, 22.7, 14.2.

[4-(Hexyloxy)phenyl]methanamine 4-(Hexyloxy)benzonitrile (35.8 g, 176 mmol) was taken up in 350 mL of THF, and the mixture was cooled by an ice bath. LAH (7 g, 184 mmol) was added cautiously in portions. After 1 hr, the mixture was heated at reflux. After 15 hr, the mixture was cooled with an ice bath. Cautiously, with thorough stirring, in portions and in sequence, 7 mL of H₂O, 7 mL of 15% NaOH, and 21 mL of H₂O were added to the ice-cold mixture. The resultant heterogenous mixture was diluted with 350 mL of IPA. The mixture was filtered through a bed of Celite, and the solids were washed with 200 mL of IPA. The filtrate was concentrated to give 34.4 g of the product that contained residual IPA. Rf 0.25 (5% MeOH/DCM+2% TEA, ninhydrin (+)); ¹H NMR (CDCl₃) δ 7.17 and 6.83 (m, 4H, AA'BB'), 3.90 (t, 2H, J=6.7 Hz), 3.74 (s, 2H), 2.00 (br s, 2H, NH₂), 1.78 (m, 2H), 1.48-1.27 (m, 6H), 0.88 (m, 3H).

N-[4-(Hexyloxy)benzyl]quinolin-4-amine [4-(Hexyloxy)phenyl]methanamine (166 mmol) was taken up in 400 mL of 1-pentanol, and 150 mL of volatile material was removed by distillation in order to ensure anhydrous conditions. The mixture was allowed to cool to 70° C., and tripropylamine (63 mL, 330 mmol) and 4-chloroquinoline (28 g, 172 mmol) were added. Heating at reflux was resumed. After 16 hr, TLC of an aliquot indicated very little ninhydrin (+) starting material remained. Volatile material was removed by distillation and evaporation. The cooled mixture was diluted with 1:2 DCM/EA and washed with 3N NaOH (60 mL), H₂O, and brine. The combined organic phases were dried over Na₂SO₄, filtered, and concentrated. SPE, eluting with 50% EA/Hex and then 15% EtOH/DCM, gave a brown oil. The oil was taken up in EA and washed with 5% Na₂CO₃ and brine. The organic phase was dried over $Na_2SO_4$, filtered, and concentrated. EA (10 mL) and then hexanes (20 mL) were added to the residue. A precipitate was obtained. The colorless precipitate was collected by filtration and washed with 100 mL of 50% EA/Hex and then 50 mL of 30% EA/Hex. A second crop was obtained from the combined filtrates. The crops were combined and dried in vacuo to give 38.4 g. Rf 0.25 (5% MeOH/DCM); mp 103.5-104.0° C.; $^1$H NMR ($CDCl_3$) δ 8.55 (d, 1H, J=5.5 Hz) 8.00 (d, 1H, J=0.7 Hz), 7.98 (d, 1H, J=0.7 Hz), 7.74 (m, 1H), 7.65-7.61 (m, 1H), 7.41 (m, 1H), 7.30 and 6.90 (m, 4H, AA'BB'), 6.46 (d, 1H, J=5.1 Hz), 5.33 (m, 1H), 4.43 (m, 2H, AB), 3.96 (t, 2H, J=6.6 Hz), 1.79 (m, 2H), 1.46 (m, 2H), 1.39-1.30 (m, 4H), 0.90 (m, 3H); $^{13}$C NMR ($CDCl_3$) δ 159.2, 151.4, 149.6, 148.7, 130.3, 129.5, 129.2, 129.1, 124.9, 119.5, 119.0, 115.2, 99.5, 68.4, 47.4, 31.8, 29.4, 25.9, 22.8, 14.2.

Example 65

N-[3-(Hexyloxy)benzyl]quinolin-4-amine

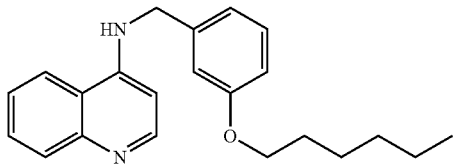 [SMILES: CCCCCCOc1cccc(CNc2ccnc3ccccc23)c1]

3-(Hexyloxy)benzaldehyde A mixture of 3-hydroxybenzaldehyde (10.3 g, 84.4 mmol), $K_2CO_3$ (13.9 g, 100.7 mmol), and 1-bromohexane (11.2 mL, 80.0 mmol) in 90 mL of DMF was heated at 60° C. for 12 hr. The mixture was cooled to room temperature, poured into 30% EA/Hex, and washed with $H_2O$, 5% $Na_2CO_3$, $H_2O$, 0.1M HCl, and brine. The organic phases were dried over $Na_2SO_4$, filtered through a pad of silica gel, and concentrated to give 15.8 g of brown oil. Rf 0.56 (20% EA/Hex), $^1$H NMR ($CDCl_3$) δ 9.94 (s, 1H), 7.43-7.36 (m, 3H), 7.14 (m, 1H), 3.99 (t, 2H, J=6.6 Hz), 1.79 (m, 2H), 1.45 (m, 2H), 1.37-1.28 (m, 4H), 0.89 (m, 3H); $^{13}$C NMR ($CDCl_3$) δ 192.4, 159.9, 137.9, 130.1, 123.4, 122.1, 113.0, 68.4, 31.7, 29.2, 25.8, 22.7, 14.2.

[3-(Hexyloxy)phenyl]methanol 3-(Hexyloxy)benzaldehyde was taken up in 160 mL of MeOH, and the mixture was cooled using an ice bath. $NaBH_4$ (3.17 g, 83 mmol) was added in three portions, during which gas was evolved from the mixture. Three hours after the final addition, 10 mL of acetone was added, and the mixture was allowed to stand for 3 days. Then, the volatile material was evaporated, and the residue was partitioned between 1:1 EA/Hex and $H_2O$, 5% $Na_2CO_3$ (2×), $H_2O$, 0.1M HCl (2×), and brine. The organic phases were dried over $Na_2SO_4$, filtered through a pad of silica gel, and concentrated to give 15.3 g of light brown oil. Rf 0.28 (20% EA/Hex); $^1$H NMR ($CDCl_3$) δ 8.16 (m, 1H), 7.83-7.81 (m, 2H), 7.73 (m, 1H), 5.55 (s, 2H), 4.86 (t, 2H, J=6.6 Hz), 2.86 (br s, 1H, OH), 2.69 (m, 2H), 2.37 (m, 2H), 2.27-2.23 (m, 4H), 1.82 (t, 3H, J=7.0 Hz); $^{13}$C NMR ($CDCl_3$) δ 159.6, 142.7, 129.7, 119.1, 114.0, 113.1, 69.2, 65.4, 31.8, 29.4, 25.9, 22.8, 14.2.

3-(Hexyloxy)benzyl methanesulfonate [3-(Hexyloxy)phenyl]methanol was taken up in 180 mL of THF and 100 mL of EA and cooled using an ice bath. TEA (12.4 mL, 88 mmol) and then methanesulfonyl chloride (6.30 mL, 80 mmol) were added. A white precipitate formed rapidly. After 2 hr, 5 mL of $H_2O$ were added, and the volatile components were evaporated. The residue was partitioned between EA (3×300 mL) and $H_2O$, saturated $NaHCO_3$, $H_2O$, 0.1M HCl, and brine (100 mL each). The combined organic phases were dried over $Na_2SO_4$, filtered through a pad of silica gel, and concentrated to give 20.75 g of light brown oil. Rf 0.50 (30% EA/Hex); $^1$H NMR ($CDCl_3$) δ 7.3 (m, 1H), 6.9-6.8 (m, 3H), 5.2 (s, 2H), 4.0 (t, 2H, J=6.6 Hz), 2.9 (2s, 3H), 1.8 (m, 2H), 1.4 (m, 2H), 1.4-1.3 (m, 4H), 0.9 (m, 3H); $^{13}$C NMR ($CDCl_3$) δ 159.7, 134.9, 130.1, 120.9, 115.7, 114.9, 71.7, 68.3, 38.6, 31.7, 29.4, 25.9, 22.8, 14.2.

N-[3-(Hexyloxy)benzyl]phthalimide A mixture of 3-(hexyloxy)benzyl methanesulfonate and potassium phthalimide (15.4 g, 83.2 mmol) in 200 mL of DMF was stirred using a mechanical stirrer at room temperature for 4 hr and then at 50° C. for 4 hr. Then, $H_2O$ (100 mL) was added, and the volatile material was evaporated. The residue was partitioned between EA and 5% $Na_2CO_3$ (2×), $H_2O$, 0.1M HCl, and brine. The organic phases were dried over $Na_2SO_4$, filtered through a pad of silica gel, and concentrated. Crystallization from IPA gave 20.74 g of colorless solid. Rf 0.56 (30% EA/Hex); $^1$H NMR ($CDCl_3$) δ 7.9 and 7.7 (m, 4H, AA'BB'), 7.2 (m, 1H), 7.0-6.9 (m, 2H), 6.8 (m, 1H), 4.8 (s, 2H), 3.9 (t, 2H, J=6.6 Hz), 1.8 (m, 2H), 1.5 (m, 2H), 1.3-1.2 (m, 4H), 0.9 (m, 3H); $^{13}$C NMR ($CDCl_3$) δ 168.2, 159.6, 138.0, 134.2, 132.3, 129.8, 123.6, 120.8, 114.8, 114.1, 68.1, 41.8, 31.8, 29.4, 25.9, 22.8, 14.2.

[3-(Hexyloxy)phenyl]methanamine Hydrazine monohydrate (2.20 mL, 45.3 mmol) was added to a mixture of N-[3-(hexyloxy)benzyl]phthalimide (10.1 g, 30.0 mmol) and 90 mL of denatured EtOH with mechanical stirring. The mixture was heated at reflux for 15 hr, during which time a colorless precipitate formed. The mixture was concentrated by evaporation, and the residue was partitioned between DCM (150, 2×80 mL) and 5% $Na_2CO_3$ (2×100 mL). The combined organic phases were dried over $Na_2SO_4$, filtered, and concentrated. SPE, washing with 50% isopropyl acetate/Hex and then eluting with 3% MeOH/DCM+2% TEA gave 4.40 g of the product as a pale yellow liquid, which was carried on without additional drying. Rf 0.26 (10% MeOH/DCM, ninhydrin (+)); $^1$H NMR ($CDCl_3$) δ 7.22 (m, 1H), 6.87-6.84 (m, 2H), 6.76 (dd, 1H, J=2.4, 8.0 Hz), 3.94 (t, 2H, J=6.6 Hz), 3.82 (br s, 2H, AB), 1.76 (m, 2H), 1.59 (br s, 2H, N$\underline{H}_2$), 1.47-1.29 (m, 6H), 0.89 (t, 3H, J=6.8 Hz).

N-[3-(Hexyloxy)benzyl]quinolin-4-amine [3-(Hexyloxy)phenyl]methanamine (7.20 g, 34.8 mmol) was taken up in 100 mL of 1-pentanol, and then 25 mL of volatile material was removed by distillation. The mixture was cooled below boiling, and tripropylamine (10.0 mL, 52.4 mmol) and 4-chloroquinoline (5.67 g, 34.8 mmol) were added. Heating at reflux was resumed. After 26 hr, volatile material was removed by evaporation. The mixture was diluted with DCM (350 mL) and washed with 1N NaOH (50 mL) and 5% $Na_2CO_3$ (50 mL). The aqueous phases were extracted with DCM (100 mL). The combined organic phases were dried over $Na_2SO_4$, filtered, and concentrated. SPE, washing with 50% EA/Hex and then eluting with 50% EA/Hex+2% TEA, gave product fractions that were combined and concentrated. The residue was partitioned between EA (400, 175 mL) and 5% $Na_2CO_3$ and brine (50 mL each). The combined organic phases were dried over $Na_2SO_4$, filtered, and concentrated to approximately 50 mL, whereupon substantial precipitate formed. The precipitate was recrystallized by heating and cooling, at the end of which 20 mL of hexanes was added. After standing overnight, the colorless precipitate was collected by filtration and washed with 30% EA/Hex. (The mother liquor contained approximately 2.4 g of material, but it was not treated further.) Drying in vacuo gave 4.05 g. Rf 0.20 (10% MeOH/DCM); mp 109.5-110.0° C.; $^1$H NMR (CDCl$_3$) δ 8.55 (d, 1H, J=5.1 Hz), 8.00 (dd, 1H, J=0.7, 8.4 Hz), 7.76 (dd, 1H, J=1.1, 8.5 Hz), 7.65 (ddd, 1H, J=1.4, 6.9, 8.4 Hz), 7.44 (m, 1H), 7.29 (t, 1H), 6.98-6.94 (m, 2H), 6.86 (dd, 1H, J=1.8, 8.1 Hz), 6.46 (d, 1H, J=5.2 Hz), 5.34 (t, 1H, NH), 4.50 (m, 2H, AB), 3.94 (t, 2H, J=6.6 Hz), 1.80-1.73 (m, 2H), 1.46-1.40 (m, 2H), 1.35-1.30 (m, 4H), 0.91-0.87 (m, 3H); $^{13}$C NMR (CDCl$_3$) δ 160.0, 151.4, 149.6, 148.8, 139.4, 130.4, 130.2, 129.2, 125.0, 119.8, 119.5, 119.1, 114.2, 113.9, 99.7, 68.3, 47.9, 31.8, 29.5, 25.9, 22.8, 14.2.

Example 66

N-[2-(Hexyloxy)benzyl]quinolin-4-amine

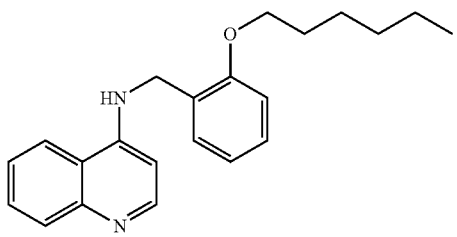 [SMILES: CCCCCCOc1ccccc1CNc1ccnc2ccccc12]

[2-(Hexyloxy)phenyl]methanol A mixture of 3-hydroxybenzyl alcohol (3.06 g, 24.7 mmol), 1-bromohexane (3.20 mL, 22.9 mmol), K$_2$CO$_3$ (3.50 g, 25.4 mmol), and 10 mL of DMF was reacted for 40 hr. The mixture was partitioned between EA and H$_2$O, 5% Na$_2$CO$_3$, H$_2$O, 0.1M HCl, and brine. The organic phases were dried over anhydrous Na$_2$SO$_4$ and concentrated. SPE, washing with 5% EA/Hex and eluting with 15% EA/Hex, gave 2.86 g of product. Rf 0.31 (15% EA/Hex); $^1$H NMR (CDCl$_3$) δ 7.27-7.22 (m, 2H), 6.95-6.85 (m, 2H), 4.69 (s, 2H), 4.01 (t, 2H, J=6.5 Hz), 2.45 (br s, 1H, OH), 1.81 (m, 2H), 1.52-1.32 (m, 6H), 0.91 (m, 3H).

N-[2-(Hexyloxy)benzyl]phthalimide DIEA (4.90 mL, 28.1 mmol) was added to a mixture of [2-(hexyloxy)phenyl]methanol (2.86 g, 13.8 mmol) and methanesulfonyl chloride (2.10 mL, 26.8 mmol) in 25 mL of dioxane and 10 mL of EA cooled by an ice bath. After 2 hr, the mixture was partitioned between EA and H$_2$O, saturated NaHCO$_3$, H$_2$O, 0.1M HCl, and brine. The organic phases were dried over anhydrous Na$_2$SO$_4$ and concentrated. The residue was filtered through a pad of silica gel using 50% EA/Hex and the filtrate was concentrated to give crude 2-(hexyloxy)benzyl methanesulfonate. The crude 2-(hexyloxy)benzyl methanesulfonate was taken up in 150 mL of acetone, sodium iodide (3.1 g, 21 mmol) was added, and the mixture was heated at reflux for 1.5 hr. Then, the solvent was evaporated, and the solid residue was partitioned between EA and H$_2$O. The organic phase was decolorized with aqueous Na$_2$S$_2$O$_3$ and washed with H$_2$O and brine, dried over anhydrous MgSO$_4$, and concentrated. The residue was filtered through a pad of silica gel using 25% EA/Hex and the filtrate was concentrated to give crude 1-(hexyloxy)-2-(iodomethyl)benzene. A mixture of the crude 1-(hexyloxy)-2-(iodomethyl)benzene and potassium phthalimide (3.8 g, 20 mmol) in 12 mL of DMF was reacted at room temperature for 24 hr. The mixture was partitioned between EA and H$_2$O, aqueous Na$_2$S$_2$O$_3$, H$_2$O, 5% Na$_2$CO$_3$, H$_2$O, 0.1M HCl, and brine, and the organic phases were dried over anhydrous MgSO$_4$ and concentrated. SPE, washing with 5% EA/Hex and eluting with 15% EA/Hex, gave 2.30 g of oil. Careful TLC (avoiding overloading and using a longer plate) showed that the product contained a nearly co-migratory impurity. Rf 0.37 (15% EA/Hex); $^1$H NMR (CDCl$_3$) δ 7.84 and 7.71 (m, 4H, AA'BB'), 7.27-7.14 (m, 2H), 6.88-6.81 (m, 2H), 4.91 (s, 2H), 3.96 (t, 2H, J=6.5 Hz), 1.77 (p, 2H, J=6.7 Hz), 1.46-1.22 (m, 6H), 0.88 (m, 3H).

[2-(Hexyloxy)phenyl]methanamine Hydrazine monohydrate was added to a mixture of N-[2-(hexyloxy)benzyl] phthalimide and 80 mL of EtOH, and the mixture was heated at reflux for 20 hr. The mixture was cooled, and the volatile components were evaporated. The residue was partitioned between EA and 5% Na$_2$CO$_3$ and brine, dried over anhydrous Na$_2$SO$_4$, and concentrated. SPE, washing with 18% EA/Hex followed by 4% MeOH/DCM and eluting with 6% MeOH/DCM+2% TEA, gave the ninhydrin (+) product. Rf 0.61 (5% MeOH/DCM+2% TEA).

N-[2-(Hexyloxy)benzyl]quinolin-4-amine A mixture of [2-(hexyloxy)phenyl]methanamine (417 mg, 2.01 mmol), 4-chloroquinoline (430 mg, 2.64 mmol), and DIEA (0.50 mL, 2.86 mmol) in 1 mL of NMP was heated at 150° C. in a sealed tube for 18 hr. Then, the mixture was cooled and partitioned between EA and 5% Na$_2$CO$_3$ and brine. The organic phase was dried over Na$_2$SO$_4$ and concentrated. SPE, washing with 2.5% MeOH/DCM and then eluting with 7% MeOH/DCM, gave 545 mg of solid. Rf 0.20 (10% MeOH/DCM); mp 90-91° C. (from EA/Hex);

$^1$H NMR (CDCl$_3$) δ $^1$H NMR (CDCl$_3$) δ 8.52 (d, 1H, J=5.5 Hz), 7.98 (dd, 1H, J=0.7, 8.4 Hz), 7.77 (dd, 1H, J=1.0, 8.4 Hz), 7.61 (ddd, 1H, J=1.5, 6.9, 8.4 Hz), 7.39 (ddd, 1H, J=1.2, 6.9, 8.1 Hz), 7.31-7.23 (m, 2H), 6.92-6.87 (m, 2H), 6.48 (d, 1H, J=5.2 Hz), 5.71 (bt, 1H, J=5.2 Hz, NH), 4.54 (m, 2H, AB), 4.02 (t, 2H, J=6.4 Hz), 1.84-1.74 (m, 2H), 1.50-1.17 (m, 6H), 0.87-0.81 (m, 3H).

Example 67

N-[3-Fluoro-4-(hexyloxy)benzyl]quinolin-4-amine

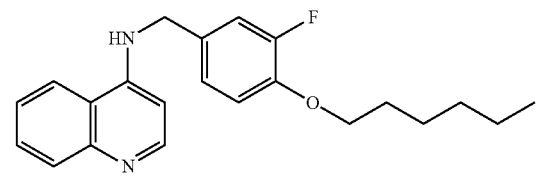 [SMILES: CCCCCCOc1ccc(CNc2ccnc3ccccc23)cc1F]

3-Fluoro-4-(hexyloxy)benzonitrile (721 mg) was prepared from 3-fluoro-4-hydroxybenzonitrile (1.5 g, 10.9 mmol), 60% sodium hydride (654 mg), 1-bromohexane (1.30 mL), and 10 mL of DMF following the method for 1-(8-bromooctyloxy)-3-methylbenzene. $^1$H NMR (CDCl$_3$) δ 7.5 (t, 1H), 6.8-6.6 (m, 2H), 3.95 (t, 2H), 1.8 (m, 2H), 1.5-1.2 (m, 6H), 0.9 (m, 3H).

[3-Fluoro-4-(hexyloxy)phenyl]methanamine (212 mg, 0.9 mmol) was prepared from 3-fluoro-(4-hexyloxy)benzonitrile (721 mg, 3.3 mmol) and LAH (6.6 mmol) in THF (50 mL) at 0° C. for 4 hr and room temperature for 12 hr following the method for [4-(hexyloxy)phenyl]methanamine. $^1$H NMR (CDCl$_3$) δ 7.15 (t, 1H), 6.7-6.5 (m, 2H), 3.9 (t, 2H), 3.75 (s, 2H), 1.75 (m, 2H), 1.6-1.2 (m, 8H), 0.9 (m, 3H).

N-[3-Fluoro-4-(hexyloxy)benzyl]quinolin-4-amine (325 mg) was prepared from [3-fluoro-4-(hexyloxy)phenyl]methanamine (486 mg, 2.2 mmol), 4-chloroquinoline (541 mg, 3.3 mmol), TEA (4 mL), and NMP (0.5 mL) at 130° C. in a sealed tube for 5 days following the method for N-[8-(3-ethoxypropoxy)octyl]quinolin-4-amine. $^1$H NMR (CDCl$_3$) δ 8.5 (d, 1H), 8.0 (d, 1H), 7.8 (d, 1H), 7.6 (m, 1H), 7.4 (m, 1H), 7.25 (t, 1H), 6.6 (m, 2H), 6.45 (d, 1H), 5.8 (br s, 1H, NH̲), 4.5 (m, 2H, AB), 3.9 (t, 2H), 1.8 (m, 2H), 1.6-1.2 (m, 6H), 0.9 (m, 3H).

Example 68

N-[4-(Decyloxy)benzyl]quinolin-4-amine

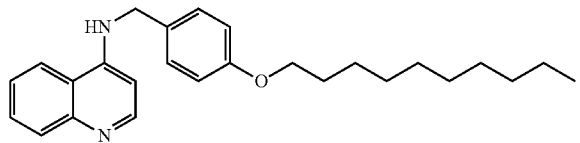 [SMILES: CCCCCCCCCCOc1ccc(CNc2ccnc3ccccc23)cc1]

4-(Decyloxy)benzonitrile A mixture of 4-hydroxybenzonitrile (4.32 g, 36.3 mmol), 1-bromodecane (6.80 mL, 32.9 mmol), and K$_2$CO$_3$ (6.61 g, 47.8 mmol) in 20 mL of DMF was reacted for 2 days. The solvent was evaporated in vacuo. The residue was partitioned between 50% EA/Hex (3×150 mL) and 5% Na$_2$CO$_3$ (3×80 mL), H$_2$O (40 mL), 0.1M HCl (40 mL), and brine (80 mL). The organic phases were dried over anhydrous Na$_2$SO$_4$ and concentrated to give 8.30 g of colorless oil that solidified upon standing. $^1$H NMR (CDCl$_3$) δ 7.54 and 6.90 (m, 4H, AA'BB'), 3.97 (t, 2H, J=6.6 Hz), 1.78 (m, 2H), 1.42 (m, 2H), 1.34-1.25 (m, 12H), 0.86 (m, 3H); $^{13}$C NMR (CDCl$_3$) δ 162.6, 134.0, 119.4, 115.3, 103.7, 68.5, 32.0, 29.6, 29.4, 29.4, 29.1, 26.0, 22.8, 14.2.

[4-(Decyloxy)phenyl]methanamine Lithium aluminum hydride (2.0 g, 53 mmol) was added in portions to a mixture of 4-(decyloxy)benzonitrile (8.30 g, 32.0 mmol) and 80 mL of THF cooled by an ice bath. Then, the mixture was allowed to warm to room temperature. After 2 hr, the mixture was cooled by an ice bath, and 2 mL H$_2$O, 2 mL 15% NaOH, and 6 mL H$_2$O were added sequentially and cautiously. The resulting solids were filtered, and the solids were washed with 5% MeOH/DCM+1% TEA. The filtrate was concentrated, then taken up in DCM and washed with 5% Na$_2$CO$_3$. The organic phase was dried over anhydrous Na$_2$SO$_4$ and concentrated. SPE, washing with 40% isopropyl acetate/Hex and eluting with 3% MeOH/DCM+2% TEA, gave ninhydrin (+) fractions. These fractions were concentrated, and the residue was taken up in DCM, washed with 5% Na$_2$CO$_3$, dried over anhydrous Na$_2$SO$_4$, and concentrated to give 7.61 g of colorless solid. Rf 0.11 (10% MeOH/DCM); $^1$H NMR (CDCl$_3$) δ 7.18 and 6.83 (m, 4H, AA'BB'), 3.90 (t, 2H, J=6.6 Hz), 3.76 (s, 2H), 1.75 (m, 2H), 1.56 (br s, 2H, NH̲$_2$), 1.43 (m, 2H), 1.39-1.26 (m, 12H), 0.87 (t, 3H, J=6.9 Hz); $^{13}$C NMR (CDCl$_3$) δ 158.1, 135.4, 128.2, 114.5, 68.0, 46.0, 32.0, 29.6, 29.6, 29.5, 29.4, 26.1, 22.7, 14.2.

N-[4-(Decyloxy)benzyl]quinolin-4-amine [4-(Decyloxy)phenyl]methanamine (5.90 g, 22.4 mmol) was taken up in 100 mL of 1-pentanol, and 25 mL was removed by distillation. The mixture was cooled slightly, and tripropylamine (6.50 mL, 34.1 mmol) and 4-chloroquinoline (3.63 g, 22.3 mmol) were added. Heating at reflux was continued for 24 hr. Then, the volatile components were evaporated, and the residue was partitioned between DCM and 5% Na$_2$CO$_3$. The organic phase was dried over anhydrous Na$_2$SO$_4$ and concentrated onto silica gel. SPE, washing with 50% EA/Hex and then eluting with 10% MeOH/DCM, gave a solid. The solid was taken up in DCM, washed with 5% Na$_2$CO$_3$, dried over anhydrous Na$_2$SO$_4$, and concentrated to give a solid. Recrystallization from EA/Hex gave 3.70 g colorless solid. Rf 0.13 (10% MeOH/DCM); mp 96.5-97.0° C.; $^1$H NMR (CDCl$_3$) δ 8.55 (d, 1H, J=5.2 Hz), 7.99 (d, 1H, J=8.5 Hz), 7.74 (d, 1H, J=8.4 Hz), 7.63 (m, 1H), 7.42 (m, 1H), 7.30 and 6.90 (m, 4H, AA'BB'), 6.47 (d, 1H, J=5.1 Hz), 5.30 (br s, 1H, NH̲), 4.44 (m, 2H, AB), 3.95 (m, 2H), 1.79 (m, 2H), 1.46 (m, 2H), 1.32-1.27 (m, 10H), 0.88 (m, 3H); $^{13}$C NMR (CDCl$_3$) δ 159.1, 151.3, 149.6, 148.7, 130.2, 129.4, 129.2, 129.2, 124.9, 119.5, 118.9, 115.1, 99.5, 68.3, 47.3, 32.1, 29.8, 29.8, 29.6, 29.5, 29.5, 26.2, 22.9, 14.3.

Example 69

N-[3-(Decyloxy)benzyl]quinolin-4-amine

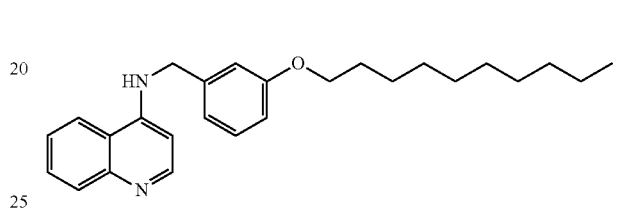

3-(Decyloxy)benzaldehyde 1-Bromodecane (15.0 mL, 72.6 mmol) was added to a mixture of 3-hydroxybenzaldehyde (9.75 g, 79.9 mmol) and K$_2$CO$_3$ (12.2 g, 88.4 mmol) in 80 mL of DMF heated at 50° C. using mechanical stirring. After 22 hr, the mixture was diluted with H$_2$O (100 mL) and extracted with EA (3×100 mL), and the organic phases were washed with 5% Na$_2$CO$_3$ and H$_2$O (100 mL each), 0.1M HCl (2×100 mL), and brine (100 mL), and dried over anhydrous Na$_2$SO$_4$. Evaporation of the volatile components yielded 18.74 g of product as a brown oil. Rf 0.54 (10% EA/Hex); $^1$H NMR (CDCl$_3$) δ 9.96 (s, 1H), 7.44-7.37 (m, 3H), 7.18 (m, 1H), 4.00 (t, 2H, J=6.6 Hz), 1.80 (m, 2H), 1.46 (m, 2H), 1.36-1.23 (m, 12H), 0.88 (m, 3H); $^{13}$C NMR (CDCl$_3$) δ 192.4, 159.9, 138.0, 130.2, 123.5, 122.2, 113.0, 68.5, 32.1, 29.8, 29.7, 29.6, 29.5, 29.3, 26.2, 22.9, 14.3.

[3-(Decyloxy)phenyl]methanol Sodium borohydride (2.63 g, 69.2 mmol) was added to a mixture of 3-(decyloxy)benzaldehyde (18.74 g) and 160 mL of MeOH cooled by an ice bath. After 1 hr, residual hydride was quenched by adding H$_2$O, and 80 mL of 1M HCl was added slowly, resulting in precipitation. The volatile components were evaporated, and the residue was partitioned between 50% EA/Hex and H$_2$O, 5% Na$_2$CO$_3$ (2×), H$_2$O, and brine. The organic phases were dried over anhydrous Na$_2$SO$_4$, filtered through a pad of silica gel, and concentrated to give 21.05 g of product as a light brown solid. Rf 0.11 (10% EA/Hex) 0.28 (1:4:5 EA/toluene/Hex); $^1$H NMR (CDCl$_3$) δ 7.24 (m, 1H), 6.90-6.88 (m, 2H), 6.81 (m, 1H), 4.60 (br s, 2H, AB), 3.94 (t, 2H, J=6.6 Hz), 2.55 (br s, 1H, OH̲), 1.78 (m, 2H), 1.46 (m, 2H), 1.38-1.24 (m, 12H), 0.91 (m, 3H); $^{13}$C NMR (CDCl$_3$) δ 159.5, 142.7, 129.6, 119.0, 113.8, 113.0, 68.1, 65.2, 32.0, 29.8, 29.7, 29.6, 29.5, 29.4, 26.2, 22.8, 14.3.

3-(Decyloxy)benzyl methanesulfonate Triethylamine (11.8 mL, 84.4 mmol) was added to a mixture of [3-(Decyloxy)phenyl]methanamine (21.05 g, mmol) and methanesulfonyl chloride (6.60 mL, 84.4 mmol) in 120 mL of THF cooled by an ice bath. A precipitate formed rapidly. After 1 hr, 5 mL of H$_2$O was added, and the volatile components were evaporated. The residue was partitioned between EA and H$_2$O, saturated NaHCO$_3$, H$_2$O, 0.1M HCl, and brine. The organic phases were dried over anhydrous Na₂SO₄, filtered through a pad of silica gel, and concentrated to give 23.53 g of 3-(decyloxy)benzyl methanesulfonate as an amber oil that solidified upon standing. Rf 0.45 (1:4:5 EA/toluene/Hex) 0.35 (20% EA/Hex); ¹H NMR (CDCl₃) δ 7.29 (m, 1H), 6.98-6.90 (m, 3H), 5.19 (m, 2H, AB), 3.95 (t, 2H, J=6.6 Hz), 2.90 (s, 3H), 1.78 (m, 2H), 1.43 (m, 2H), 1.36-1.28 (m, 12H), 0.88 (m, 3H); ¹³C NMR (CDCl₃) δ 159.6, 134.9, 130.1, 120.8, 115.6, 114.8, 71.7, 68.2, 38.4, 32.0, 29.7, 29.7, 29.5, 29.4, 29.4, 26.2, 22.8, 14.3.

N-[3-(Decyloxy)benzyl]phthalimide A mixture of 3-(decyloxy)benzyl methanesulfonate (23.53 g, 68.8 mmol) and potassium phthalimide (14.00 g, 75.7 mmol) in 90 mL of DMF was reacted at room temperature for 16 hr and at 50-60° C. for 3 hr. The mixture was cooled, diluted with 350 mL H₂O, and extracted with EA (3×400 mL). The organic phases were washed with H₂O (3×200 mL) and brine (2×200 mL), dried over anhydrous Na₂SO₄, and concentrated to give a colorless solid. The solid was broken up and washed with 10% EA/Hex to give 11.40 g of solid as a colorless solid. The washes were partially concentrated to give an additional 6.95 g of colorless solid. Rf 0.50 (20% EA/Hex); ¹H NMR (CDCl₃) δ 7.84 and 7.70 (m, 4H, AA'BB'), 7.21 (m, 1H), 7.00-6.96 (m, 2H), 6.79 (m, 1H), 4.81 (s, 2H, AB), 3.92 (t, 2H, J=6.6 Hz), 1.74 (m, 2H), 1.43 (m, 2H), 1.30-1.26 (m, 12H), 0.88 (m, 3H); ¹³C NMR (CDCl₃) δ 168.2, 159.6, 137.9, 134.2, 132.4, 129.9, 123.6, 120.8, 114.8, 114.1, 68.2, 41.8, 32.1, 29.8, 29.8, 29.6, 29.5, 29.5, 29.5, 26.2, 22.9, 14.3.

[3-(Decyloxy)phenyl]methanamine Hydrazine monohydrate (3.90 mL, 80.3 mmol) was added in three portions to a mixture of N-[3-(decyloxy)benzyl]phthalimide (5.12 g, 13.0 mmol) and IPA heated at reflux. After the starting material was consumed as observed by TLC (30 hr), the mixture was cooled and concentrated. The residue was partitioned between isopropyl acetate and 5% Na₂CO₃ and brine, and the organic phases were dried over anhydrous Na₂SO₄ and concentrated. SPE, washing with 50% isopropyl acetate/Hex and then eluting with 3% MeOH/DCM+2% TEA, gave ninhydrin (+) material. Partial concentration and washing of the filtrate with 5% Na₂CO₃ and drying over Na₂SO₄ gave 3.25 g of yellow oil after drying in vacuo.

N-[3-(Decyloxy)benzyl]quinolin-4-amine A mixture of [3-(decyloxy)phenyl]methanamine (2.54 g, 9.66 mmol), 4-chloroquinoline (1.73 g, 10.62 mmol), and tripropylamine (4.00 mL, 21.0 mmol) in 65 mL of 1-pentanol was heated at reflux for 16 hr. Analytical TLC indicated a substantial quantity of unreacted [3-(decyloxy)phenyl]methanamine. 4-Chloroquinoline (0.85 g, 5.21 mmol) and tripropylamine (2.00 mL, 10.5 mmol) were added. After 24 hr, the mixture was cooled and 15 mL of 1N NaOH were added. The volatile components were evaporated, the residue was taken up in DCM and washed with 5% Na₂CO₃, and the organic phase was dried over anhydrous Na₂SO₄ and evaporated onto silica gel. SPE, washing with 70% EA/Hex and eluting with 50% EA/Hex+2% TEA, gave 2.62 g of white solid after crystallization from IPA. Recrystallization from 30% EA/Hex gave 2.00 g of N-[3-(decyloxy)benzyl]quinolin-4-amine as a white powdery solid. Rf 0.24 (50% EA/Hex+2% TEA) 0.40 (10% MeOH/DCM); mp 71.0-72.0° C.; ¹H NMR (CDCl₃) δ 8.55 (d, 1H, J=5.1 Hz), 8.00 (m, 1H), 7.77 (m, 1H), 7.64 (ddd, 1H, J=1.5, 7.0, 8.5 Hz), 7.43 (ddd, 1H, J=1.5, 7.0, 8.5 Hz), 7.28 (m, 1H), 6.97-6.93 (m, 2H), 6.85 (dd, 1H, J=1.8, 8.1 Hz), 6.45 (d, 1H, J=5.5 Hz), 5.38 (m, 1H, NH), 4.49 (m, 2H, AB), 3.94 (m, 2H), 1.77 (m, 2H), 1.42 (m, 2H), 1.34-1.26 (m, 10H), 0.87 (m, 3H); 159.9, 151.4, 149.6, 148.7, 139.3, 130.3, 130.2, 129.2, 125.0, 119.7, 119.5, 18.95, 114.1, 113.8, 99.6, 68.3, 47.8, 32.1, 29.8, 29.8, 29.6, 29.5, 29.5, 26.3, 22.9, 14.3.

Example 70

N-(3-Phenoxybenzyl)quinolin-4-amine

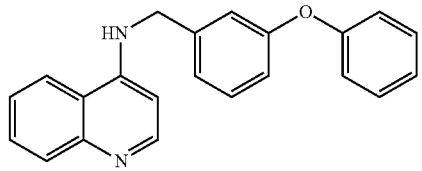 [SMILES: c1ccc(Oc2cccc(CNc3ccnc4ccccc34)c2)cc1]

3-Phenoxybenzyl methanesulfonate A mixture of 3-phenoxybenzyl alcohol (15.44 g, 77.2 mmol) and TEA (13.1 mL, 93.4 mmol) in 180 mL of THF and 100 mL of EA was cooled using an ice bath. Then, methanesulfonyl chloride (6.60 mL, 84.4 mmol) was added. A white precipitate formed rapidly. After 2 hr, 5 mL of H₂O were added, and the volatile components were evaporated. The residue was partitioned between EA (3×300 mL) and H₂O, saturated NaHCO₃, H₂O, 0.1M HCl, and brine (100 mL each). The combined organic phases were dried over Na₂SO₄, filtered through a pad of silica gel, and concentrated to give 22.02 g of colorless oil. Rf 0.38 (30% EA/Hex); ¹H NMR (CDCl₃) δ 7.4-7.3 (m, 3H), 7.2-7.1 (m, 2H), 7.1-7.0 (m, 4H), 5.2 (m, 2H, AB), 2.9 (s, 3H); ¹³C NMR (CDCl₃) δ 158.0, 156.7, 135.5, 130.4, 130.1, 124.0, 123.4, 119.5, 119.4, 118.8, 71.0, 38.4.

N-(3-Phenoxybenzyl)phthalimide A mixture of 3-phenoxybenzyl methanesulfonate (22.5 g, 80.9 mmol) and potassium phthalimide (16.4 g, 88.6 mmol) in 200 mL of NMP was stirred at 50° C. for 17 hr using a mechanical stirrer. Then, H₂O (100 mL) was added, and the volatile material was evaporated. The residue was partitioned between EA and 5% Na₂CO₃ (2×), H₂O, 0.1M HCl, and brine. The organic phases were dried over Na₂SO₄, filtered through a pad of silica gel, and concentrated. Crystallization from IPA gave 23.55 g of colorless solid. Rf 0.53 (30% EA/Hex);

¹H NMR (CDCl₃) δ 7.85 and 7.73 (m, 4H, AA'BB'), 7.34-7.24 (m, 3H), 7.15-7.07 (m, 3H), 6.99-6.97 (m, 2H), 6.88-6.85 (m, 1H), 4.82 (m, 2H, AB); ¹³C NMR (CDCl₃) δ 168.1, 157.6, 157.1, 138.4, 134.5, 134.2, 132.2, 130.2, 129.9, 123.8, 123.6, 123.6, 123.2, 119.1, 119.1, 118.1, 41.4.

(3-Phenoxyphenyl)methanamine Hydrazine monohydrate (3.50 mL, 72.1 mmol) was added to a mixture of N-(3-phenoxybenzyl)phthalimide (6.28 g, 19.1 mmol) and 200 mL of IPA while using mechanical stirring. The mixture was heated at reflux for 7 hr. After standing overnight, a precipitate had formed. The mixture was concentrated by evaporation, and the residue was partitioned between isopropyl acetate and 5% Na₂CO₃ and brine. The organic phases were dried over Na₂SO₄, filtered, and concentrated. SPE, washing with 50% isopropyl acetate/Hex and then eluting with 3% MeOH/DCM+2% TEA gave fractions that contained ninhydrin (+) product. The combined product fractions were washed with 5% Na₂CO₃, dried over Na₂SO₄, filtered, and concentrated to give 3.25 g of yellow oil. Rf 0.28 (10% MeOH/DCM); ¹H NMR (CDCl₃) δ 7.36-7.25 (m, 3H), 7.12-6.95 (m, 5H), 6.87 (ddd, 1H, J=1.0, 2.5, 8.2 Hz), 3.82 (br s, 2H), 2.15 (br s, 2H, NH₂).

N-(3-Phenoxybenzyl)quinolin-4-amine (3-Phenoxyphenyl)methanamine (2.02 g, 10.2 mmol) was taken up in 60 mL of 1-pentanol, and then 15 mL of volatile material was removed by distillation. The mixture was cooled below boiling, and tripropylamine (3.80 mL, 19.9 mmol) and 4-chloroquinoline (1.65 g, 10.2 mmol) were added. Heating at reflux was resumed. After 66 hr, volatile material was removed by evaporation. The mixture was partitioned between DCM (150, 100 mL) and 5% $Na_2CO_3$ (80 mL). The combined organic phases were dried over $Na_2SO_4$, filtered, and concentrated to give a solid. Recrystallization from EA/Hex gave 2.08 g of colorless solid. Rf 0.34 (10% MeOH/DCM); mp 163.0-164.0° C.; $^1$H NMR (CDCl$_3$) δ 8.54 (d, 1H, J=5.5 Hz), 8.00 (m, 1H), 7.76 (d, 1H, J=8.1 Hz), 7.64 (m, 1H), 7.43 (m, 1H), 7.34-7.29 (m, 3H), 7.11 (m, 1H), 7.05 (s, 1H), 7.02-6.99 (m, 2H), 6.94 (dd, 1H, J=2.2, 8.0 Hz), 6.42 (d, 1H, J=5.5 Hz), 5.46 (br s, 1H, NH) 4.51 (m, 2H, AB); $^{13}$C NMR (CDCl$_3$) δ 158.2, 156.9, 151.3, 149.5, 148.7, 139.9, 130.5, 130.3, 130.0, 129.3, 125.0, 123.8, 122.2, 119.5, 119.3, 118.9, 118.0, 117.8, 99.7, 47.4.

Example 71

N-[3-(Benzyloxy)benzyl]quinolin-4-amine

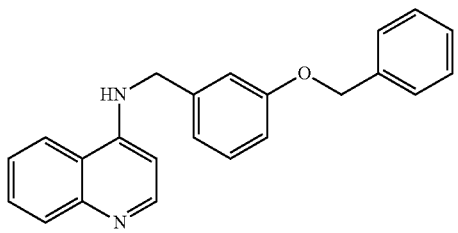 [SMILES: c1ccc(COc2cccc(CNc3ccnc4ccccc34)c2)cc1]

3-(Benzyloxy)benzonitrile A mixture of 3-hydroxybenzonitrile (504 mg, 4.24 mmol), benzyl chloride (607 mg, 4.78 mmol), and $K_2CO_3$ (605 mg, 4.38 mmol) in 2 mL of DMF reacted for 42 hr. The mixture was diluted with 50% EA/Hex and washed with 5% $Na_2CO_3$ (2×) and brine made acidic with 1M HCl. The organic phase was dried over anhydrous $MgSO_4$ and concentrated. FC (15% EA/Hex) gave 780 mg of colorless oil. Rf 0.50 (20% EA/Hex); $^1$H NMR (CDCl$_3$) δ 7.43-7.31 (m, 6H), 7.26-7.17 (m, 3H), 5.08 (m, 2H, AB).

[3-(Benzyloxy)phenyl]methanamine A mixture of 3-(benzyloxy)benzonitrile and 30 mL of THF was cooled by an ice path. LAH (195 mg and then 190 mg) was added. The mixture was allowed to warm to room temperature. After 24 hr, the mixture was cooled by an ice bath, and 0.40 mL $H_2O$, 0.40 mL 15% NaOH, and 1.2 mL $H_2O$ were added in succession. The heterogeneous mixture was diluted with 5% MeOH/DCM and preloaded on silica gel. SPE, washing with 5% MeOH and eluting with 10% MeOH/DCM+2% TEA gave 672 mg of colorless oil that solidified upon standing. $^1$H NMR (CDCl$_3$) δ 7.48-7.23 (m, 6H), 6.98-6.83 (m, 3H), 5.07 (m, 2H, AB), 3.83 (m, 2H, AB).

N-[3-(Benzyloxy)benzyl]quinolin-4-amine (600 mg) was prepared from [3-(benzyloxy)phenyl]methanamine (670 mg, 3.14 mmol), 4-chloroquinoline (767 mg, 4.70 mmol), and DIEA (1.20 mL, 6.88 mmol) in 0.5 mL DMF heated in a sealed tube. FC (7% MeOH/DCM) gave 600 mg of product. Rf 0.38 (10% MeOH/DCM); $^1$H NMR (CDCl$_3$) δ 8.43 (d, 1H, J=5.4 Hz), 8.01-7.96 (m, 2H), 7.62-7.56 (m, 1H), 7.40-7.22 (m, 7H), 6.99-6.88 (m, 3), 6.53 (br s, 1H, NH), 6.34 (d, 1H, J=5.5 Hz), 4.99 (s, 2H), 4.48 (m, 2H, AB).

Example 72

N-(3-Phenethoxybenzyl)quinolin-4-amine

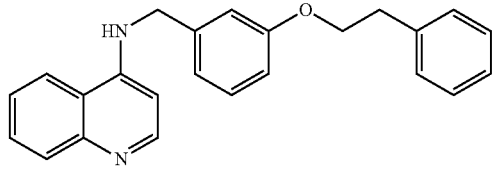 [SMILES: c1ccc(CCOc2cccc(CNc3ccnc4ccccc34)c2)cc1]

N-(3-Phenethoxybenzyl)quinolin-4-amine was prepared by the method for N-[3-(benzyloxy)benzyl]quinolin-4-amine starting with 3-hydroxybenzonitrile (561 mg, 4.71 mmol), 2-bromoethylbenzene (1.34 g, 7.24 mmol), and $K_2CO_3$ (1.00 g, 7.25 mmol) in 2 mL of DMF heated at 60° C.

3-(Phenethoxy)benzonitrile (454 mg): Rf 0.46 (20% EA/Hex): $^1$H NMR (CDCl$_3$) δ 7.38-7.20 (m, 7H), 7.10 (m, 2H), 4.18 (t, 2H, J=6.9 Hz), 3.11 (t, 2H, J=6.9 Hz).

(3-(Phenethoxyphenyl)methanamine (480 mg): $^1$H NMR (CDCl$_3$) δ 7.36-7.20 (m, 6H), 6.87 (m, 2H), 6.78 (m, 1H), 4.18 (t, 2H, J=7.2 Hz), 3.82 (m, 2H, AB), 3.10 (t, 2H, J=7.2 Hz), 2.16 (br s, 2H, NH$_2$).

N-(3-Phenethoxybenzyl)quinolin-4-amine (358 mg): Rf 0.12 (5% MeOH/DCM); $^1$H NMR (CDCl$_3$) δ 8.39 (d, 1H, J=5.4 Hz), 7.96 (d, 1H, J=8.4 Hz), 7.91 (d, 1H, J=8.4 Hz), 7.59 (m, 1H), 7.38 (m, 1H), 7.31-7.18 (m, 6H), 6.94-6.90 (m, 2H), 6.80 (dd, 1H, J=2.4, 8.1 Hz), 6.35 (d, 1H, J=5.5 Hz), 6.26 (br s, 1H), 4.48 (m, 2H, AB), 4.12 (t, 2H, J=7.0 Hz), 3.05 (m, 2H).

Example 73

N-[4-(Quinolin-4-ylamino)butyl]benzamide

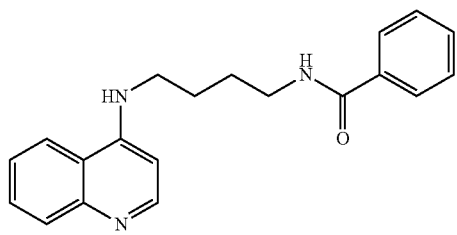 [SMILES: O=C(NCCCCNc1ccnc2ccccc12)c1ccccc1]

$N^1$-(Quinolin-4-yl)butane-1,4-diamine A mixture of 1,4-butanediamine (1.54 g, 17.5 mmol), 4-chloroquinoline (357 mg, 2.19 mmol), and DIEA (0.50 mL, 2.87 mmol) was heated at 130° C. in a sealed tube for 24 hr. The mixture was cooled, taken up in EA, and washed with 5% $Na_2CO_3$ (3×) and brine. The organic phase was dried over $Na_2SO_4$ and concentrated. $^1$H NMR (20% CD$_3$OD/CDCl$_3$) δ 8.33 (d, 1H, J=5.5 Hz), 7.86 (ddd, 1H, J=0.5, 1.5, 8.4 Hz), 7.81 (ddd, 1H, J=0.5, 1.2, 8.4 Hz), 7.53 (ddd, 1H, J=1.3, 6.7, 8.4 Hz), 7.33 (ddd, 1H, J=1.2, 6.9, 8.4 Hz), 6.29 (d, 1H, J=5.5 Hz), 3.20 (m, 2H), 2.66 (t, 2H, J=6.9 Hz), 1.69 (m, 2H), 1.51 (m, 2H).

N-[4-(Quinolin-4-ylamino)butyl]benzamide $N^1$-(Quinolin-4-yl)butane-1,4-diamine (185 mg, 0.86 mmol) was taken up in 5 mL of pyridine, and the mixture was concentrated. The residue was taken up in 10 mL of DCM, cooled by an ice bath, and TEA (0.49 mL, 3.5 mmol) and then benzoyl chloride (0.40 mL, 3.43 mmol) were added. The mixture was allowed to warm to room temperature. After 2 hr, 3.43 mL of 1N NaOH were added, and the volatile components were removed by distillation. The residue was partitioned between EA and 5% Na$_2$CO$_3$ and brine. The organic phases were dried over Na$_2$SO$_4$ and concentrated. SPE, washing with 5% MeOH/DCM and eluting with 15% MeOH/DCM, gave an oily solid. Repurification by preparative TLC (15% MeOH/DCM) gave the product as a solid. Rf 0.21 (15% MeOH/DCM); $^1$H NMR (CDCl$_3$) δ 8.31 (d, 1H, J=5.7 Hz), 8.10 (m, 1H), 7.80-7.77 (m, 3H), 7.62 (ddd, 1H, J=1.2, 6.6, 8.4 Hz), 7.55-7.39 (m, 4H), 6.51 (d, 1H, J=5.5 Hz), 3.45 (q, 2H, J=7 Hz), 1.86-1.76 (m, 4H).

Example 74

N-[6-(Quinolin-4-ylamino)hexyl]benzamide

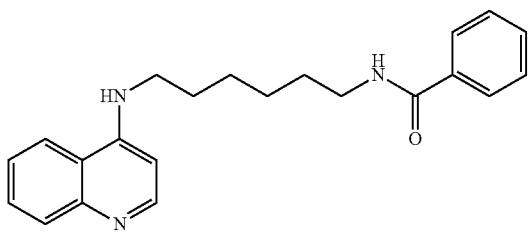 [SMILES: O=C(NCCCCCCNc1ccnc2ccccc12)c1ccccc1]

N$^1$-(Quinolin-4-yl)hexane-1,6-diamine A mixture of 1,6-hexanediamine (2.05 g, 17.7 mmol) and 4-chloroquinoline (297 mg, 1.82 mmol) was heated at 130° C. in a sealed tube for 24 hr. The mixture was cooled, partitioned between EA (3×) and 5% Na$_2$CO$_3$ (3×) and brine. The organic phases were dried over Na$_2$SO$_4$ and concentrated. $^1$H NMR (20% CD$_3$OD/CDCl$_3$) δ 8.39 (d, 1H, J=5.4 Hz), 7.87 (d, 1H, J=8.1 Hz), 7.75 (d, 1H, J=8.4 Hz), 7.56 (ddd, 1H, J=1.3, 6.9, 8.4 Hz), 7.36 (m, 1H), 6.35 (d, 1H, J=5.4 Hz), 3.26 (m, 2H), 2.63 (m, 2H), 1.71 (m, 2H), 1.49-1.38 (m, 6H).

N-[6-(Quinolin-4-ylamino)hexyl]benzamide N$^1$-(Quinolin-4-yl)hexane-1,6-diamine (230 mg, 0.946 mmol) was taken up in 5 mL of pyridine, and the mixture was concentrated. The residue was taken up in 10 mL of DCM, cooled by an ice bath, and TEA (0.53 mL, 3.8 mmol) and then benzoyl chloride (0.44 mL, 3.78 mmol) were added. The mixture was allowed to warm to room temperature. After 2 hr, 3.78 mL of 1N NaOH were added. The mixture was partitioned between DCM and 5% Na$_2$CO$_3$. The organic phase was dried over Na$_2$SO$_4$ and concentrated. Purification by preparative TLC (15% MeOH/DCM) gave the product. The residue from concentration of the eluate was taken up in DCM, washed with 5% Na$_2$CO$_3$, dried over Na$_2$SO$_4$ and concentrated to give the product. Rf 0.23 (15% MeOH/DCM); $^1$H NMR (CDCl$_3$) δ 8.30 (d, 1H, J=6.0 Hz), 8.09 (d, 1H, J=8.4 Hz), 7.91 (d, 1H, J=8.4 Hz), 7.82-7.78 (m, 2H), 7.55 (m, 1H), 7.45-7.30 (m, 4H), 6.94 (t, 1H, J=6 Hz), 6.81 (br s, 1H), 6.24 (d, 1H, J=6.2 Hz), 3.40 (m, 2H), 3.25 (m, 2H), 1.68-1.54 (m, 8H).

Example 75

N-[8-(Quinolin-4-ylamino)octyl]benzamide

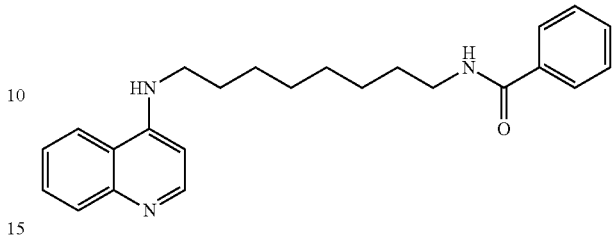

N-(8-Aminooctyl)benzamide A mixture of 1,8-octanediamine (3.27 g, 22.7 mmol) and methyl benzoate (0.40 mL, 3.20 mmol) was heated at 115° C. for 24 hr. The mixture was cooled and partitioned between EA and H$_2$O. The organic phase, which contained a 1:1 molar ratio of diamine and monoamide, was concentrated. Reverse-phase SPE, washing with 20% MeOH/H$_2$O and eluting with MeOH, gave the product fraction, which was concentrated, taken up in DCM, washed with 5% Na$_2$CO$_3$, dried over Na$_2$SO$_4$, and concentrated to give 698 mg of product. $^1$H NMR (20% CD$_3$OD/CDCl$_3$) δ 7.64-7.59 (m, 2H), 7.43 (br s, 1H, NH), 7.32-7.18 (m, 3H), 3.19 (m, 2H), 2.45 (m, 2H), 1.42 (m, 2H), 1.27-1.04 (m, 10H).

N-[8-(Quinolin-4-ylamino)octyl]benzamide A mixture of N-(8-aminooctyl)benzamide (357 mg, 1.44 mmol), 4-chloroquinoline (312 mg, 1.91 mmol), and DIEA (0.50 mL, 2.87 mmol) in 1 mL of NMP was heated at 160° C. in a sealed tube for 24 hr. The mixture was cooled, diluted with DCM, and washed with 5% Na$_2$CO$_3$. The organic phase was dried over Na$_2$SO$_4$ and concentrated. SPE, washing with 5% MeOH/DCM and eluting with 2.5% MeOH/DCM+2% TEA, gave the product as an oil, which was crystallized from EtOH. Rf 0.33 (50% EA/Hex+2% TEA); $^1$H NMR (CDCl$_3$) δ 8.33 (d, 1H, J=5.7 Hz), 7.87 (dd, 1H, J=0.7, 8.4 Hz), 7.80 (d, 1H, J=8.7 Hz), 7.74-7.71 (m, 2H), 7.58 (ddd, 1H, J=1.5, 6.9, 8.4 Hz), 7.48-7.34 (m, 4H), 6.38 (d, 1H, J=5.7 Hz), 3.38-3.26 (m, 4H), 1.74-1.35 (m, 12H).

Example 76

3-Methoxy-N-[8-(quinolin-4-ylamino)octyl]benzamide

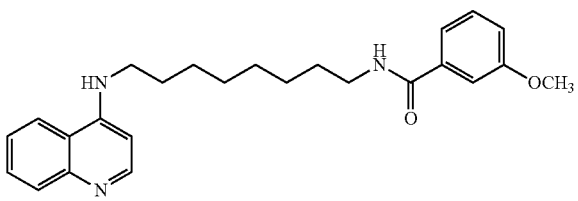 [SMILES: COc1cccc(C(=O)NCCCCCCCCNc2ccnc3ccccc23)c1]

N-(8-Aminooctyl)-3-methoxybenzamide A mixture of methyl 3-methoxybenzoate (863 mg, 5.20 mmol) and 1,8-octanediamine (6.90 g) was heated at 110-120° C. for 24 hr. The mixture was cooled and partitioned between EA (3×60 mL) and H$_2$O, 2.5% Na$_2$CO$_3$ (3×), and brine (60 mL each). The organic phases were dried over anhydrous Na$_2$SO$_4$ and concentrated. NMR showed the residue consisted of 2.3:1 ratio of amide and diamine. Reverse-phase SPE (ODS-silica gel), washing with 20% MeOH/H$_2$O and then eluting with MeOH, gave 1.43 g yellow oil. NMR showed the oil consisted of 7.3:1 ratio of amide and diamine.

3-Methoxy-N-[8-(quinolin-4-ylamino)octyl]benzamide A mixture of N-(8-aminooctyl)-3-methoxybenzamide (540 mg, 1.94 mmol), 4-chloroquinoline (340 mg, 2.08 mmol), and DIEA (0.80 mL, 4.59 mmol) in 2.5 mL of NMP was heated at 160° C. in a sealed tube for 3 days. The mixture was cooled, diluted with EA, washed with 5% Na$_2$CO$_3$ and brine, dried over Na$_2$SO$_4$, and concentrated. SPE, washing with 1% MeOH/DCM and then eluting with 7.5% MeOH/DCM+2% TEA, gave the product as a solid. Rf 0.19 (EA+2% TEA); mp 162-165° C. (from MeOH);

$^1$H NMR (20% CD$_3$OD/CDCl$_3$) δ 8.38 (d, 1H, J=5.7 Hz), 8.04 (d, 1H, J=8.4 Hz), 7.92 (d, 1H, J=8.4 Hz), 7.57 (m, 1H), 7.40-7.21 (m, 4H), 6.95 (ddd, 1H, J=1.2, 2.7, 8.1 Hz), 6.85 (m, 1H), 6.36 (d, 1H, J=5.7 Hz), 6.31 (br s, 1H, NH̲), 3.75 (s, 3H), 3.41-3.25 (m, 4H), 1.72-1.16 (m, 12H).

Example 77

4-Methoxy-N-[8-(quinolin-4-ylamino)octyl]benzamide

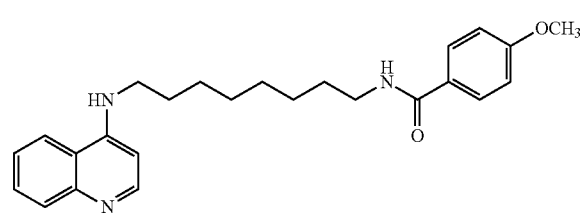 [SMILES: COc1ccc(C(=O)NCCCCCCCCNc2ccnc3ccccc23)cc1]

N-(8-Aminooctyl)-4-methoxybenzamide A mixture of methyl 4-methoxybenzoate (874 mg, 5.26 mmol) and 1,8-octanediamine (6.18 g) was heated at 110-120° C. for 4 days. The mixture was cooled and partitioned between EA (3×60 mL) and H$_2$O, 2.5% Na$_2$CO$_3$ (3×), and brine (60 mL each). The organic phases were dried over anhydrous Na$_2$SO$_4$ and concentrated. Reverse-phase SPE (ODS-silica gel), washing with 20% MeOH/H$_2$O and then eluting with MeOH, gave an oil. The oil was taken up in DCM and washed with 5% Na$_2$CO$_3$, dried over Na$_2$SO$_4$, and concentrated to give 533 mg of sticky yellow solid. $^1$H NMR (CD$_3$OD) δ 7.77 and 6.96 (m, 4H, AA'BB'), 4.88 (s, 3H), 3.34 (m, 2H), 3.13 (m, 1H, NH̲), 2.60 (m, 2H), 1.91 (2×s, 2H, NH̲$_2$), 1.62-1.33 (m, 12H).

4-Methoxy-N-[8-(quinolin-4-ylamino)octyl]benzamide A mixture of N-(8-aminooctyl)-4-methoxybenzamide (533 mg, 1.92 mmol) and 7.5 mL of anhydrous pyridine was evaporated to dryness. Then, 4-chloroquinoline (335 mg, 2.08 mmol) and DIEA (0.80 mL, 4.59 mmol) in 2.5 mL of NMP was added and the mixture was heated at 160° C. in a sealed tube for 3 days. The mixture was cooled, diluted with EA, washed with 5% Na$_2$CO$_3$ and brine, dried over Na$_2$SO$_4$, and concentrated. SPE, washing with 1% MeOH/DCM and then eluting with 7.5% MeOH/DCM+2% TEA, gave the product as a solid. Rf 0.00 (5% MeOH/DCM) 0.20 (EA+2% TEA); $^1$H NMR (20% CD$_3$OD/CDCl$_3$) δ 8.30 (d, 1H, J=5.7), 7.82-7.76 (m, 2H), 7.65 and 6.82 (m, 4H, AA'BB'), 7.53 (ddd, 1H, J=1.5, 6.9, 8.4 Hz), 7.33 (ddd, 1H, J=1.2, 6.9, 8.4 Hz), 6.32 (d, 1H, J=5.5 Hz), 3.74 (s, 3H), 3.32-3.19 (m, 4H), 1.70-1.25 (m, 12H).

Example 78

2-(Hexyloxy)-N-[2-(quinolin-4-ylamino)ethyl]benzamide

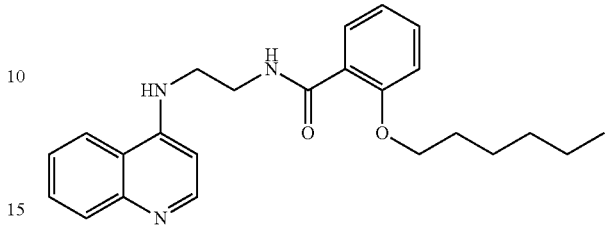

Methyl 2-(hexyloxy)benzoate A mixture of methyl salicylate (7.76 g, 51.1 mmol), K$_2$CO$_3$ (8.8 g, 64 mmol), and 1-bromohexane (8.60 mL, 61.5 mmol) in 30 mL of DMF was heated at 50° C. for 20.5 hr. The mixture was partitioned between 1:1 EA/Hex (3×150 mL) and 0.2M HCl, 0.1M HCl, and brine (50 mL of each). The organic phases were dried over Na$_2$SO$_4$ and concentrated. SPE, washing with Hex and eluting with 20% EA/Hex, gave 11.7 g colorless liquid.

N-(2-Aminoethyl)-2-(hexyloxy)benzamide A mixture of methyl 2-(hexyloxy)benzoate (2.11 g, 8.94 mmol) and 1,2-ethanediamine (5.40 mL, 81.0 mmol) was heated at 115° C. in a sealed tube for 72 hr. Then, the volatile components were evaporated in vacuo. The residue was taken up in 10 mL of MeOH and evaporated in vacuo to give 2.34 g amber liquid. $^1$H NMR (CD$_3$OD) δ 7.84 (m, 1H), 7.45 (ddd, 1H, J=1.9, 7.4, 9.2 Hz), 7.09 (d, 1H, J=8.1 Hz), 7.02 (m, 1H), 4.13 (t, 2H, J=6.5 Hz), 3.47 (m, 2H), 2.84 (m, 2H), 1.86 (m, 2H), 1.49 (m, 2H), 1.39-1.34 (m, 4H), 0.93 (m, 3H); $^{13}$C NMR (CD$_3$OD) δ 169.0, 158.5, 134.1, 132.0, 123.7, 122.0, 114.0, 70.4, 43.5, 42.3, 32.9, 30.4, 27.2, 23.9, 14.6.

2-(Hexyloxy)-N-[2-(quinolin-4-ylamino)ethyl]benzamide N-(2-Aminoethyl)-2-(hexyloxy)benzamide (2.34 g, 8.86 mmol) was taken up in 65 mL of 1-pentanol, and 15 mL was removed by distillation. The mixture was cooled slightly, and tripropylamine 3.40 mL, 17.8 mmol) and 4-chloroquinoline (1.60 g, 9.82 mmol) were added. The mixture was heated at reflux for 63 hr. Then, the mixture was concentrated in vacuo. The residue was partitioned between DCM and 5% Na$_2$CO$_3$, and the organic phase was dried over Na$_2$SO$_4$ and concentrated. FC (5% MeOH/DCM+2% TEA) gave 1.84 g of brown syrup, which solidified upon standing. The solid was rinsed with 20%, 33%, and 50% Et$_2$O/Hex and dried in vacuo to give 1.67 g of solid. Rf 0.30 (5% MeOH/DCM+2% TEA); $^1$H NMR (CDCl$_3$) δ 8.56-8.51 (m, 2H), 8.28 (dd, 1H, J=1.8, 8.1 Hz), 7.92 (d, 1H, J=8.8 Hz), 7.60 (m, 1H), 7.46-7.41 (m, 2H), 7.08 (m, 1H), 6.93 (d, 1H, J=8.0 Hz), 6.77 (br s, 1H, NH̲), 6.33 (d, 1H, J=5.1 Hz), 4.06 (t, 2H, J=6.6 Hz), 3.90 (m, 2H), 3.50 (m, 2H), 1.77 (m, 2H), 1.42-1.23 (m, 6H), 0.87 (t, 3H, J=7 Hz); $^{13}$C NMR (CDCl$_3$) δ 168.1, 157.3, 151.2, 150.3, 148.6, 133.5, 132.5, 129.8, 129.1, 124.9, 121.5, 120.9, 120.6, 119.1, 112.5, 98.1, 69.3, 46.1, 39.1, 31.5, 29.2, 26.0, 22.7, 14.2.

Example 79

2-(Hexyloxy)-N-[3-(quinolin-4-ylamino)propyl]benzamide

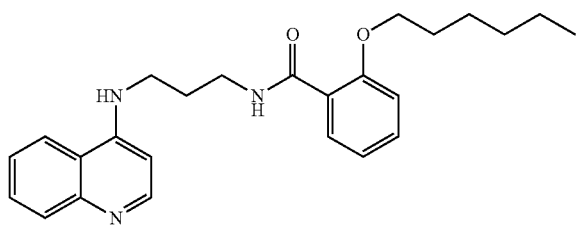 [SMILES: CCCCCCOc1ccccc1C(=O)NCCCNc1ccnc2ccccc12]

2-(Hexyloxy)-N-[3-(quinolin-4-ylamino)propyl]benzamide (1.6 g) was prepared by the method for 2-(hexyloxy)-N-[4-(quinolin-4-ylamino)butyl]benzamide, starting with methyl 2-(hexyloxy)benzoate (2.13 g) and 1,3-diaminopropane (6.00 mL) and using 4-chloroquinoline (1.70 g).

N-(3-Aminopropyl)-2-(hexyloxy)benzamide: $^1$H NMR (CDCl$_3$) δ 7.85 (dd, 1H, J=1.8, 7.7 Hz), 7.44 (ddd, 1H, J=1.8, 7.3, 9.2 Hz), 7.10 (d, 1H, J=8.4 Hz), 7.02 (m, 1H), 4.14 (m, 2H), 3.48 (m, 2H), 3.30 (m, 2H), 2.72 (m, 2H), 1.86 (m, 2H), 1.75 (m, 2H), 1.40-1.35 (m, 4H), 0.93 (m, 3H); $^{13}$C NMR (CDCl$_3$) δ 168.8, 158.5, 134.1, 132.0, 123.6, 122.0, 114.0, 70.4, 40.0, 38.2, 33.9, 32.9, 30.4, 27.2, 23.9, 14.6.

2-(Hexyloxy)-N-[3-(quinolin-4-ylamino)propyl]benzamide: Rf 0.08 (5% MeOH/DCM); $^1$H NMR (CDCl$_3$) δ 8.50 (d, 1H, J=5.5 Hz), 8.25 (dd, 1H, J=1.8, 7.7 Hz), 8.24-8.20 (m, 1H), 8.01-7.98 (m, 1H), 7.93 (dd, 1H, J=0.7, 8.4 Hz), 7.58 (ddd, 1H, J=1.1, 7.0, 8.1 Hz), 7.44-7.36 (m, 2H), 7.10-7.06 (m, 1H), 6.92 (d, 1H, J=8.1 Hz), 6.49-6.46 (t, 1H, J=6 Hz, NH), 6.39 (d, 1H, J=5.5 Hz), 4.03 (t, 2H), 3.63-3.59 (m, 2H), 3.46-3.42 (m, 2H), 2.64 (br s, 1H, NH), 1.95-1.89 (m, 2H), 1.81-1.74 (m, 2H), 1.45-1.27 (m, 6H), 0.89-0.86 (m, 3H); $^{13}$C NMR (CDCl$_3$) δ 166.8, 157.2, 151.0, 150.0, 148.7, 133.1, 132.4, 129.7, 129.1, 124.7, 121.4, 21.3, 120.4, 119.3, 112.4, 98.3, 69.2, 39.6, 39.6, 36.8, 31.6, 29.3, 28.7, 26.0, 22.7, 14.1.

Example 80

2-(Hexyloxy)-N-[4-(quinolin-4-ylamino)butyl]benzamide

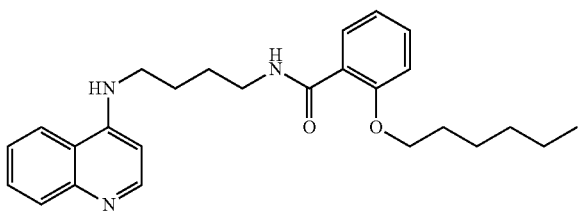 [SMILES: CCCCCCOc1ccccc1C(=O)NCCCCNc1ccnc2ccccc12]

N-(4-Aminobutyl)-2-(hexyloxy)benzamide A mixture of 1,4-diaminobutane (5.37 g, 61 mmol) and methyl 2-(hexyloxy)benzoate (1.80 g, 7.63 mmol) was heated at 110° C. in a sealed tube for 48 hr. The mixture was partitioned between isopropyl acetate (3×125 mL) and H$_2$O (100 mL), 5% Na$_2$CO$_3$ (2×100 mL), and brine (100 mL). The organic phases were dried over anhydrous Na$_2$SO$_4$ and concentrated to give 2.10 g of colorless syrup. $^1$H NMR (CDCl$_3$) δ 8.15 (dd, 1H, J=7.7, 1.8 Hz), 8.01 (br s, 1H), 7.33 (ddd, 1H, J=9.2, 7.3, 1.8 Hz), 6.98 (m, 1H), 6.88 (d, 1H, J=8.4 Hz), 4.04 (m, 2H), 3.41 (m, 2H), 2.68 (m, 2H), 1.80 (m, 2H), 1.59 (m, 2H), 1.52-1.40 (m, 4H), 1.32-1.25 (m, 4H), 1.12 (br, s, 2H), 0.86 (m, 3H); $^{13}$C NMR (CDCl$_3$) δ 165.3, 157.0, 132.6, 132.2, 121.6, 121.1, 112.2, 69.0, 42.0, 39.6, 31.6, 31.3, 29.3, 27.1, 26.0, 22.6, 14.0.

2-(Hexyloxy)-N-[4-(quinolin-4-ylamino)butyl]benzamide N-(4-Aminobutyl)-2-(hexyloxy)benzamide was taken up in 60 mL of 1-pentanol, and 15 mL of volatile liquid was removed by distillation. The mixture was cooled slightly, and tripropylamine (2.70 mL, 14.2 mmol) and 4-chloroquinoline (1.29 g, 7.91 mmol) were added. Heating at reflux was resumed for 42 hr. The cooled mixture was concentrated and partitioned between DCM and 5% Na$_2$CO$_3$, and the organic phase was dried over anhydrous Na$_2$SO$_4$ and concentrated. The residue was taken up in EA and then concentrated again. The resulting oil solidified upon standing. The solid was broken up and washed with 20%, 50%, and 100% Et$_2$O/Hex. Drying in vacuo gave 1.53 g of yellow-gray solid. Rf 0.21 (5% MeOH/DCM+2% TEA); $^1$H NMR (CD$_3$OD) δ 8.53 (d, 1H, J=5.5 Hz), 8.24 (dd, 1H, J=1.9, 7.7 Hz), 8.16 (m, 1H, NH), 7.95 (d, 1H, J=8.4 Hz), 7.85 (d, 1H, J=8.4 Hz), 7.61 (m, 1H), 7.44-7.38 (m, 2H), 7.07 (m, 1H), 6.94 (d, 1H, J=8.4 Hz), 6.41 (d, 1H, J=5.1 Hz), 5.44 (br s, 1H, NH), 4.08 (m, 2H), 3.57 (m, 2H), 3.39 (m, 2H), 1.91-1.75 (m, 6H), 1.44 (m, 2H), 1.34-1.27 (m, 4H), 0.86 (m, 3H); $^{13}$C NMR (CDCl$_3$) δ 165.9, 157.2, 151.2, 149.9, 148.7, 133.0, 132.5, 130.1, 129.1, 124.8, 121.5, 121.4, 119.8, 119.0, 112.4, 98.9, 69.2, 43.2, 39.3, 31.7, 29.4, 28.0, 26.2, 26.1, 22.8, 14.2.

Example 81

N-[8-(Quinolin-4-ylamino)octyl]picolinamide

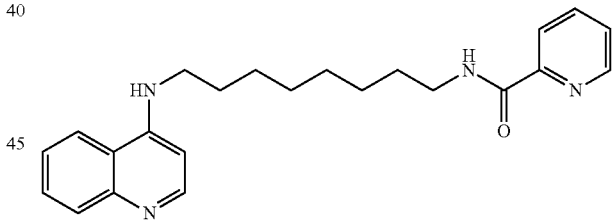

N-(8-Aminooctyl)picolinamide A mixture of 1,8-octanediamine (8.19 g, 56.9 mmol) and methyl picolinate (970 mg, 7.08 mmol) was heated at 130° C. for 60 hr. The mixture was cooled, taken up in methanol, and evaporated onto silica gel. The pre-loaded silica gel was loaded on top of a flash column and eluted using 15% MeOH/DCM+2% TEA. Concentration of the product-containing fractions gave 1.28 g of liquid. Rf 0.23 (15% MeOH/DCM+2% TEA); $^1$H NMR (20% CD$_3$OD/CDCl$_3$) δ 8.5 (ddd, 1H, J=1.0, 1.7, 4.9 Hz), 8.2 (m, 1H), 8.0 (br s, 1H, NH), 7.8 (m, 1H), 7.4 (ddd, 1H, J=1.5, 4.9, 7.7 Hz), 3.43 (m, 2H), 2.66 (m, 2H), 2.17 (br s, 2H, NH$_2$), 1.65-1.28 (m, 12H).

N-[8-(Quinolin-4-ylamino)octyl]picolinamide A mixture of N-(8-aminooctyl)picolinamide (557 mg, 2.24 mmol), 4-chloroquinoline (544 mg, 3.34 mmol), DIEA (1 mL, 6 mmol) and 0.5 mL of DMF was heated at 140° C. in a sealed tube for 89 hr. Then, the volatile components were evaporated, and the residue was purified by FC (8% MeOH/DCM)

to give 520 mg of product. Rf 0.38 (10% MeOH/DCM); $^1$H NMR (CDCl$_3$) δ 8.6 (d, 1H), 8.4 (d, 1H), 8.1 (d, 1H), 8.1-7.9 (m, 3H), 7.7 (m, 1H), 7.5 (m, 1H), 7.30 (m, 1H), 6.3 (d, 1H), 3.4-3.3 (m, 4H), 1.7 (m, 2H), 1.5 (m, 2H), 1.3-1.0 (m, 8H).

Example 82

N-[8-(Quinolin-4-ylamino)octyl]nicotinamide

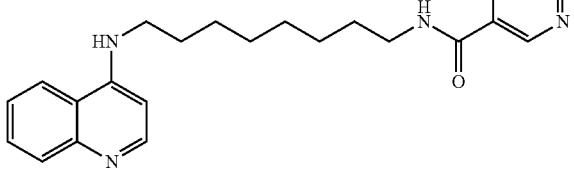

N-(8-Aminooctyl)nicotinamide A mixture of 1,8-diaminooctane (9.78 g, 67.0 mmol) and methyl nicotinate (1.50 g, 10.9 mmol) was heated at 84° C. for 16 hr and 110-120° C. for an additional 56 hr. The cooled mixture was separated by SPE, washing with 5% MeOH/DCM+2% TEA to remove the octane-1,8-bis(amide) and residual methyl nicotinate and then with 15% MeOH/DCM+2% TEA to elute ninhydrin (+) product fractions. The product fractions were concentrated, taken up in DCM, washed with 5% Na$_2$CO$_3$, dried over Na$_2$SO$_4$, filtered, and dried to give 2.07 g of pale yellow solid. Rf 0.10 (15% MeOH/DCM+2% TEA); $^1$H NMR (CD$_3$OD) δ 8.95 (dd, 1H, J=0.8, 2.2 Hz), 8.67 (m, 1H), 8.23 (m, 1H), 7.53 (m, 1H), 3.38 (t, 2H, J=7.3 Hz), 2.60 (t, 2H), 1.61 (m, 2H), 1.47-1.33 (m, 10H); $^{13}$C NMR (CD$_3$OD) δ 167.8, 152.7, 149.2, 137.1, 132.4, 125.3, 42.8, 41.3, 34.1, 30.7, 30.6, 28.2, 28.2, 22.2.

N-[8-(Quinolin-4-ylamino)octyl]nicotinamide N-(8-aminooctyl)nicotinamide (5.66 g, 22.7 mmol) was taken up in 100 mL of 1-pentanol, and then 50 mL of volatile material was removed by distillation. The mixture was cooled below boiling, and tripropylamine (9.50 mL, 49.8 mmol) and 4-chloroquinoline (4.08 g, 25.0 mmol) were added. Heating at reflux was resumed. After 22 hr, volatile material was removed by evaporation. The mixture was partitioned between DCM (175, 2×100 mL) and a combination of 25 mL of 1N NaOH and 25 mL of 5% Na$_2$CO$_3$. The combined organic phases were dried over Na$_2$SO$_4$, filtered, and concentrated to give a dark syrup. Two crystallizations from MeOH/H$_2$O and drying in vacuo over P$_2$O$_5$ gave 2.31 g of tan solid. Rf 0.56 (15% MeOH/DCM+2% TEA); mp 139.5-141.0° C.; $^1$H NMR (DMSO-d$_6$) δ 8.97 (m, 1H), 8.66 (m, 1H), 8.61 (t, 1H, J=5.5 Hz), 8.35 (d, 1H, J=5.1 Hz), 8.19 (d, 1H, J=8.8 Hz), 8.14 (ddd, 1H, J=1.4, 2.2, 7.7 Hz), 7.74 (dd, 1H, J=1.1, 8.5 Hz), 7.57 (m, 1H), 7.46 (m, 1H), 7.38 (ddd, 1H, J=1.4, 7.0, 8.4 Hz), 7.16 (t, 1H, J=5 Hz), 6.40 (d, 1H, J=5.5 Hz), 3.27-3.22 (m, 4H), 1.65 (m, 2H), 1.44 (m, 2H), 1.30 (m, 8H); $^{13}$C NMR (DMSO-d$_6$) δ 164.6, 151.6, 150.4, 150.2, 148.3, 148.0, 134.8, 130.1, 128.7, 123.7, 123.4, 121.7, 118.8, 98.0, 42.4, 39.2, 29.0, 28.8, 28.7, 27.8, 26.6, 26.4.

Example 83

N-[8-(Quinolin-4-ylamino)octyl]isonicotinamide

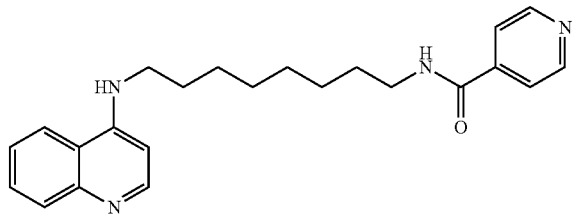 [SMILES: O=C(NCCCCCCCCNc1ccnc2ccccc12)c1ccncc1]

N-(8-Aminooctyl)isonicotinamide A mixture of 1,8-diaminooctane (7.66 g, 53 mmol) and methyl isonicotinate (910 mg, 6.64 mmol) was heated at 130° C. for 60 hr. The cooled mixture was partitioned between DCM and 5% Na$_2$CO$_3$, and the organic phase was dried over anhydrous Na$_2$SO$_4$ and concentrated. FC (15% MeOH/DCM+2% TEA) gave 539 mg of oily solid. Rf 0.15 (15% MeOH/DCM+2% TEA); $^1$H NMR (20% CD$_3$OD/CDCl$_3$) δ 8.59 and 7.66 (m, 4H, AA'BB'), 3.33 (m, 2H), 3.10 (m, 1H, NH), 2.78 (m, 2H), 1.85 (s, 2H, NH$_2$), 1.57-1.24 (m, 12H).

N-[8-(Quinolin-4-ylamino)octyl]isonicotinamide A mixture of N-(8-aminooctyl)isonicotinamide (539 mg, 2.16 mmol), 4-chloroquinoline (536 mg, 3.29 mmol), DIEA (2 mL, 12 mmol) and 0.5 mL of DMF was heated at 140° C. in a sealed tube for 89 hr. Then, the volatile components were evaporated, and the residue was purified by FC (8% MeOH/DCM) to give 113 mg of product. Rf 0.13 (10% MeOH/DCM); $^1$H NMR (20% CD$_3$OD/CDCl$_3$) δ 8.58 and 7.62 (m, 4H, AA'BB'), 8.35 (d, 1H, J=5.4 Hz), 7.83 (dd, 1H, J=0.7, 8.4 Hz), 7.71 (m, 1H), 7.55 (ddd, 1H, J=1.3, 7.0, 8.2 Hz), 7.35 (ddd, 1H, J=1.2, 6.9, 8.4 Hz), 6.34 (d, 1H, J=5.5 Hz), 3.37-3.21 (m, 4H), 1.70-1.22 (m, 12H).

Example 84

N-(Pyridin-4-ylmethyl)quinolin-4-amine

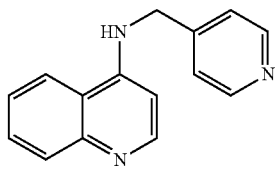 [SMILES: c1ccc2c(NCc3ccncc3)ccnc2c1]

N-(Pyridin-4-ylmethyl)quinolin-4-amine was prepared following the method for N-(pyridin-2-ylmethyl)quinolin-4-amine. Rf 0.29 (5% MeOH/DCM+2% TEA); $^1$H NMR (CDCl$_3$) δ 8.51-8.47 (m, 2H), 8.39 (d, 1H, J=5.4 Hz), 8.03-8.00 (m, 1H), 7.95 (dd, 1H, J=1.0, 8.4 Hz), 7.59 (ddd, 1, J=1.2, 6.9, 8.4 Hz), 7.40 (ddd, 1H, J=1.5, 6.9, 8.4 Hz), 7.28-7.22 (m, 2H), 6.61 (br s, 1H), 6.19 (d, 1H, J=5.4 Hz), 4.56 (br s, 2H).

Example 85

N-(Pyridin-3-ylmethyl)quinolin-4-amine

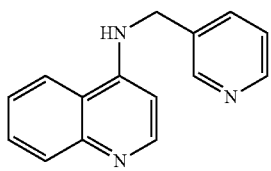 [SMILES: c1cncc(CNc2ccnc3ccccc23)c1]

N-(Pyridin-3-ylmethyl)quinolin-4-amine was prepared following the method for N-(pyridin-2-ylmethyl)quinolin-4-amine. Rf 0.36 (5% MeOH/DCM+2% TEA); $^1$H NMR (CDCl$_3$) δ 8.56 (d, 1H, J=2.0 Hz), 8.45 (dd, 1H, J=1.7, 5.0 Hz), 8.41 (d, 1H, J=5.2 Hz), 7.98 (d, 1H, J=8.4 Hz), 7.91 (dd, 1H, J=1.0, 8.4 Hz), 7.61 (ddd, 1H, J=1.7, 2.0, 7.9 Hz), 7.54 (ddd, 1H, J=1.2, 6.9, 8.2 Hz), 7.33 (ddd, 1H, J=1.2, 6.9, 8.4 Hz), 7.17 (dd, 1H, J=5.0, 7.9 Hz), 6.61 (br s, 1H), 6.29 (d, 1H, J=5.5 Hz), 4.50 (m, 2H, AB).

Example 86

N-(Pyridin-2-ylmethyl)quinolin-4-amine

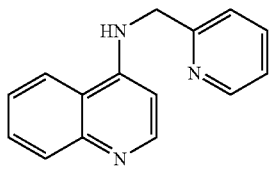 [SMILES: c1ccc(CNc2ccnc3ccccc23)nc1]

A mixture of 4-chloroquinoline (228 mg, 1.40 mmol), 2-(aminomethyl)pyridine (144 mg, 1.33 mmol), and DIEA (0.50 mL) was heated at 130° C. in a sealed tube for 48 hr. Then, the mixture was cooled, partitioned between EA and 5% Na$_2$CO$_3$ and brine, dried over Na$_2$SO$_4$, and concentrated. FC (3% MeOH/DCM+2% TEA) gave product-containing fractions, which were concentrated. The residue was taken up in DCM and washed with 5% Na$_2$CO$_3$, dried over Na$_2$SO$_4$, and concentrated to give the product. Rf 0.54 (5% MeOH/DCM+2% TEA); $^1$H NMR (CDCl$_3$) δ 8.57-8.54 (m, 1H), 8.46 (d, 1H, J=5.4 Hz), 7.99-7.91 (m, 2H), 7.62-7.52 (m, 2H), 7.37 (ddd, 1H, J=1.2, 6.9, 8.1 Hz), 7.26-7.23 (m, 1H), 7.18-7.13 (m, 1H), 7.03 (br s, 1H), 6.32 (d, 1H, J=5.4 Hz), 4.52 (m, 2H, AB).

Example 87

N-Hexylquinolin-4-amine

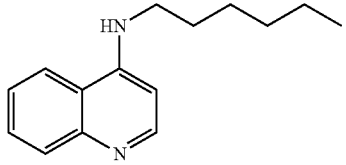 [SMILES: CCCCCCNc1ccnc2ccccc12]

A mixture of 4-chloroquinoline (248 mg, 1.52 mmol) and 1-hexylamine (2 mL, 15 mmol) was heated in a sealed tube at 100° C. for 2 days, 120-130° C. for 2 days, and 150° C. for 1 day. The mixture was cooled and partitioned between EA and 5% Na$_2$CO$_3$ and brine, and the organic phase was dried over Na$_2$SO$_4$ and concentrated in vacuo. SPE, washing with 25% EA/Hex and eluting with 12% MeOH/DCM, followed by repurification by preparative TLC (10% MeOH/DCM), gave the product as an oil. Rf 0.16 (5% MeOH/DCM); $^1$H NMR (CDCl$_3$) δ 8.48 (d, 1H, J=5.4 Hz), 7.97 (dd, 1H, J=1.0, 8.4 Hz), 7.87 (d, 1H, J=8.4 Hz), 7.60 (ddd, 1H, J=1.5, 6.9, 8.4 Hz), 7.40 (ddd, 1H, J=1.2, 6.9, 8.4 Hz), 6.40 (d, 1H, J=5.7 Hz), 5.66 (br s, 1H, NH), 3.32 (m, 2H), 1.75 (m, 2H), 1.46-1.26 (m, 6H), 0.89 (m, 3H).

Example 88

N-(Decyl)quinolin-4-amine

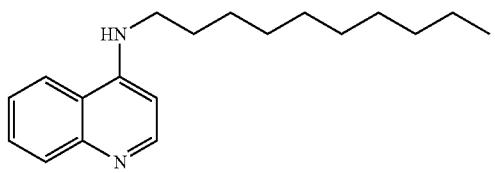 [SMILES: CCCCCCCCCCNc1ccnc2ccccc12]

A mixture of 1-aminodecane (4.36 g, 27.8 mmol), tripropylamine (8.00 mL, 42.0 mmol), and 4-chloroquinoline (4.55 g, 27.9 mmol) in 25 mL of 1-pentanol was heated at reflux for 3 days. Then, the volatile components were evaporated. The residue was take up in DCM (150 mL) and washed with 5% Na$_2$CO$_3$ (100 mL). The aqueous phase was extracted with DCM (100 mL), and the combined organic phases were dried over Na$_2$SO$_4$, filtered, and concentrated to give a dark liquid. SPE, eluting with 1% and then 5% MeOH/DCM+2% TEA, gave product fractions that were concentrated, partitioned between DCM (150, 100 mL) and 5% Na$_2$CO$_3$ (100 mL), dried over Na$_2$SO$_4$, filtered, and concentrated. Recrystallization from EA/Hex gave 4.14 g colorless solid. Rf 0.30 (5% MeOH/DCM+2% TEA); mp 79.0-80.0° C.; $^1$H NMR (CDCl$_3$) δ 8.56 (d, 1H, J=5.5 Hz), 7.97 (dd, 1H, J=1.1, 8.4 Hz), 7.72 (m, 1H), 7.62 (ddd, 1H, J=1.4, 7.0, 8.4 Hz), 7.41 (m, 1H), 6.43 (d, 1H, J=5.5 Hz), 4.97 (br s, 1H, NH), 3.31 (m, 2H), 1.76 (m, 2H), 1.46 (m, 2H), 1.39-1.27 (m, 12H), 0.88 (m, 3H); $^{13}$C NMR (CDCl$_3$) δ 152.2, 149.9, 149.6, 129.2, 128.2, 125.0, 122.7, 121.0, 102.4, 62.0, 51.8, 32.6, 28.0, 25.7, 22.4, 14.0.

Example 89

N-(Dodecyl)quinolin-4-amine

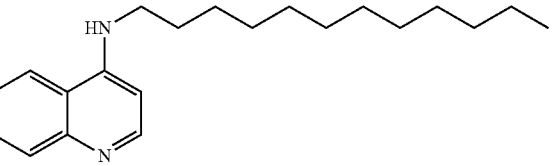

A mixture of 4-chloroquinoline (3.25 g, 19.9 mmol), 1-dodecylamine (3.80 g, 20.5 mmol), and tripropylamine (5.90 mL, 30.9 mmol) in 30 mL of 1-pentanol was heated at reflux for 16.5 hr. Then, the volatile components were evaporated in vacuo. The residue was partitioned between DCM (150, 100 mL) and a mixture of 1N NaOH and 5% $Na_2CO_3$ (20 mL each). The organic phases were dried over $Na_2SO_4$ and concentrated. Crystallization from ice-cold 10% EA/Hex, washing the collected solid with ice-cold 20% $Et_2O$/Hex, gave 4.95 g colorless solid (mp 81.5-82.0° C.). LC/MS (230 nm) indicated the presence of 5-10% impurity. SPE (1% TEA/EA) separated an impurity with predominantly aryl hydrogens by NMR. The product was recrystallized from ice-cold 10% EA/Hex to give 4.70 g colorless solid. Rf 0.12 (10% MeOH/DCM); mp 80.5-81.5° C.; $^1$H NMR ($CDCl_3$) δ 8.56 (d, 1H, J=5.1 Hz), 7.97 (dd, 1H, J=1.1, 8.4 Hz), 7.72 (m, 1H), 7.62 (ddd, 1H, J=1.5, 7.0, 8.5 Hz), 7.42 (ddd, 1H, J=1.5, 7.0, 8.5 Hz), 6.42 (d, 1H, J=5.5 Hz), 4.98 (br s, 1H, NH), 3.31 (m, 2H), 1.76 (p, 2H, J=7.3 Hz), 1.47 (m, 2H), 1.38-1.26 (m, 16H), 0.88 (t, 3H, J=6.8 Hz); $^{13}$C NMR ($CDCl_3$) δ 151.3, 149.8, 148.7, 130.3, 129.1, 124.7, 119.3, 118.9, 99.0, 43.5, 32.1, 29.8, 29.8, 29.8, 29.8, 29.6, 29.5, 29.2, 27.4, 22.9, 14.3.

Example 90

$N^1,N^8$-Di(quinolin-4-yl)octane-1,8-diamine

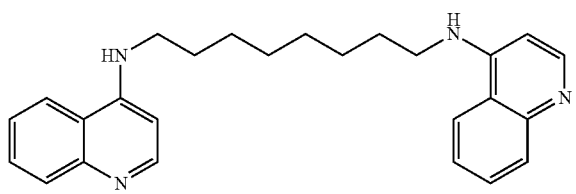 [SMILES: c1ccc2c(NCCCCCCCCNc3ccnc4ccccc34)ccnc2c1]

A mixture of 1,8-octanediamine and excess 4-chloroquinoline and DIEA in NMP was heated at 160° C. in a sealed tube for 3 days. The mixture was cooled and purified by SPE, washing with 1% MeOH/DCM and then eluting with 7.5% MeOH/DCM+2% TEA to give the product as a solid. Rf 0.05 (EA+2% TEA); $^1$H NMR (20% $CD_3OD/CDCl_3$) δ 8.32 (d, 2H, J=5.7 Hz), 7.85-7.80 (m, 4), 7.58 (ddd, 2H, J=1.2, 6.9, 8.2 Hz), 7.38 (ddd, 2H, J=1.2, 6.9, 8.4 Hz), 6.37 (d, 2H, J=5.7 Hz), 3.38-3.25 (m, 4H), 1.73-1.24 (m, 12H).

Example 91

N-[8-(Hexyloxy)octyl]quinolin-6-amine

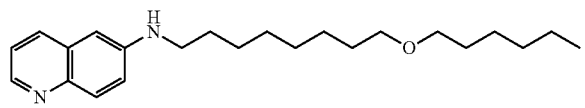 [SMILES: CCCCCCOCCCCCCCCNc1ccc2ncccc2c1]

8-(Hexyloxy)octanoic acid Approximately 6.0 mL of Jones reagent was added to a mixture of 8-(hexyloxy)octan-1-ol (2.1 g, 9.1 mmol) and 50 mL of DCM cooled by an ice bath, after which the green color of the mixture did not persist. Then, the mixture was washed with $H_2O$ and 0.1M HCl, and the organic phase was dried over $MgSO_4$, diluted with 5 mL of MeOH, filtered through a pad of silica gel, washing the pad with 5% MeOH/DCM, and concentrated. FC (5% MeOH/DCM) gave 1.6 g of product. Rf 0.3 (5% MeOH/DCM); $^1$H NMR ($CDCl_3$) δ 3.4 (t, 4H), 2.3 (m, 2H), 1.7-1.4 (m, 6H), 1.4-1.2 (m, 12H), 0.9 (m, 3H).

8-(Hexyloxy)-N-(quinolin-6-yl)octanamide A mixture of 6-aminoquinoline (0.5 g, 3.5 mmol), 8-(hexyloxy)octanoic acid (847 mg, 3.47 mmol), 1-hydroxybenzotriazole (469 mg, 3.47 mmol), 4-dimethylaminopyridine (42 mg, 0.3 mmol), and EDC (663 mg, 3.47 mmol) in 20 mL of DCM was reacted until the starting material was consumed, as observed by TLC. Then, the volatile components were evaporated, and the residue was partitioned between EA and $H_2O$, 5% $Na_2CO_3$, $H_2O$, and brine, and the organic phases were dried over $Na_2SO_4$ and concentrated. FC (50% EA/Hex) gave 225 mg of the product. Rf 0.4 (50% EA/Hex); $^1$H NMR ($CDCl_3$) δ 8.8 (m, 1H), 8.4 (m, 1H), 8.15 (m, 1H), 8.05 (m, 1H), 7.9 (br s, 1H, NH), 7.6 (m, 1H), 7.4 (m, 1H), 3.4 (t, 4H), 2.4 (t, 2H), 1.7 (m, 2H), 1.6-1.4 (m, 4H), 1.4-1.2 (m, 12H), 0.85 (m, 3H).

N-[8-(Hexyloxy)octyl]quinolin-6-amine A mixture of 8-(hexyloxy)-N-(quinolin-6-yl)octanamide (171 mg, 0.46 mmol) and 20 mL of THF was cooled by an ice bath before 70 mg of lithium aluminum hydride was added. The mixture was allowed to warm slowly to room temperature overnight. Then, the mixture was recooled, and 0.7 mL of $H_2O$, 0.7 mL of 15% NaOH, and 2.1 mL of $H_2O$ were added cautiously. The mixture was filtered through a pad of Celite, washing with 5% MeOH/DCM, and the filtrate was concentrated. The residue was partitioned between EA and 5% $Na_2CO_3$ and brine, and the organic phase was dried over $Na_2SO_4$ and concentrated. FC (50% EA/Hex) gave 100 mg of the product. Rf 0.3 (50% EA/Hex); $^1$H NMR ($CDCl_3$) δ 8.6 (m, 1H), 7.95-7.85 (m, 2H), 7.3 (m, 1H), 7.1 (m, 1H), 7.7 (m, 1H), 3.4 (t, 4H), 3.2 (t, 2H), 1.8-1.2 (m, 20H), 0.85 (t, 3H).

Example 92

N-[8-(Hexyloxy)octyl]quinolin-3-amine

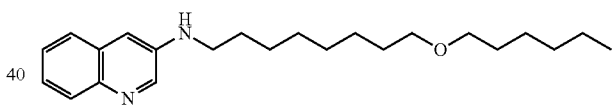

N-[8-(Hexyloxy)octyl]quinolin-3-amine (66 mg) was prepared following the method for N-[8-(hexyloxy)octyl]quinolin-6-amine starting with 3-aminoquinoline (728 mg).

8-(Hexyloxy)-N-(quinolin-3-yl)octanamide: $^1$H NMR ($CDCl_3$) δ 9.05 (br s, 1H), 8.95 (br s, 1H), 8.5 (br s, 1H, NH), 8.1 (d, 1H), 7.8 (d, 1H), 7.7-7.5 (m, 2H), 3.4 (m, 4H), 2.5 (t, 2H), 1.8 (m, 2H), 1.7-1.2 (m, 16H), 0.85 (t, 3H).

206-181   N-[8-(Hexyloxy)octyl]quinolin-3-amine  $^1$H NMR ($CDCl_3$) δ 8.6 (d, 1H), 8.0 (d, 1H), 7.6 (d, 1H), 7.5-7.3 (m, 2H), 7.0 (m, 1H), 4.3 (br s, 1H, NH), 3.5-3.3 (m, 4H), 3.2 (m, 2H), 1.8-1.2 (m, 20H), 0.9 (m, 3H).

Example 93

N-[8-(Hexyloxy)octyl]quinolin-8-amine

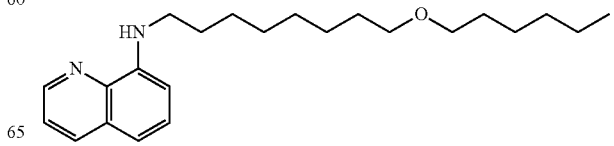

N-[8-(Hexyloxy)octyl]quinolin-8-amine (58 mg) was prepared following the method for N-[8-(hexyloxy)octyl]quinolin-6-amine starting with 8-aminoquinoline (472 mg).

8-(Hexyloxy)-N-(quinolin-8-yl)octanamide: Rf 0.7 (10% EA/Hex); $^1$H NMR (CDCl$_3$) δ 9.8 (br s, 1H, N$\underline{H}$), 8.85-8.75 (m, 2H), 8.2 (m, 1H), 7.6-7.4 (m, 3H), 3.4 (m, 4H), 2.6 (t, 2H), 1.8 (m, 2H), 1.7-1.2 (m, 16H), 0.9 (m, 3H).

N-[8-(Hexyloxy)octyl]quinolin-8-amine: Rf 0.6 (50% EA/Hex); $^1$H NMR (CDCl$_3$) δ 8.7 (d, 1H), 8.1 (br s, 1H), 7.5-7.3 (m, 2H), 7.0 (d, 1H), 6.7 (d, 1H), 3.5-3.3 (m, 4H), 3.3 (m, 2H), 1.8 (m, 2H), 1.7-1.2 (m, 18H), 0.9 (m, 3H).

Example 94

N-[8-(Hexyloxy)octyl]-2-(trifluoromethyl)quinolin-4-amine

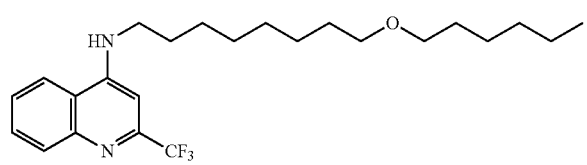 [SMILES: CCCCCCOCCCCCCCCNc1cc(C(F)(F)F)nc2ccccc12]

A mixture of 8-(hexyloxy)octan-1-amine (350 mg, 1.53 mmol), 4-chloro-2-trifluoromethylquinoline (420 mg, 1.81 mmol) and TEA (0.32 mL, 1.84 mmol) in 1 mL of NMP was heated at 150° C. for 16 hr. The mixture was cooled and partitioned between EA and 5% Na$_2$CO$_3$. The organic phases were washed with brine, dried over Na$_2$SO$_4$, and concentrated. Purification by preparative TLC gave the product. Rf 0.38 (20% EA/Hex); $^1$H NMR (CDCl$_3$) δ 8.01 (m, 1H), 7.75 (d, 1H, J=8.4 Hz), 7.62 (ddd, 1H, J=1.2, 6.9, 8.4 Hz), 7.42 (ddd, 1H, J=1.2, 7.0, 8.4 Hz), 6.65 (s, 1H), 5.45 (m, 1H, N$\underline{H}$), 3.38-3.34 (m, 4H), 3.27 (m, 2H), 1.76-1.18 (m, 20H), 0.85 (m, 3H).

Example 95

7-Chloro-N-decylquinolin-4-amine

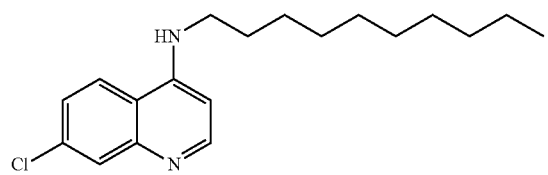 [SMILES: CCCCCCCCCCNc1ccnc2cc(Cl)ccc12]

7-Chloro-N-decylquinolin-4-amine (8.10 g) was prepared following the method for 7-chloro-N-dodecylquinolin-4-amine, starting with 5.18 g of 1-decylamine and 6.53 g of 4,7-dichloroquinoline. Mp 102.5-103.0° C. (EA/Hex); $^1$H NMR (CDCl$_3$) δ 88.5 (d, 1H, J=5.5 Hz), 7.9 (d, 1H, J=1.9 Hz), 7.6 (d, 1H, J=8.8 Hz), 7.3 (m, 1H), 6.4 (d, 1H, J=5.5 Hz), 5.1 (br m, 1H, N$\underline{H}$), 3.3 (m, 2H), 1.7 (m, 2H), 1.5-1.3 (m, 14H), 0.8 (m, 3H); $^{13}$C NMR (CDCl$_3$) δ 152.2, 149.9, 149.4, 134.9, 129.0, 125.4, 121.1, 117.3, 99.2, 43.5, 32.1, 29.7, 29.7, 29.6, 29.5, 29.1, 27.3, 22.9, 14.3.

Example 96

7-Chloro-N-dodecylquinolin-4-amine

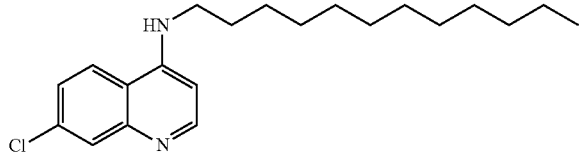 [SMILES: CCCCCCCCCCCCNc1ccnc2cc(Cl)ccc12]

A mixture of 1-dodecylamine (4.57 g, 24.7 mmol), tripropylamine (9.4 mL, 49 mmol), 4,7-dichloroquinoline (4.89 g, 24.7 mmol) and 50 mL of 1-pentanol were heated at reflux for 22 hr. Then, the volatile components were evaporated. The residue was partitioned between EA and 5% Na$_2$CO$_3$ and brine, and the organic phase was dried over Na$_2$SO$_4$ and concentrated. SPE (50% EA/Hex) gave the product as a yellow solid. The product was taken up in DCM, washed with 5% Na$_2$CO$_3$, dried over Na$_2$SO$_4$, and concentrated. The product was crystallized from ice-cold 20% EA/Hex to give 7.50 g colorless solid. Rf 0.30 (50% EA/Hex); mp 95.0-97.0° C.; $^1$H NMR (CDCl$_3$) δ 8.5 (d, 1H, J=5.1 Hz), 7.9 (d, 1H, J=1.9 Hz), 7.6 (d, 1H, J=8.8 Hz), 7.3 (m, 1H), 6.39 (d, 1H, J=5.5 Hz), 5.0 (br m, 1H, N$\underline{H}$), 3.3 (m, 2H), 1.8 (m, 2H), 1.5-1.2 (m, 20H, 0.9 (m, 3H);

$^{13}$C NMR (CDCl$_3$) δ 152.3, 149.9, 149.4, 135.0, 129.1, 125.4, 121.0, 117.3, 99.3, 43.5, 32.1, 29.8, 29.8, 29.8, 29.7, 29.6, 29.5, 29.1, 27.3, 22.9, 14.3.

Example 97

N-(Decyl)quinazolin-4-amine

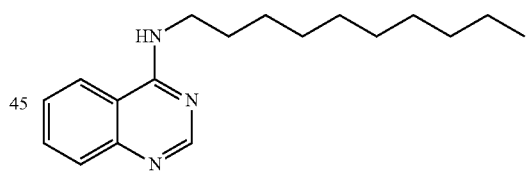

A mixture of 4-chloroquinazoline (6.90 g, 42.1 mmol), 1-decylamine (10.8 mL, 54.3 mmol), and TEA (8.90 mL, 62.7 mmol) in 50 mL of IPA was heated at reflux for 6 hr, then allowed to stand overnight. Then, the volatile components were evaporated, and the residue was taken up in DCM and washed with a mixture of 20 mL of 1N NaOH and 20 mL of 5% Na$_2$CO$_3$. The organic phase was dried over anhydrous Na$_2$SO$_4$ and filtered through a pad of silica gel, washing with 5% MeOH/DCM. The filtrate was concentrated to give a solid. The solid was washed with 25 mL and 10 mL portions of 20% Et$_2$O/Hex, then dried in vacuo to give 11.22 g of colorless solid. Rf 0.41 (10% MeOH/DCM); mp 72.5-73.0° C.; $^1$H NMR (CDCl$_3$) δ 8.66 (s, 1H), 7.82 (dd, 1H, J=1.1, 8.8 Hz), 7.73-7.69 (m, 2H), 7.44 (m, 1H), 5.83 (br s, 1H, N$\underline{H}$), 3.65 (m, 2H), 1.72 (m, 2H), 1.46-1.25 (m, 14H), 0.86 (t, 3H, J=7.0 Hz); $^{13}$C NMR (CDCl$_3$) δ 159.7, 155.7, 149.6, 132.7, 128.8, 126.1, 120.6, 115.2, 41.6, 32.1, 29.8, 29.7, 29.6, 29.5, 27.6, 22.9, 14.3.

Example 98

N-Dodecylquinazolin-4-amine

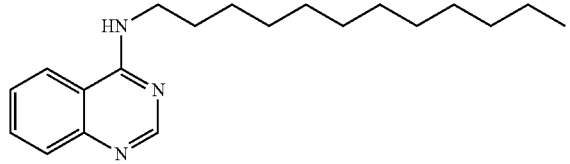

1-Dodecylamine (4.20 g, 22.7 mmol) was taken up in 45 mL of IPA, and 10 mL was removed by distillation. Then, the mixture was cooled slightly, and TEA (6.5 mL, 46 mmol) and 4-chloroquinazoline (3.72 g, 22.7 mmol) were added. The mixture was heated at reflux for 7 hr. Then, most of the volatile components were removed by distillation. The residue was partitioned between DCM (150, 100 mL) and a mixture of 1N NaOH and 5% $Na_2CO_3$ (20 mL each). The organic phases were dried over $Na_2SO_4$ and concentrated. SPE (30, 50, and 60% EA/Hex step gradient) gave product-containing fractions that were concentrated, taken up in DCM, washed with 5% $Na_2CO_3$, dried over $Na_2SO_4$, and concentrated to a syrup. Crystallization from ice-cold 30% EA/Hex gave 6.05 g colorless solid. Rf 0.20 (50% EA/Hex); mp 74.0-75.0° C.; $^1$H NMR (CDCl$_3$) δ 866 (s, 1H), 7.82 (m, 1H), 7.74-7.69 (m, 2H), 7.45 (m, 1H), 5.76 (br s, 1H, N$\underline{H}$), 3.65 (m, 2H), 1.72 (m, 2H), 1.46-1.25 (m, 18H), 0.87 (m, 3H); $^{13}$C NMR (CDCl$_3$) δ 159.6, 155.7, 149.6, 132.7, 128.9, 126.1, 120.6, 115.1, 41.6, 32.1, 29.8, 29.8, 29.8, 29.6, 29.6, 29.5, 27.3, 22.9, 14.3.

Example 99

N-Decyl-7-fluoroquinazolin-4-amine

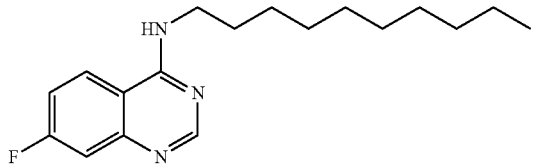 [SMILES: CCCCCCCCCCNc1ncnc2cc(F)ccc12]

A mixture of 1-decylamine (1.2 mL, 6.0 mmol), 4-chloro-7-fluoroquinazoline (1.1 g, 6.0 mmol), and TEA (1.3 mL, 9.3 mmol) in 10 mL of IPA was heated at reflux for 6 hr. Then, the volatile components were evaporated, and the residue was partitioned between DCM (400, 300 mL) and 5% $Na_2CO_3$ (400 mL). The organic phases were dried over anhydrous $Na_2SO_4$, filtered through a pad of silica gel, washing with 10% MeOH/DCM, and concentrated. The product was crystallized from EA/Hex.

Example 100

N-Dodecyl-7-fluoroquinazolin-4-amine

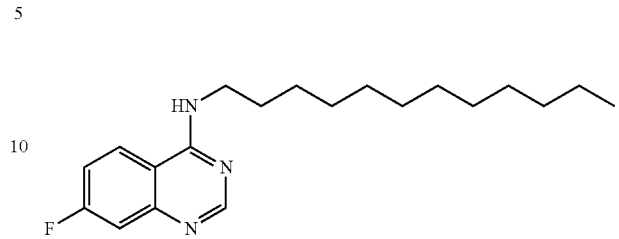

N-Dodecyl-7-fluoroquinazolin-4-amine was made from 1-dodecylamine (1.2 mL, 5.2 mmol), 4-chloro-7-fluoroquinazoline (1.0 g, 5.5 mmol), and TEA (1.2 mL, 8.6 mmol) in 10 mL of IPA following the method for the preparation of N-decyl-7-fluoroquinazolin-4-amine.

Example 101

7-Chloro-N-decylquinazolin-4-amine

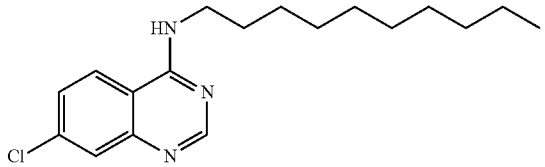

7-Chloro-N-decylquinazolin-4-amine was made from 1-decylamine (1.5 mL, 7.0 mmol), 4,7-dichloroquinazoline (1.4 g, 7.0 mmol), and TEA (2.0 mL, 14 mmol) in 15 mL of IPA following the method for the preparation of N-decyl-7-fluoroquinazolin-4-amine.

Example 102

7-Chloro-N-dodecylquinazolin-4-amine

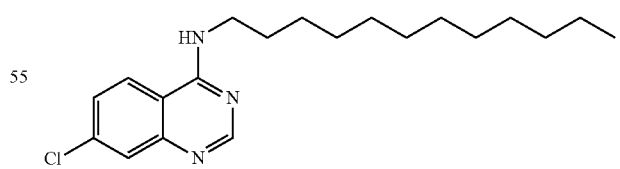

7-Chloro-N-dodecylquinazolin-4-amine was made from 1-dodecylamine (1.3 g, 7.0 mmol), 4,7-dichloroquinazoline (1.4 g, 7.0 mmol), and TEA (2.0 mL, 14 mmol) in 15 mL of IPA following the method for the preparation of N-decyl-7-fluoroquinazolin-4-amine.

Example 103

N-(6-Butoxyhexyl)quinazolin-4-amine

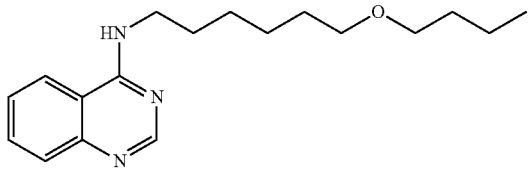 [SMILES: CCCCOCCCCCCNc1ncnc2ccccc12]

6-Butoxyhexan-1-amine (7.20 g, 41.1 mmol) was taken up in 200 mL, and 50 mL was removed by distillation. The mixture was cooled slightly, and TEA (17.4 mL, 124 mmol) and 4-chloroquinazoline (11.11 g, 67.7 mmol) were added. The mixture was heated at reflux for 38 hr, then allowed to stand at room temperature for 3 days. The volatile components were evaporated. The residue was partitioned between DCM (150, 2×50 mL) and a mixture of 40 mL 1N NaOH and 40 mL of 5% $Na_2CO_3$. The organic phases were dried over anhydrous $Na_2SO_4$ and evaporated onto silica gel. SPE, washing with 30% EA/Hex and eluting with 60% EA/Hex, gave a yellow syrup that crystallized from 10% EA/Hex at −20° C. to give 4.64 g of colorless solid. Rf 0.25 (50% EA/Hex); mp 40-46° C.; $^1$H NMR ($CDCl_3$) δ 8.64 (s, 1H), 7.84 (d, 1H, J=8.4 Hz), 7.78-7.70 (m, 2H), 7.46 (ddd, 1H, J=1.4, 7.3, 8.4 Hz), 6.12 (br s, 1H, N$\underline{H}$), 3.66 (m, 2H), 3.41-3.37 (m, 4H), 1.74 (m, 2H), 1.62-1.30 (m, 10H), 0.90 (t, 3H, J=7.3 Hz); $^{13}$C NMR ($CDCl_3$) δ 159.8, 155.2, 148.6, 133.0, 128.1, 126.3, 120.9, 115.0, 70.9, 70.9, 41.6, 32.0, 29.8, 29.4, 27.1, 26.2, 19.6, 14.1.

Example 104

N-[8-(Hexyloxy)octyl]quinazolin-4-amine

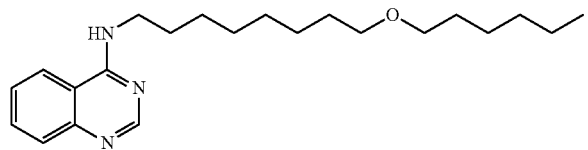 [SMILES: CCCCCCOCCCCCCCCNc1ncnc2ccccc12]

8-(Hexyloxy)octan-1-ol 1,8-Octanediol (201.4 g, 1.38 mol) was taken up in 1.3 L of IPA, and 250 mL of volatile material was removed by distillation. The mixture was allowed to cool below boiling, and sodium metal (6.9 g, 0.30 mol) was added in portions while maintaining a blanket of argon. After the addition was completed, the mixture was boiled for one hour, and then it was allowed to stir at room temperature overnight. 1-Bromohexane (32.2 mL, 0.23 mol) was added in a slow stream. After 25 hr, the mixture was warmed gently. Precipitate began to form. After 2 days of warming, the mixture was heated to distill 400 mL of volatile material. Then, heating was halted, and 16 g of $NH_4Cl$ in 48 mL of $H_2O$ was added. After 1 hr, the distillation was resumed and 450 mL of distillate was collected. Heating was halted, and 214 g of silica gel was added to the hot mixture. The warm mixture was blended well and cooled. The excess diol was removed by SPE using 30% EA/Hex, which afforded 25.9 g of light yellow oil containing the desired product. Rf 0.19 (20% EA/Hex); $^1$H NMR ($CDCl_3$) δ 3.63-3.58 (m, 2H), 3.37 (t, 4H, J=6.7 Hz), 1.66 (br s, 1H, O$\underline{H}$), 1.57-1.50 (m, 6H), 1.30-1.28 (m, 14H), 0.87 (t, 3H, J=6.6 Hz). 1,8-Octanediol was recovered by eluting with 5% MeOH/DCM, evaporation of solvent, and crystallization of three crops from EA/Hex, which afforded 182.4 g of colorless solid.

8-(Hexyloxy)octyl methanesulfonate 8-(Hexyloxy)octan-1-ol was taken up in 250 mL of DCM and cooled using an ice bath. TEA (21.0 mL, 150 mmol) and methanesulfonyl chloride (10.5 mL, 134 mmol) were added in turn. After 1.25 hr, 20 g of ice chips were added. Most of the volatile material was evaporated. The residue was partitioned between 1:1 EA/Hex (3×300 mL) and $H_2O$, saturated $NaHCO_3$, $H_2O$, 1M HCl, $H_2O$, and brine (100 mL each). The combined organic phases were dried over $Na_2SO_4$, filtered through a pad of silica gel, and concentrated. Rf 0.28 (20% EA/Hex); $^1$H NMR ($CDCl_3$) δ 4.21 (t, 2H, J=6.6 Hz), 3.38 (t, 2H, J=6.4 Hz), 3.37 (t, 2H, J=6.7 Hz), 2.98 (s, 3H), 1.72 (m, 2H), 1.61-1.46 (m, 4H), 1.40-1.24 (m, 14H), 0.87 (t, 3H, J=6.8 Hz).

N-[8-(Hexyloxy)octyl]phthalimide Toluene (100 mL) was mixed with the crude 8-(hexyloxy)octyl methanesulfonate and then was evaporated. The residue was taken up in 120 mL of DMF and 60 mL of NMP. Potassium phthalimide (25.0 g, 135 mmol) was added. After mixing for 21.5 hr, 50 mL of $H_2O$ was added, and the volatile material was evaporated. The residue was partitioned between EA (3×300 mL) and $H_2O$ (150 mL), saturated $NaHCO_3$ (150 mL), and brine (2×150 mL). The combined organic phases were dried over $Na_2SO_4$, filtered through a pad of silica gel, and concentrated. Rf 0.50 (10% EA/Hex); $^1$H NMR ($CDCl_3$) δ 7.81 and 7.68 (m, 4H, AA'BB'), 3.65 (t, 2H, J=7.3 Hz), 3.36 (t, 2H, J=6.7 Hz), 3.35 (t, 2H, J=6.7 Hz), 1.67-1.48 (m, 6H), 1.29-1.22 (m, 14H), 0.86 (t, 3H, J=6.8 Hz).

8-(Hexyloxy)octan-1-amine IPA (100 mL) was mixed with the crude N-[8-(hexyloxy)octyl]phthalimide and then was evaporated. The residue was taken up in 450 mL of EtOH, hydrazine monohydrate (6.60 mL, 136 mmol) was added, and the mixture was heated at reflux overnight. The mixture was concentrated by distillation of 300 mL of volatile material. Heating was halted, 150 mL of 1M HCl was added to the hot mixture, and the mixture was allowed to cool. The precipitate was removed by filtration, and it was washed with 1:1 EtOH/$H_2O$ (2×100 mL). The filtrate was concentrated to 100 mL, and the pH was adjusted to >10 using NaOH pellets. The mixture was extracted with DCM (3×250 mL), and the combined organic phases were dried over $Na_2SO_4$, filtered, and concentrated to give 27.6 g of cloudy liquid. $^1$H NMR ($CDCl_3$) δ 3.36 (t, 4H, J=6.7 Hz), 2.66 (t, 2H, J=6.9 Hz), 1.52 (m, 2H), 1.44-1.28 (m, 18H), 0.86 (m, 3H).

N-[8-(Hexyloxy)octyl]quinazolin-4-amine Crude 8-(hexyloxy)octan-1-amine was taken up in 400 mL of IPA, and 250 mL of volatile material was removed by distillation. The mixture was cooled, and TEA (16.8 mL, 120 mmol) and 4-chloroquinazoline (9.8 g, 60 mmol) were added. The mixture was heated at reflux for 4 hr. TLC of an aliquot indicated a substantial quantity of ninhydrin (+) material remained. TEA (11.2 mL, 80 mmol) and 4-chloroquinazoline (6.5 g, 38 mmol) were added. After 5 hr additional heating the mixture was allowed to cool and stirred 12 hr. Then, the volatile components were evaporated, and the residue was partitioned between DCM (300, 2×150 mL) and 1N NaOH and 5% $Na_2CO_3$ (100 mL each). The combined organic phases were dried over $Na_2SO_4$, filtered, and concentrated. SPE, eluting with 20%, 30%, and 50% EA/Hex, gave product fractions that were combined and concentrated. The residue was taken up in 300 mL of EA, filtered, and concentrated. The resulting yellow solid was recrystallized twice from 10% EA/Hex to give 30.3 g of pale yellow solid. Rf 0.11 (40% EA/Hex); mp 67.0-67.5° C.; $^1$H NMR (CDCl$_3$) δ 8.66 (s, 1H), 7.83 (d, 1H, J=7.8 Hz), 7.75-7.70 (m, 2H), 7.46 (m, 1H), 5.81 (br s, 1H, NH), 3.65 (dt, 2H, J=5.5, 7.4 Hz), 3.38 (t, 4H), 1.73 (m, 2H), 1.59-1.52 (m, 4H), 1.46-1.24 (m, 14H), 0.87 (t, 3H, J=6.9 Hz); $^{13}$C NMR (CDCl$_3$) δ 159.7, 155.6, 149.4, 132.8, 128.7, 126.2, 120.6, 115.1, 71.2, 71.1, 41.7, 41.5, 31.9, 30.0, 29.6, 29.6, 29.5, 27.2, 26.4, 26.1, 22.8, 14.3.

Example 105

N-[8-(4-Methoxyphenoxy)octyl]quinazolin-4-amine

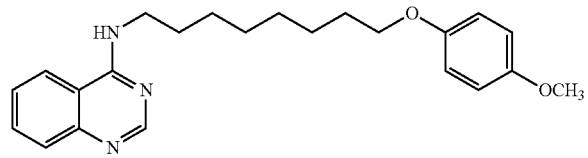 [SMILES: COc1ccc(OCCCCCCCCNc2ncnc3ccccc23)cc1]

8-(4-Methoxyphenoxy)octan-1-amine (4.03 g, 16.1 mm) was taken up in 125 mL of IPA, and 50 mL of volatile components were removed by distillation. The mixture was cooled slightly, and TEA (4.50 mL, 32.1 mmol) and 4-chloroquinazoline (2.92 g, 17.7 mmol) were added. Heating at reflux was resumed. After 24 hr, the mixture was allowed to cool, and 15 mL of 1N NaOH were added. The volatile components were evaporated. The residue was diluted with DCM, washed with 5% Na$_2$CO$_3$, dried over anhydrous Na$_2$SO$_4$, and concentrated onto silica gel. SPE, washing with 50% EA/Hex and eluting with 40% EA/Hex+2% TEA, gave product-containing fractions, which were concentrated, taken up in DCM, washed with 5% Na$_2$CO$_3$, dried over anhydrous Na$_2$SO$_4$, and concentrated to give a yellow solid. Recrystallization form EA/Hex gave 3.93 g of white solid. Rf 0.41 (50% EA/Hex+2% TEA); mp 97.0-98.0° C.; $^1$H NMR (CDCl$_3$) δ 8.66 (s, 1H), 7.81 (dd, 1H, J=0.7, 8.4 Hz), 7.51 (m, 1H), 7.69 (ddd, 1H, J=1.5, 7.0, 8.5 Hz), 7.41 (ddd, 1H, J=1.5, 7.0, 8.4 Hz), 6.83-6.78 (m, 4H, AA'BB'), 6.09 (m, 1H, NH), 3.87 (t, 2H, J=6.6 Hz), 3.74 (s, 3H), 3.67 (m, 2H), 1.76-1.66 (m, 4H), 1.46-1.33 (m, 8H); $^{13}$C NMR (CDCl$_3$) δ 159.7, 155.6, 153.8, 153.4, 149.5, 132.6, 128.6, 126.0, 120.8, 115.6, 115.2, 114.8, 68.7, 55.9, 41.5, 29.5, 29.4, 29.4, 27.1, 26.1.

Example 106

N-{2-[2-(Hexyloxy)phenoxy]ethyl}quinazolin-4-amine

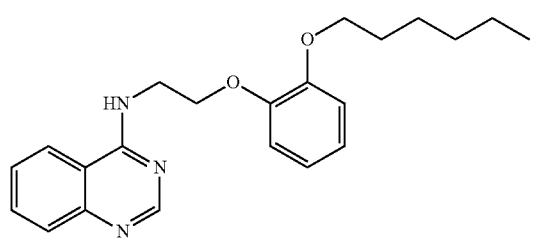 [SMILES: CCCCCCOc1ccccc1OCCNc1ncnc2ccccc12]

2-[2-(Hexyloxy)phenoxy]ethanamine (15.32 g, 64.6 mmol) was taken up in 350 mL of IPA, and 50 mL was removed by distillation. The mixture was cooled slightly, and TEA (18.0 mL, 128 mmol) and 4-chloroquinazoline (11.0 g, 67.1 mmol) were added. The mixture was heated at reflux for 16 hr. Then, the volatile components were evaporated and the residue was partitioned between DCM and 5% Na$_2$CO$_3$ (500 mL of each). The organic phase was dried over Na$_2$SO$_4$ and concentrated. The solid was recrystallized from EA/Hex to give 16.0 g of solid. $^1$H NMR (CDCl$_3$) δ 8.6 (s, 1H), 7.9-7.7 (m, 3H), 7.4 (m, 1H), 7.0-6.8 (m, 4H), 6.6 (br s, 1H, NH), 4.3 (m, 2H), 4.1-4.0 (m, 4H), 1.8 (m, 2H), 1.4 (m, 2H), 1.3-1.2 (m, 4H), 0.8 (m, 3H).

Example 107

N-{3-[2-(Hexyloxy)phenoxy]propyl}quinazolin-4-amine

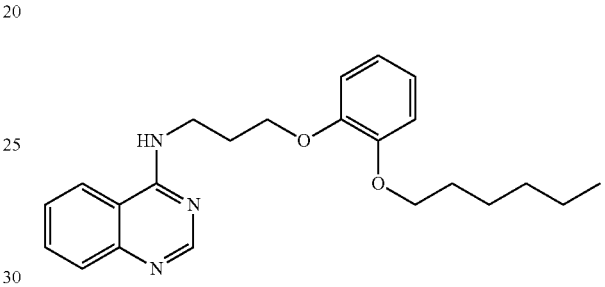

2-(Hexyloxy)phenol A mixture of catechol (47.5 g, 432 mmol), 1-bromohexane (71.2 g, 432 mmol), and K$_2$CO$_3$ (71.5 g, 518 mmol) in 120 mL of NMP and 240 mL of DMF was heated at 60° C. for 24 hr. Then, the volatile components were evaporated, and the slurry was partitioned between EA (600, 2×250 mL) and H$_2$O, 5% Na$_2$CO$_3$ (2×), H$_2$O, 0.1M HCl, and brine (150 mL each). The organic phases were dried over Na$_2$SO$_4$ and evaporated onto silica gel. SPE (10% EA/Hex) gave 75.5 g of a colorless liquid that contained a 2.5:1 mole ratio of 2-(hexyloxy)phenol and 1,2-bis(hexyloxy)benzene, as calculated from the NMR spectrum. The reaction was repeated using catechol (71.68 g, 652 mmol), 1-bromohexane (91.0 mL, 651 mmol), and K$_2$CO$_3$ (108 g, 783 mmol) in 240 mL of DMF at room temperature. The reaction gave 96.3 g pale yellow liquid that contained a 1:1 mole ratio of 2-(hexyloxy)phenol and 1,2-bis(hexyloxy) benzene.

N-{3-[2-(Hexyloxy)phenoxy]propyl}phthalimide A 1:1 mixture of 2-(hexyloxy)phenol and 1,2-bis(hexyloxy)benzene (47.2 g, 100 mmol of phenol), K$_2$CO$_3$ (18.7 g, 136 mmol), and N-(3-bromopropyl)phthalimide (26.8 g, 100 mmol) in 100 mL of DMF was heated at 55° C. for 24 hr. Then, the mixture was cooled, and most of the volatile components were evaporated. The residue was partitioned between EA (3×250 mL) and H$_2$O (3×200 mL), 0.05M HCl (2×150 mL), and brine (150 mL). The combined organic phases were dried over Na$_2$SO$_4$ and concentrated. SPE, washing with 5% EA/Hex to elute residual starting materials and then eluting the product with 20% EA/Hex, gave 29.8 g of white solid. Rf 0.41 (20% EA/Hex).

3-[2-(Hexyloxy)phenoxy]propan-1-amine A mixture of N-{3-[2-(hexyloxy)phenoxy]propyl}phthalimide (29.8 g, 78.2 mmol) and hydrazine monohydrate (4.80 mL, 101 mmol) in 300 mL of EtOH was heated at reflux for 16 hr. Then, heating was stopped, and 50 mL of 2M HCl was added. The slurry was mixed for 2 hr, then filtered through a pad of Celite, washing with 100 mL of 10% aqueous EtOH. The filtrate was adjusted to pH 10 using NaOH pellets and concentrated. SPE, washing with 3% MeOH/DCM and eluting with 8% MeOH/DCM+2% TEA, gave 15.5 g of yellow oil.

3-[2-(Hexyloxy)phenoxy]propan-1-amine (15.5 g, 61.8 mmol) was taken up in 250 mL of IPA, and 50 mL was removed by distillation. The mixture was cooled slightly, and TEA (10.5 mL, 74.8 mmol) and 4-chloroquinazoline (11.1 g, 67.6 mmol) were added. The mixture was heated at reflux for 16 hr. Then, most of the volatile components were evaporated, and the residue was partitioned between EA (300, 2×250 mL) and 5% $Na_2CO_3$ and brine (150 mL each). The organic phases were dried over anhydrous $Na_2SO_4$ and concentrated to a dark liquid. Trituration with two portions of ice-cold 50% $Et_2O$/Hex gave 14.9 g of light tan solid. Rf 0.20 (50% EA/Hex+2% TEA) 0.28 (5% MeOH/DCM+2% TEA); mp 67.0-67.5° C.; $^1$H NMR (CDCl$_3$) δ 8.65 (s, 1H), 7.85-7.81 (m, 2H), 7.70 (ddd, 1H, J=1.5, 7.0, 8.4 Hz), 7.38 (ddd, 1H, J=1.1, 6.9, 8.0 Hz), 7.11 (br s, 1H, NH), 7.00-6.89 (m, 4H), 4.24 (m, 2H), 4.04 (m, 2H), 3.93 (m, 2H), 2.24 (m, 2H), 1.71 (m, 2H), 1.37 (m, 2H), 1.23-1.17 (m, 4H), 0.81 (m, 3H); $^{13}$C NMR (CDCl$_3$) δ 159.7, 155.5, 149.5, 149.2, 148.6, 132.6, 128.3, 126.0, 122.5, 121.6, 121.3, 115.5, 115.3, 113.8, 70.5, 69.2, 40.9, 31.6, 29.2, 28.5, 25.8, 22.7, 14.1.

Example 108

N-{4-[2-(Hexyloxy)phenoxy]butyl}quinazolin-4-amine

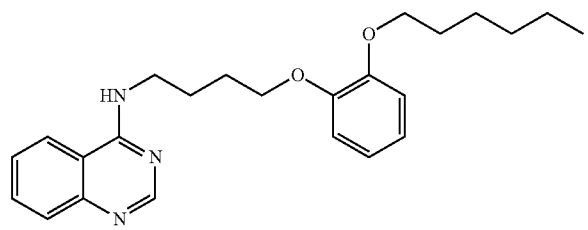 [SMILES: CCCCCCOc1ccccc1OCCCCNc1ncnc2ccccc12]

4-[2-(Hexyloxy)phenoxy]butan-1-amine (13.82 g, 52.2 mmol) was taken up in 300 mL of IPA, and 50 mL was removed by distillation. Then, the mixture was cooled slightly, and TEA (15 mL, 107 mmol) and 4-chloroquinazoline (8.6 g, 52 mmol) were added. The mixture was heated at reflux for 16 hr. Then, the volatile components were evaporated and the residue was partitioned between DCM and 5% $Na_2CO_3$ (500 mL of each). The organic phase was dried over $Na_2SO_4$ and concentrated. The solid was recrystallized from EA/Hex to give 8.3 g of colorless solid.

Example 109

N-[8-(Quinazolin-4-ylamino)octyl]nicotinamide

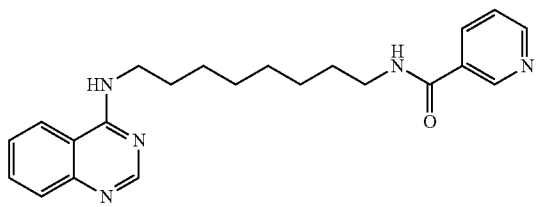 [SMILES: O=C(NCCCCCCCCNc1ncnc2ccccc12)c1cccnc1]

N-(8-Aminooctyl)nicotinamide (2.60 g, 10.4 mmol) was taken up in 65 mL of IPA, and 30 mL of volatile components were removed by distillation. The mixture was cooled, and TEA (2.90 mL, 20.7 mmol) and 4-chloroquinazoline (1.88 g, 11.5 mmol) were added. The mixture was heated at reflux for 6 hr. Then, the volatile components were evaporated, and the residue was partitioned between DCM and a mixture of 20 mL of 1N NaOH and 20 mL of 5% $Na_2CO_3$. The dark aqueous phase was extracted with 40 mL of 1-butanol. The combined organic phases were concentrated. The residue was taken up in 10% MeOH/DCM+2% TEA and filtered through a pad of silica gel. The filtrate was concentrated to give a dark solid. The solid was recrystallized from 10% aqueous MeOH, which removed some of the color. Recrystallization from EtOH gave two crops of light tan solid with comparable $^1$H NMR spectra; the crops were combined to give 2.08 g with mp 173-176° C. and 67% purity by LC (230 nm). FC (10% to 12% MeOH/DCM step gradient) and recrystallization from IPA/$H_2O$ gave 1.52 g of pale yellow solid, 89% purity by LC (230 nm). Trituration with ice-cold $Et_2O$ and then 30% EA/Hex at room temperature gave a solid with mp 172.5-176.0° C. and 90% purity by LC (230 nm). $^1$H NMR (40° C., DMSO-d$_6$) δ 8.96 (d, 1H, J=1.5 Hz), 8.66 (d, 1H, J=3.3 Hz), 8.56 (br s, 1H), 8.42 (s, 1H), 8.21-8.13 (m, 3H), 7.72 (m, 1H), 7.63 (m, 1H), 7.48-7.44 (m, 2H), 3.51 (m, 2H), 3.23 (m, 2H), 1.62 (m, 2H), 1.51 (m, 2H), 1.4-1.2 (m, 8H); $^{13}$C NMR (DMSO-d$_6$) δ 164.6, 159.3, 155.1, 151.6, 149.0, 148.3, 134.8, 132.3, 130.1, 127.4, 125.4, 123.4, 122.6, 114.9, 40.4, 39.2, 29.0, 28.8, 28.7, 28.5, 26.5, 26.4.

Example 110

N-[3-(Hexyloxy)benzyl]quinazolin-4-amine

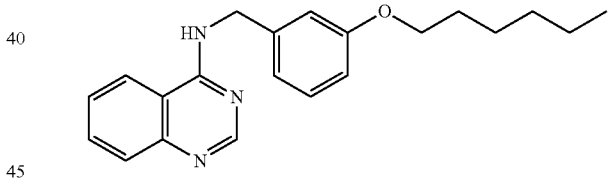

[3-(Hexyloxy)phenyl]methanamine (18.5 g 89.3 mmol) was taken up in 300 mL of IPA, and 100 mL of volatile material was removed by distillation. The mixture was cooled, and TEA (25.3 mL, 180 mmol) and 4-chloroquinazoline (16.1 g, 98.3 mmol) were added. The mixture was heated at reflux for 5 hr, and then stirred at room temperature overnight. Then, the volatile components were evaporated, and the residue was taken up in DCM (200 mL) and washed with 1N NaOH (100 mL). The aqueous phase was extracted with DCM (100 mL). The combined organic phases were dried over $Na_2SO_4$, filtered, and concentrated to give a red-brown solid. SPE, eluting with 20%, 30%, and 50% EA/Hex, gave product fractions that were combined and concentrated to yield a brown solid. Recrystallization from EA/Hex gave 21.8 g of the product as a colorless solid. Rf 0.21 (50% EA/Hex); mp 106.0-107.0° C.; $^1$H NMR (CDCl$_3$) δ 8.69 (s, 1H), 7.84 (d, 1H), 7.74-7.71 (m, 2H), 7.44 (m, 1H), 7.25 (m, 1H), 6.96-6.93 (m, 2H), 6.83 (dd, 1H, J=2.2, 8.5 Hz), 6.18 (br s, 1H), 4.83 (m, 2H, AB), 3.92 (t, 2H, J=6.6 Hz), 1.75 (m, 2H), 1.42 (m, 2H), 1.33-1.28 (m, 4H), 0.89 (m, 3H); $^{13}$C NMR (CDCl$_3$) δ 159.8, 159.5, 155.8, 149.6, 139.7, 132.9, 130.1, 128.8, 126.3, 120.8, 120.2, 115.0, 114.5, 113.8, 68.2, 45.5, 31.8, 29.4, 25.9, 22.8, 14.2.

Example 111

N-[3-(Decyloxy)benzyl]quinazolin-4-amine

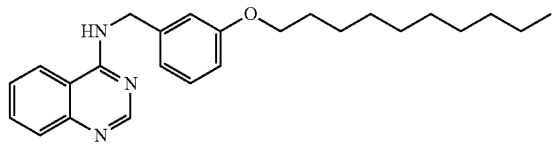 [SMILES: CCCCCCCCCCOc1cccc(CNc2ncnc3ccccc23)c1]

(3-(Decyloxy)phenyl)methanol A mixture of 3-hydroxybenzyl alcohol (36.2 g, 292 mmol), 1-bromodecane (55.5 mL, 269 mmol), and K$_2$CO$_3$ (44.3 g, 321 mmol) in 60 mL of NMP and 120 mL of DMF was mixed at 60° C. for 2 days with the aid of a mechanical stirrer. Then, the volatile components were removed in vacuo. The resulting slurry was partitioned between 50% EA/Hex (300, 2×250 mL) and H$_2$O (400 mL), 0.2N NaOH (150 mL), H$_2$O (150 mL), 2M HCl (150 mL), H$_2$O (150 mL), and brine (150 mL). The organic phases were dried over anhydrous Na$_2$SO$_4$, filtered through a pad of silica gel, and concentrated to 67.8 g of amber oil. The oil solidified exothermically. NMR indicated the presence of residual 1-bromodecane and EA. $^1$H NMR (CDCl$_3$) δ 7.2 (m, 1H), 6.9 (m, 2H), 6.8 (m, 1H), 3.9 (br s, 2H, AB), 3.9 (t, 2H, J=6.6 Hz), 2.6 (br s, 1H, OH), 1.8 (m, 2H), 1.5 (m, 2H), 1.4-1.2 (m, 12H), 0.9 (m, 3H); $^{13}$C NMR (CDCl$_3$) δ 159.5, 142.7, 129.6, 119.0, 113.8, 113.0, 68.1, 65.2, 32.0, 29.8, 29.7, 29.6, 29.5, 29.4, 26.2, 22.8, 14.3.

1-(Chloromethyl)-3-(decyloxy)benzene A mixture of [3-(decyloxy)phenyl]methanol (58.4 g, 221 mmol) and 150 mL of toluene was added dropwise to a mixture of thionyl chloride (19.4 mL, 266 mmol) and 50 mL of toluene. During the addition, gas evolution was observed. After 16 hr, the mixture was heated at reflux. After 1 hr, 150 mL of volatile material was removed by distillation. Then, the remaining volatiles were evaporated in vacuo.

N-[3-(Decyloxy)benzyl]phthalimide The residue was taken up in 120 mL of DMF and 60 mL of NMP, potassium phthalimide (49.2 g, 266 mmol) was added, and the mixture was heated at 60° C. for 24 hr. Then, the mixture was cooled and partitioned between 50% EA/Hex and H$_2$O (2×), 0.1M HCl, and brine. The organic phases were dried over Na$_2$SO$_4$, filtered through a pad of silica gel, and concentrated to 90.4 g of amber oil. $^1$H NMR (CDCl$_3$) δ 7.8 and 7.7 (m, 4H, AA'BB'), 7.2 (m, 1H), 7.0 (m, 2H), 6.8 (m, 1H), 4.8 (s, 2H), 3.9 (t, 2H, J=6.6 Hz), 1.7 (m, 2H), 1.4 (m, 2H), 1.4-1.2 (m, 12H), 0.9 (m, 3H); $^{13}$C NMR (CDCl$_3$) δ 168.2, 159.6, 137.9, 134.2, 132.3, 129.9, 123.6, 120.8, 114.8, 114.1, 68.2, 41.8, 32.1, 29.8, 29.8, 29.6, 29.5, 29.5, 26.2, 22.9, 14.3.

[3-(Decyloxy)phenyl]methanamine IPA (50 mL) was mixed with the residue and then evaporated to remove residual EA. The residue was taken up in 400 mL of EtOH, hydrazine monohydrate (14.5 mL, 299 mmol) was added, and the mixture was heated at reflux. After 6 hr, the mixture was cooled, and 150 mL of 2M HCl was added. The solid precipitate was broken up to form a slurry, which was filtered and washed with 20% aqueous IPA. The filtrate was adjusted to pH 10 by adding NaOH pellets. Then, the mixture was concentrated. The resulting liquid was partitioned between DCM and 5% Na$_2$CO$_3$, and the organic phase was dried over anhydrous Na$_2$SO$_4$ and concentrated.

N-[3-(Decyloxy)benzyl]quinazolin-4-amine Crude [3-(decyloxy)phenyl]methanamine was taken up in 400 mL of IPA, and 100 mL of volatile components were removed by distillation. The mixture was allowed to cool slightly. TEA (39 mL, 278 mmol) and 4-chloroquinazoline 22.4 g, 136 mmol) were added. The mixture was heated at reflux for 20 hr. Then, the mixture was allowed to cool, and the volatile components were evaporated. The mixture was partitioned between DCM (350, 2×100 mL) and 2N NaOH (150 mL). The organic phases were dried over anhydrous Na$_2$SO$_4$, 150 mL of MeOH were added, and the mixture was filtered through a pad of silica gel. The filtrate was concentrated to give a pink solid. The solid was recrystallized from EA/Hex to give a lightly colored solid. The solid was recrystallized from IPA to give 43.4 g of colorless solid. Rf 0.47 (10% MeOH/DCM); mp 93.0-95.5° C.; $^1$H NMR (CDCl$_3$) δ 8.71 (s, 1H), 7.86 (d, 1H, J=8.4 Hz), 7.76-7.68 (m, 2H), 7.46 (m, 1H), 7.27 (m, 1H), 6.98-6.94 (m, 2H), 6.84 (m, 1H), 5.95 (br s, 1H, NH), 4.84 (m, 2H, AB), 3.94 (t, 2H, J=6.6 Hz), 1.77 (m, 2H), 1.43 (m, 2H), 1.29-1.26 (m, 12H), 0.87 (m, 3H); $^{13}$C NMR (CDCl$_3$) δ 159.8, 159.4, 155.6, 149.8, 139.8, 132.9, 130.1, 128.9, 126.3, 120.7, 120.2, 115.0, 114.6, 113.8, 68.3, 45.6, 32.1, 29.8, 29.8, 29.6, 29.5, 29.5, 26.3, 22.9, 14.3.

Example 112

N-(3-Phenoxybenzyl)quinazolin-4-amine

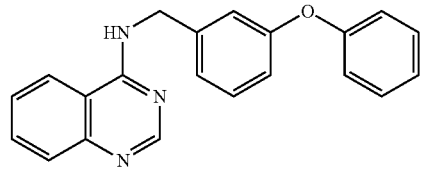 [SMILES: c1ccc(Oc2cccc(CNc3ncnc4ccccc34)c2)cc1]

(3-Phenoxyphenyl)methanamine (1.55 g, 7.79 mmol) was taken up in 60 mL of IPA, and 15 mL of volatile material was removed by distillation. The mixture was cooled, and TEA (1.50 mL, 10.7 mmol) and 4-chloroquinazoline (1.20 g, 7.32 mmol) in 15 mL of IPA were added. The mixture was heated at reflux for 5.5 hr, and then stirred at room temperature overnight. Then, the volatile components were evaporated, and the residue was partitioned between DCM (3×70 mL) and 5% Na$_2$CO$_3$ (40 mL). The combined organic phases were dried over Na$_2$SO$_4$, filtered, and concentrated. SPE, eluting with 25% and then 55% EA/Hex, gave product fractions that were combined and concentrated to yield an orange solid. Recrystallization from EA/Hex gave a pink solid, and then from MeOH gave 1.29 g of a light pink solid. Rf 0.19 (50% EA/Hex); mp 146.5-148.0° C.; $^1$H NMR (CDCl$_3$) δ 8.66 (s, 1H), 7.83 (d, 1H, J=8.5 Hz), 7.77 (d, 1H, J=8.1 Hz), 7.71 (m, 1H), 7.42 (m, 1H), 7.30 (m, 3H), 7.10 (m, 2H), 7.04 (br s, 1H), 6.99 (m, 2H), 6.90 (m, 1H), 6.44 (m, 1H, NH), 4.84 (m, 2H, AB); $^{13}$C NMR (CDCl$_3$) δ 159.5, 157.9, 157.0, 155.5, 149.6, 140.4, 132.9, 130.3, 130.0, 128.7, 126.3, 123.7, 122.6, 120.9, 119.2, 118.3, 117.9, 115.1, 45.1.

Example 113

N-[4-(Decyloxy)benzyl]quinazolin-4-amine

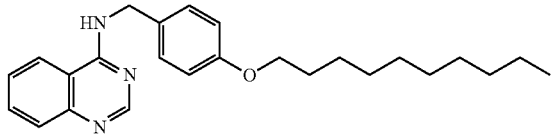 [SMILES: CCCCCCCCCCOc1ccc(CNc2ncnc3ccccc23)cc1]

4-(Decyloxy)benzonitrile A mixture of 4-hydroxybenzonitrile (4.32 g, 36.3 mmol), 1-bromodecane (6.80 mL, 32.9 mmol), and $K_2CO_3$ (6.61 g, 47.8 mmol) in 20 mL of DMF was reacted for 2 days. The solvent was evaporated in vacuo. The residue was partitioned between 50% EA/Hex (3×150 mL) and 5% $Na_2CO_3$ (3×80 mL), $H_2O$ (40 mL), 0.1M HCl (40 mL), and brine (80 mL). The organic phases were dried over anhydrous $Na_2SO_4$ and concentrated to give 8.30 g of colorless oil that solidified upon standing. $^1H$ NMR (CDCl$_3$) δ 7.54 and 6.90 (m, 4H, AA'BB'), 3.97 (t, 2H, J=6.6 Hz), 1.78 (m, 2H), 1.42 (m, 2H), 1.34-1.25 (m, 12H), 0.86 (m, 3H);
$^{13}C$ NMR (CDCl$_3$) δ 162.6, 134.0, 119.4, 115.3, 103.7, 68.5, 32.0, 29.6, 29.4, 29.4, 29.1, 26.0, 22.8, 14.2.

[4-(Decyloxy)phenyl]methanamine (7.61 g) was prepared as a colorless solid by the method for [4-(hexyloxy)phenyl]methanamine by treating 4-(decyloxy)benzonitrile with 2 g of LAH. $^1H$ NMR (CDCl$_3$) δ 7.2 (m, 2H), 6.8 (m, 2H), 3.90 (t, 2H, J=6.6 Hz), 3.76 (s, 2H), 1.75 (m, 2H), 1.55 (m, 2H), 1.43 (m, 2H), 1.4-1.2 (m, 10H), 0.87 (m, 3H); $^{13}C$ NMR (CDCl$_3$) δ 158.1, 135.4, 128.3, 114.5, 68.0, 46.0, 32.0, 29.6, 29.6, 29.5, 29.4, 29.4, 28.1, 26.1, 22.7, 14.2.

N-[4-(Decyloxy)benzyl]quinazolin-4-amine (3.77 g) was prepared from [4-(decyloxy)phenyl]methanamine (3.04 g, 11.6 mmol), 4-chloroquinazoline (2.60 g, 15.8 mmol), TEA (3.40 mL, 24.2 mmol), and IPA (50 mL) using the method for N-(3-phenoxybenzyl)quinazolin-4-amine. The product was recrystallized from 30% EA/Hex. Rf 0.24 (5% MeOH/DCM); mp 103.0-104.5° C.; $^1H$ NMR (CDCl$_3$) δ 8.71 (s, 1H), 7.85 (dd, 1H, J=0.7, 8.4 Hz), 7.74 (dd, 1H, J=1.5, 6.9 Hz), 7.69 (m, 1H), 7.44 (ddd, 1H, J=1.1, 7.0, 8.1 Hz), 7.31 (m, 2H), 6.88 (m, 2H), 5.90 (br s, 1H, NH), 4.78 (m, 2H, AB), 3.95 (t, 2H, J=6.6 Hz), 1.77 (m, 2H), 1.45 (m, 2H), 1.4-1.2 (m, 12H), 0.88 (m, 3H); $^{13}C$ NMR (CDCl$_3$) δ 159.6, 159.1, 155.7, 149.7, 132.8, 130.0, 129.7, 128.9, 126.2, 120.8, 115.0, 68.3, 45.2, 32.1, 29.8, 29.8, 29.6, 29.5, 29.4, 26.2, 22.9, 14.3.

Example 114

N-[4-(Hexyloxy)benzyl]quinazolin-4-amine

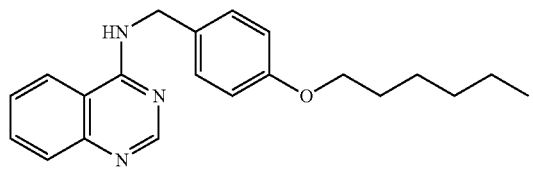 [SMILES: CCCCCCOc1ccc(CNc2ncnc3ccccc23)cc1]

N-[4-(Hexyloxy)benzyl]quinazolin-4-amine (31.9 g) was prepared from [4-(hexyloxy)phenyl]methanamine (32 g), 4-chloroquinazoline (19 g), TEA (32.5 mL), and IPA (250 mL) following the method for the preparation of N-(3-phenoxybenzyl)quinazolin-4-amine. Mp 109.0-111.0° C. (from IPA); $^1H$ NMR (CDCl$_3$) δ 8.68 (s, 1H), 7.82 (m, 1H), 7.71 (m, 2H), 7.41 (m, 1H), 7.29 (m, 2H, J=2.9, 4.8, 9.5 Hz, AA'BB'), 6.87 (m, 2H, J=2.9, 5.1, 9.5 Hz, AA'BB'), 6.11 (br s, 1H, NH), 4.77 (m, 2H, AB), 3.93 (t, 2H, J=6.6 Hz), 1.76 (m, 2H), 1.5 (m, 2H), 1.4-1.3 (m, 4H), 0.89 (m, 3H); $^{13}C$ NMR (CDCl$_3$) δ 159.4, 150.0, 155.6, 149.6, 132.8, 130.0, 129.6, 128.7, 126.2, 120.8, 115.0, 115.0, 68.3, 45.1, 31.8, 29.4, 25.9, 22.8, 14.2.

Example 115

1-[2-(Ethoxymethyl)-1H-imidazo[4,5-c]quinolin-1-yl]-2-methylpropan-2-ol

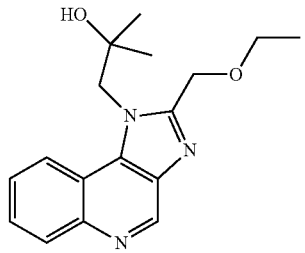 [SMILES: CCOCc1nc2cnc3ccccc3c2n1CC(C)(C)O]

3-Nitroquinolin-4-ol 70% Aqueous nitric acid (6.1 mL) was added dropwise to a mixture of 4-hydroxyquinoline (10 g, 69 mmol) and 100 mL of acetic acid heated at reflux. After 15 min, the mixture was allowed to cool to room temperature. Dilution with EtOH resulted in the formation of a precipitate, which was filtered and washed sequentially with EtOH, $H_2O$, and EtOH. Drying of the filtrate in vacuo gave 4.62 g of a light yellow powder. $^1H$ NMR (DMSO-d$_6$) δ 9.2 (s, 1H), 8.3 (d, 1H), 7.9-7.7 (m, 2H), 7.5 (m, 1H).

4-Chloro-3-nitroquinoline Phosphorus oxychloride (2.5 mL, 27 mmol) was added dropwise to a mixture of 3-nitroquinolin-4-ol (4.6 g, 24 mmol) and 100 mL of DMF. The mixture was heated at 100° C. for 15 min, and then poured onto stirred ice. The slurry was neutralized with solid NaHCO$_3$, and the precipitate was filtered and washed with saturated NaHCO$_3$ and $H_2O$. The filtrate was taken up in DCM, dried over anhydrous $Na_2SO_4$, and concentrated to give 2.3 g of solid.

2-Methyl-1-(3-nitroquinolin-4-yl)propan-2-ol A mixture of 4-chloro-3-nitroquinoline (2.3 g, 11 mmol), 1-amino-2-methylpropan-2-ol (1.0 g, 11 mmol), TEA (9.3 mL), and 100 mL of DCM was heated at reflux until the starting material was consumed. The mixture was allowed to cool, washed with saturated NaHCO$_3$ and $H_2O$, dried over anhydrous $Na_2SO_4$, and concentrated to give 1.01 g of product. $^1H$ NMR (DMSO-d$_6$) δ 9.9 (br s, 1H, NH), 9.2 (s, 1H), 8.5 (d, 1H), 7.9-7.8 (m, 2H), 7.6 (m, 1H), 5.1 (s, 1H, OH), 3.8 (m, 2H, ABX), 1.2 (s, 6H).

1-(3-Aminoquinolin-4-ylamino)-2-methylpropan-2-ol 2-Methyl-1-(3-nitroquinolin-4-yl)propan-2-ol (1.01 g, mmol), 10% Pd—C (200 mg), and 20 mL of toluene were stirred under an atmosphere of hydrogen until the starting material was consumed. The hydrogen was replaced by argon, and the mixture was filtered through a pad of Celite and concentrated by evaporation to give 586 mg of product. $^1H$ NMR (CD$_3$OD) δ 8.3 (s, 1H), 8.1 (m, 1H), 7.8 (m, 1H), 7.5-7.4 (m, 2H), 7.2-7.0 (m, 2H, ABX), 1.2 (s, 6H).

1-[2-(Ethoxymethyl)-1H-imidazo [4,5-c]quinolin-1-yl]-2-methylpropan-2-ol A mixture of 1-(3-aminoquinolin-4-ylamino)-2-methylpropan-2-ol (586 mg, 2.54 mmol) and 0.4 mL of ethoxyacetic acid was heated at 130° C. for 3 hr. The cooled mixture was poured into 5 mL of H$_2$O and made basic with 6N NaOH. The resulting solid was collected by filtration, washed with H$_2$O, and dried in vacuo to give 655 mg of product. $^1$H NMR (CDCl$_3$) δ 9.1 (s, 1H), 8.3 (m, 1H), 8.1 (m, 1H), 7.7-7.5 (m, 2H), 4.9 (br s, 2H), 4.8 (br s, 2H), 3.6 (q, 2H), 1.3 (s, 6H), 1.2 (t, 3H).

Example 116

1-(4-Amino-1-isobutyl-1H-imidazo[4,5-c]quinolin-2-yl)pentyl acetate

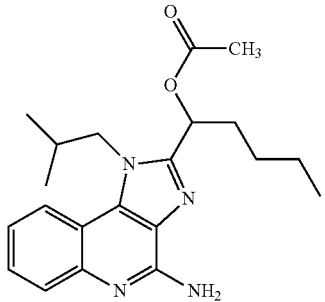 [SMILES: CCCCC(OC(C)=O)c1nc2c(N)nc3ccccc3c2n1CC(C)C]

N-Isobutyl-3-nitroquinolin-4-amine 4-Chloro-3-nitroquinoline was prepared from 3-nitroquinolin-4-ol (5.5 g, 28.8 mmol). Isobutylamine (3.2 mL, 32 mmol) was added slowly to a mixture of the 4-chloro-3-nitroquinoline, TEA (24 mL, 170 mmol), and 40 mL of DCM. The mixture was heated at reflux for 30 min. Then, the volatile components were evaporated, and the residue was taken up in aqueous acid and filtered. The filtrate was adjusted to pH 8-9 by adding concentrated NH$_4$OH, and the resulting solid was filtered and washed with H$_2$O. Drying in vacuo gave 6.49 g of product. $^1$H NMR (CDCl$_3$) δ 9.8 (br s, 1H, NH), 9.3 (s, 1H), 8.3 (m, 1H), 8.0 (m, 1H), 7.8 (m, 1H), 7.4 (m, 1H), 3.8 (m, 2H), 2.1 (m, 1H), 1.1 (d, 6H).

N$^4$-Isobutylquinoline-3,4-diamine A mixture of N-isobutyl-3-nitroquinolin-4-amine (19.0 g, 77.6 mmol) and 10% Pd—C (700 mg) in 200 mL of EA was reacted under an atmosphere of hydrogen at 42 psi until the starting material was consumed. Then, the hydrogen was replaced by argon, and the mixture was filtered through a pad of Celite. The filtrate was concentrated to give 15.2 g of product. $^1$H NMR (CDCl$_3$) δ 8.4 (s, 1H), 7.9 (m, 1H), 7.8 (m, 1H), 7.5-7.4 (m, 2H), 3.9-3.6 (br m, 3H, NH), 3.0 (d, 2H), 1.9 (m, 1H), 1.0 (d, 6H).

1-Isobutyl-1H-imidazo[4,5-c]quinoline A mixture of N$^4$-isobutylquinoline-3,4-diamine (2.33 g, 10.8 mmol) and 17 mL of formic acid was heated at 100° C. for 3 hr. The volatile components were evaporated in vacuo. The residue was diluted with H$_2$O, made basic using concentrated NH$_4$OH, and extracted with DCM. The organic solvent was replaced with Et$_2$O, treated with activated charcoal, filtered through a pad of Celite, and concentrated. NMR indicated the presence of starting material. The crude was mixed with triethyl orthoformate, heated at 100° C. for 3 hr, and processed as before to give 1.4 g of product. $^1$H NMR (CDCl$_3$) δ 9.3 (s, 1H), 8.3 (m, 1H), 8.1 (m, 1H), 7.9 (s, 1H), 7.7-7.5 (m, 2H), 4.3 (d, 2H), 2.3 (m, 1H), 1.0 (d, 6H).

1-(1-Isobutyl-1H-imidazo[4,5-c]quinolin-2-yl)pentan-1-ol n-Butyllithium (1.5M in hexanes, 3.6 mL) was added to a mixture of 1-isobutyl-1H-imidazo[4,5-c]quinoline (1.4 g, 4.9 mmol) and 25 mL of THF cooled by a dry ice/IPA bath. After 15 min, valeraldehyde (0.80 mL, 7.5 mmol) was added. The mixture was allowed to warm to room temperature. After 3 hr, H$_2$O and Et$_2$O were added, and the organic phase was separated, dried over anhydrous MgSO$_4$, and concentrated. FC, eluting with EA, gave 990 mg of the product. $^1$H NMR (CDCl$_3$) δ 9.2 (s, 1H), 8.1 (m, 1H), 7.9 (m, 1H), 7.7-7.5 (m, 2H), 4.95 (m, 1H), 4.5 (m, 1H), 4.3 (m, 1H), 2.3 (m, 2H), 1.6-1.3 (m, 4H), 1.1 (d, 3H), 1.0-0.8 (m, 6H).

1-(1-Isobutyl-1H-imidazo[4,5-c]quinolin-2-yl)pentyl acetate Acetic anhydride (0.400 mL, 4.24 mmol) and TEA (0.510 mL, 3.64 mmol) were added sequentially to a mixture of 1-(1-isobutyl-1H-imidazo[4,5-c]quinolin-2-yl)pentan-1-ol (818 mg, 2.75 mmol) and 20 mL of DCM. After 16 hr, the mixture was diluted with 1 volume of DCM and washed with H$_2$O and saturated NaHCO$_3$. The organic phase was dried over anhydrous MgSO$_4$ and concentrated to give 1.00 g of product. $^1$H NMR (CDCl$_3$) δ 9.3 (s, 1H), 8.25 (m, 1H), 8.1 (m, 1H), 7.75-7.55 (m, 2H), 6.1 (m, 1H), 4.5 (m, 2H, ABX), 2.3 (m, 2H), 2.1 (s, 3H), 1.5-1.3 (m, 4H), 1.1 (d, 3H), 1.0-0.8 (m, 6H).

2-(1-Acetoxypentyl)-1-isobutyl-1H-imidazo[4,5-c]quinoline 5-oxide A mixture of 1-(1-isobutyl-1H-imidazo[4,5-c]quinolin-2-yl)pentyl acetate (980 mg, 2.91 mmol) and 32% peracetic acid (0.22 mL, 3.2 mmol) in 20 mL of EA was heated at reflux for 1 hr and stirred at room temperature overnight. The volatile components were evaporated in vacuo, and the residue was partitioned between DCM and saturated NaHCO$_3$ and H$_2$O. The organic phase was dried over anhydrous Na$_2$SO$_4$ and concentrated to give a solid. The solid was slurried with cold acetone, filtered, and dried to give 750 mg of product. $^1$H NMR (CDCl$_3$) δ 9.3 (s, 1H), 9.0 (m, 1H), 8.5 (br s, 2H, NH$_2$), 8.15 (m, 1H), 7.85-7.75 (m, 2H), 6.0 (dd, 1H), 4.5 (m, 2H, ABX), 2.3 (m, 2H), 2.1 (s, 3H), 1.5-1.3 (m, 4H), 1.1 (d, 3H), 0.95 (d, 3H), 0.9 (m, 3H).

1-(4-Amino-1-isobutyl-1H-imidazo[4,5-c]quinolin-2-yl)pentyl acetate A mixture of 4-toluenesulfonyl chloride (447 mg, 2.34 mmol) and 15 mL of DCM was added slowly to a mixture of 2-(1-acetoxypentyl)-1-isobutyl-1H-imidazo[4,5-c]quinoline 5-oxide (750 mg, 2.13 mmol) and 8 mL of concentrated NH$_4$OH cooled by an ice bath. The mixture was allowed to warm to room temperature overnight. The mixture was diluted with DCM and washed with saturated NaHCO$_3$, and the organic phase was dried over anhydrous Na$_2$SO$_4$ and concentrated to give 650 mg of colorless solid. $^1$H NMR (CDCl$_3$) δ 7.9 (d, 1H), 7.7 (d, 1H), 7.5 (m, 1H), 7.3 (m, 1H), 6.1 (dd, 1H), 5.5 (br s, 2H, NH$_2$), 4.4 (m, 2H, ABX), 2.3 (m, 2H), 2.15 (m, 1H), 2.1 (s, 3), 1.5-1.3 (m, 4H), 1.1 (d, 3H), 1.0-0.8 (m, 6H).

Example 117

1-Isobutyl-2-pentadecyl-1H-imidazo[4,5-c]quinolin-4-ol

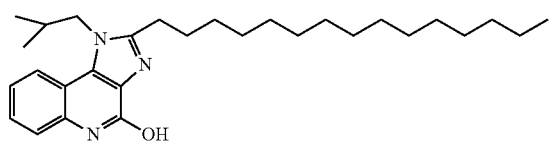 [SMILES: CCCCCCCCCCCCCCCc1nc2c(O)nc3ccccc3c2n1CC(C)C]

2-Chloro-N-isobutyl-3-nitroquinolin-4-amine A mixture of isobutylamine (10.0 mL, 101 mmol) and TEA (15.6 mL, 111 mmol) in 10 mL of 1:1 DMF/DCM was added slowly to 2,4-dichloro-3-nitroquinoline (26.94 g, 111 mmol) in 100 mL of 4:1 DMF/DCM cooled with an ice bath. The mixture was allowed to warm to room temperature overnight. Then, the volatile components were evaporated, and the residue was partitioned between EA and saturated NaHCO$_3$ and brine, dried over Na$_2$SO$_4$, and concentrated. FC (15% EA/Hex) gave the product as an orange solid. Recrystallization from EA/Hex gave 3 crops of the product (17.97 g) as a light orange solid.

2-Chloro-N$^4$-isobutylquinoline-3,4-diamine A mixture of 2-chloro-N-isobutyl-3-nitroquinolin-4-amine (996 mg, 3.57 mmol) and 35 mg of 5% Pt—C in 15 mL of MeOH was stirred under 2 atmospheres of hydrogen for 90 min. Then, the mixture was blanketed with argon, filtered through a pad of Celite and concentrated to dryness.

4-Chloro-1-isobutyl-2-pentadecyl-1H-imidazo[4,5-c]quinoline A mixture of the crude 2-chloro-N$^4$-isobutylquinoline-3,4-diamine and palmitic acid (3.66 g, 14.3 mmol) was heated at 180° C. for 4 hr. Then, the mixture was partially cooled and, while mixing, diluted with 400 mL of EA and 10 mL of 1M NaOH and 40 mL of 5% Na$_2$CO$_3$. The warm mixture was cooled with an ice bath, and a solid (presumably sodium palmitate) formed. The liquid was decanted from the solid, the layers were separated, and the aqueous layer was extracted with EA (2×150 mL). The organic phases were washed with 5% Na$_2$CO$_3$ (3×50 mL) and brine, dried over Na$_2$SO$_4$, and concentrated. FC (4% MeOH/DCM) gave fractions that contained the product, observed by TLC. The fractions were concentrated, and two crops of the product (1.14 g) were crystallized from DCM/Hex. Rf 0.27 (5% MeOH/DCM); $^1$H NMR (CDCl$_3$) δ 7.8 (m, 2H), 7.4 (m, 1H), 7.3 (m, 1H), 4.2 (d, 2H, ABX), 2.9 (m, 2H), 2.3 (m, 1H), 1.9 (m, 2H), 1.5-1.2 (m, 24H), 1.0 (d, 6H), 0.85 (t, 3H).

1-Isobutyl-2-pentadec yl-1H-imidazo[4,5-c]quinolin-4-ol A mixture of 4-chloro-1-isobutyl-2-pentadecyl-1H-imidazo[4,5-c]quinoline (165 mg, 0.35 mmol) in 5 mL of 50% concentrated NH$_4$OH/MeOH was heated at 160° C. for 72 hr. Then, the mixture was cooled and evaporated to a solid. The solid was washed with saturated NaHCO$_3$ and H$_2$O and dried in vacuo to give 160 mg light gray solid. Rf 0.29 (10% MeOH/DCM); $^1$H NMR (CDCl$_3$) δ 12.1 (br s, 1H, OH), 7.8 (m, 2H), 7.4 (m, 1H), 7.3 (m, 1H), 4.2 (d, 2H, ABX), 2.9 (m, 2H), 2.3 (m, 1H), 1.9 (m, 2H), 1.5-1.2 (m, 24H), 1.0 (d, 6H), 0.85 (t, 3H).

Example 118

1-Octyl-1H-imidazo[4,5-c]quinoline

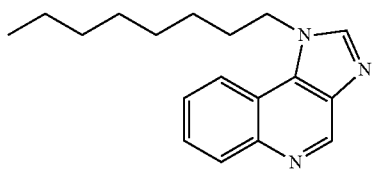 [SMILES: CCCCCCCCn1cnc2cnc3ccccc3c21]

2,4-Dihydroxy-3-nitroquinoline Concentrated nitric acid (12.4 mL) was added to a mechanically-stirred mixture of 2,4-dihydroxyquinoline (20.2 g, 125 mmol) in 160 mL of acetic acid at reflux. After 20 min, heating was stopped. After a further 15 min, 3 volumes of ice chips were added, and the mixture was stirred 30 min. The precipitate was filtered and washed with four times with 1 volume of ice-cold H$_2$O. After drying in vacuo, 23.0 g of orange solid was obtained.

2,4-Dichloro-3-nitroquinoline A mixture of 2,4-dihydroxy-3-nitroquinoline (5.08 g, 24.7 mmol) and phenylphosphonic dichloride (13.9 mL, 98.4 mmol) was heated at 140° C. for 3 hr. After the mixture had cooled somewhat, it was added to 18.5 g of NaHCO$_3$ in 150 mL ice-cold H$_2$O. The pH was at least 6. The solid was filtered and washed twice with H$_2$O. After drying in vacuo, 5.09 g of a tan solid was obtained.

2-Chloro-3-nitro-N-octylquinolin-4-amine A mixture of 2,4-dichloro-3-nitroquinoline (1.0 g, 4.1 mmol), 1-octylamine (0.75 mL), TEA (3.5 mL), and 20 mL of DCM were heated at reflux for 1 hr. Then, the volatile material was evaporated, the residue was taken up in H$_2$O, and the pH was adjusted to 8-9 with concentrated HCl and concentrated NH$_4$OH. The precipitate was collected and washed with H$_2$O. After drying in vacuo, 1.65 g of a solid was obtained.

N$^4$-Octylquinoline-3,4-diamine (515 mg) was obtained by treating 2-chloro-3-nitro-N-octylquinolin-4-amine (1.33 g) with the conditions used to prepare N-[8-(hexyloxy)octyl]pyrimidin-4-amine. $^1$H NMR (CDCl$_3$) δ 8.5 (s, 1H), 8.05 (d, 1H), 7.9 (d, 1H), 7.5 (m, 1H), 7.35 (m, 1H), 4.1 (br s, 2H, NH$_2$), 3.5 (m, 2H), 1.75 (m, 2H), 1.6-1.1 (m, 10H), 0.85 (m, 3H).

1-Octyl-1H-imidazo[4,5-c]quinoline (400 mg) was obtained by treating N$^4$-octylquinoline-3,4-diamine (515 mg) with the conditions used to prepare 1-[8-(hexyloxy)octyl]-1H-imidazo[4,5-c]pyridine.

$^1$H NMR (CDCl$_3$) δ 9.35 (s, 1H), 8.6 (m, 1H), 8.2 (d, 1H), 8.0 (s, 1H), 7.75 (m, 2H), 4.6 (t, 2H), 2.0 (m, 2H), 1.5-1.1 (m, 10H), 0.9 (m, 3H).

Example 119

1-Hexadecyl-1H-imidazo[4,5-c]quinoline

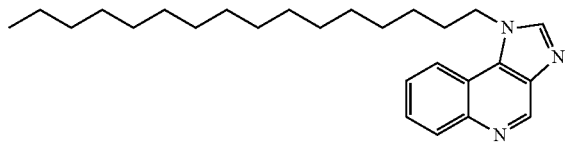 [SMILES: CCCCCCCCCCCCCCCCn1cnc2cnc3ccccc3c21]

2-Chloro-3-nitro-N-octylquinolin-4-amine A mixture of 2,4-dichloro-3-nitroquinoline (1.0 g, 4.1 mmol), 1-octylamine (0.75 mL), TEA (3.5 mL), and 20 mL of DCM were heated at reflux for 1 hr. Then, the volatile material was evaporated, the residue was taken up in H$_2$O, and the pH was adjusted to 8-9 with concentrated HCl and concentrated NH$_4$OH. The precipitate was collected and washed with H$_2$O. After drying in vacuo, 1.65 g of a solid was obtained.

N$^4$-Octylquinoline-3,4-diamine (515 mg) was obtained by treating 2-chloro-3-nitro-N-octylquinolin-4-amine (1.33 g) with the conditions used to prepare N-[8-(hexyloxy)octyl]pyrimidin-4-amine. $^1$H NMR (CDCl$_3$) δ 8.5 (s, 1H), 8.05 (d, 1H), 7.9 (d, 1H), 7.5 (m, 1H), 7.35 (m, 1H), 4.1 (br s, 2H, NH$_2$), 3.5 (m, 2H), 1.75 (m, 2H), 1.6-1.1 (m, 10H), 0.85 (m, 3H).

1-Octyl-1H-imidazo[4,5-c]quinoline (400 mg) was obtained by treating N$^4$-octylquinoline-3,4-diamine (515 mg) with the conditions used to prepare 1-[8-(hexyloxy) octyl]-1H-imidazo[4,5-c]pyridine.

$^1$H NMR (CDCl$_3$) δ 9.35 (s, 1H), 8.6 (m, 1H), 8.2 (d, 1H), 8.0 (s, 1H), 7.75 (m, 2H), 4.6 (t, 2H), 2.0 (m, 2H), 1.5-1.1 (m, 10H), 0.9 (m, 3H).

Example 120

1-Hexadecyl-1H-imidazo[4,5-c]quinolin-4-amine

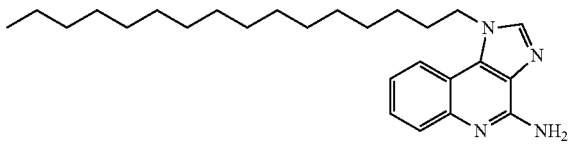 [SMILES: CCCCCCCCCCCCCCCCn1cnc2c(N)nc3ccccc3c21]

1-Hexadecyl-1H-imidazo[4,5-c]quinolin-4-amine was made following the method for the preparation of 1-isobutyl-2-pentadecyl-1H-imidazo[4,5-c]quinolin-4-ol, using 2,4-dichloro-3-nitroquinoline (1.00 g), 1-hexadecylamine (1.00 g), 8 mL of triethyl orthoformate at reflux for imidazole ring formation, and a solution of 1 mL of anhydrous NH$_3$ in 8 mL of anhydrous IPA in the final reaction. Final purification used FC (5% MeOH/DCM, Rf 0.17). $^1$H NMR (CDCl$_3$) δ 7.9 (m, 1H), 7.8 (m, 1H), 7.75 (s, 1H), 7.5 (m, 1H), 7.3 (m, 1H), 5.6 (br s, 1H, N$\underline{H}$), 4.5 (t, 2H), 2.0 (m, 2H), 1.5-1.2 (m, 26H), 0.85 (t, 3H).

Example 121

1-[2-(Dodecyloxy)ethyl]-1H-imidazo[4,5-c]quinoline

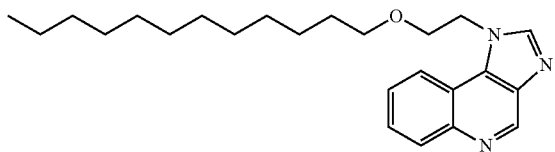 [SMILES: CCCCCCCCCCCCOCCn1cnc2cnc3ccccc3c21]

2-(Dodecyloxy)ethanol 60% Dispersion of sodium hydride in mineral oil (8.3 g, 208 mmol) was washed in Hex (2×). Then, a mixture of ethylene glycol (17.4 mL, 312 mmol) in 250 mL of DMF and 25 mL of DCM was added slowly while cooling with an ice bath. After 1 hr, 1-iodododecane (104 mmol) was added. The mixture was allowed to warm to room temperature.

After 24 hr, the volatile components were evaporated, and the residue was partitioned between EA and 100 mL of 1M HCl, then 0.1M HCl and 5% Na$_2$S$_2$O$_3$, then 0.1M HCl, then brine, and the organic phases were dried over MgSO$_4$ and concentrated. SPE, washing with 5% EA/Hex and eluting with 40% EA/Hex, gave 10.15 g of product. Rf 0.48 (40% EA/Hex); $^1$H NMR (CDCl$_3$) δ 3.7 (m, 2H), 3.55-3.40 (m, 4H), 2.1 (br s, 1H, O$\underline{H}$), 1.6 (m, 2H), 1.4-1.2 (m, 18H), 0.85 (t, 3H).

2-(Dodecyloxy)ethyl methanesulfonate as a crude material was prepared from 2-(dodecyloxy)ethanol (10.15 g, 44.1 mmol), methanesulfonyl chloride (4.3 mL, 53 mmol), and triethylamine (7.5 mL, 53 mmol) in 200 mL of THF, and carried on. Rf 0.56 (40% EA/Hex).

1-(2-Iodoethoxy)dodecane (14.9 g) was prepared from 2-(dodecyloxy)ethyl methanesulfonate and 12.9 g of sodium iodide by the Finkelstein reaction. Rf 0.94 (40% EA/Hex) 0.46 (5% EA/Hex); $^1$H NMR (CDCl$_3$) δ 3.7 (t, 2H), 3.45 (t, 2H), 3.25 (t, 2H), 1.6 (m, 2H), 1.4-1.2 (m, 18H), 0.85 (t, 3H).

1-(2-Azidoethoxy)dodecane as a crude was prepared from 1-(2-iodoethoxy)dodecane (14.9 g, 43.8 mmol) and sodium azide (2.85 g, 43.8 mmol) in 33 mL of DMF. Rf 0.28 (5% EA/Hex); $^1$H NMR (CDCl$_3$) δ 3.6 (t, 2H), 3.45 (t, 2H), 3.35 (t, 2H), 1.6 (m, 2H), 1.4-1.2 (m, 18H), 0.85 (t, 3H).

2-(Dodecyloxy)ethanamine was prepared by the catalytic hydrogenation of the crude 1-(2-azidoethoxy)dodecane using 1.5 g of 5% Pd—C in 150 mL of MeOH. SPE, washing with 50% EA/Hex and eluting with 15% MeOH/DCM+2% TEA, gave 8.0 g of product.

1-[2-(Dodecyloxy)ethyl]-1H-imidazo[4,5-c]quinoline (103 mg) was prepared by the method for the preparation of 1-hexadecyl-1H-imidazo[4,5-c]quinolin-4-amine starting with 2-(dodecyloxy)ethanamine (2.73 g, 11.9 mmol) and 2,4-dichloro-3-nitroquinoline (2.94 g, 12.1 mmol), using reduction of both nitro and aryl chloride by zinc/HCl, and formation of the imidazole ring using 7 mL of triethyl orthoformate at reflux. Final purification was by FC (5% MeOH/DCM, Rf 0.10). $^1$H NMR (CDCl$_3$) δ 9.3 (s, 1H), 8.2 (d, 1H), 8.1 (d, 1H), 7.95 (s, 1H), 7.7-7.5 (m, 2H), 4.7 (m, 2H), 3.85 (m, 2H), 3.3 (m, 2H), 1.4 (m, 2H), 1.3-1.1 (m, 18H), 0.8 (m, 3H).

Example 122

1-[2-(Dodecyloxy)ethyl]-N,N-dimethyl-1H-imidazo [4,5-c]quinolin-4-amine

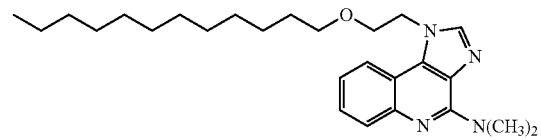 [SMILES: CCCCCCCCCCCCOCCn1cnc2c(N(C)C)nc3ccccc3c21]

N$^4$-[2-(Dodecyloxy)ethyl]-N$^2$,N$^2$-dimethyl-3-nitroquinoline-2,4-diamine A stoichiometric excess of 2-(dodecyloxy) ethanamine and 2,4-dichloro-3-nitroquinoline (486 mg, 2.0 mmol) and DIEA (0.38 mL, 2.18 mmol) in 10 ml of DMF and 10 mL of DCM was mixed at room temperature for 2 days. No reaction was observed by TLC. The DCM was evaporated and replaced by toluene, and the mixture was heated at reflux for 6 hr. Then, the reaction was cooled, partitioned between EA and saturated NaHCO$_3$ and brine, and the organic phase was dried over Na$_2$SO$_4$ and concentrated. FC (10% to 20% EA/Hex step gradient) gave 306 mg of N$^4$-[2-(Dodecyloxy)ethyl]-N$^2$,N$^2$-dimethyl-3-nitroquinoline-2,4-diamine as orange oil, as well as 376 mg of N$^2$,N$^4$-bis[2-(dodecyloxy)ethyl]-3-nitroquinoline-2,4-diamine as orange oil. $^1$H NMR (CDCl$_3$) δ 7.9 (m, 2H), 7.6-7.55 (m, 2H), 7.1 (m, 1H), 3.8 (m, 2H), 3.5-3.4 (m, 4H), 3.0 (s, 6H), 1.6 (m, 2H), 1.4-1.2 (m, 18H), 0.85 (t, 3H).

1-[2-(Dodecyloxy)ethyl]-N,N-dimethyl-1H-imidazo[4,5-c]quinolin-4-amine The nitro group of N$^4$-[2-(dodecyloxy) ethyl]-N$^2$,N$^2$-dimethyl-3-nitroquinoline-2,4-diamine (306 mg, 0.70 mmol) was reduced using zinc/HCl, and the ortho diamine was reacted with triethyl orthoformate at reflux to give 197 mg of the product after FC (5% MeOH/DCM). Rf 0.15 (5% MeOH/DCM); $^1$H NMR (CDCl$_3$) δ 7.9 (m, 2H), 7.8 (s, 1H), 7.45 (m, 1H), 7.2 (m, 1H), 4.6 (t, 2H), 3.85 (t, 2H), 3.6 (s, 6H), 3.3 (t, 2H), 1.5 (m, 2H), 1.3-1.1 (m, 18H), 0.85 (t, 3H).

Example 123

1-[6-(Octyloxy)hexyl]-1H-imidazo[4,5-c]quinoline

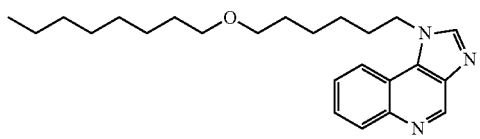 [SMILES: CCCCCCCCOCCCCCCn1cnc2cnc3ccccc3c21]

6-(Octyloxy)hexan-1-ol Sodium hydride (6.38 g, 266 mmol) was added cautiously to a mixture of 1,6-hexanediol (47.2 g, 400 mmol) and 120 mL of DMF cooled by an ice bath. After 15 min, a mixture of 1-iodooctane (31.9 g, 133 mmol) in 120 mL of DCM was added. The mixture was allowed to warm to room temperature overnight. Then, the volatile components were evaporated, and the residue was partitioned between EA and 0.1M HCl, 5% Na₂S₂O₃, H₂O, and brine. The organic phases were dried over anhydrous MgSO₄ and concentrated. SPE, washing with 2% EA/Hex and eluting with 40% EA/Hex, gave 13.0 g of colorless oil. Rf 0.40 (50% EA/Hex); ¹H NMR (CDCl₃) δ 3.59 (t, 2H, J=6.7 Hz), 3.36 (t, 2H, J=6.7 Hz), 3.35 (t, 2H, J=6.7 Hz), 2.02 (br s, 1H, OH), 1.56-1.47 (m, 6H), 1.40-1.20 (m, 14H), 0.84 (m, 3H).

2-Chloro-3-nitro-N-[6-(octyloxy)hexyl]quinolin-4-amine TEA (8.40 mL, 59.9 mmol) was added to a mixture of 6-(octyloxy)hexan-1-ol (7.60 g, 33.0 mmol) and methanesulfonyl chloride (4.56 mL, 58.3 mmol) in 190 mL of DME cooled by an ice bath. The mixture was allowed to warm to room temperature. After 4 hr, 5 mL of H₂O were added and the volatile components were evaporated. The residue was partitioned between EA (3×150 mL) and H₂O, saturated NaHCO₃, H₂O, 1M HCl, H₂O, and brine (100 mL each). The organic phases were dried over MgSO₄ and concentrated to a colorless oil. The oil was taken up in 250 mL of acetone, sodium iodide (9.9 g, 66 mmol) was added, and the mixture was heated at reflux for 2 hr. The volatile components were evaporated, and the residue was partitioned between EA and H₂O, 5% Na₂S₂O₃, H₂O, and brine. The organic phases were dried over MgSO₄ and concentrated. SPE (5% EA/Hex) gave a purple oil. The oil was taken up in 25 mL of DMF and 10 mL of toluene, potassium phthalimide (5.55 g, 30 mmol) was added, and the mixture was heated at reflux for 4 hr. Then, the mixture was cooled and partitioned between EA and 0.1M HCl, 5% Na₂S₂O₃, H₂O, and brine. The organic phases were dried over MgSO₄ and concentrated. SPE, washing with 5% EA/Hex and eluting with 7.5% EA/Hex, gave 10.05 g colorless oil. The oil was taken up in 500 mL of 5% IPA/EtOH, hydrazine monohydrate (2.0 mL, 41 mmol) was added, and the mixture was heated at reflux for 4 hr. The mixture was cooled and concentrated. The residue was partitioned between DCM and 5% Na₂CO₃. The organic phase was dried over anhydrous Na₂SO₄ and concentrated. SPE, washing with 50% EA/Hex and eluting with 15% MeOH/DCM+2% TEA, gave 1.91 g of colorless oil. The oil was taken up in a mixture of 9 mL of DMA and 9 mL of toluene, and 2,4-dichloro-3-nitroquinoline (2.16 g, 8.87 mmol) and DIEA (1.45 mL, 8.32 mmol) were added. The mixture was reacted at room temperature for 88 hr and at reflux for 2 days. The mixture was cooled, the volatile components were evaporated, and the residue was partitioned between EA and 5% Na₂CO₃ and brine. The organic phases were dried over Na₂SO₄ and concentrated. SPE (20% EA/Hex) gave product-containing fractions with impurities. FC (20% EA/Hex) gave 2.06 g of yellow oil that solidified upon standing. The solid was recrystallized from EA/Hex to give 1.70 g of yellow solid. Rf 0.22 (20% EA/Hex); ¹H NMR (CDCl₃) δ 7.84 (d, 1H, J=7.9 Hz), 7.76 (dd, 1H, J=1.2, 8.4 Hz), 7.63 (ddd, 1H, J=1.2, 6.9, 8.1 Hz), 7.42 (ddd, 1H, J=1.3, 7.0, 8.4 Hz), 5.98 (t, 1H, J=4.7 Hz, NH), 3.38-3.29 (m, 6H), 1.66 (m, 2H), 1.56-1.42 (m, 4H), 1.36-1.34 (m, 4H), 1.2-1.1 (m, 10H), 0.8 (m, 3H).

1-[6-(Octyloxy)hexyl]-1H-imidazo[4,5-c]quinoline Four mL of a 1:3 mixture of concentrated HCl and MeOH added slowly to a mixture of 2-chloro-3-nitro-N-[6-(octyloxy)hexyl]quinolin-4-amine (357 mg, 0.82 mmol), zinc dust (320 mg), and 20 mL of DCM cooled by an ice bath. The mixture was allowed to warm to room temperature. After 16 hr, the volatile components were evaporated, the residue was diluted with 75 mL of DCM, and the pH was adjusted to >8 using 5% Na₂CO₃. The organic phase was separated, dried over anhydrous Na₂SO₄, and concentrated. Triethyl orthoformate (5 mL) was added to the crude product, and the mixture was heated at 130° C. for 6 hr. Then, the mixture was cooled and concentrated. The residue was partitioned between DCM and 5% Na₂CO₃. The organic phase was dried over Na₂SO₄ and concentrated. FC (3% and 5% MeOH/DCM step gradient) gave 101 mg of brown oil. Rf 0.21 (5% MeOH/DCM); ¹H NMR (CDCl₃) δ 9.31 (s, 1H), 8.26 (m, 1H), 8.12 (m, 1H), 7.92 (s, 1H), 7.70-7.58 (m, 2H), 4.54 (t, 2H, J=7.2 Hz), 3.34 (t, 2H, J=6.2 Hz), 3.33 (t, 2H, J=6.7 Hz), 2.00 (m, 2H), 1.56-1.39 (m, 6H), 1.3-1.1 (m, 12H), 0.83 (m, 3H).

Example 124

1-(8-Ethoxyoctyl)-1H-imidazo[4,5-c]quinoline

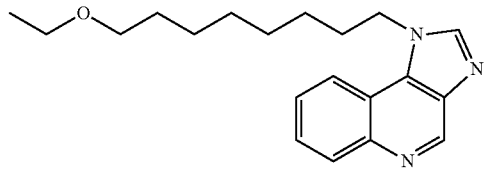 [SMILES: CCOCCCCCCCCn1cnc2cnc3ccccc3c21]

1-(8-Ethoxyoctyl)-1H-imidazo[4,5-c]quinoline was made by the method used for the preparation of 1-octyl-1H-imidazo[4,5-c]quinoline, substituting 8-ethoxyoctan-1-amine for 1-octylamine. 8-Ethoxyoctan-1-amine was made by the method used for the preparation of 8-(hexyloxy)octan-1-amine, using iodoethane and 1,8-octanediol as starting materials.

Example 125

1-(8-Methoxyoctyl)-1H-imidazo[4,5-c]quinoline

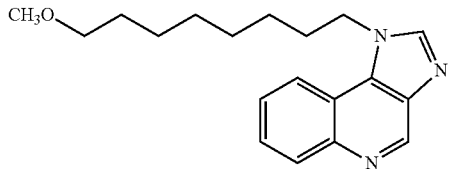

1-(8-Methoxyoctyl)-1H-imidazo[4,5-c]quinoline was made by the method used for the preparation of 1-octyl-1H-imidazo[4,5-c]quinoline, substituting 8-methoxyoctan-1-amine for 1-octylamine.

Example 126

1-(8-Butoxyoctyl)-1H-imidazo[4,5-c]quinoline

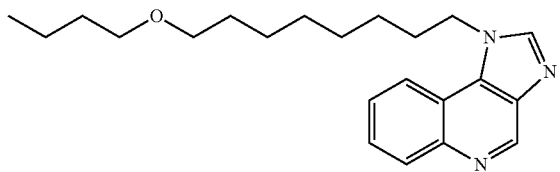 [SMILES: CCCCOCCCCCCCCn1cnc2cnc3ccccc3c21]

1-(8-Butoxyoctyl)-1H-imidazo[4,5-c]quinoline was made by the method used for the preparation of 1-octyl-1H-imidazo[4,5-c]quinoline, substituting 8-butoxyoctan-1-amine for 1-octylamine. 8-Butoxyoctan-1-amine was made by the method used for the preparation of 10-(hexyloxy)decan-1-amine, using 1-bromobutane and 1,8-octanediol as starting materials.

Example 127

1-[9-(Hexyloxy)nonyl]-1H-imidazo[4,5-c]quinoline

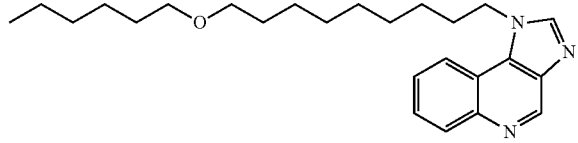

9-(Benzyloxy)nonan-1-ol, as 8.79 g of colorless oil, was made by the method used for the preparation of 8-(benzyloxy)octan-1-ol, using 27.1 g of 1,9-nonanediol, 7.85 mL of benzyl chloride in 20 mL of DME, 1.80 g of sodium hydride, 60% dispersion in mineral oil, and 300 mL of DMF. Rf 0.12 (20% EA/Hex); $^1$H NMR (CDCl$_3$) δ 7.37-7.22 (m, 5H), 4.49 (s, 2H), 3.61 (t, 2H, J=6.6 Hz), 3.45 (t, 2H, J=6.7 Hz), 1.65-1.49 (m, 4H), 1.36-1.21 (m, 10H).

{[9-(Hexyloxy)nonyloxy]methyl}benzene Sodium hydride (920 mg, 38.3 mmol) was added to a mixture of 9-(benzyloxy)nonan-1-ol (8.79 g, 35.2 mmol) and 200 mL of DME. After 1 hr, 1-iodohexane (10.6 g, 50 mmol) was added. After 40 hr, analysis by TLC indicated little conversion. Another portion of sodium hydride was added. After 8 hr, another portion of sodium hydride and 1-bromohexane (7.0 mL, 50 mmol) were added. The mixture was stirred 48 hr, then allowed to stand for several weeks. Then, 6 mL of concentrated NH$_4$OH were added cautiously. After 16 hr, the volatile components were evaporated. The residue was partitioned between EA (3×250 mL) and H$_2$O (100 mL), 5% Na$_2$S$_2$O$_3$ (100 mL), H$_2$O (100 mL), 0.1M HCl (2×100 mL), and brine (100 mL). The organic phases were dried over anhydrous Na$_2$SO$_4$ and concentrated. SPE (5% EA/Hex) gave 8.47 g of colorless oil. Rf 0.75 (20% EA/Hex); $^1$H NMR (CDCl$_3$) δ 7.34-7.23 (m, 5H), 4.49 (s, 2H), 3.48-3.36 (m, 6H), 1.68-1.51 (m, 6H), 1.5-1.2 (m, 16H), 0.88 (t, 3H, J+6.8 Hz).

1-(Hexyloxy)-9-iodononane A mixture of {[9-(hexyloxy)nonyloxy]methyl}benzene (8.47 g, 25.4 mmol), chlorotrimethylsilane (20 mL, 158 mmol), and sodium iodide (23.7 g, 158 mmol) in 150 mL of DCM was heated at reflux for 60 hr, then mixed at room temperature for 48 hr. Then, the volatile components were evaporated. The residue was partitioned between EA (3×250 mL) and saturated NaHCO$_3$ (100 mL), 5% Na$_2$S$_2$O$_3$ (100 mL), H$_2$O (100 mL), and brine (100 mL). The organic phases were dried over anhydrous MgSO$_4$ and concentrated. Analysis by TLC suggested the presence of 9-(hexyloxy)nonan-1-ol with low Rf. The mixture was taken up in 25 mL of toluene and then concentrated. The purple oil was taken up in another 25 mL of toluene, 5 mL of phosphorus oxychloride was added, and the mixture was heated at reflux until the suspected alcohol was consumed, as observed by TLC analysis. The mixture was cooled with an ice bath, and saturated NaHCO$_3$ was added slowly, accompanied by gas evolution. The mixture was extracted with EA (3×250 mL), and the organic phases were washed with H$_2$O, 0.1M HCl, and brine (100 mL each), dried over MgSO$_4$, and concentrated. SPE (2% EA/Hex), discarding early fractions that contained benzyl halides, gave 3.76 g of product as amber oil. Rf 0.53 (5% EA/Hex); $^1$H NMR (CDCl$_3$) δ 3.37 (t, 4H, J=6.7 Hz), 3.16 (m, 2H), 1.80 (m, 2H), 1.57-1.49 (m, 4H), 1.4-1.2 (m, 16H), 0.87 (m, 3H).

N-[9-(Hexyloxy)nonyl]phthalimide A mixture of 1-(hexyloxy)-9-iodononane (3.80 g, 14.4 mmol), and potassium phthalimide (2.70 g, 14.6 mmol) in 8 mL of DMF was heated at 100° C. for 5 hr. The mixture was cooled and partitioned between EA (3×250 mL) and 5% Na$_2$CO$_3$, H$_2$O, 5% Na$_2$S$_2$O$_3$, H$_2$O, 0.1M HCl, and brine (100 mL each). The organic phases were dried over anhydrous MgSO$_4$ and concentrated. SPE, washing with 5% EA/Hex and eluting with 7.5% EA/Hex, gave 3.30 g of product as a solid. Rf 0.26 (10% EA/Hex); $^1$H NMR (CDCl$_3$) δ 7.80 and 7.67 (m, 4H, AA'BB'), 3.64 (m, 2H), 3.35 (t, 2H, J=6.7 Hz), 3.34 (t, 2H, J=6.7 Hz), 1.77-1.47 (m, 6H), 1.28-1.22 (m, 16H), 0.86 (m, 3H).

9-(Hexyloxy)nonan-1-amine A mixture of N-[9-(hexyloxy)nonyl]phthalimide (3.05 g, 8.18 mmol) and hydrazine monohydrate (0.58 mL, 12 mmol) in 50 mL of 5% IPA/EtOH was heated at reflux for 4 hr. The mixture was cooled and concentrated. The residue was partitioned between DCM and 5% Na$_2$CO$_3$. The organic phase was dried over anhydrous Na$_2$SO$_4$ and concentrated. SPE, washing with 50% EA/Hex and eluting with 15% MeOH/DCM+2% TEA, gave 1.08 g of a mixture of 9-(hexyloxy)nonan-1-amine and phthalhydrazide. Rf 0.11 (15% MeOH/DCM+2% TEA); $^1$H NMR (CDCl$_3$) δ 4.6 (br s, 2H, NH$_2$), 3.4-3.3 (m, 4H), 2.7 (t, 2H), 1.7-1.1 (m, 22H), 0.8 (m, 3H).

2-Chloro-N-[9-(hexyloxy)nonyl]-3-nitroquinolin-4-amine The mixture of 9-(hexyloxy)nonan-1-amine and phthalhydrazide was reacted with 2,4-dichloro-3-nitroquinoline (1.11 g, 4.56 mmol) and TEA (0.63 mL, 4.49 mmol) in 9 mL of DMF and 16 mL of toluene heated at reflux. After 24 hr, the mixture was cooled, partitioned between EA and H$_2$O, 5% Na$_2$CO$_3$, and brine, dried over anhydrous Na$_2$SO$_4$, and concentrated. FC, eluting with 15% and then 20% EA/Hex, gave 1.35 g of yellow product as an oil that solidified upon standing. Recrystallization from cold EA/Hex gave 650 mg of yellow solid. Rf 0.18 (20% EA/Hex); $^1$H NMR (CDCl$_3$) δ 7.87 (d, 1H, J=8.6 Hz), 7.78 (dd, 1H, J=1.3, 9.5 Hz), 7.67.65 (m, 1H), 7.45 (m, 1H), 5.99 (t, 1H, J=4.7 Hz, NH), 3.39-3.31 (m, 6H), 1.66 (m, 2H), 1.53-1.45 (m, 4H), 1.4-1.1 (m, 16H), 0.82 (m, 3H).

1-[9-(Hexyloxy)nonyl]-1H-imidazo[4,5-c]quinoline Six mL of a 1:3 mixture of concentrated HCl and MeOH was added slowly to a mixture of 2-chloro-N-[9-(hexyloxy)nonyl]-3-nitroquinolin-4-amine (674 mg, 1.50 mmol), zinc dust (585 mg), and 25 mL of DCM cooled by an ice bath. The mixture was allowed to warm to room temperature. After 1 hr, the volatile components were evaporated, the residue was diluted with 75 mL of DCM, and the pH was adjusted to >8 using 5% Na$_2$CO$_3$. The organic phase was separated, dried over anhydrous Na$_2$SO$_4$, and concentrated. Rf 0.41 (15% MeOH/DCM) Triethyl orthoformate (4 mL) was added to the crude product, and the mixture was heated at 130° C. for 6 hr. Then, the mixture was cooled and concentrated. FC (3% and 5% MeOH/DCM step gradient) gave 273 mg of brown oil. Rf 0.27 (5% MeOH/DCM);

$^1$H NMR (CDCl$_3$) δ 9.22 (s, 1H), 8.16 (m, 1H), 7.98 (m, 1H), 7.60-7.47 (m, 2H), 4.38 (t, 2H, J=7.1 Hz), 3.27 (t, 2H, J=6.7 Hz), 3.26 (t, 2H, J=6.7 Hz), 1.86 (m, 2H), 1.45-1.41 (m, 4H), 1.4-1.1 (m, 16H), 0.78 (m, 3H).

Example 128

1-(10-Butoxydecyl)-1H-imidazo[4,5-c]quinoline

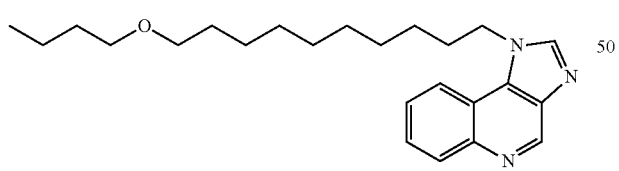

1-(10-Butoxydecyl)-1H-imidazo[4,5-c]quinoline was made by the method used for the preparation of 1-octyl-1H-imidazo[4,5-c]quinoline, substituting 10-butoxydecan-1-amine for 1-octylamine. 10-Butoxydecan-1-amine was made by the method used for the preparation of 10-(hexyloxy)decan-1-amine, using 1-bromobutane and 1,10-decanediol as starting materials. Rf 0.23 (5% MeOH/DCM); $^1$H NMR (CDCl$_3$) δ 9.32 (s, 1H), 8.27 (m, 1H), 8.12 (m, 1H), 7.93 (s, 1H), 7.66 (m, 2H), 4.54 (t, 2H, J=7.2 Hz), 3.36 (t, 2H, J=6.5 Hz), 3.35 (t, 2H, J=6.5 Hz), 1.99 (m, 2H), 1.57-1.13 (m, 18H), 0.88 (t, 3H, J=7.3 Hz).

Example 129

4-Amino-1-[8-(hexyloxy)octyl]pyridinium salts

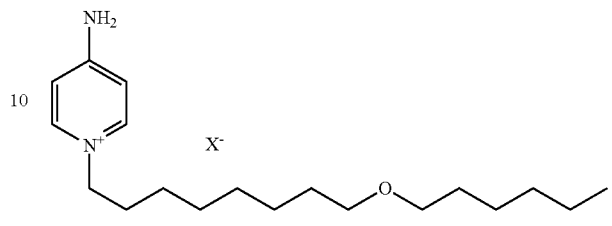

A mixture of 8-(hexyloxy)octyl methanesulfonate (0.5 g, 1.62 mmol) and 4-aminopyridine (450 mg) in 20 mL of THF was heated at reflux for 18 hr. The mixture was concentrated and purified by FC (5% MeOH/DCM) to give 396 mg of an oily solid. Recrystallization from MeOH gave a solid. Mp 108-110° C.; $^1$H NMR (CDCl$_3$) δ 8.4 (br s, 1.4H), 7.8 (d, 2H), 7.2 (d, 2H), 4.1 (m, 2H), 3.35 (m, 4H), 2.4 (br s, 4.5H), 1.8 (m, 2H), 1.6 (m, 4H), 1.4-1.2 (m, 14H), 0.8 (m, 3H).

Example 130

4-(8-Methoxyoctylamino)-1-methylpyridinium iodide

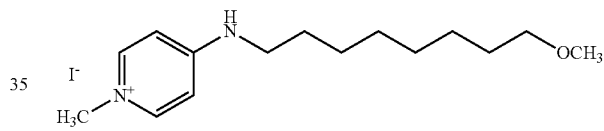

A mixture of N-(8-methoxyoctyl)pyridin-4-amine (176 mg, 0.74 mmol) and iodomethane (0.5 mL, 8 mmol) in 4 mL of acetone was heated at 80° C. in a sealed tube for 1.5 hr, then allowed to stand at room temperature for 2 days, during which a precipitate formed. The volatile components were evaporated from the precipitated product. $^1$H NMR (CDCl$_3$) δ 8.47 (m, 1H), 7.99 (m, 2H), 7.57 (m, 1H), 6.59 (m, 1H), 4.04 (s, 3H), 3.35-3.21 (m, 4H), 3.29 (s, 3H), 1.71 (m, 2H), 1.54-1.28 (m, 10H).

Example 131

1-[8-(Hexyloxy)octyl]-1H-imidazo[4,5-c]pyridine

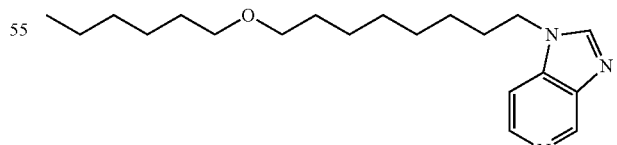

N-[8-(Hexyloxy)octyl]-3-nitropyridin-4-amine A mixture of 3-nitropyridin-4-ol (510 mg, 3.64 mmol) in 1 mL of phenylphosphonic dichloride was heated at 170-140° C. for 3 hr. Then, the mixture was cooled and partitioned between EA and saturated NaHCO$_3$. The organic phase was washed with brine, dried over Na$_2$SO$_4$, filtered through a pad of silica gel, and concentrated to give crude 4-chloro-3-nitropyridine. 8-(Hexyloxy)octan-1-amine was taken up in 10 mL of pyridine, and 5 mL of volatile material was evaporated from the mixture. The mixture was cooled with an ice bath, TEA (0.44 mL, 3.14 mol) was added, and then a mixture of the chloropyridine prepared above and 10 mL of DCM was added. The mixture was allowed to warm to room temperature overnight. Then, the reaction was concentrated by evaporation, and the residue was partitioned between EA and saturated NaHCO$_3$. The organic phases were washed with brine, dried over Na$_2$SO$_4$, and concentrated. Purification by FC (50% EA/Hex) gave 405 mg of N-[8-(hexyloxy)octyl]-3-nitropyridin-4-amine as a yellow oil. Rf 0.28 (50% EA/Hex); $^1$H NMR (CDCl$_3$) δ 9.16 (s, 1H), 8.24 d, 1H, J=6.2 Hz), 8.12 (br s, 1H), 6.66 (d, 1H, J=6.2 Hz), 3.38-3.25 (m, 6H), 1.70 (m, 2H), 1.52-1.47 (m, 4H), 1.39-1.18 (m, 14H), 0.84 (t, 3H, J=6.7 Hz).

N$^4$-[8-(Hexyloxy)octyl]pyridine-3,4-diamine A mixture of N-[8-(hexyloxy)octyl]-3-nitropyridin-4-amine (405 mg, 1.15 mol) and 45 mg of 10% Pd/C in 30 mL of MeOH was stirred under an atmosphere of hydrogen for 5 hr. Then, the catalyst was removed by filtration through Celite, and the filtrate was concentrated. Purification by SPE, washing with 10% MeOH/DCM and then eluting with 15% MeOH/DCM+ 2% TEA, gave 216 mg of N$^4$-[8-(hexyloxy)octyl]pyridine-3,4-diamine. Rf 0.05 (15% MeOH/DCM, ninhydrin (+)); $^1$H NMR (CDCl$_3$) δ 7.86 (d, 1H, J=5.4 Hz), 7.79 (s, 1H), 6.38 (d, 1H, J=5.4 Hz), 4.53 (br s, 1H), 3.62 (br s, 2H), 3.34 (t, 4H, J=6.7 Hz), 3.08 (m, 2H), 1.62-1.46 (m, 6H), 1.27-1.24 (m, 14H), 0.83 (t, 3H, J=6.8 Hz).

1-[8-(Hexyloxy)octyl]-1H-imidazo[4,5-c]pyridine A mixture of N$^4$-[8-(hexyloxy)octyl]pyridine-3,4-diamine (216 mg, 0.67 mol) in 2 mL of triethyl orthoformate was heated at reflux for 6 hr. Then, volatile material was removed by evaporation, and the residue was partitioned between EA and saturated NaHCO$_3$. The organic phases were washed with brine, dried over Na$_2$SO$_4$, and concentrated. Purification by FC (7% MeOH/DCM) gave 217 mg of 1-[8-(hexyloxy)octyl]-1H-imidazo[4,5-c]pyridine as an amber oil. Rf 0.11 (5% MeOH/DCM); $^1$H NMR (CDCl$_3$) δ 9.02 (s, 1H), 8.34 (d, 1H, J=5.7 Hz), 7.86 (s, 1H), 7.25 (m, 1H), 4.08 (t, 2H, J=7.0 Hz), 3.30-3.25 (m, 4H), 1.78 (m, 2H), 1.45-1.43 (m, 4H), 1.22-1.19 (m, 14H), 0.78 (t, 3H, J=6.7 Hz).

Example 132

1-Hexadecyl-1H-imidazo[4,5-c]pyridine

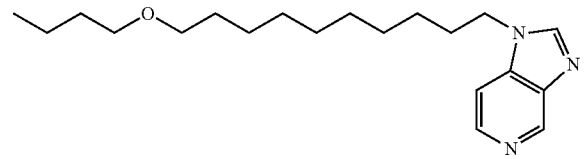 [SMILES: CCCCOCCCCCCCCCCn1cnc2cnccc21]

N-Hexadecyl-3-nitropyridin-4-amine 1-Hexadecylamine was taken up in 10 mL of pyridine, and 6 mL of volatile components were removed by distillation. The mixture was cooled, and a mixture of 4-chloro-3-nitropyridine in 10 mL of DCM and 10 mL of DMF was added. Then, TEA (0.46 mL, 3.28 mmol) was added and the mixture was heated at gentle reflux. After 16 hr, the cooled mixture was taken up in EA and washed with saturated NaHCO$_3$, H$_2$O, and brine. The organic phase was dried over anhydrous Na$_2$SO$_4$ and concentrated. SPE, washing with 10% EA/Hex and eluting with 20% EA/Hex, gave 626 mg of solid. Rf 0.34 (50% EA/Hex); $^1$H NMR (CDCl$_3$) δ 9.19 (s, 1H), 8.26 (d, 1H, J=6.1 Hz), 8.15 (br s, 1H, N<u>H</u>), 6.68 (d, 1H, J=6.2 Hz), 3.30 (m, 2H), 1.72 (m, 2H), 1.42-1.17 (m, 26H), 0.86 (m, 3H).

1-Hexadecyl-1H-imidazo[4,5-c]pyridine A mixture of N-hexadecyl-3-nitropyridin-4-amine (626 mg, 1.79 mmol) and 65 mg of 10% Pd—C in 25 mL of 1:1 EA/MeOH was stirred under a blanket of hydrogen for 40 hr. The hydrogen atmosphere was replaced by argon, and the mixture was filtered through a pad of Celite and concentrated. SPE, washing with 10% MeOH/DCM and eluting with 10% MeOH/DCM+2% TEA, gave 540 mg of colorless solid. The solid was taken up in 8 mL of triethyl orthoformate and heated at reflux for 4 hr. Then, the volatile components were evaporated. The residue was taken up in a fresh 8-mL portion of triethyl orthoformate and heated at reflux for 6 hr. The volatile components were evaporated. FC of the residue (5% MeOH/DCM) gave 375 mg of tan solid. Rf 0.10 (5% MeOH/DCM); $^1$H NMR (CDCl$_3$) δ 9.06 (s, 1H), 8.39 (d, 1H, J=5.7 Hz), 7.92 (s, 1H), 7.31 (dd, 1H, J=1.0, 5.7 Hz), 4.12 (m, 2H), 1.82 (m, 2H), 1.26-1.18 (m, 26H), 0.81 (t, 3H, J=6.6 Hz).

Example 133

1-(10-Butoxydecyl)-1H-imidazo[4,5-c]pyridine

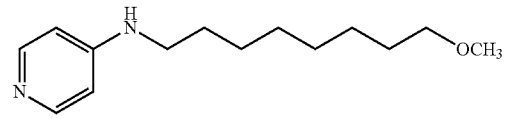 [SMILES: COCCCCCCCCNc1ccncc1]

1-(10-Butoxydecyl)-1H-imidazo[4,5-c]pyridine (231 mg) as an amber oil was prepared following the method for 1-[8-(hexyloxy)octyl]-1H-imidazo[4,5-c]pyridine, using 492 mg of 4-hydroxy-3-nitropyridine and 535 mg of 10-butoxydecan-1-amine.

N-(10-Butoxydecyl)-3-nitropyridin-4-amine: Rf 0.30 (50% EA/Hex); $^1$H NMR (CDCl$_3$) δ 9.18 (s, 1H), 8.25 (d, 1H, J=6.0 Hz), 8.14 (br s, 1H, N<u>H</u>), 6.68 (d, 1H, J=6.2 Hz), 3.39-3.26 (m, 6H), 1.71 (m, 2H), 1.57-1.47 (m, 4H), 1.40-1.27 (m, 14H), 0.88 (t, 3H, J=7.2 Hz).

N$^4$-(10-Butoxydecyl)pyridine-3,4-diamine: Rf 0.08 (15% MeOH/DCM); $^1$H NMR (CDCl$_3$) δ 7.89 (d, 1H, J=6.4 Hz), 7.83 (s, 1H), 6.41 (d, 1H, J=6.4 Hz), 4.41 (br s, 1H, N<u>H</u>), 3.58 (br s, 2H, N<u>H</u>$_2$), 3.39-3.33 (m, 4H), 3.11-3.10 (br m, 2H), 1.66-1.47 (m, 6H), 1.40-1.26 (m, 14H), 0.88 (t, 3H, J=7.2 Hz).

1-(10-Butoxydecyl)-1H-imidazo[4,5-c]pyridine: Rf 0.15 (5% MeOH/DCM); $^1$H NMR (CDCl$_3$) δ 9.06 (s, 1H), 8.38 (d, 1H, J=5.7 Hz), 7.88 (d, 1H), 7.28 (d, 1H, J=5.4 Hz), 4.12 (m, 2H), 3.35-3.29 (m, 4H), 1.82 (m, 2H), 1.53-1.43 (m, 4H), 1.36-1.20 (m, 14H), 0.84 (m, 3H).

Example 134

N-(8-Methoxyoctyl)pyridin-4-amine

A mixture of 4-chloropyridine hydrochloride (1.50 g, 10.0 mmol), 8-methoxyoctan-1-amine (894 mg, 5.62 mmol), TEA (1.80 mL, 10.4 mmol), and 4 mL of IPA was heated at 130-140° C. in a sealed tube for 48 hr. Then, the mixture was cooled and the volatile components were evaporated. The residue was partitioned between DCM and 5% Na$_2$CO$_3$, and the organic phase was dried over Na$_2$SO$_4$ and concentrated. FC (1% TEA+0%, 2%, 3% MeOH/DCM step gradient) gave 176 mg of solid. Rf 0.13 (10% MeOH/DCM); $^1$H NMR (CDCl$_3$) δ 8.6 (m, 1H), 7.8 (m, 2H), 6.9 (m, 2H), 3.3 (m, 5H), 3.2 (m, 2H), 1.7 (m, 2H), 1.5 (m, 2H), 1.4-1.2 (m, 8H).

Example 135

N-[8-(Hexyloxy)octyl]pyridin-3-amine

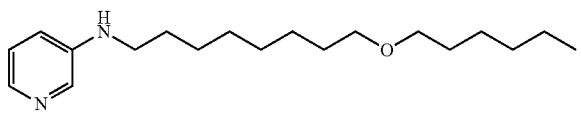 [SMILES: CCCCCCOCCCCCCCCNc1cccnc1]

8-(Hexyloxy)octanal (1.12 g, 4.91 mmol), prepared by the Swern oxidation of 8-(hexyloxy)octan-1-ol, was mixed with 3-aminopyridine (500 mg, 5.32 mmol) in 5 mL of acetonitrile and 0.4 mL of 1M HCl. Then, 0.37 mL of 1M sodium cyanoborohydride in THF was added. After 20 hr, the mixture was partitioned between EA and 5% Na$_2$CO$_3$ and brine, and the organic phase was dried over Na$_2$SO$_4$ and concentrated. FC (70% EA/Hex) gave 160 mg of the product. $^1$H NMR (CDCl$_3$) δ 8.0 (m, 1H), 7.9 (m, 1H), 7.1 (m, 1H), 6.9 (m, 1H), 3.4 (t, 4H), 3.1 (t, 2H), 1.7-1.5 (m, 6H), 1.5-1.2 (m, 14H), 0.85 (m, 3H).

Example 136

N-[8-(Hexyloxy)octyl]pyridin-2-amine

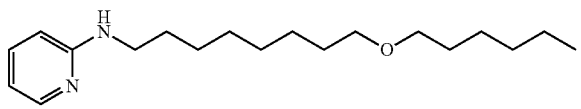 [SMILES: CCCCCCOCCCCCCCCNc1ccccn1]

A mixture of 2-aminopyridine (458 mg, 4.8 mmol) and 8-(hexyloxy)octyl methanesulfonate (0.5 g, 1.6 mmol) in 20 mL of THF was heated at reflux for 3 hr. Then, the reaction was cooled and worked up following the procedure for N-[8-(hexyloxy)octyl]pyridin-3-amine to give 100 mg of product. $^1$H NMR (CDCl$_3$) δ 8.0 (m, 1H), 7.4 (m, 1H), 6.55 (m, 1H), 6.35 (m, 1H), 4.6 (br s, 1H, NH), 3.4 (t, 4H), 3.2 (m, 2H), 1.7-1.5 (m, 6H), 1.5-1.2 (m, 14H), 0.85 (m, 3H).

Example 137

N-[8-(Hexyloxy)octyl]pyrimidin-4-amine

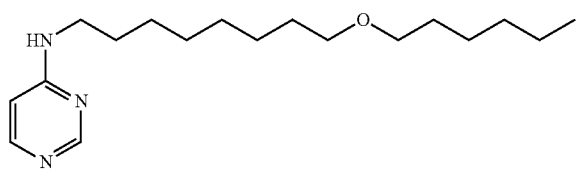 [SMILES: CCCCCCOCCCCCCCCNc1ccncn1]

6-Chloro-N-[8-(Hexyloxy)octyl]pyrimidin-4-amine 8-(Hexyloxy)octan-1-amine (636 mg, 2.78 mmol) was taken up in 15 mL of pyridine, and then 10 mL of volatile material was removed by distillation. The mixture was cooled to room temperature, and 15 mL of DCM, 4,6-dichloropyrimidine (621 mg, 4.17 mmol), and TEA (0.47 mL, 3.35 mmol) were added sequentially. After being stirred overnight, TLC indicated the presence of the amine starting material, so a second quantity of 4,6-dichloropyrimidine was added and the mixture was heated at reflux for 3 hr. Then, the mixture was cooled, the volatile material was evaporated, and the residue was partitioned between EA and 5% Na$_2$CO$_3$. The organic phases were washed with brine, dried over Na$_2$SO$_4$, filtered through a pad of silica gel, and concentrated. Purification by FC (30% EA/Hex) gave 767 mg of 6-chloro-N-[8-(hexyloxy)octyl]pyrimidin-4-amine as a tan solid. Rf 0.18 (20% EA/Hex); $^1$H NMR (CDCl$_3$) δ 8.30 (s, 1H), 6.30 (d, 1H, J=1.0 Hz), 5.36 (br s, 1H, NH), 3.37 (t, 4H, J=6.9 Hz), 3.24 (m, 2H, AB), 1.6-1.5 (m, 6H), 1.3-1.2 (m, 14H), 0.87 (m, 3H).

N-[8-(Hexyloxy)octyl]pyrimidin-4-amine A mixture of 6-chloro-N-[8-(hexyloxy)octyl]pyrimidin-4-amine (767 mg, 2.25 mmol) in 30 mL of DCM and 6.8 mL of 2M HCl/IPA was cooled using an ice bath. Then, 876 mg of zinc dust was added. After 45 min, the mixture was allowed to warm to room temperature. After being stirred overnight, the mixture was partitioned between DCM and 5% Na$_2$CO$_3$. The organic phase was dried over Na$_2$SO$_4$ and concentrated. Purification by FC (5% MeOH/DCM) gave 229 mg of N-[8-(hexyloxy)octyl]pyrimidin-4-amine as a colorless solid. Rf 0.21 (5% MeOH/DCM); $^1$H NMR (CDCl$_3$) δ 8.46 (s, 1H), 8.08 (d, 1H, J=5.7 Hz), 6.25 (dd, 1H, J=1.2, 5.9 Hz), 5.59 (br s, 1H), 3.33 (t, 4H, J=6.7 Hz), 3.21 (m, 2H, AB), 1.58-1.45 (m, 6H), 1.26-1.17 (m, 14H), 0.83 (m, 3H).

Example 138

N-[8-Hexyloxy)octyl)pyrimidin-2-amine

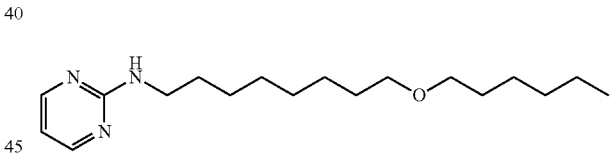

A mixture of 2-chloropyrimidine (272 mg, 2.39 mmol), 8-(hexyloxy)octan-1-amine (548 mg, 2.39 mmol), and TEA (0.34 mL, 2.42 mmol) in 10 mL of DMF was heated at 80-90° C. for 2 hr. Then, the mixture was partitioned between EA and 5% Na$_2$CO$_3$ (2×) and brine, and the organic phase was dried over Na$_2$SO$_4$ and concentrated. FC (50% EA/Hex) gave 227 mg of product as a yellow solid. $^1$H NMR (CDCl$_3$) δ 8.2 (d, 2H), 6.4 (d, 2H), 5.6 (br s, 1H, NH), 3.3 (m, 4H), 1.6-1.4 (m, 6H), 1.4-1.2 (m, 14H), 0.8 (m, 3H).

Example 139

1-[8-(Hexyloxy)octyl]-4-phenyl-1H-imidazole

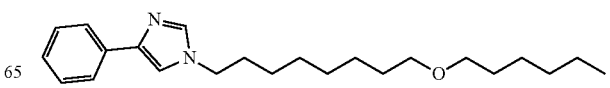

4-Phenylimidazole (1.0 g, 6.9 mmol) was added to a mixture of sodium tert-butoxide (7.9 mmol) in 20 mL of DMF cooled by an ice bath. After 30 min, 8-(hexyloxy)octyl methanesulfonate (2.14 g, 6.95 mmol) was added, and the mixture was allowed to come to room temperature. After 6 hr, volatile components were evaporated. The residue was taken up in EA and washed with saturated NaHCO$_3$, 0.1M HCl, and H$_2$O. The organic phase was dried over anhydrous Na$_2$SO$_4$ and concentrated. FC (70% EA/Hex) gave 2.5 g of 1-[8-(hexyloxy)octyl]-4-phenyl-1H-imidazole.

$^1$H NMR (CDCl$_3$) δ 7.8 (m, 2H), 7.6 (s, 1H), 7.4 (m, 2H), 7.2 (m, 2H), 3.9 (t, 2H), 3.4 (m, 4H), 1.8 (m, 2H), 1.6-1.5 (m, 4H), 1.4-1.2 (m, 14H), 0.9 (m, 3H).

Example 140

N-[8-(Hexyloxy)octyl]isoquinolin-1-amine

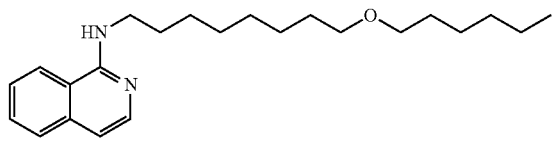 [SMILES: CCCCCCOCCCCCCCCNc1nccc2ccccc12]

1-Chloroisoquinoline (390 mg, 2.38 mmol), 8-(hexyloxy) octan-1-amine (360 mg, 1.57 mmol), and triethylamine (0.22 mL, 1.57 mmol) in 2 mL of DMA was heated at 80° C. for 24 hr. Then the mixture was cooled and partitioned between EA and 5% Na$_2$CO$_3$ and brine, and the organic phase was dried over Na$_2$SO$_4$ and concentrated. FC (20% EA/Hex) gave 87 mg of the product. Rf 0.25 (20% EA/Hex); $^1$H NMR (CDCl$_3$) δ 7.97 (d, 1, J=6.0 Hz), 7.76-7.73 (m, 1), 7.67-7.64 (m, 1), 7.59-7.53 (m, 1), 7.47-7.41 (m, 1), 6.89 (d, 1, J=5.9 Hz), 5.25 (br s, 1), 3.62-3.55 (m, 2), 3.38 (t, 4, J=6.7 Hz), 1.77-1.67 (m, 2), 1.58-1.24 (m, 18), 0.89-0.84 (m, 4).

Example 141

N-[8-(Hexyloxy)octyl]isoquinolin-5-amine

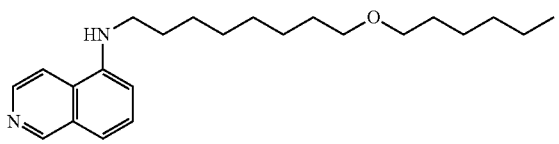 [SMILES: CCCCCCOCCCCCCCCNc1cccc2cnccc12]

N-[8-(Hexyloxy)octyl]isoquinolin-5-amine (123 mg) was prepared following the method for N-[8-(hexyloxy)octyl] quinolin-6-amine starting with 8-(hexyloxy)octanoic acid (300 mg, 123 mmol) and 5-aminoisoquinoline (174 mg, 1.21 mmol). $^1$H NMR (CDCl$_3$) δ 9.14 (d, 1, J=0.7 Hz), 8.44 (d, 1, J=6.1 Hz), 7.57-7.54 (m, 1), 7.45 (t, 1, J=7.9 Hz), 7.30-7.25 (m, 1), 6.74 (dd, 1, J=0.7, 7.7 Hz), 4.35 (br s, 1), 3.41-3.35 (m, 4), 3.27-3.22 (m, 2), 1.80-1.70 (m, 2), 1.57-1.21 (m, 18), 0.89-0.84 (m, 3).

Example 142

N-[8-(Hexyloxy)octyl]quinoxalin-2-amine

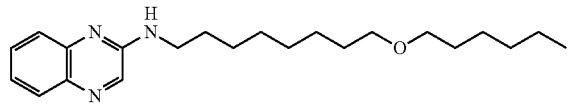

N-[8-(Hexyloxy)octyl]quinoxalin-2-amine (238 mg) was prepared following the method for N-[8-(hexyloxy)octyl] isoquinolin-1-amine starting with 8-(hexyloxy)octan-1-amine (380 mg, 1.66 mmol) and 2-chloroquinoxaline (413 mg, 2.50 mmol), but the reaction proceeded at room temperature over 4 days. Rf 0.20 (20% EA/Hex); $^1$H NMR (CDCl$_3$) δ 8.14 (s, 1), 7.80 (dd, 1, J=1.2, 8.1 Hz), 7.64 (m, 1), 7.50 (m, 1), 7.29 (m, 1), 5.24 (br t, 1), 3.46 (m, 2), 3.37-3.32 (m, 4), 1.66-1.47 (m, 6), 1.31-1.25 (m, 14), 0.84 (m, 3).

Example 143

1-[8-(Hexyloxy)octyl]-1H-benzimidazole

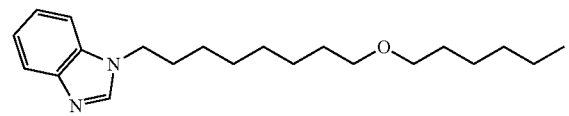 [SMILES: CCCCCCOCCCCCCCCn1cnc2ccccc21]

8-(Hexyloxy)octyl methanesulfonate (9.4 g, 31 mmol) was added to a mixture of benzimidazole (4.0 g, 31 mmol) and sodium tert-butoxide (31 mmol) in 100 mL of DMF. After 6 hr, the volatile components were evaporated, and the residue was partitioned between EA and saturated NaHCO$_3$, 0.1M HCl, and H$_2$O, and the organic phases were dried over Na$_2$SO$_4$ and concentrated. FC (70% EA/Hex) gave 7.4 g of the product. $^1$H NMR (CDCl$_3$) δ 7.9 (s, 1H), 7.8 (m, 1H), 7.4 (m, 1H), 7.2 (m, 2H), 4.1 (t, 2H), 3.3 (m, 4H), 1.9 (m, 2H), 1.7-1.5 (m, 4H), 1.4-1.2 (m, 14H), 0.9 (m, 3H).

Example 144

N-[8-(Hexyloxy)octyl]pyrazin-2-amine

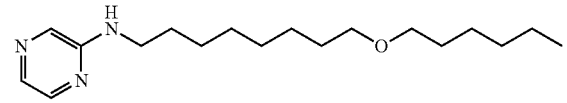

N-[8-(Hexyloxy)octyl]pyrazin-2-amine (102 mg) was prepared following the method for N-[8-(hexyloxy)octyl] isoquinolin-1-amine starting with 8-(hexyloxy)octan-1-amine (583 mg, 2.54 mmol) and 2-chloropyrazine (0.25 mL, 2.81 mmol) and heating at 70° C. for 5 days. Rf 0.26 (40% EA/Hex); $^1$H NMR (CDCl$_3$) δ 7.9 (m, 1H), 7.8 (m, 1H), 7.7 (m, 1H), 4.8 (br s, 1H, NH), 3.4-3.2 (m, 6H), 1.6-1.4 (m, 6H), 1.4-1.2 (m, 14H), 0.8 (m, 3H).

Example 145

1-[8-(Hexyloxy)octyl]-1H-indole

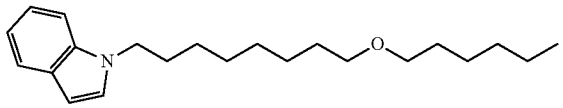 [SMILES: CCCCCCOCCCCCCCCn1ccc2ccccc21]

1-[8-(Hexyloxy)octyl]-1H-indole (1.0 g) was prepared following the method for 1-[8-(hexyloxy)octyl]-1H-benzimidazole starting with indole (836 mg, 7.1 mmol), 8-(hexyloxy)octyl methanesulfonate (1.1 g, 3.6 mmol), and 7.1 mmol of sodium tert-butoxide. $^1$H NMR (CDCl$_3$) δ 7.6 (d, 1H), 7.3 (d, 1H), 7.2 (m, 1H), 7.1 (m, 2H), 6.5 (d, 1H), 4.1 (t, 2H), 3.4 (m, 4H), 1.8 (m, 2H), 1.7-1.5 (m, 4H), 1.4-1.2 (m, 14H), 0.9 (m, 3H).

Example 146

3-[8-(Hexyloxy)octyl]-3H-imidazo[4,5-b]pyridine

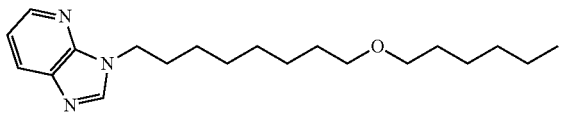 [SMILES: CCCCCCOCCCCCCCCn1cnc2cccnc21]

3-[8-(Hexyloxy)octyl]-3H-imidazo[4,5-b]pyridine was prepared following the method for 1-[8-(hexyloxy)octyl]-1H-imidazo[4,5-c]pyridine starting from 2-chloro-3-nitropyridine (479 mg, 3.0 mmol) and 8-(hexyloxy)octan-1-amine (0.69 g, 3.0 mmol). Since 2-chloro-3-nitropyridine was commercially available, the first step in the 1-[8-(hexyloxy)octyl]-1H-imidazo[4,5-c]pyridine preparation (chlorination using phenylphosphonic dichloride) was not performed. Rf 0.31 (5% MeOH/DCCM); $^1$H NMR (CDCl$_3$) δ 8.21 (dd, 1, J=1.5, 4.7 Hz), 7.89 (s, 1), 7.87 (m, 1), 7.02 (dd, 1, J=4.7, 7.9 Hz), 4.09 (m, 2), 3.21-3.15 (m, 4), 1.74 (m, 2), 1.36-1.32 (m, 4), 1.14-1.10 (m, 14), 0.69 (m, 3).

Example 147

1-Dodecyl-1H-imidazo[4,5-c]quinoline

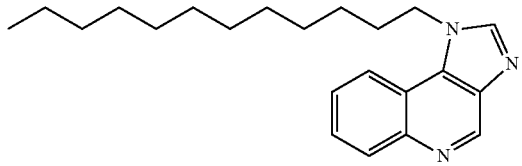 [SMILES: CCCCCCCCCCCCn1cnc2cnc3ccccc3c21]

1-Dodecyl-1H-imidazo[4,5-c]quinoline (510 mg) was prepared following the method for the preparation of 1-octyl-1H-imidazo[4,5-c]quinoline, starting with 2,4-dichloro-3-nitroquinoline (1.0 g, 4.1 mmol) and 1-dodecylamine (1.0 g, 4.5 mmol). $^1$H NMR (CDCl$_3$) δ 8.5 (s, 1H), 8.15 (d, 1H), 8.05 (d, 1H), 7.5 (m, 1H), 7.3 (m, 1H), 3.7 (t, 2H), 1.8 (m, 2H), 1.5-1.1 (m, 18H), 0.8 (m, 3H).

Example 148

1-[3-(Decyloxy)propyl]-1H-imidazo[4,5-c]quinoline

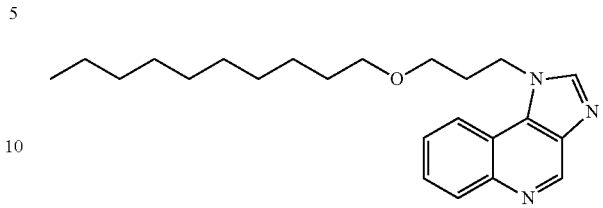

3-(Decyloxy)propan-1-amine (7.17 g of a solid) was prepared following the method for the preparation of 8-butoxyoctan-1-amine, starting from 1,3-propanediol (26.3 mL, 363 mmol) and 1-iododecane (121 mmol) mixed in 240 mL of 1:1 DCM/DMF.

1-[3-(Decyloxy)propyl]-1H-imidazo[4,5-c]quinoline (127 mg) was prepared following the method for the preparation of 1-octyl-1H-imidazo[4,5-c]quinoline, starting with 2,4-dichloro-3-nitroquinoline (1.94 g, 7.99 mmol) and 3-(decyloxy)propan-1-amine (1.72 g, 7.99 mmol). $^1$H NMR (CDCl$_3$) δ 8.9.3 (s, 1H), 8.3 (m, 2H), 7.95 (s, 1H), 7.7-7.5 (m 2H), 4.7 (t, 2H), 3.5-3.3 (m, 4H), 2.2 (m, 2H), 1.6 (m, 2H), 1.4-1.2 (m, 14H), 0.8 (t, 3H).

Example 149

1-[4-(Decyloxy)butyl]-1H-imidazo[4,5-c]quinoline

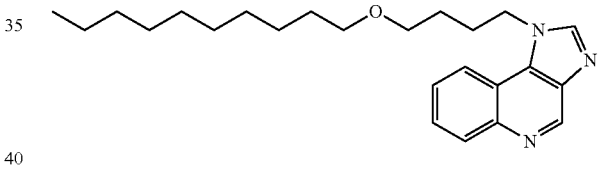

4-(Decyloxy)butan-1-amine (2.42 g, 7.28 mmol) was prepared by lithium aluminum hydride reduction of 4-(decyloxy)butyronitrile, which was prepared in poor yield from the sodium alkoxide of 1-decanol and 4-bromobutyronitrile.

1-[4-(Decyloxy)butyl]-1H-imidazo[4,5-c]quinoline (78 mg) was prepared following the method for the preparation of 1-octyl-1H-imidazo[4,5-c]quinoline, starting with 2,4-dichloro-3-nitroquinoline (1.77 g, 7.28 mmol) and 4-(decyloxy)butan-1-amine (2.42 g, 7.28 mmol). $^1$H NMR (CDCl$_3$) δ 9.3 (s, 1H), 8.25 (m, 1H), 8.15 (m, 1H), 7.95 (s, 1H), 7.7-7.5 (m, 2H), 4.6 (t, 2H), 3.5-3.3 (m, 4H), 2.1 (m, 2H), 1.7 (m, 2H), 1.5 (m, 2H), 1.4-1.1 (m, 14H), 0.8 (t, 3H).

Example 150

1-[8-(Hexyloxy)octyl]-1H-imidazo[4,5-c]quinoline

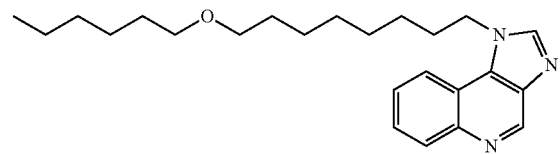 [SMILES: CCCCCCOCCCCCCCCn1cnc2cnc3ccccc3c21]

1-[8-(Hexyloxy)octyl]-1H-imidazo[4,5-c]quinoline was made by the method used for the preparation of 1-octyl-1H-imidazo[4,5-c]quinoline, substituting 8-(hexyloxy)octan-1-amine for 1-octylamine.

Example 151

1-{5-[3-(Hexyloxy)propoxy]pentyl}-1H-imidazo[4,5-c]quinoline

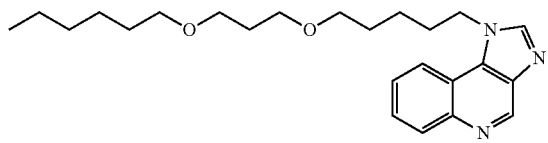 [SMILES: CCCCCCOCCCOCCCCCn1cnc2cnc3ccccc3c21]

1-{5-[3-(Hexyloxy)propoxy]pentyl}-1H-imidazo[4,5-c]quinoline (2.75 g of brown oil) was made by the method used for the preparation of 1-octyl-1H-imidazo[4,5-c]quinoline, starting with 2,4-dichloro-3-nitroquinoline (5.35 g, 22 mmol) and 5-[3-(hexyloxy)propoxy]pentan-1-amine (4.90 g, 20 mmol). $^1$H NMR (CDCl$_3$) δ 9.3 (s, 1H), 8.25 (m, 1H), 8.1 (m, 1H), 7.9 (s, 1H), 7.7-7.5 (m, 2H), 4.5 (t, 2H), 3.5-3.3 (m, 8H), 2.0 (m, 2H), 1.8 (m, 2H), 1.7-1.4 (m, 6H), 1.4-1.2 (m, 6H), 0.8 (m, 3H).

Example 152

1-{3-[3-(Hexyloxy)phenoxy]propyl}-1H-imidazo[4,5-c]quinoline

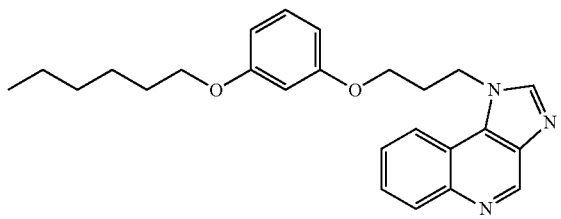 [SMILES: CCCCCCOc1cccc(OCCCn2cnc3cnc4ccccc4c32)c1]

1-{3-[3-(Hexyloxy)phenoxy]propyl}-1H-imidazo[4,5-c]quinoline (1.33 g of brown oil) was made by the method used for the preparation of 1-octyl-1H-imidazo[4,5-c]quinoline, starting with 2,4-dichloro-3-nitroquinoline (4.33 g, 17.8 mmol) and 3-[2-(hexyloxy)phenoxy]propan-1-amine (4.37 g, 17.8 mmol). $^1$H NMR (CDCl$_3$) δ 9.3 (s, 1H), 8.3-8.1 (m, 2H), 7.9 (s, 1H), 7.7-7.5 (m, 2H), 7.1 (m, 1H), 6.6-6.4 (m, 3H), 4.7 (t, 2H), 3.95-3.80 (m, 4H), 2.4 (m, 2H), 1.7 (m, 2H), 1.5-1.2 (m, 6H), 0.8 (m, 3H).

Biological Activity Examples

Anti-Inflammatory Examples

Example A

Selective Killing of LPS-Activated Inflammatory Macrophages by Compound AC

Summary: THP-1 is a human AML cell line that can be induced into a macrophage-like cell by treatment with 0.2 μM vitamin-D3 (vit-D3) for 3-5 days. In the absence of an inflammatory activator (LPS; bacterial endotoxin), AC exerted little effect on cell viability in THP-1 cells over a 6 hour period. Similarly, LPS in the absence of AC induced only a low level of cell death. In contrast, when both components, LPS and AC were added to vit-D3 activated THP-1 cells, massive cytotoxicity was observed within 6 hours. These observations indicate that stimulated macrophages participating in an inflammatory reaction may be specifically targeted for deactivation with AC.

Experiment Overview:
1. Vit-D3 activated THP-1 cells were transferred to the wells of a 24-well dish
2. Compound AC, LPS from *E. coli* 0111:B4 or both components were added
3. After 6 hours at 37 C the wells viable cell counts were performed by FACS Experimental Procedures Cell Culture:

THP-1 cells (ATCC) treated with 0.2 μM vitamin-D3 (EMD Biosciences) for 4 days prior to day 0 were transferred to the wells of 24-well dishes (1×10$^6$ cells in 1 ml cRPMI [RPMI (ATCC)+10% ΔFBS (ATCC)]. LPS from *E. coli* 0111:B4 (Sigma-Aldrich) and compound AC were added to appropriate wells and the plates placed in a 37 C incubator. After 6 hours the wells were processed for Annexin V apoptosis assay.

FACS Cell Count and Viability Assay:

After 6 hours, 5000 of the cell suspension from each well was transferred to 3 ml FACS tubes and 500 CountBright beads (Invitrogen) were added to each tube. Samples were vortexed, 2 μl propidium iodide (150 μM) (Sigma-Aldrich) added then acquired on the FACSCalibur.

Results:

As shown in Table 1, in the absence of a second pro-inflammatory signal (LPS), AC exerted little effect on cell viability in THP-1 cells over a 6 hour period. Similarly, LPS in the absence of AC induced only a low level of cell death. In marked contrast, when both LPS and AC were added to vit-D3 activated THP-1 cells, massive cytotoxicity was observed within 6 hours. Cytotoxicity increased in a AC dose-dependent manner.

TABLE 1

Dose-dependent acute cell death in AC-treated THP-1 cells primed with LPS (Viable cell percent change from 0 hours)

| Compound AC concentration | No LPS | | Plus LPS (100 ng/ml) | |
|---|---|---|---|---|
| | Mean | SE | Mean | SE |
| 0 (0.1% DMSO) | 0.00 | 4.30 | −21.47 | 3.50 |
| 0.5 μM AC | −8.75 | 5.92 | −55.63 | 4.61 |
| 1.0 μM AC | −2.43 | 4.24 | −65.93 | 3.13 |
| 2.0 μM AC | −10.63 | 1.49 | −77.43 | 3.44 |

As shown in Table 2, in the absence of a second signal (LPS), AC, in a concentration range of 0.1 to 2 μM, exerted little effect on cell viability in THP-1 cells over a 6 hour period. Similarly, LPS in the absence of AC induced a low level of cell death that increased in a dose dependent manner. In contrast, when both components, LPS and AC, were added to vit-D3 activated THP-1 cells, massive cytotoxicity was observed within 6 hours. Cytotoxicity appeared to have reached maximal level with the lowest dose of LPS used (1 ng/ml).

TABLE 2

Titration of LPS in the THP-1 acute/5-hour AC + LPS-induced cell death model (Viable cell percent change from 0 hours)

| LPS concentration | THP-1 viable cell % from 0 hours 5 hours treatment | | | |
|---|---|---|---|---|
| | No AC | | 0.1 µM AC | |
| | Mean | SE | Mean | SE |
| 0 ng/ml | 0.00 | 0.80 | −13.24 | 0.73 |
| 1 ng/ml | −23.36 | 1.77 | −53.79 | 2.57 |
| 5 ng/ml | −30.23 | 2.57 | −53.64 | 1.73 |
| 10 ng/ml | −31.25 | 1.45 | −58.85 | 0.79 |
| 20 ng/ml | −40.17 | 1.38 | −58.76 | 1.44 |

Conclusion:

AC selectively reduces viability of pro-inflammatory LPS-activated macrophages, with relative sparing of non-stimulated macrophages. A very low dose of LPS (1 ng/ml) provided sufficient activation of macrophages to make them susceptible to AC.

Example B

Relative Potency of Compound AC and Chloroquine for Inactivation of Inflammatory Macrophages Background: THP-1 is a human AML cell line that can be induced into a macrophage-like cell with vitamin-D3 (vit-D3) then activated into an inflammatory state by stimulation with LPS (bacterial endotoxin). In the macrophage, LPS binding to toll-like receptor 4 (TLR-4) leads to NF-κB activation and secretion of inflammatory cytokines which can lead to tissue damage in inflammatory diseases.

Compounds of the invention inactivate inflammatory macrophages by accumulating in acidic vacuoles and disrupting their structure and function, inhibiting release of vesicular inflammatory mediators and inducing cytosolic changes that trigger macrophage death or dysfunction, including inhibition of autophagy; autophagy is important for differentiation of monocytes into macrophages. The aim of this study was to compare relative potency of a compound of the invention, AC, with chloroquine. Both AC and chloroquine are 4-aminoquinoline derivatives, and chloroquine is known to be useful for treatment of several clinical inflammatory diseases.

In this experiment, cell viability was monitored and uptake and accumulation of acridine orange, a lysosomotropic fluorescent dye, was used to assess lysosomal acidification and integrity. JC-1 dye was used to measure effects of test compounds on mitochondrial membrane potential (MMP); reduction of MMP is a feature of apoptotic cell death.

Experimental Procedures:
1. Vit-D3 activated THP-1 cells (0.5×10⁶ cells in 2 ml) were transferred to the wells of a 24-well dish
2. Compound AC was added at a concentration of 0.5 µM, 1.0 µM or 5.0 µM
3. Chloroquine was added at a concentration of 25.0 µM, 50.0 µM or 100.0 µM
4. LPS from *E. coli* 0111:B4 (1 ng/ml final concentration) was added to some wells
5. After 5 hours viable cell count, Acridine Orange (A.O.) uptake and JC-1 mitochondrial loading were determined by fluorescence-activated cell sorting (FACS)

Cell Line Information:

| THP-1: ATCC TIB-202 Organ: Peripheral blood Cell type: Monocyte | Organism: Human, male, one-year infant Disease: Acute Monocytic Leukemia (AML) Growth properties: Suspension in RPMI plus 10% FBS |
|---|---|

Test Compounds:

| Compound | Conc. | Supplier | Batch info. |
|---|---|---|---|
| DMSO | 100% | Alfa Aesar 43998 | E26X026 |
| AC | 10 mM | N/A | 073112DZ |
| Chloroquine diphosphate (C.Q.) | 25 mM | SIGMA C6628 | 100912JR |
| Bafilomycin A1 (Baf A1) | 100 µM | SIGMA B1793 | 040912JR |
| Crude-LPS *E. coli* 0111:B4 | 100 µg/ml | SIGMA L4391 | 111611JR |
| Acridine Orange (A.O.) | 50 µg/ml | Invitrogen A3568 | 092311JR |
| JC-1 | 200 µM | Invitrogen T3168 | 040611JR |
| CCCP | 50 mM | Invitrogen M34152 | 818978 |
| Sterile water | N/A | HyClone SH30529.03 | AXF39335 |
| Sterile DPBS | N/A | HyClone SH30529.03 | AWJ21253 |

Cell Culture:

THP-1 cells (p39) treated with 0.1 µM vit-D3 (100 µM) in DMSO] for 3 days were counted, spun down, resuspended in serum-free RPMI (Lonza 12-115F) and transferred to the wells of two 24-well dishes (0.5×10⁶ cells in 2 ml). Compound AC was added (in triplicate) at 0.1 µM, 0.5 µM and 1.0 µM, Chloroquine diphosphate was added (in triplicate) at 10.0 µM, 50.0 µM and 100.0 µM. Crude-LPS from *E. coli* 0111:B4 was added to some wells (1 ng/ml final conc) and the plates placed in a 37 C incubator. 10 of Baf A1 (50 nM final conc) was added to one well (no LPS) at T=4 hours to serve as a compensation control for Acridine Orange loading. After 5 hours, 5000 aliquots of cells were transferred to FACS tubes and viable cell counts, A.O. loading and JC-1 accumulation determined by FACS.

Acridine Orange (A.O.) uptake and viability cell count assay—5 hour time point:

Samples were vortexed, 2 µl of 50 µg/ml A.O. stock solution was added (200 ng/ml final) and the tubes incubated at 37 C for 15 minutes. The tubes were washed twice in DPBS, resuspended in 5000 DPBS and acquired on the FACSCalibur. Acridine Orange exhibits strong fluorescence in both FL-1 (green—RNA binding) and FL-3 (far red—acidic lysosomes).

Results:

As shown in Table 3 below, in the absence of LPS, low doses of AC had low direct cytotoxic effects that increased in a concentration dependent manner at the acute/(5-hour) time point. Chloroquine followed a similar trend though this required 100-fold more drug versus AC; 100 µM Chloroquine was approximately equivalent to 1 µM AC.

In the presence of a low dose of LPS (1 ng/ml), cytotoxicity was increased with addition of 0.1 µM (100 nM) AC. Addition of 10 µM, 50 µM or 100 µM Chloroquine had a smaller effect on LPS-induced cell death than did 1 µM AC, indicating approximately 100× higher potency of AC than chloroquine for inactivating LPS-stimulated as well as basal THP-1 cells.

Both AC and chloroquine reduced acridine orange fluorescence in THP-1 cells primed with vitamin D3 and activated with 0.1 ng/ml LPS (Table 4), indicating deacidification or disruption of lysosomal integrity. AC was approximately 50× more potent than chloroquine for reducing acridine orange fluorescence.

AC treatment led to a dose-dependent reduction in mitochondrial depolarization, resulting in a decrease mitochondrial accumulation of red JC-1 dimers.

LPS alone (1 ng/ml) had no effect on mitochondrial integrity but potentiated AC-induced mitochondrial depolarization. In contrast Chloroquine had little or no direct effect on mitochondrial integrity at concentrations up to 100 µM in the absence or presence of LPS.

TABLE 3

Effect of AC and chloroquine on cell viability after 5 hours +/−LPS in vit-D3 activated THP-1 cells

| Test compound concentration | THP-1 viable cell count/well percent change from 0 hrs | |
|---|---|---|
| | No LPS Mean ± SE | 1 ng/ml LPS Mean ± SE |
| DMSO (Vehicle) | 0.00 ± 2.37 | −10.20 ± 6.47 |
| 0.1 µM AC | −17.46 ± 2.84 | −32.77 ± 1.98 |
| 0.5 µM AC | −17.01 ± 2.27 | −40.99 ± 5.01 |
| 1.0 µM AC | −31.20 ± 2.71 | −49.63 ± 0.96 |
| 10.0 µM C.Q. | −7.34 ± 0.53 | −17.38 ± 4.44 |
| 50.0 µM C.Q. | −17.11 ± 2.70 | −30.13 ± 1.23 |
| 100.0 µM C.Q. | −31.44 ± 1.37 | −43.98 ± 1.73 |

TABLE 4

Effect of AC and chloroquine on acridine orange fluorescence after 5 hours +/−LPS in vit-D3 activated THP-1 cells

| Treatment | A.O. FL-3 fluorescence (MFI) percent change from DMSO no LPS | |
|---|---|---|
| | No LPS Mean ± SE | 1 ng/ml LPS Mean ± SE |
| DMSO | 0.00 ± 3.89 | −21.06 ± 0.45 |
| 0.1 µM AC | −27.64 ± 9.68 | −54.72 ± 2.74 |
| 0.5 µM AC | −54.59 ± 4.05 | −68.24 ± 2.39 |
| 1.0 µM AC | −69.52 ± 2.05 | −81.11 ± 2.65 |
| 10.0 µM C.Q. | −49.37 ± 6.16 | −64.76 ± 3.01 |
| 50.0 µM C.Q. | −63.45 ± 2.36 | −72.28 ± 0.78 |
| 100.0 µM C.Q. | −91.25 ± 0.60 | −88.28 ± 1.60 |

TABLE 5

Effect of AC and chloroquine on JC-1 accumulation in mitochondria after 5 hours +/−LPS in vit-D3 activated THP-1 cells

| Treatment | JC-1 Red cells (functional mitochondria) percent change from DMSO (no LPS) | |
|---|---|---|
| | No LPS Mean ± SE | 1 ng/ml LPS Mean ± SE |
| DMSO | 0.00 ± 1.59 | −0.33 ± 0.69 |
| 0.1 µM AC | 1.18 ± 0.91 | −1.66 ± 0.96 |
| 0.5 µM AC | −4.39 ± 1.40 | −7.19 ± 1.52 |
| 1.0 µM AC | −10.40 ± 2.08 | −16.41 ± 2.60 |
| 10.0 µM C.Q. | 2.58 ± 0.81 | 4.39 ± 0.81 |
| 50.0 µM C.Q. | −0.70 ± 1.24 | 2.21 ± 0.63 |
| 100.0 µM C.Q. | −1.40 ± 0.67 | 1.07 ± 0.39 |

Conclusion:

AC displays selectivity for inactivating LPS-activated macrophages versus unstimulated cells. AC also attenuated acridine orange accumulation in lysosomes, indicating that it caused lysosomal disruption. AC was approximately 100 fold more potent than chloroquine for inactivating macrophages, and about 50 times more potent than chloroquine for disrupting lysosomal integrity as measured by acridine orange accumulation.

Example C

Screen of Compounds of the Invention for Anti-Inflammatory Activity In Vitro

Background: THP-1 is a human acute myeloid leukemia (AML) cell line that can be induced into a macrophage-like cell with vitamin-D3 (vit-D3). In the macrophage, LPS (lipopolysaccharide; endotoxin) stimulation of toll-like receptor 4 (TLR-4) leads to NF-κB activation and secretion of inflammatory cytokines but also the priming of programmed death pathways through RIP and Caspase 8. The balance of this complex regulatory network is dependent on highly specific kinases, enzymes that require ATP. Disruption of either cytosolic pH or ATP availability/energy level uncouples this control network and the can macrophage shift away from production of inflammatory cytokines towards a programmed death event, which has the net effect of limiting inflammatory damage.

Compounds of the invention have been shown to inactivate macrophages rapidly (within 5 to 6 hours) when the macrophages have been put into a pro-inflammatory state activated with LPS. More than 200 compounds of the invention were screened for anti-inflammatory activity in the THP-1 system to assess their relative potency and activity in vitro.

Summary:

Addition of LPS to compound-treated macrophages resulted in acute/5-hour cell death; this activity increased in a concentration dependent manner. Treatment with test compounds alone exhibited only a low level of acute cytotoxicity.

The majority of compounds tested displayed significant ability to inactivate pro-inflammatory THP-1 cells in accord with the proposed mechanism of action involving lysosome disruption, which is not dependent upon binding to a specific protein target. Of the compounds tested, seven demonstrated higher activity than the active benchmark compound AC: CJ, AM, AG, CX, AF, BM and AH.

At the lowest concentration tested (0.1 µM), all seven tested compounds were more active than AC in causing death of cells treated with LPS. At concentrations of 0.5 µM and above all compounds, including AC, reached a maximum activity threshold.

Results:

Addition of LPS to test compound-treated macrophages resulted in massive acute/5-hour cell death; this activity increased in a concentration dependent manner (Table 6). Treatment with compounds alone without pro-inflammatory activation of the macrophages with LPS exhibited only a low level of acute cytotoxicity.

At the lowest concentration tested (0.1 µM), seven compounds were more active than AC in conditioning the cells for LPS-induced cell death. At concentrations of 0.5 µM and above, all eight compounds, including AC, reached a maximum activity threshold.

Compound CX was the most effective cytotoxic compound at the acute/5-hour time point, followed by a moderate activity group including CJ, AF, AH and BM. AG and AM exerted the lowest effect on cytoplasmic conditioning, albeit still greater than that shown by AC.

TABLE 6

Compound screen: Reduction in viable THP-1 cell count (percent change) from 0 hours after treatment with test compounds for 5 hours

| | Compound (0.1 μM) | | Compound (1.0 μM) | |
|---|---|---|---|---|
| Compound | Plus LPS Mean ± SE | No LPS Mean ± SE | Plus LPS Mean ± SE | No LPS Mean ± SE |
| Vehicle | −7.42 ± 3.07 | 0.00 ± 4.71 | −7.42 ± 3.07 | 0.00 ± 4.71 |
| AC | −15.14 ± 2.06 | −7.48 ± 5.82 | −44.25 ± 2.53 | −9.60 ± 1.96 |
| CJ | −30.15 ± 4.41 | −5.53 ± 3.89 | −41.62 ± 1.80 | −6.99 ± 1.55 |
| AM | −19.80 ± 1.96 | −5.57 ± 2.67 | −44.05 ± 1.38 | −8.47 ± 3.31 |
| AG | −21.28 ± 1.52 | −6.24 ± 0.69 | −38.58 ± 0.73 | −4.02 ± 2.83 |
| CX | −38.09 ± 0.41 | −8.00 ± 1.41 | −49.57 ± 2.44 | −9.20 ± 3.09 |
| AF | −27.32 ± 4.69 | −8.99 ± 2.00 | −44.82 ± 2.46 | −6.02 ± 2.31 |
| BM | −25.80 ± 3.26 | −3.96 ± 0.82 | −39.17 ± 2.18 | −4.18 ± 2.46 |
| AH | −26.55 ± 0.95 | −9.66 ± 1.34 | −35.51 ± 3.90 | −7.87 ± 0.98 |

Example D

Anti-Inflammatory Activity of Compounds of the Invention

Compounds of the invention have been shown to directly inhibit NF-κB, damage intracellular acidic lysosomes leading to proton leakage and acidification of the cytoplasm and also damage mitochondria reducing the cellular energy level. Together these actions result in direct cell death in some vulnerable cell types, over a period of about 48 hours. Additionally in the macrophage, cytoplasmic acidification and energy depletion by compounds of the invention prime the cell for inactivation when exposed to low concentrations of LPS, leading to an acute (5-hour) cell death event through a combination of Caspase-driven apoptosis and RIP-driven necrosis.

Compounds of the invention were tested at 0.1 μM versus AC in the LPS-triggered THP-1 cell death assay. Both acute/5-hour and chronic/48-hour phases of cell death were assessed. Compounds were screened in batches with DMSO as the negative control and AC as the high activity control. Compounds were tested at the low concentration of 0.1 μM with a view toward identifying agents more potent than the benchmark agent AC; at higher concentrations, e.g. 1 μM, most compounds of the invention are active in inducing cell death in this assay, which makes differentiation from AC less clear than at a 10 fold lower drug concentration.

Results/Summary:

Seven of the compounds not only demonstrated equivalent activity to AC at the acute/5-hour time point (cell conditioning) but were also more active than AC at the chronic/48-hour time point (retention): CJ, AM, AG, CX, AF, BM and AH.

A further 15 tested compounds demonstrated equivalent activity to AC at both the 5-hour and 48-hour time points: CI, CL, AL, AR, AN, AD, BH, CV, AJ, BD, BU, BK, EW, AK and AE.

The remaining 187 compounds exhibited lower anti-inflammatory activity than AC at the tested concentration of 0.1 μM. However, this screen was conducted at a suboptimal concentration to detect the most potent compounds in the library; low activity at a concentration of 0.1 mM in the context of this assay is still consistent with significant and potent anti-inflammatory activity when compared to chloroquine or other antimalarials.

SUMMARY TABLE 7

Compound screen: Viable cell percent change after 5 and 48 hours in the THP-1 cell death assay (10 ng/ml LPS 0.1 μM test compound)

| | Cell death time point | | | |
|---|---|---|---|---|
| | Acute/5-hour | | Chronic/48-hour | |
| Compound | Mean | SE | Mean | SE |
| DMSO | −19.09 | 6.46 | 52.22 | 6.74 |
| AC | −34.96 | 3.83 | 27.70 | 4.12 |
| CH | −23.58 | 1.41 | 53.55 | 7.24 |
| CI | −33.19 | 2.15 | 28.46 | 1.27 |
| CJ | −39.08 | 0.63 | 15.44 | 4.55 |
| CK | −22.60 | 1.68 | 42.23 | 4.37 |
| CL | −33.77 | 2.31 | 29.43 | 0.86 |
| CO | −27.62 | 2.37 | 43.95 | 1.27 |
| AR | −38.07 | 4.48 | 28.75 | 5.34 |
| AN | −38.87 | 4.25 | 31.66 | 1.43 |
| AD | −43.47 | 4.88 | 26.01 | 3.24 |
| CX | −39.48 | 1.53 | 8.50 | 4.04 |
| BH | −44.02 | 2.43 | 34.77 | 8.01 |
| CV | −39.94 | 1.23 | 23.02 | 5.00 |
| AZ | −24.00 | 1.47 | 50.12 | 1.11 |
| CW | −26.47 | 0.71 | 43.71 | 2.34 |
| DA | −25.97 | 2.71 | 43.55 | 6.40 |
| DB | −25.73 | 0.25 | 20.47 | 3.28 |
| BA | −20.15 | 1.07 | 41.79 | 6.41 |
| CY | −29.18 | 1.70 | 47.86 | 2.06 |
| CZ | −29.41 | 1.34 | 53.70 | 1.63 |
| CP | −21.87 | 1.68 | 49.81 | 4.04 |
| CR | −24.54 | 2.32 | 40.02 | 10.49 |
| BG | −26.46 | 3.81 | 38.39 | 10.97 |

SUMMARY TABLE 8

Compound screen: Viable cell percent change after 5 and 48 hours in the THP-1 cell death assay (10 ng/ml LPS 0.1 μM test compound)

| | Cell death time point | | | |
|---|---|---|---|---|
| | Acute/5-hour | | Chronic/48-hour | |
| Compound | Mean | SE | Mean | SE |
| DMSO | −15.79 | 2.35 | 81.91 | 10.05 |
| AC | −30.98 | 2.63 | 38.84 | 7.90 |
| CS | −15.04 | 2.29 | 66.27 | 4.64 |
| BT | −15.61 | 1.14 | 66.98 | 2.63 |
| DW | −23.38 | 1.66 | 73.97 | 0.81 |
| DX | −13.66 | 2.36 | 59.95 | 3.73 |
| DZ | −12.39 | 0.38 | 73.5 | 1.3 |
| EA | −30.40 | 2.34 | 73.48 | 17.34 |
| EG | −30.80 | 2.11 | 60.59 | 8.29 |
| ED | −29.12 | 1.27 | 81.40 | 4.16 |
| DC | −30.73 | 2.07 | 87.66 | 9.59 |
| DI | −32.79 | 1.21 | 82.24 | 3.39 |
| DK | −31.72 | 1.43 | 73.60 | 7.17 |
| DL | −35.64 | 1.88 | 61.01 | 4.54 |
| DN | −29.63 | 2.37 | 77.15 | 7.16 |
| DS | −14.93 | 2.00 | 56.67 | 7.09 |
| AF | −33.78 | 3.20 | 13.79 | 3.87 |
| BK | −30.96 | 3.05 | 43.69 | 3.12 |
| CG | −24.24 | 4.35 | 54.66 | 1.13 |
| BM | −39.97 | 2.41 | 29.97 | 2.15 |
| BN | −17.24 | 0.92 | 60.91 | 2.81 |
| AE | −37.73 | 3.86 | 4.11 | 2.24 |
| AB | −20.14 | 0.71 | 56.56 | 5.96 |

SUMMARY TABLE 9

Compound screen: Viable cell percent change after 5 and 48 hours in the THP-1 cell death assay (10 ng/ml LPS 0.1 µM test compound)

| Compound | Acute/5-hour Mean | Acute/5-hour SE | Chronic/48-hour Mean | Chronic/48-hour SE |
|---|---|---|---|---|
| DMSO | −23.30 | 0.40 | 35.66 | 3.27 |
| AC | −34.70 | 1.94 | 14.24 | 1.47 |
| AL | −36.59 | 2.17 | 19.14 | 4.63 |
| EI | −16.40 | 1.18 | 39.53 | 5.09 |
| BE | −27.08 | 2.45 | 33.86 | 1.63 |
| BF | −31.22 | 2.14 | 31.64 | 4.04 |
| BG | −24.51 | 2.07 | 31.07 | 8.11 |
| BJ | −22.42 | 4.07 | 18.03 | 3.64 |
| BI | −17.04 | 2.14 | 27.30 | 8.06 |
| CT | −15.13 | 3.87 | 34.36 | 2.98 |
| CU | −14.30 | 1.56 | 41.84 | 3.25 |
| AI | −22.65 | 2.45 | 28.60 | 12.70 |
| DY | −15.92 | 2.80 | 45.25 | 2.74 |
| EE | −17.77 | 1.15 | 24.32 | 3.49 |
| EB | −19.41 | 4.94 | 35.89 | 2.24 |
| EC | −13.74 | 0.73 | 47.40 | 8.60 |

SUMMARY TABLE 10

Compound screen: Viable cell percent change after 5 and 48 hours in the THP-1 cell death assay (10 ng/ml LPS 0.1 µM test compound)

| Compound | Acute/5-hour Mean | Acute/5-hour SE | Chronic/48-hour Mean | Chronic/48-hour SE |
|---|---|---|---|---|
| DMSO | −15.51 | 0.95 | 28.09 | 5.15 |
| AC | −28.61 | 0.31 | 11.13 | 3.65 |
| AO | −18.86 | 0.91 | 25.19 | 0.81 |
| DP | −10.67 | 2.78 | 42.36 | 6.73 |
| AP | −8.73 | 2.99 | 37.38 | 8.16 |
| DD | −22.24 | 4.26 | 44.34 | 4.25 |
| DE | −16.91 | 3.02 | 25.65 | 6.11 |
| DF | −14.22 | 3.09 | 39.26 | 1.86 |
| DJ | −13.11 | 1.57 | 22.32 | 6.35 |
| DM | −13.85 | 3.09 | 34.67 | 10.04 |
| DO | −16.45 | 3.36 | 36.46 | 8.92 |
| DR | −30.11 | 7.00 | 27.12 | 5.64 |
| DQ | −14.50 | 6.72 | 32.31 | 4.28 |
| BU | −30.95 | 2.44 | 18.10 | 2.50 |
| DV | −15.76 | 0.16 | 24.69 | 2.29 |
| BL | −14.15 | 1.42 | 32.33 | 5.20 |
| DT | −15.01 | 3.02 | 16.12 | 2.95 |
| DU | −19.46 | 3.16 | 17.10 | 2.36 |
| FR | −7.33 | 2.48 | 15.96 | 2.96 |
| AV | −12.93 | 2.26 | 38.76 | 3.70 |
| AX | −12.47 | 1.73 | 18.20 | 4.10 |

SUMMARY TABLE 11

Compound screen: Viable cell percent change after 5 and 48 hours in the THP-1 cell death assay (10 ng/ml LPS 0.1 µM test compound)

| Compound | Acute/5-hour Mean | Acute/5-hour SE | Chronic/48-hour Mean | Chronic/48-hour SE |
|---|---|---|---|---|
| DMSO | −19.10 | 0.94 | −4.46 | 1.11 |
| AC | −28.75 | 2.33 | −23.17 | 2.92 |
| BR | −16.15 | 2.85 | −5.72 | 1.19 |
| CM | −30.79 | 4.75 | −6.80 | 3.16 |
| BB | −19.89 | 2.07 | 0.65 | 3.12 |
| BC | −18.89 | 1.94 | 6.40 | 11.50 |
| BD | −28.12 | 0.36 | −17.21 | 4.61 |
| BS | −17.29 | 1.13 | −6.51 | 2.77 |

SUMMARY TABLE 12

Compound screen: Viable cell percent change after 5 and 48 hours in the THP-1 cell death assay (10 ng/ml LPS 0.1 µM test compound)

| Compound | Acute/5-hour Mean | Acute/5-hour SE | Chronic/48-hour Mean | Chronic/48-hour SE |
|---|---|---|---|---|
| DMSO | −38.16 | 2.40 | −9.13 | 2.21 |
| AC | −46.72 | 3.21 | −24.59 | 1.48 |
| FD | −34.27 | 2.34 | −3.68 | 4.14 |
| FB | −43.02 | 2.59 | −10.18 | 3.14 |
| FC | −34.17 | 7.15 | −20.85 | 1.63 |
| FH | −29.93 | 1.60 | −5.12 | 4.01 |
| FF | −25.50 | 0.78 | −4.74 | 0.92 |
| FE | −28.83 | 3.01 | −11.23 | 1.97 |
| FY | −35.57 | 2.74 | −1.84 | 3.24 |
| BP | −26.04 | 1.33 | −3.39 | 7.15 |
| FG | −24.92 | 3.17 | 1.15 | 3.75 |
| FZ | −23.87 | 1.56 | −5.31 | 3.01 |

SUMMARY TABLE 13

Compound screen: Viable cell percent change after 5 and 48 hours in the THP-1 cell death assay (10 ng/ml LPS 0.1 µM test compound)

| Compound | Acute/5-hour Mean | Acute/5-hour SE | Chronic/48-hour Mean | Chronic/48-hour SE |
|---|---|---|---|---|
| DMSO | −24.88 | 2.82 | 26.90 | 5.17 |
| AC | −36.91 | 0.49 | −9.22 | 3.97 |
| GA | −22.33 | 1.00 | 16.51 | 4.55 |
| FI | −23.79 | 2.33 | 12.70 | 1.85 |
| GB | −25.77 | 0.93 | 19.29 | 4.19 |
| CD | −28.27 | 0.57 | 7.55 | 2.55 |
| CE | −30.76 | 3.40 | 4.71 | 2.96 |
| BQ | −23.07 | 1.07 | 13.70 | 1.17 |
| FJ | −31.23 | 2.21 | 27.44 | 2.43 |
| FK | −27.64 | 1.45 | 16.57 | 2.59 |
| GC | −27.62 | 3.64 | 19.30 | 7.07 |
| CF | −26.02 | 1.80 | 27.26 | 3.66 |
| FO | −20.14 | 1.51 | 20.18 | 2.47 |
| FP | −29.59 | 2.59 | 30.44 | 4.50 |
| FQ | −31.29 | 0.86 | 25.62 | 3.30 |
| AU | −29.50 | 3.48 | 16.86 | 3.41 |
| FV | −31.34 | 0.29 | 17.51 | 2.28 |
| EK | −22.83 | 2.09 | 15.50 | 2.40 |

SUMMARY TABLE 14

Compound screen: Viable cell percent change after 5 and 48 hours in the THP-1 cell death assay (10 ng/ml LPS 0.1 μM test compound)

| Compound | Acute/5-hour Mean | Acute/5-hour SE | Chronic/48-hour Mean | Chronic/48-hour SE |
|---|---|---|---|---|
| DMSO | −40.83 | 3.04 | 9.11 | 9.96 |
| AC | −43.44 | 2.32 | −16.35 | 2.21 |
| EL | −32.95 | 1.57 | −3.09 | 6.02 |
| FS | −28.46 | 1.15 | −0.47 | 2.36 |
| EM | −35.35 | 1.22 | −1.83 | 3.18 |
| FT | −27.22 | 1.21 | 3.59 | 3.14 |
| FU | −30.02 | 1.79 | −2.75 | 1.97 |
| CB | −34.76 | 1.69 | 10.62 | 5.40 |
| CC | −31.14 | 1.04 | −1.09 | 0.38 |
| FW | −34.49 | 1.96 | 1.27 | 3.15 |
| FX | −31.28 | 2.66 | −3.62 | 2.06 |
| AS | −32.02 | 3.71 | 3.86 | 1.52 |
| EN | −27.16 | 2.48 | 6.64 | 2.20 |
| AY | −36.14 | 1.27 | 7.71 | 4.95 |
| CN | −32.16 | 2.34 | 3.70 | 2.76 |
| FN | −27.54 | 2.71 | 3.54 | 4.49 |
| FM | −46.22 | 2.64 | 9.74 | 2.98 |

SUMMARY TABLE 15

Compound screen: Viable cell percent change after 5 and 48 hours in the THP-1 cell death assay (10 ng/ml LPS 0.1 μM test compound)

| Compound | Acute/5-hour Mean | Acute/5-hour SE | Chronic/48-hour Mean | Chronic/48-hour SE |
|---|---|---|---|---|
| DMSO | −28.93 | 2.75 | 40.68 | 6.03 |
| AC | −41.20 | 2.33 | 16.40 | 3.98 |
| DG | −25.02 | 0.28 | 37.90 | 7.88 |
| DH | −27.53 | 1.35 | 50.89 | 5.57 |
| AQ | −26.78 | 1.89 | 24.71 | 1.45 |
| BV | −27.24 | 2.50 | 42.14 | 2.90 |
| BW | −34.15 | 0.75 | 36.08 | 4.32 |
| BX | −34.84 | 1.60 | 25.10 | 6.23 |
| EH | −29.46 | 3.65 | 32.85 | 4.45 |
| BY | −29.40 | 1.20 | 39.64 | 5.24 |
| BZ | −27.55 | 2.27 | 30.72 | 2.28 |
| AT | −32.45 | 1.49 | 30.34 | 2.30 |
| BO | −32.29 | 1.45 | 28.35 | 4.70 |
| FL | −30.26 | 2.85 | 38.59 | 1.87 |

Example E

Anti-Inflammatory Properties of Compound AC in a Model of Skin Inflammation

Objective: To evaluate the anti-inflammatory properties of compounds of the invention in a 12-O-tetradecanoylphorbol-13-acetate (TPA) induced chronic skin inflammation mouse model. Topically applied phorbol esters such as TPA induce skin inflammation involving edema, macrophage and T cell infiltration and epidermal hyperplasia (Alford et al., 1992), and this system has been used as an animal model for dermatitis, mimicking aspects of human inflammatory skin disorders. TPA is also known as a tumor promoter, so that agents which inhibit hyperproliferative or angiogenic actions of TPA may inhibit tumor promotion.

Methods

Drug formulations: Compound AC was dissolved in isopropyl myristate:propylene glycol (1:1)+0.9% DMSO at the indicated concentrations. TPA was dissolved in acetone:water (99:1). Dexamethasone (0.06%) was dissolved in normal saline.

Mice: HSD-ICR(CD-1R) female mice at 8-10 weeks of age were used in this experiment.

Experimental Design: Mice were placed into six groups of 10 mice each. 20 μL of 0.01% TPA was administered to each ear on days 0, 2, 4, 7, 9, 11, 13, 15, 18, 20, and 22. 20 μL of AC at various concentrations or 20 μL of dexamethasone solution was applied to the ears daily beginning on day 7, after inflammatory changes in ear thickness were established. Ear thickness was measured with calipers every three days.

Results

Compound AC treatment prevented inflammatory thickening of mouse ears treated with TPA. Histology indicated that both TPA-induced edema and epidermal hyperplasia were reduced by AC, as was angiogenesis. The potency of AC was comparable to that of dexamethasone, with significant activity observed at the lowest dose of 12.5 micrograms of AC per ear per day.

TABLE 16

Ear thickness of vehicle and compound-treated mice: day 22

| Treatment | Ear thickness (mm) |
|---|---|
| Vehicle | 0.646 ± 0.1161 |
| Dexamethasone, 0.05 mg/ear | 0.301 ± 0.0722 |
| AC, 0.0125 mg/ear | 0.362 ± 0.0394 |
| AC, 0.025 mg/ear | 0.390 ± 0.0319 |
| AC, 0.05 mg/ear | 0.391 ± 0.0334 |
| AC, 0.075 mg/ear | 0.395 ± 0.0438 |

REFERENCE

Alford J G, Stanley P L, Todderud G, Tramposch K M. (1992) Temporal infiltration of leukocyte subsets into mouse skin inflamed with phorbol ester. Agents Actions. 37(3-4):260-7

Example F

Anti-Inflammatory Effects of Compounds of the Invention on Psoriasiform Dermatitis in Mice Topical imiquimod (IMQ), a toll-like receptor agonist, has been established as a model of Inflammatory skin diseases including psoriasis and atopic dermatitis. Dermal inflammatory changes and gene expression in mice treated with topical imiquimod mimic human psoriasis and dermatitis (van der Fits et al., 2009; Swindell et al., 2011). The effect of a set of compounds of the invention were tested in a mouse model of imiquimod-induced dermatitis, with topical tacrolimus and dexamethasone as comparators for assessing safety and efficacy relative to standard agents used to treat dermatitis in humans.

Compounds to be tested for anti-inflammatory activity were individually dissolved in ethanol at a concentration of 0.6% and then mixed with 9 volumes of petrolatum (melted on a heated water bath at 50 degrees C.), yielding ointments containing 0.06% active drug. Dexamethasone ointment was prepared similarly, though at a final concentration of 0.03%, because 0.06% dexamethasone applied topically in preliminary experiments had caused significant weight loss due to systemic absorption. Commercial 0.1% tacrolimus ointment (ProTopic™; Novartis) was also used as an active comparator. Petrolatum containing 10% ethanol was used as a control treatment.

Female Balb/C mice (8 weeks old) were randomized and divided into groups of 5 animals each. Polyethylene collars were affixed to the mice to prevent them from easily scratching their ears.

5% imiquimod was applied to both ears of each mouse (20 microliters per ear) daily for 5 days, and then every other day for the full duration of the study Inflammatory changes, including a doubling of ear thickness were apparent by day 5. On day 7 after initiation of imiquimod, treatment with topical agents was started. Both ears of each mouse were treated with test ointments, with one compound per mouse.

Ear thickness and PASI assessments (Psoriasis Area and Severity Index, a standard psoriasis scoring system) were recorded twice per week throughout the study. The PASI score comprises the sum of evaluations of swelling, erythema and scaling on scales from 0 to 4; the maximum PASI score is 12, and the minimum, in unaffected skin, is 0).

Results

Imiquimod treatment resulted in significant inflammatory changes, including an increase in ear thickness and a change in PASI scores; control ears reached the maximum possible value in the PASI scoring system, with severe thickening, erythema and scaling. Compounds of the invention, applied topically in an ointment base, reduced imiquimod-induced inflammatory damage to mouse ears, as assessed by caliper measurements of thickness and PASI scoring of appearance. The comparator drugs tacrolimus and dexamethasone also reduced ear thickness and PASI scores. Notably, AF was superior to the commercial clinical form of topical 0.1% tacrolimus (Protopic ointment) in reducing ear thickness and PASI score. The anti-inflammatory activity of dexamethasone was accompanied by significant loss of body weight, indicating systemic toxicity due to dexamethasone absorption. Neither compounds of the invention nor tacrolimus affected body weight. In addition to inducing inflammation of the ears imiquimod transfer from the ears to the scalps of mice resulted in loss of hair and psoriasiform dermatitis on the head, from between the ears, forward to the nose. In dexamethasone-treated mice, this area remained hairless after treatment at the end of the experiment; in contrast, hair growth was maintained in this area during daily treatment with AF, indicating that AF inhibited pathologic inflammation without also impairing tissue normal tissue maintenance. A known side effect of treatment with dexamethasone and other topical corticosteroids is thinning and weakening of the treated areas; the lack of hair regrowth may reflect the clinical problem of skin atrophy known as a side effect of topical dexamethasone. AF was equally effective at 0.06% and 0.6% concentrations in the ointment base, indicating a wide therapeutic window. All of the tested compounds of the invention reduced IMQ-induced changes in ear thickness, thus demonstrating their anti-inflammatory activity in vivo.

TABLE 17

Ear thickness in mice with imiquimod-induced dermatitis

| Treatment | Mean ± SEM |
|---|---|
| Untreated (no IMQ) | 0.220 ± 0.004 |
| Control | 1.355 ± 0.004 |
| AF 0.06% | 0.355 ± 0.005* |
| AF 0.6% | 0.390 ± 0.008* |
| AC | 0.501 ± 0.030* |
| BM | 0.577 ± 0.019* |

TABLE 17-continued

Ear thickness in mice with imiquimod-induced dermatitis

| Treatment | Mean ± SEM |
|---|---|
| EF | 0.613 ± 0.010* |
| DD | 0.589 ± 0.018* |
| DU | 0.607 ± 0.027* |
| DE | 0.593 ± 0.016* |
| AE | 0.846 ± 0.023* |
| Dexamethasone | 0.305 ± 0.111* |
| Tacrolimus 0.1% | 0.428 ± 0.007* |

*= less than control ear thickness, p < .05

TABLE 18

PASI Scores in mice with imiquimod-induced psoriasiform dermatitis

| Treatment | Mean ± SEM |
|---|---|
| Untreated (no IMQ) | 0.000 ± 0.000 |
| Control | 12.000 ± 0.000 |
| AF 0.06% | 3.575 ± 0.158* |
| AF 0.6% | 4.875 ± 0.155* |
| AC | 7.150 ± 0.221* |
| BM | 9.250 ± 0.183* |
| EF | 7.275 ± 0.199* |
| DD | 7.450 ± 0.322* |
| DU | 7.975 ± 0.621* |
| DE | 7.250 ± 0.183* |
| AE | 11.550 ± 0.281 |
| Dexamethasone | 4.525 ± 0.375* |
| Tacrolimus 0.1% | 6.075 ± 0.0990* |

*= less than control PASI score, p < .05

TABLE 19

Body weights of mice with imiquimod-induced psoriasiform dermatitis

| Treatment | Initial (g) | Final (g) | D BW (g) |
|---|---|---|---|
| Control | 21.2 ± 0.8 | 21.9 ± 0.7 | +0.7 |
| AF 0.06% | 20.5 ± 0.8 | 20.9 ± 0.6 | +0.4 |
| AF 0.6% | 20.8 ± 0.6 | 20.4 ± 0.6 | −0.4 |
| AC | 21.1 ± 0.7 | 21.3 ± 0.6 | +0.2 |
| BM | 20.8 ± 0.7 | 20.9 ± 0.6 | +0.1 |
| EF | 21.5 ± 0.6 | 21.3 ± 0.2 | −0.2 |
| DD | 20.9 ± 0.8 | 20.7 ± 0.6 | −0.2 |
| DU | 20.4 ± 0.7 | 20.9 ± 0.5 | +0.5 |
| DE | 20.6 ± 0.5 | 20.5 ± 0.5 | −0.1 |
| AE | 20.9 ± 0.5 | 21.3 ± 0.4 | +0.4 |
| Dexamethasone | 20.5 ± 0.6 | 18.1 ± 0.5* | −2.4* |
| Tacrolimus 0.1% | 20.9 ± 0.7 | 20.4 ± 0.6 | −0.5 |

*Less than initial body weight, P < .02

REFERENCES

Swindell W R, Johnston A, Carbajal S, Han G, Wohn C, Lu J, Xing X, Nair R P, Voorhees J J, Elder J T, Wang X J, Sano S, Prens E P, DiGiovanni J, Pittelkow M R, Ward N L, Gudjonsson J E. (2011) Genome-wide expression profiling of five mouse models identifies similarities and differences with human psoriasis. PLoS One. 6(4):e18266 van der Fits L, Mourits S, Voerman J S, Kant M, Boon L, Laman J D, Cornelissen F, Mus A M, Florencia E, Prens E P, Lubberts E. (2009) Imiquimod-induced psoriasis-like skin inflammation in mice is mediated via the IL-23/IL-17 axis. J Immunol. 182(9):5836-45

Example G

Effects of Compounds of the Invention in a Mouse Model of Multiple Sclerosis Multiple sclerosis (MS) is an autoimmune disease mediated involving destruction by the immune system of myelin sheaths surrounding neuron axons in the brain. An established animal model for this disease is Experimental Autoiimune Encephalitis (EAE), induced by immunization of mice with proteins or peptides that induce an immune response to myelin-specific proteins.

In this experiment, EAE was induced by immunization of mice with a peptide from proteolipid protein (PLP), a known antigenic target in MS. Several compounds of the invention were administered orally to assess their effect on the course of EAE, with quantitative evaluation of disease symptoms as an endpoint. Linomide, a small molecule immunomodulator with known activity in EAE models was used as a comparator drug.

Materials and Methods 41 mice received subcutaneous injections of 90 μg PLP139-151 in 200 μL of PBS on Day 0.

The PLP was prepared in incomplete Freund's adjuvant (IFA) by mixing 10 mL IFA with 40 mg *M. tuberculosis* H37Ra (final concentration 4 mg/ml *M. tuberculosis*). The resulting mixture is complete Freund's adjuvant (CFA).

For injection, an emulsion of PLP139-151 and CFA was prepared by mixing 1 mL of stock solution with 1 mL of CFA while vortexing for 15 minutes to form an emulsion.

Mice received vehicle or a test compound (60 mol/kg; suspended in 1% aqueous hydroxypropylmethylcellulose) by oral gavage, three times per week for 2 weeks followed by once daily treatment for 4 additional weeks, beginning on Day 14. Vials with vehicle and with compounds were coded by letters (A-E) in order to obtain blind readings of disease severity.

| Group 1 (n = 7) | Vehicle |
| --- | --- |
| Group 2 (n = 6): | AZ |
| Group 3 (n = 7): | CZ |
| Group 4 (n = 7): | CP |
| Group 5 (n = 7): | CQ |
| Group 6 (n = 7) | Linomide |

Mice were monitored every other day for the development of clinical symptoms according to the grading system below.

Grading System for Clinical Assessment of EAE

| Score | Clinical Signs |
| --- | --- |
| 0 | Normal mouse, no overt signs of disease |
| 1 | Limp tail[a] and hind limb weakness[b], but not both |
| 2 | Limp tail[a] and hind limb weakness[b] |
| 3 | Partial hind limb paralysis[c] |
| 4 | Complete hind limb paralysis[d] |
| 5 | Moribund state; death by EAE; sacrifice for humane reasons |

[a] Limp tail: complete flaccidity of the tail, and absence of curling at the tip of the tail when mouse is picked up.
[b] Hind limb weakness: observed as a waddling gait, the objective sign being that, in walking, mouse's hind limbs fall through the wire cage tops.
[c] Partial hind limb paralysis: mouse can no longer use hind limbs to maintain rump posture or walk but can still move one or both limbs to some extent.
[d] Complete hind limb paralysis: total loss of movement in hind limbs; mouse drags itself only on its forelimbs. Mice at this stage are given food on the cage floor, long sipper tubes, and daily subcutaneous saline injections to prevent death by dehydration.

Results:

Mice in all groups were displaying comparable mild EAE disease symptoms by day 14 after PLP injection, at which time oral treatment with the test agents was initiated. At the termination of the study, on Day 46, Vehicle-treated mice displayed more severe disease symptom scores than did the treatment groups. Compounds of the invention displayed protective activity comparable to the positive control compound linomide.

TABLE 20

| Treatment | EAE Score on Day 14 (Before Treatment) | EAE Score on Day 46 |
| --- | --- | --- |
| Vehicle | 0.71 ± 0.18 | 3.57 ± 0.48 |
| Linomide | 0.93 ± 0.19 | 2.29 ± 0.48 |
| AZ | 0.83 ± 0.41 | 2.50 ± 0.29 |
| CZ | 1.00 ± 0.00 | 2.29 ± 0.20 |
| CP | 0.86 ± 0.14 | 1.86 ± 0.34 |

Antifungal and Antiparasitic Examples

Example H

Anti-Candida Activity of Compounds of the Invention

| Reagents | Manufacturer/Catalog # | Lot # |
| --- | --- | --- |
| *Candida albicans* strain 3153 | ATCC 28367 | 61794 |
| YPD Broth | KD Medical YLF-3260 | 032111-03 |
| Sabouraud Dextrose Agar | KD Medical #YPL-1050 | C21-03 |
| Sterile PBS, pH 7.4 | Quality Biological Inc; #114-058-131 | |
| DMSO | Sigma; cat#D2650 | |

Experiment Overview:

A single colony of *Candida Albicans* was grown in 50 ml YPD broth overnight (19 hr). The cells were washed with PBS and $3.5 \times 10^4$ CFU/ml of *C. Albicans* (144 μl/well) in YPD medium were plated in 96 well plates. Test compounds were then added to each well with concentration ranged from 5 to 40 μM as final concentrations. The plates were incubated at 30° C. overnight (24 hrs) and OD at 600 nm was read at the end of incubation as an index of yeast cell density.

Results:

Most of the compounds tested showed inhibition of Candida growth. Based on inhibition curves, IC50 (50% inhibition of fungal growth) and MIC (99% of inhibition of fungal growth) values of compounds were calculated using XLfit and listed in the following table. The compounds with higher antifungal activity have the lower numerical values.

TABLE 21

50% Inhibition (IC50) and Maximum Inhibition Concentration (MIC) Value

| Compound | IC50 (uM) | MIC (uM) | inactive compound |
| --- | --- | --- | --- |
| AL | 7.08 | 20.07 | BR |
| AM | 6.52 | 16.17 | BS |
| AG | 8.92 | 16.01 | BU |
| AR | 46.06 | 69.76 | CB |
| BH | 18.05 | 30.12 | CC |
| AZ | 10.40 | 21.10 | AY |
| BE | 12.19 | 29.70 | CD |
| BF | 14.19 | 26.95 | CE |
| BG | 11.47 | 20.86 | CF |
| BJ | 13.32 | 23.48 | CG |
| BI | 17.48 | 27.76 | BN |

TABLE 21-continued

50% Inhibition (IC50) and Maximum Inhibition Concentration (MIC) Value

| Compound | IC50 (uM) | MIC (uM) | inactive compound |
|---|---|---|---|
| BA | 34.64 | 96.74 | BV |
| BB | 50.92 | 99.69 | BW |
| BC | 45.71 | 107.71 | BX |
| AJ | 43.18 | 113.41 | BY |
| BD | 37.45 | 133.84 | BZ |
| AI | 18.29 | 56.38 | |
| AO | 34.70 | 84.94 | |
| AP | 25.03 | 41.95 | |
| AA | 10.97 | 27.31 | |
| AC | 45.71 | 107.71 | |
| AF | 45.50 | 74.16 | |
| BK | 11.17 | 19.03 | |
| BL | 33.51 | 44.80 | |
| AU | 16.28 | 30.95 | |
| AS | 15.34 | 37.79 | |
| AV | 13.42 | 19.82 | |
| AW | 13.30 | 24.81 | |
| AX | 11.19 | 26.63 | |
| AT | 14.50 | 51.21 | |
| BO | 19.01 | 42.47 | |
| BP | 28.75 | 90.56 | |
| BQ | 51.70 | * | |
| AK | 10.71 | * | |
| BM | 20.23 | 44.47 | |
| AE | 7.82 | * | |
| AH | 5.24 | 15.41 | |
| AB | 10.98 | 33.00 | |
| AQ | 41.20 | * | |

* The MIC cannot be calculated for these compounds due to insufficient data points.

Procedure:

Part-I: Preparation of *Candida albicans* Cells

1. One day prior to the inoculum preparation, pick a single colony of *Candida albicans* strain 3153 (lot #61794) from the Sabouraud Dextrose Agar plate using the inoculum loop and inoculate into a 250 mL flask containing 50 ml of YPD growth medium
2. Incubate at 30° C. with shaking at 150 rpm for at least 18 hours with loosened lid to allow air in and facilitate growth.
3. Examine an aliquot of the culture under a microscope for *Candida* cell morphology and lack of bacterial contamination; >95% of *Candida* cells should be blastoconidia.
4. Transfer 25 ml the overnight culture into a 50-ml plastic disposable centrifuge tube, and centrifuge at 1000×g for 20 min.
5. Discard the supernatant and wash the pellet with 4 ml of PBS at three times. Vortex and centrifuge, 1000×g for 10 min.
6. After the third wash, dispense the pellet with 2 ml PBS and vortex.
7. Make three 1:10 serial dilutions in sterile PBS ($10^{-1}$, $10^{-2}$, $10^{-3}$) from the 2 ml cell suspension using 15 ml culture tubes. The final volume in each tube is 5 ml.
8. Count the number of cells in cell suspension from the $10^{-3}$ dilution tube on the hemocytometer.
   To calculate cell concentration per ml:
   Average number of cells in one large square x dilution factor x $10^4$
   $10^4$=conversion factor to convert $10^{-4}$ ml to 1 ml
      The cell number in 50-fold dilution of $10^{-3}$ was: $14 \times 10^4$ CFU/ml
9. Make a 1:4 dilution in YPD medium from the 50-fold dilution of $10^{-3}$ cell suspension for testing compounds.
   The final *C. albicans* cell concentration for the test: $3.5 \times 10^4$ CFU/ml
10. Plated 144 ul/well of the above dilution of cell on 96-well plates.

Part-II: *C. Albicans* Growth Inhibition Testing with Compounds

1. From 10 mM DMSO stock solutions, make serial dilutions of compounds to 0.13, 0.25, 0.40, 0.55, 0.75 and 1.0 mM solutions
2. Add 6 ul each of diluted compound solutions per well in duplicates. The final concentrations were 0, 5, 10, 16, 22, 30 and 40 micromolar.
3. Incubated all plates at 30 C for overnight (~24 hours).
4. Read absorbance at OD600 for each plate.
6. Calculate the % inhibition of each compound against the DMSO treated cell.

Example I

Evaluation of Activity of Compounds against *Saccharomyces cerevisiae*

| Reagents | Manufacturer/Catalog # | Lot # |
|---|---|---|
| Baker's yeast | Red Star | |
| YPD Broth | KD Medical YLF-3260 | 032111-03 |
| Sabouraud Dextrose Agar | KD Medical #YPL-1050 | C21-03 |
| Sterile PBS, pH 7.4 | Quality Biological Inc; #114-058-131 | |
| DMSO | Sigma; cat#D2650 | |

Experiment Overview:

An overnight culture of *S. cereviseae* was dilution in YPD broth to concentration of 40,000/ml and 150 μl/well was plated in 96 well plates. Compounds were then added to each well with concentration ranged from 4 to 50 μM as final concentration. The plates were inoculated at 30° C. overnight with shaking at 220 rpm and absorbance at 600 nm was read after 18 hour incubation.

Results:

Among all the effect compounds against *S. cerevisiae*, compounds AL, BG, and AW were the most effective ones. Compound AI generated lower $IC_{50}$ from XLfit calculation, even though it could not reach near 100% kill at high concentration like other compounds did. Chloroquine (C.Q.) did not show any inhibition of yeast growth up to 50 uM. Following listed IC50 (50% inhibition of fungal growth) and MIC (99% of inhibition of fungal growth) values of compounds (calculated using XLfit) based on inhibition curves.

TABLE 22

Anti-*S. cerevisiae* - 50% Inhibition (IC50) and Maximum Inhibition Concentration (MIC) Value

| Compound | IC50, uM | MIC, uM | inactive compound |
|---|---|---|---|
| AL | 9.67 | 10.48 | BA |
| AM | 13.41 | 18.88 | BT |
| AG | 19.39 | 24.35 | AC |
| AN | 19.11 | 24.26 | CA |
| AZ | 18.63 | 24.07 | CB |
| BE | 19.23 | 24.13 | Chloroquine |
| BF | 20.82 | 32.04 | |
| BG | 9.88 | 11.84 | |
| BJ | 21.44 | 37.80 | |
| BI | 28.58 | 47.08 | |
| AI | 6.31 | * | |

TABLE 22-continued

Anti-*S. cerevisiae* - 50% Inhibition (IC50) and Maximum Inhibition Concentration (MIC) Value

| Compound | IC50, uM | MIC, uM | inactive compound |
|---|---|---|---|
| AP | 26.29 | 46.47 | |
| AC | 27.73 | 47.67 | |
| BK | 21.40 | 29.38 | |
| AU | 18.03 | 24.26 | |
| AS | 38.47 | 48.91 | |
| AV | 19.65 | 19.76 | |
| AW | 9.73 | 10.24 | |
| AX | 19.61 | 19.92 | |
| AY | 16.86 | 21.88 | |
| BP | 35.56 | 50.81 | |
| AK | 23.47 | * | |
| BM | 30.57 | 50.45 | |
| BV | 12.35 | 25.01 | |
| C12-lm | 15.21 | 29.04 | |

* The MIC cannot be calculated for these compounds due to insufficient data points.

Procedure:
Part-I: Preparation of Yeast Cells
1. One days prior to the inoculum preparation, pick a single colony of *S. cereviseae* from the Sabouraud Dextrose Agar plate using the inoculum loop and inoculate into a 50 mL tube containing 10 ml of YPD growth medium
2. Incubate at 30° C. with shaking at 220 rpm for 24 hours with loosen lid to allow air in and facilitates growth.
3. Examine an aliquot of the culture under a microscope for yeast cell morphology and lack of bacterial contamination.
4. Dilute the overnight culture with YPD medium at 1:30 dilution (70 ul to 2.1 ml) and count the number of cells as 4,230,000/ml.
5. Mix 620 μl of 1:30 dilution and 64.4 ml YPD to make final concentration of 40,000/ml cells
6. Plated 144 μl/well in four 96-well plates.

Part-II: Yeast Growth Inhibition Testing
1. From 10 mM DMSO stock solutions, make serial dilutions of compounds to 0.1, 0.2, 0.3, 0.63 and 1.25 mM solutions
2. Add 6 μl each of diluted compound solutions per well in duplicates. The final concentrations were 0, 4, 8, 12, 25 and 50 micromolar.
3. Incubated all plates at 30 C for overnight (~18 hours) with 220 rpm shaking.
4. Read absorbance at OD600 for each plate on Spectra Max Plus plate reader.
5. Calculate the % inhibition of each compound against the DMSO treated cell and plotted.

Example J

Anti-*Trichophyton* Activity of Compounds of the Invention

*Tricophyton rubrum* is one of the primary fungi responsible for persistent, treatment-resistant toenail infections.

| Reagents | Manufacturer/Catalog # | Lot # |
|---|---|---|
| *Trichophyton rubrum* | ACTT, MYA-4438 | 59404737 |
| PDB (potato dextrose broth) | VWR 61000-102 | 0000130316 |
| PDA (potato dextrose agar) | VWR 90008-416 | 2214381 |
| Sterile PBS, pH 7.4 | Quality Biological Inc; #114-058-131 | |
| DMSO | Sigma; cat#D2650 | |
| Transwell plate (Costar 3422, 24well with 8 μm) | VWR 29442-120 | 04709006 |

Experiment Overview:
Trichophyton grown on two agar plates were collected by scraping into 10 ml saline and filtered through 8 μm filters. The filtered solution was diluted (1:75) and plated in 96 well plates and treated with selected compounds of the invention.

Results:
This experiment included some active compounds from previous experiment and added several untested compounds. Culture treated by compounds AW, AX, AT, AE or AH showed no visible fungal grow with even the lowest concentration (6 μM) tested, representing their strongest inhibitory effect against trichophyton growth. Most of rest compounds also inhibited fungal growth with higher concentration (12-18 μM). AO, AP, AF, BL, AQ and BO showed only partial or no inhibition on fungal grow with highest concentration (40 μM) tested. Following table listed the maximum inhibition concentration (MIC) based on scoring by eye.

TABLE 23

| Compound | MIC, μM | Compound | MIC, μM | Compound | MIC, μM |
|---|---|---|---|---|---|
| AL | 12 | AO | >40 | AX | 6 |
| AM | 12 | AP | ~40 | AT | 6 |
| AG | 18 | AC | 18 | BO | >40 |
| AN | 18 | AF | >40 | BP | 12 |
| AZ | 18 | BL | >40 | AK | 18 |
| BE | 12 | AQ | >40 | BM | 18 |
| BF | 18 | AU | 12 | AE | 6 |
| BG | 12 | AS | 25 | AH | 6 |
| BJ | 18 | AV | 25 | AB | 18 |
| BI | 18 | AW | 6 | C12-lm | 18 |

Procedure:
Part-I: Preparation of *Trichophyton rubrum* Cells
Scrape frozen Trichophyton culture from ATCC vial and suspended in 100 μl PDB, and then plate on a PDA plate. Incubate plate at 30 C for 4 days.
The plate was covered almost full. Scrap colonies from two plates in 10 ml saline and filter through 8 μm filter in a 24 well transwell plate (used 2 wells). Take OD of collected solution at 520 nm and 600 nm:

| A 520 nm = 0.13; | A 600 nm = 0.092 | 1x without dilution |
| A 520 nm = 0.061; | A 600 nm = 0.037 | 1:2.5 dilution |

Make 90 ml of 1:75 dilution in PDB broth from the filtered cell suspension by mixing 1.2 ml of cell solution with 88.8 ml PDB and aliquot 144 μl/well in 5×96 well plates.

Part-II: *Trichophyton* Growth Inhibition Testing with Compounds
1. From 10 mM DMSO stock solutions, make serial dilutions of compounds to 0.15, 0.3, 0.45, 0.63 and 1 mM solutions
2. Add 6 μl each of diluted compound solutions per well in triplicates. The final concentrations were 0, 6, 12, 18, 25 and 40 micromolar.

3. Wrap the plates with parafilms and incubate all plates at 30° C. for 6 days.
   Take picture of the plates on KODAK imager with 17 captures of 1.5 sec/capture for total of 25.5 second exposure.

Example K

Anti-Cryptococcus Activity of Compounds of the Invention

| Reagents | Manufacturer/Catalog # | Lot # |
|---|---|---|
| *Cryptococcus neoformans* Stain ID 52 | ATCC 24067 | 4282211 |
| YM Broth | TEKNOVA #Y0731 | Y073105J1101 |
| Sabouraud Dextrose Agar | KD Medical #YPL-1050 | C21-03 |
| Sterile PBS, pH 7.4 | Quality Biological Inc; #114-058-131 | |
| DMSO | Sigma; cat#D2650 | |

Experiment Overview:

*Cryptococcus neoformans* (serotype D) were plated in 96 well plates with 144 µl/well of 8×10e5 CFU/ml in YM growth medium. Diluted compounds were then added to each well with concentration ranged from 4 to 60 µM as final concentration in duplicates. The plates were inoculated at 37° C. for total of 48 hours. Two readings of OD at 600 nm were measured after 30 and 48 hour treatments.

Results:

Most compounds tested in this assay inhibited the growth of Cryptococcus, with compounds AL, AG, AW, AX, AA, AE, AH, AK, BM, and BN as the most effective ones. It is noteworthy that compounds AA and AC were quite active against Cryptococcus, comparing with their relative weak activities against Candida and *S. cereviseae*. Overall it seems that Cryptococcus is more susceptible to compounds of the invention than the other fungi tested. Chloroquine had very weak activity against *Cryptococcus*, with a maximum growth inhibition of 40% at a concentration of 100 micromolar, so that its IC50 is greater than this concentration. $IC_{50}$ (concentration for 50% of inhibition) and MIC (concentration for maximum-99% of inhibition) were calculated using XLfit based on OD of 48 hour reading are listed in the following table.

TABLE 24

| compound | IC50 | MIC | compound | IC50 | MIC |
|---|---|---|---|---|---|
| AL | 1.88 | 11.54 | AS | 1.46 | 26.81 |
| AM | 3.32 | 13.32 | AV | 5.12 | 22.85 |
| AG | 1.78 | 17.55 | AW | 0.90 | 8.73 |
| AD | 3.98 | 45.20 | AX | 1.06 | 10.56 |
| AZ | 2.01 | 15.83 | AT | 1.29 | 41.78 |
| BE | 3.45 | 13.15 | BO | 2.00 | 13.40 |
| BG | 2.13 | 12.54 | BP | * | * |
| BJ | 1.86 | 18.54 | AK | 0.85 | 24.62 |
| BI | 2.23 | 19.56 | BM | 0.72 | 22.55 |
| PA | 3.34 | 40.55 | BN | 1.03 | * |
| AC | 3.35 | 19.39 | AE | 0.53 | 6.99 |
| AF | 5.18 | 55.87 | AN | 0.76 | 9.54 |
| BK | 2.44 | 16.51 | AB | 1.15 | 40.75 |
| AU | 1.63 | 14.36 | C12-lm | 1.81 | 20.54 |

Procedure:

Part-I: Preparation of Fungal Cells

1. Pick a single colony of *Cryptococcus* from the YM agar plate using the inoculum loop and inoculate into a 125 ml flask containing 25 ml of YM growth medium.
2. Incubate at 37° C. with shaking at 220 rpm for 24 hours with loosen lid to allow air in and facilitates growth.
3. Examine an aliquot of the culture under a microscope for yeast cell morphology and lack of bacterial contamination.
4. Dilute the overnight culture with YM medium at 1:100 dilution and count the number of cells as $1 \times 10^6$ cfu/ml.
5. Make a final concentration of cells suspension at $8 \times 10^5$ cfu/ml in YM medium.
6. Plate 144 µl/well of $8 \times 10^5$ cfu/ml cell suspension on 96-well plates.

Part-II: Cryptococcus Growth Inhibition Testing with Compounds

1. From 10 mM DMSO stock solutions, make serial dilutions of compounds to 0.1, 0.2, 0.3, 0.5, 1.0 and 1.5 mM solution
2. Add 6 ul each of diluted compound solutions per well in duplicates. The final concentrations were 0, 4, 8, 12, 20, 40 and 60 micromolar.
3. Incubated all plates at 37° C. overnight (30 hours) with 150 rpm shaking.
4. Read absorbance at OD600 for each plate.
5. Leave plates in 37° C. incubator for another day and read absorbance at OD600 again at 48 hours to ensure the inhibitory effect of the compounds.
6. Calculated the % inhibition and IC50 of each compound against untreated cells.

Example L

Anti-Cryptococcus (Serotype A) Activity of Compounds of the Invention

| Reagents | Manufacturer/Catalog # | Lot # |
|---|---|---|
| *Cryptococcus neoformans* serotype A | ATCC MYA-1017 | 58178990 |
| YPD Broth | KD Medical YLF-3260 | 090712-04 |
| Sabouraud Dextrose Agar | KD Medical #YPL-1050 | C21-03 |
| Sterile PBS, pH 7.4 | Quality Biological Inc; #114-058-131 | |
| DMSO | Sigma; cat#D2650 | |

Experiment Overview:

*Cryptococcus neoformans* (serotype A) were plated in 96 well plates with 144 µl/well of 5×10e5 CFU/ml in YPD growth medium. Diluted compounds were then added to each well with concentration ranged from 0.05 to 10 µM as final concentration in duplicates. The plates were inoculated at 30° C. Two readings of OD at 600 nm were measured after 18 hr and 48 hour treatments.

Results:

Most compounds tested in this assay inhibited the growth of *Cryptococcus* (serotype A), with AX, AK, BM, AE and AH as the most effective ones. C12-imidazol had relative weak activity against *Cryptococcus* serotype A at low concentration. Data plotted was based on 26 hour reading because 18 hour reading was too low. $IC_{50}$ (concentration for 50% of inhibition) and MIC (concentration for maximum—99% of inhibition) were calculated using XLfit based on OD of 26 hour reading are listed in the following table.

TABLE 25

50% Inhibition (IC50) and Maximum Inhibition Concentration (MIC) Value

| compound | IC50, uM | MIC, uM |
|---|---|---|
| AL | 3.01 | 10.47 |
| AM | 1.57 | 10.53 |
| AG | 2.14 | 11.37 |
| AC | 1.15 | 12.56 |
| AW | 1.74 | 13.75 |
| AX | 0.91 | 17.29 |
| AK | 0.25 | 19.50 |
| BM | 0.69 | 17.50 |
| BN | 3.73 | 56.10 |
| AE | 0.54 | 14.74 |
| AH | 0.39 | 12.00 |
| C12-Im | 3.67 | 10.83 |

It is worthy of note that C. neoformans (serotype A) is the most sensitive fungus to the compounds compared to the other tested species, including C. Albicans, S. cerevisiae, Trichophyton rubrum, and Cryptococcus serotype D Procedure:

Part-I: Preparation of Fungal Cells
1. Pick a single colony of Cryptococcus from the Sabouraud Dextrose agar plate using the inoculum loop and inoculate into a 125 ml flask containing 25 ml of YPD growth medium
2. Incubate at 30° C. with shaking at 220 rpm for 24 hours with loosen lid to allow air in and facilitates growth.
3. Examine an aliquot of the culture under a microscope for yeast cell morphology and lack of bacterial contamination.
4. Dilute the overnight culture with YPD medium at 1:100 dilution and count the number of cells as $8 \times 10^6$ cfu/ml.
5. Make a final concentration of cells suspension at $5 \times 10^5$ cfu/ml in YPD medium after the stock culture had been stored at 4° C. for 3 days.
6. Plate 144 μl/well of $5 \times 10^5$ cfu/ml cell suspension on 96-well plates.

Part-II: Cryptococcus Growth Inhibition Testing with Compounds
1. From 10 mM DMSO stock solutions, make serial dilutions of compounds to 0.0013, 0.0025, 0.0125, 0.025, 0.05, 0.125 and 0.25 mM solution
2. Add 6 ul each of diluted compound solutions per well in duplicates. The final concentrations were 0, 0.05, 0.1, 0.5, 1.0, 2.0, 5.0 and 10 micromolar.
3. Incubated all plates at 30° C. overnight with 175 rpm shaking.
4. Read absorbance at OD600 after 18 and 26 hours for each plate.
5. Calculated the % inhibition and IC50 of each compound against the untreated cell.

Example M

Effects of Compounds of the Invention on THP-1-Derived Macrophage Antifungal Activity; Development of a Phagocytosed Cryptococcus neoformans Antifungal Screen Background: In the preceding examples compounds have been shown to possess direct anti-fungal activity against Cryptococcus neoformans at concentrations less than 5 μM. The compounds, being weak bases, are lysosomotropic, concentrating in the acidic lysosomal compartment of macrophages. Some pathogenic fungi, such as Cryptococcus neoformans, reside in acidic lysosomes of macrophages in an effort to avoid the host immune system (Srikanta et al., 2011).

Another lysosomotropic drug, chloroquine, which has some direct anti-fungal activity at the much higher concentration of 100 μM in C. neoformans, has been shown to enhance anti-fungal activity of macrophages against C. neoformans when tested at only 10 μM. This effect was shown to be due to the drug concentrating in lysosomes housing the yeast (Harrison et al., 2000) The potential therefore exists for compounds of the invention to behave in a manner similar to chloroquine for attacking Cryptococcus or other organisms residing in macrophages, but at much lower concentrations.

Results/Summary:

The compounds tested (AM, BM, AH and AC) all showed clear dose dependent inhibition of fungal growth after phagocytosis and lysis. AH showed the highest potency with near 100% inhibition of the fungal growth at 2 μM.

The IC50 values after macrophage phagocytosis were comparable to the IC50 values for direct inhibition of fungal growth, in the absence of macrophages reported in an earlier study.

The compounds were capable of killing C. neoformans (serotype A) even when the fungus was located within live macrophages.

References:
1: A sensitive high-throughput assay for evaluating host-pathogen interactions in Cryptococcus neoformans infection Srikanta, D et al (2011) PLoS ONE 6(7): e22773
2: Conditional lethality of the diprotic weak bases Chloroquine and Quinacrine against Cryptococcus neoformans Harrison, T. S et al (2000) J Infect Disease 182: p 283-289

Results:

Two concentrations of macrophages ($1 \times 10^5$ and $2 \times 10^5$/well) and a high concentration of C. neoformans ($4 \times 10^6$/well) (MOI values of 40 and 20 respectively) were tested in this experiment.

All of the compounds tested showed clear dose dependent inhibition of fungal growth after phagocytosis and lysis. Phagocytosis by macrophages did not protect the fungus cells from antifungal activity of compounds of the invention.

The IC50 values after macrophage phagocytosis were comparable to the IC50 values for direct inhibition of fungal growth, in the absence of macrophages.

TABLE 26

IC50 for inhibition of fungal growth by compounds directly or after macrophage phagocytosis

| | IC50 value (μM) | | |
|---|---|---|---|
| Compound | No macrophages | $1 \times 10^5$ macrophages | $2 \times 10^5$ macrophages |
| AM | 1.57 | 1.13 | 0.85 |
| BM | 0.69 | 1.80 | 1.31 |
| AH | 0.39 | 0.29 | 0.25 |
| AC | 1.15 | 1.29 | 1.35 |

Experimental Procedures:

Experiment Overview for assay development plate #4:

THP-1 cells were adjusted to $5 \times 10^5$/ml or $1 \times 10^6$/ml in cRPMI+PMA 200 μl was transferred to a flat-bottomed 96-well dish ($1 \times 10^5$ and $2 \times 10^5$/well) (48 hrs at 37 C)

Media was removed and fresh cRPMI+PMA added (further 24 hrs at 37 C)

*C. neoformans* cells in DPBS were opsonized with human serum (60 mins at 30 C)

The opsonized yeast was washed (DPBS) and resuspended at $1\times10^7$/ml or $2\times10^7$/ml in cRPMI.

100 µl added to macrophage plate ($1\times10^6$ and $2\times10^6$/well) (4 hrs at 37 C) washed ×4 with DPBS 100 µl of cRPMI was added to each well (18 hrs at 37 C) Compound AC was added to some wells.

Media was removed, no wash, 25 µl 0.05% Triton X-100 added to lyse cells (3 mins RT rocking)

125 µl YPD broth was added and the plate incubated (24 hrs at 30 C then 24 hrs at 37 C)

*C. neoformans* growth was determined on a Spectrophotometer (600 nm) after 24 and 48 hours Cell Line Information:

| | |
|---|---|
| THP-1: ATCC TIB-202 | Organism: Human, male, one-year old infant |
| Organ: Peripheral blood | Disease: Acute Monocytic Leukemia (AML) |
| Cell type: Monocyte | Growth properties: Suspension in RPMI plus 10% FBS |

THP-1-derived macrophage differentiation protocol (PMA):

THP-1 cells (p15) grown in cRPMI [RPMI (Lonza 12-115F) plus 10% AFBS (Lonza DE14-701F)] were counted on a hemacytometer. Cells were spun at 1,800 rpm, RT for 5 mins, supernatant aspirated, pellet disturbed then adjusted to $5.0\times10^5$/ml and $1.0\times10^6$/ml in cRPMI supplemented with 0.2 µg/ml phorbol 12-myristate 13-acetate (PMA) (1 mg/ml in DMSO Sigma P8139). 2000 aliquots of each cell concentration were transferred to 42 wells (half a plate) of a flat-bottomed 96-well dish ($1\times10^5$ and $2\times10^5$/well) and placed in a 37 C incubator for 48 hours, media was then removed and 200 µl of fresh cRPMI+PMA added. The plate was incubated for an additional 24 hours at 37 C then processed for yeast uptake.

Yeast Strain Information:

*Cryptococcus neoformans*: ATCC MYA-1017 Designation: CDC21

Isolation: Derived from strain H99 from patient with Hodgkin's disease, New York Antigenic properties: Serotype-A Growth properties: Suspension in YEPD broth 25 C Opsonization of *Cryptococcus neoformans* cells (human serum only):

In parallel to macrophage preparation, *C. neoformans* cells were grown from a single colony in 20 ml YPD broth at 30 C overnight. Absorbance of 1:10 dilution of the overnight (ON) culture gave 0.89 OD at 600 nm. Estimated concentration of this stock was $4\times10^8$ cells/ml ($2\times10^8$ cells/ml gave an OD 600 nm of 0.426 in an earlier study Cryptococcus macrophage development plate 3 ML113012). The cells were washed with DPBS once and resuspended in 2 ml DPBS. 230 µl of this stock (~$60\times10^7$ cells) was brought up to 500 µl with DPBS in an Eppendorf tube. For opsonization, 500 µl of human serum (SIGMA 57023) was added and the tube incubated at 30 C for 60 mins with orbital shaking. The opsonized fungal cells were washed three times with 8000 DPBS (1,100 g for 2 min) and resuspended in 8000 DPBS. A 1:200 dilution of cells was counted ($4.25\times10^6$/ml), equivalent to $8.5\times10^8$/ml for the 1× stock. 470 µl of the 1× stock was brought up to 10 ml with cRPMI for a final concentration of $4\times10^7$/ml.

Macrophage Mediated Anti-Fungal Activity Assay:

Media was aspirated from the prepared macrophage plate and 100 µl of the opsonized fungal cell suspension added to the wells. Media without yeast was added to triplicate wells for each macrophage concentration to provide background readings. Three empty wells (no macrophages) were seeded with fungus to serve as the wash control. The plates were then incubated at 37 C for 4 hours then washed 4 times with DPBS (plates were shakes briefly after addition of DPBS to increase wash efficiency). 144 µl of cRPMI was added to each well and 60 of 12.5 µM, 25 µM and 50 µM stocks of compounds AM, BM, AH, and AC added in triplicate for final concentrations of 0.5 µM, 1 µM or 2 µM. The plate was incubated at 37 C, 5% $CO_2$ for 18 hours. Media was removed, 25 µl of 0.05% Triton X-100 (SIGMA T-9284) in DPBS was added to each well and the plate rocked at RT for 3 min, to lyse the cells. 125 µl YPD broth (KD Medical YLF-3260) was then added to each well and the plate placed in a 30 C incubator. *C. neoformans* cell growth was determined by measuring absorbance at 600 nm on a Spectrophotometer (Spectra Max Plus using program SoftMax Pro) after 30 hours.

Example N

Antifungal Activity as Determined by Minimum Inhibitory and Fungicidal Concentrations Objective The objective of this study was to determine the antifungal activity of eight experimental compounds against a representative panel of fungal isolates, including *Candida albicans, C. glabrata, Cryptococcus neoformans, Trichophyton rubrum, Aspergillus fumigatus*, and *Rhizopus* spp. Antifungal activity was measured by minimum inhibitory concentration (MIC) and minimum fungicidal concentration (MFC).

Materials

Isolates

Three recent clinical strains of each species, taken from the culture collection at the Center for Medical Mycology, Case Western University, were tested.

Antifungal Agents

Compounds in powder form were dissolved in DMSO. Serial dilutions of each compound were then prepared in RPMI-1640 in a range of 0.125-64 µg/ml.

Methods

MIC testing was performed according to the CLSI M27-A3 and M38-A2 standards for the susceptibility testing of yeasts and filamentous fungi, respectively (1, 2). Test isolates were subcultured from frozen slants onto potato dextrose agar plates (*Trichophyton rubrum* was subcultured onto oatmeal plates for conidia production) and checked for purity. Inocula were then prepared in RPMI-1640 (YNB for *Cryptococcus*) to a concentration of $0.5\text{-}2.5\times10^3$ colony-forming units (CFU)/ml or $0.4\text{-}5\times10^4$ conidia/ml for yeast and filamentous fungi, respectively. MIC endpoints were read at 50% and 100% inhibition, as compared to the growth control, at both 24 and 48 hrs (*C. neoformans* were incubated for 72 hrs and *T. rubrum* strains were incubated for 96 hrs).

MFC determinations were performed according to the modifications previously described by Canton et al. and Ghannoum and Isham. (3, 4) Specifically, the total contents of each clear well from the MIC assay were subcultured onto potato dextrose agar. To avoid antifungal carryover, the aliquots were allowed to soak into the agar and then were streaked for isolation once dry, thus removing the cells from the drug source. Fungicidal activity was defined as a ≥99.9% reduction in the number of colony forming units (CFU)/ml from the starting inoculum count, with compounds being determined as cidal if the MFC fell within 4 dilutions of the MIC.

Results

The data shows that all eight compounds demonstrated antifungal activity against the strains tested, although MIC and MFC results were strain specific. As can be seen in Table 27, compound AC showed the lowest MIC values against the *C. albicans* strains at both the 50% and 100% inhibition at 24 hrs (<0.12-0.25 and <0.12-1 µg/ml, respectively) and 48 hrs (<0.12-1 and 0.5-2 µg/ml, respectively). Importantly, compound AC was cidal against 2 of the 3 *C. albicans* strains tested. Compound AG demonstrated similar MIC and MFC values against the *C. albicans* strains.

Table 28 shows that compounds AG and AC were also the most active against the *C. glabrata* strains tested. After 24 hrs, the MIC at 50% for compound AG was 0.25-1 m/ml and 0.5-2 at 100%. After 48 hrs, the corresponding compound AG values were both 0.5-2 µg/ml. After 24 hrs, the MIC at 50% for compound AC was 0.5-1 µg/ml and 1-2 at 100%. After 48 hrs, the corresponding compound AC values were 1-2 (50%) and 2-4 µg/ml (100%). Both compounds AG and AC were cidal against all of the *C. glabrata* strains tested.

As can be seen in Table 29, compounds AX and AH demonstrated the greatest antifungal activity against the *Cryptococcus neoformans* strains tested. Compound AX had MIC values of 0.12-2 and 0.5-4 µg/ml at 50% and 100% inhibition, respectively, while compound AH had corresponding values of 0.004-2 and 0.25-2 µg/ml. Both compounds were cidal against all 3 *neoformans* isolates.

Table 30 shows the MIC and MFC values of the eight compounds against the *Aspergillus fumigatus* strains. Compounds AE, AH, and AC showed equivalent inhibitory activity, with compound AE demonstrating MIC values of <0.12-0.5 and <0.12-1 µg/ml at 50% and 100% inhibition, respectively, after 24 hrs. After 48 hrs, the corresponding values for compound AE were 0.5-2 and 1-4 µg/ml. Compound AH demonstrated MIC values of <0.12 and 0.25-0.5 µg/ml at 50% and 100% inhibition, respectively, after 24 hrs. After 48 hrs, the corresponding values for compound AH were 0.25-1 and 0.25-4 µg/ml. For compound AC, the MIC values at 24 hrs were <0.12 and 0.25-0.5 µg/ml for 50% and 100% inhibition, respectively, while the corresponding values at 48 hrs were 0.5-1 and 1 µg/ml. However, only compounds AL, AM, and AG were cidal against one of the *A. fumigatus* strains (MRL 28397).

In Table 31, it can be seen that compounds AE, AH, and AC were the most active against the *Rhizopus* strains. At 24 hrs, compound AE showed MIC values of <0.12 and 1-2 µg/ml for 50% and 100% inhibition, respectively, with corresponding 48 hr values of 1-2 and 1-4 µg/ml. Compound AH showed MIC values of 0.25-0.5 and 2 µg/ml for 50% and 100% inhibition, respectively, at 24 hrs and 2 µg/ml for both endpoint readings at 48 hrs. At 24 hrs, compound AC showed MIC values of <0.12-0.25 and 0.5 µg/ml for 50% and 100% inhibition, respectively, with corresponding 48 hr values of 0.5 and 0.5-1 µg/ml. Generally, no cidal activity was demonstrated against the *Rhizopus* strains tested.

Finally, Table 32 shows the MIC and MFC values of the eight compound against *T. rubrum*. At the 50% inhibition endpoint, compounds AG, AX, AE, AH, and AC showed equivalent activity (<0.12-4 µg/ml overall). At the 100% inhibition endpoint, compounds AG, AH, and AC were equivalent (0.25-4 µg/ml overall), with compounds AX and AE ranging slightly higher (0.25-16 µg/ml). Within the definition of cidality (MFC within 4 dilutions of the MIC) all compounds were considered cidal against the *T. rubrum* strains, though the MFC were high in some strains (8-16 µg/ml).

Overall, compounds AE, AH, and AC appeared to demonstrate the greatest inhibitory activity against the most fungal strains tested.

REFERENCES FOR EXAMPLE N

1. CLSI. *Reference Method for Broth Dilution Antifungal Susceptibility Testing of Yeasts; Approved Standard—Second Edition.* CLSI document M27-A2 (ISBN 1-56238-469-4). CLSI, 940 West Valley Road, Suite 1400, Wayne, Pa. 19087-1898 USA, 2002.
2. CLSI. *Reference Method for Broth Dilution Antifungal Susceptibility Testing of Filamentous Fungi; Approved Standard—Second Edition.* CLSI document M38-A2 [ISBN 1-56238-668-9]. CLSI, 940 West Valley Road, Suite 1400, Wayne, Pa. 19087-1898 USA, 2008.
3. Canton E, Peman J, Viudes A, Quindos G, Gobernado M, Espinel-Ingroff A. 2003. Minimum fungicidal concentrations of amphotericin B for bloodstream *Candida* species. Diagn Microbiol Infect Dis. 45:203-6.
4. Ghannoum M A, Isham N. 2007. Voriconazole and Caspofungin Cidality Against Non-*Albicans Candida* Species. Infectious Diseases in Clinical Practice. 15(4): 250-253.

TABLE 27

MIC and MFC ranges against *Candida albicans* strains (in µg/ml).

| | Compound | | | | | | | |
|---|---|---|---|---|---|---|---|---|
| | AL | | AM | | AG | | AW | |
| *C. albicans* | 24 hr | 48 hr | 24 hr | 48 hr | 24 hr | 48 hr | 24 hr | 48 hr |
| Range | | | | | | | | |
| MIC 50% | 0.5-2 | 2-4 | 0.5-2 | 0.5-4 | 0.25-0.5 | 0.5-2 | 1-4 | 4-8 |
| MIC 100% | 2-4 | 2-4 | 2-4 | 2-4 | 0.5-2 | 1-4 | 4-8 | 8 |
| MFC | | 4-8 | | 4 | | 2-4 | | 8-32 |

TABLE 27-continued

| C. albicans | Compound | | | | | | | |
|---|---|---|---|---|---|---|---|---|
| | AX | | AE | | AH | | AC | |
| | 24 hr | 48 hr | 24 hr | 48 hr | 24 hr | 48 hr | 24 hr | 48 hr |
| Range | | | | | | | | |
| MIC 50% | 0.12-0.5 | 1-4 | 0.12-1 | 2-4 | <0.12-1 | 0.25-2 | <0.12-0.25 | <0.12-1 |
| MIC 100% | 0.5-4 | 2-4 | 0.5-4 | 4 | <0.12-4 | 1-4 | <0.12-1 | 0.5-2 |
| MFC | | 4-32 | | 8-64 | | 4-32 | | 2 |

TABLE 28

MIC and MFC ranges against *Candida glabrata* strains (in μg/ml).

| C. glabrata | Compound | | | | | | | | | | | | | | | |
|---|---|---|---|---|---|---|---|---|---|---|---|---|---|---|---|---|
| | AL | | AM | | AG | | AW | | AX | | AE | | AH | | AC | |
| | 24 hr | 48 hr | 24 hr | 48 hr | 24 hr | 48 hr | 24 hr | 48 hr | 24 hr | 48 hr | 24 hr | 48 hr | 24 hr | 48 hr | 24 hr | 48 hr |
| Range | | | | | | | | | | | | | | | | |
| MIC 50% | 2 | 2-4 | 1-2 | 2-4 | 0.25-1 | 0.5-2 | 4 | 8 | 2 | 8 | 4 | 4-8 | 2 | 4-8 | 0.5-1 | 1-2 |
| MIC 100% | 2 | 4 | 2-4 | 2-4 | 0.5-2 | 0.5-2 | 8 | 8-16 | 8 | 8 | 4 | 4-8 | 4-8 | 4-8 | 1-2 | 2-4 |
| MFC | | 4 | | 4-8 | | 4 | | 16-32 | | 8-64 | | 16-64 | | 8-64 | | 4-8 |

TABLE 29

MIC and MFC ranges against *Cryptococcus neoformans* strains (in μg/ml).

| Cr. neoformans | Compound | | | | | | | |
|---|---|---|---|---|---|---|---|---|
| | AL | AM | AG | AW | AX | AE | AH | AC |
| Range | | | | | | | | |
| MIC 50% | 1-2 | 0.5-4 | 2-4 | 0.5-2 | 0.12-2 | 0.03-4 | 0.004-2 | 0.12-4 |
| MIC 100% | 2 | 2-4 | 4 | 2 | 0.5-4 | 0.25-4 | 0.25-2 | 0.25-4 |
| MFC | 2-4 | 8 | 8-16 | 2-8 | 4-8 | >1-8 | 1-2 | 8 |

TABLE 30

MIC and MFC ranges against *Aspergillus fumigatus* strains (in μg/ml).

| A. fumigatus | Compound | | | | | | | |
|---|---|---|---|---|---|---|---|---|
| | AL | | AM | | AG | | AW | |
| | 24 hr | 48 hr | 24 hr | 48 hr | 24 hr | 48 hr | 24 hr | 48 hr |
| Range | | | | | | | | |
| MIC 50% | 2 | 2-4 | 0.5-1 | 2-4 | 0.5-1 | 1-2 | 2-4 | 8 |
| MIC 100% | 2 | 4 | 1-2 | 4 | 1 | 1-2 | 4-8 | 16 |
| MFC | | 4-32 | | 4-32 | | 4->64 | | 64->64 |

TABLE 30-continued

| A. fumigatus | Compound | | | | | | | |
|---|---|---|---|---|---|---|---|---|
| | AX | | AE | | AH | | AC | |
| | 24 hr | 48 hr | 24 hr | 48 hr | 24 hr | 48 hr | 24 hr | 48 hr |
| Range | | | | | | | | |
| MIC 50% | 0.12-0.25 | 1-4 | <0.12-0.5 | 0.5-2 | <0.12 | 0.25-1 | <0.12 | 0.5-1 |
| MIC 100% | 0.5-1 | 4-8 | <0.12-1 | 1-4 | 0.25-0.5 | 0.25-4 | 0.25-0.5 | 1 |
| MFC | | >64 | | >64 | | >64 | | 16->64 |

TABLE 31

MIC and MFC ranges against Rhizopus strains (in μg/ml).

| Rhizopus | Compound | | | | | | | | | | | | | | | |
|---|---|---|---|---|---|---|---|---|---|---|---|---|---|---|---|---|
| | AL | | AM | | AG | | AW | | AX | | AE | | AH | | AC | |
| | 24 hr | 48 hr | 24 hr | 48 hr | 24 hr | 48 hr | 24 hr | 48 hr | 24 hr | 48 hr | 24 hr | 48 hr | 24 hr | 48 hr | 24 hr | 48 hr |
| Range | | | | | | | | | | | | | | | | |
| MIC 50% | 4 | 4-8 | 1-2 | 2-4 | 1-2 | 2-4 | 4 | 4-8 | 0.5-1 | 1 | <0.12 | 1-2 | 0.25-0.5 | 2 | <0.12-0.25 | 0.5 |
| MIC 100% | 4 | 8 | 2-4 | 4 | 2 | 2-4 | 4-8 | 8 | 1-2 | 1-2 | 1-2 | 1-4 | 2 | 2 | 0.5 | 0.5-1 |
| MFC | | 64->64 | | 8-32 | | 4-16 | | 64->64 | | >64 | | 64 | | 64 | | 16-64 |

TABLE 32

MIC and MFC ranges against Trichophyton rubrum strains (in μg/ml).

| T. rubrum | Compound | | | | | | | |
|---|---|---|---|---|---|---|---|---|
| | AL | AM | AG | AW | AX | AE | AH | AC |
| Range | | | | | | | | |
| MIC 50% | 1-4 | 0.25-4 | <0.12-2 | 1-8 | <0.12-4 | <0.12-4 | <0.12-4 | <0.12-2 |
| MIC 100% | 1-4 | 0.5-4 | 0.25-2 | 1-16 | 0.25-8 | 4-16 | 0.25-4 | 0.5-4 |
| MFC | 2-4 | 1-4 | 0.5-2 | 8-16 | 2-8 | 4-16 | 0.25-16 | 0.5-4 |

Anticancer Examples

Example O

Compounds of the Invention Inhibit Syngeneic Breast Cancer Growth in Mice

Cancer models in mice generally either involve syngeneic murine tumors in immunocompetent mice or xenografts of human tumors in immunocompromised mice. An important aspect of using murine tumors in mice is that the tumor and host have much closer genetic similarity than do human xenografts in mice and therefore can be a very rigorous test of selectivity of agents for inhibiting proliferation of cancer cells versus normal tissues. 4T1 is breast cancer cell line commonly used as a syngeneic cancer model. Test compounds were chosen based upon their ability to selectively to kill 4T1 mouse mammary breast cancer cells relative to a normal mouse mammary cell line in vitro.

Female Balb/C mice were randomized into treatment groups and $10^3$ 4T1 cells were injected into into the mammary fat pad of each mouse in 0.1 mL PBS on 4/28/10 (day 0). Mice received test compounds by oral gavage in 1% hydroxypropylmethylcellulose from day 2 until day 30. Tumor growth was assessed by caliper measurements twice per week and tumor weight after necropsy, and body weight was also monitored.

Treatment Groups Were:
1. Vehicle (1% hydroxypropylmethylcellulose; HPMC)
2. CI (120 μmol/kg/day)
3. BA (120 μmol/kg/day)
4. CP (120 μmol/kg/day)
5. CQ (120 μmol/kg/day)
6. AA (120 μmol/kg/day)
7. AC (120 μmol/kg/day)

TABLE 33

Results

| Treatment | Final Tumor Volume (mm³) | Initial Body Weight (g) | Final Body Weight | Δ BW % |
|---|---|---|---|---|
| Vehicle | 906 ± 316 | 22.2 ± 1.1 | 21.8 ± 0.7 | -1.7% |
| CI | 702 ± 244 | 21.8 ± 0.8 | 20.6 ± 0.6 | -5.5% |

TABLE 33-continued

| Treatment | Final Tumor Volume (mm³) | Initial Body Weight (g) | Final Body Weight | Δ BW % |
|---|---|---|---|---|
| BA | 641 ± 159 | 25.5 ± 1.5 | 24.8 ± 2.0 | −2.7% |
| CP | 352 ± 114 | 24.1 ± 0.9 | 24.1 ± 1.3 | −0.0% |
| CQ | 140 ± 60 | 24.9 ± 0.6 | 24.4 ± 0.9 | −2.0% |
| AA | 563 ± 175 | 21.4 ± 1.0 | 20.3 ± 1.3 | −5.1% |
| AC | 723 ± 185 | 21.5 ± 1.0 | 19.7 ± 1.1 | −8.4% |

Compounds of the invention reduced tumor growth versus vehicle-treated mice after daily oral administration at a dose of 120 μM/kg/day for 33 days, with acceptable toxicity (less than 10% body weight loss). CQ was the most active of the compounds tested in this experiment in the 4T1 breast cancer model. Compounds were chosen for in vivo testing based upon their ability to selectively to kill 4T1 mouse mammary breast cancer cells relative to a normal mouse mammary cell line in vitro, indicating a correspondence between in vitro cancer cell line cytotoxicity in vivo anti-cancer activity of compounds of the invention.

Example P

Effects of Compound AC in Mice Bearing Xenografts of Human Hormone-Independent Prostate Cancer Experimental Procedure Standard models for prostate cancer use subcutaneous xenografts of human prostate cancer cell line. Local measurable tumors are produced at the site of injection of the cells, and they metastasize to critical tissues such as the bones, lungs and liver. Mortality in this model is due to metastases impairing tissue function. Compounds of the invention were assessed for inhibition of tumor growth and reduction or delay of mortality in the PC-3 prostate cancer model, which mimics an advanced, androgen-independent stage of prostate cancer.

10 female nude mice (female Hsd:athymic nude-Foxn1$^{nu}$) received PC-3 cells (5×10⁶ per mouse in 0.1 mL PBS) by subcutaneous injection into the right hind flank. After 8 days tumors were palpable and mice were divided into two groups with approximately equal mean tumor sizes. Mice received AC or vehicle (saline) via intraperitoneal (i.p.) injection once daily until day 79.

1. Vehicle (0.9% saline): Mean pretreatment tumor volume 55.7 mm³; body weight 26.6±0.9 g)
2. Compound AC: 120 mol/kg/day. Mean pretreatment tumor volume 59.6 mm³; body weight 26.8±0.5 g)

Tumors were measured with calipers twice per week, and body weights and mortality were also monitored.

Results

All 5 vehicle-treated mice died by day 35 (Individual days of death 20, 24, 24, 26, and 35). One mouse in the AC-treated group died on day 65 and the remaining 4 survived until the study was terminated on day 79.

In the longest-surviving vehicle-treated mouse, the tumor volume was 3007% larger at time of death on day 35 than at initiation of treatment; all other vehicle-treated animals died of metastatic disease with smaller primary tumor sizes. Among mice treated with AC, tumors had enlarged to an average of 949% of initial size at day 77; two of the mice surviving to the end of the study had no detectable tumors at that time and were deemed complete regressions, and one regressed more than 50% from the initial tumor size. AC-treated mice had a mean body weight of 28.9±1.3 g at end of study; a weight gain rather than a weight loss from the initial group body weight of 26.8±0.5 g indicates that the treatment was well tolerated. Daily injections of AC therefore markedly improved survival and decreased tumor size, including producing complete and partial regressions, in mice bearing hormone-independent prostate cancers.

Example Q

Effects of Compounds of the Invention in a Mouse Model of Liver Metastases of Human Colorectal Cancer A major cause of morbidity and mortality in patients with colorectal cancer is metastasis of the tumor into the liver; colorectal cancer can often be successfully resected from the primary site, but metastases to the liver are much less accessible to surgical treatment. A mouse model of colorectal cancer metastasis to the liver has been established, using HCT-116 colon adenocarcinoma cells injected into the spleen of athymic (nude) mice. The HCT-116 cancer cells spontaneously spread from the spleen into the liver via the circulation, and they form tumors in the liver (Ishizu, K., Sunose, N., Yamazaki, K., Tsuruo, T., Sadahiro, S., Makuuchi, H., and Yamori, T. Development and Characterization of a Model of Liver Metastasis Using Human Colon Cancer HCT-116. *Biol. Pharm. Bull.* 2007, 30(9):1779-1783).

Compounds CQ and AA were tested for antitumor activity in the HCT-116 model of metastatic colorectal cancer.

Methods:

Mice (female Hsd:athymic nude-Foxn1™) were anesthetized with xylazine/ketamine intraperitoneal injection, followed by incision approximately 10 mm on the left subcostal region (area disinfected with ethanol) to expose the peritoneum. The peritoneum was opened for about 8 mm near the spleen, and 2.5×10⁶ cells in 50 μL PBS were injected into the spleen using a 30 G needle. The spleen was repositioned, and the surgical area was closed using sutures and clips.

| N | Treatment | Dose (μmol/kg) | Dose Volume (per mouse) |
|---|---|---|---|
| 5♀ | Vehicle | N/A | 0.4 mL |
| 5♀ | CQ | 240 | 0.4 mL |
| 5♀ | AA | 240 | 0.4 mL |

The day after receiving cells, mice were randomized into groups of five based upon body weight to provide groups with approximately equivalent mean body weight. Mice received a single, daily oral dose of test article or vehicle (1% hydroxypropylmethylcellulose) beginning 48 hours following cell injection into the spleen.

At study termination 28 days after HCT-116 cell injection, body weights were recorded, and spleens and livers were removed, weighed and fixed in 10% formalin. Livers were sectioned and stained; the relative areas of normal and tumor tissue were quantified in histology sections with quantitative planimetry software.

Results:

Tumors in the Vehicle control group occupied 14% of the liver as assessed by quantitative planimetry in histology sections. Both compounds CQ and AC markedly reduced the area of liver invaded by metastatic cancer cells. The Vehicle group had a 12% higher liver weight/body weight ratio than the groups treated with either CQ or AC, corroborating the histology planimetry measurements indicating that tumors increased the total liver mass in the Vehicle group. Body weights were not significantly different between groups of mice treated with vehicle-treated versus test compounds, indicating that the compounds of the invention were well tolerated at a dose of 240 mol/kg/day for 28 days.

TABLE 34

| Treatment | Tumor Area % of Total Liver | Tumor Area % of Vehicle Group | Liver Weight % of Body Weight | Final Body Weight Grams |
|---|---|---|---|---|
| Vehicle | 14 ± 5.6% | 100% | 6.1 ± 0.3% | 27.4 ± 0.9 |
| CQ | 0.02 ± 0.01% * | 0.15% * | 5.3 ± 0.1% | 26.2 ± 0.9 NS |
| AA | 0.2 ± 0.26% * | 1.5% * | 5.3 ± 0.2% | 28.2 ± 1.5 NS |

* = less than Vehicle group, P < .02

Example R

Effects of Compounds of the Invention, Sorafenib, and Combinations in a Mouse Model of Human Hepatocellular Carcinoma Hepatocellular carcinoma (HCC) is one of the most common and lethal cancers worldwide, generally developing as a consequence of chronic infection with hepatitis B or C viruses. The tyrosine kinase inhibitor sorafenib is a multikinase inhibitor used for treatment of advanced HCC, and has both direct antitumor and antiangiogenic properties. Compounds of the invention act via a different mechanism of action than does sorafenib or other kinase inhibitors; therefore it is possible that compounds of the invention, in addition to displaying single agent activity, may also enhance the efficacy of sorafenib or other standard treatments in HCC and other cancers.

The Hep3B hepatocellular carcinoma cell line is human in origin, contains genetic traces of hepatitis B virus, and can be injected into the livers of athymic immunocompromised mice as a model of primary HCC. Oral sorafenib is active in this model and was used as both a positive control treatment and as a partner for combination therapy with a selection of compounds of the invention. The test compounds were all administered orally.

Methods:

The test compounds of the invention were suspended in 1% hydroxypropylmethylcellulose (HPMC) using a sonicator equipped with a microtip to minimize particle size and maximize uniformity of the suspension. Sorafenib was dissolved in a 1:1 mixture of Cremophor EL and ethanol by heating to 60° C. for 1 minute and then sonicating for 10 minutes to fully suspend.

Female nude mice (Hsd:athymic nude-Foxn1™) weighing approximately 25 g were anesthetized with ketamine/xylazine, laid on their backs, and a 1-cm transverse incision made through the skin and peritoneum of the left upper abdomen. The median lobe of the liver was exposed by applying gentle pressure on the abdomen. 1.5-2×10$^6$ Hep3B cells in a 20 μL volume of matrigel:EMEM serum free (1:1) were slowly implanted by subserosal injection into the liver using a 27-gauge needle on a Hamilton syringe. The liver was allowed to slip back into place, and the peritoneum was closed with sutures and wound clips.

Mice were divided into 8 groups of mice each following injection of cells; the vehicle/vehicle group comprised 12 mice and the other groups comprised 8 or 9. Mice began receiving oral test drug treatments 48 hr post cell injection.

TABLE 35

| Group No. | No. of Animals | Treatment | Daily Dose |
|---|---|---|---|
| 1 | 12 | 1% HPMC vehicle; cremophor vehicle | N/A |
| 2 | 9 | Sorafenib; 1% HPMC vehicle | 30 mg/kg/day |
| 3 | 8 | AC; cremophor vehicle | 180 μmol/kg/day |
| 4 | 8 | AC + sorafenib | 180 μmol/kg/day; 20 mg/kg/day |
| 5 | 8 | AK; cremophor vehicle | 360 μmol/kg/day |
| 6 | 9 | AK + sorafenib | 360 μmol/kg/day; 20 mg/kg/day |
| 7 | 8 | AB; cremophor vehicle | 360 μmol/kg/day |
| 8 | 9 | AB + sorafenib | 360 μmol/kg/day; 20 mg/kg/day |

The test compounds, sorafenib, and vehicles were administered by oral gavage. Sorafenib or its cremophor-containing vehicle were given in the morning and compounds of the invention or their HPMC vehicle was administered in the afternoon each day; all animals received two gavage treatments of drugs or appropriate vehicles daily. In the group with sorafenib as the only active test agent, the daily dose was 30 mg/kg; when combined with compounds of the invention, the sorafenib dose was reduced to 20 mg/kg because the tolerability of the combination was unknown, and also because possible improved anticancer activity of compounds of the invention combined with a lower dose of sorafenib over a higher dose of sorafenib alone would more clearly demonstrate advantageous activity of compounds of the invention.

Mice were sacrificed at day 35 after 2 of the initial 12 vehicle-treated mice had died from tumor progression; livers were removed and photographed, and tumors were dissected out for measurement and weighing.

Results

All vehicle-treated mice developed tumors, with a mean weight of about 2 grams at the time of sacrifice. Sorafenib (30 mg/kg/day) as a single agent reduced the tumor size by more than 50%. Compounds AC and AB alone also reduced tumor size by more than 50%; AK alone produced a numerically but not statistically significant reduction in tumor size versus vehicle. Addition of sorafenib (20 mg/kg/day) to compounds of the invention resulted in better inhibition of tumor growth than was achieved with sorafenib alone at 30 mg/kg/day. The combinations of AC or AB with sorafenib produced more complete regressions (no viable tumor detected at necropsy) than single-agent treatments. All treatments including combinations were well-tolerated as indicated by maintenance of body weight throughout the entire duration of the study.

TABLE 36

Effects of compounds of the invention alone and in combination with sorafenib on growth of hepatocellular carcinoma in nude mice

| Treatment | N | Tumor Weight (g) Mean ± SEM | Complete Regressions | Body Weight (g) Mean ± SEM Initial | Final |
|---|---|---|---|---|---|
| Vehicle | 10 | 2.03 ± 0.37 | 0 | 26.0 ± 0.4 | 26.4 ± 0.5 |
| Sorafenib | 9 | 0.81 ± 0.20 * | 1 | 25.9 ± 0.7 | 24.9 ± 0.4 |
| AC | 8 | 0.49 ± 0.17 * | 2 | 25.4 ± 0.5 | 25.6 ± 0.7 |

TABLE 36-continued

Effects of compounds of the invention alone and in combination with sorafenib on growth of hepatocellular carcinoma in nude mice

| Treatment | N | Tumor Weight (g) Mean ± SEM | Complete Re-gressions | Body Weight (g) Mean ± SEM Initial | Final |
|---|---|---|---|---|---|
| AC + Sorafenib | 8 | 0.17 ± 0.07 *+ | 4 | 24.9 ± 0.5 | 25.2 ± 0.9 |
| AK | 8 | 1.56 ± 0.39 | 2 | 25.9 ± 0.7 | 24.9 ± 0.9 |
| AK + Sorafenib | 9 | 0.48 ± 0.22 * | 2 | 25.1 ± 0.7 | 25.1 ± 1.3 |
| AB | 8 | 0.88 ± 0.33 * | 2 | 26.2 ± 0.7 | 26.0 ± 0.9 |
| AB + Sorafenib | 9 | 0.38 ± 0.18 * | 6 | 25.3 ± 0.7 | 25.7 ± 0.8 |

\* = less than Vehicle group, P < .02
+ = less than Sorafenib group, p < .02

Example S

In Vitro screen for Anticancer Activity Against 4T1 Murine Breast Cancer and PC-3 Human Prostate Cancer Compounds of the invention were screened for ability to kill or inhibit proliferation of cancer cell lines in vitro, as a complement to in vivo studies on subsets of compounds demonstrating anticancer efficacy in vivo, at doses that were well tolerated after either oral or intraperitoneal administration.

Anticancer activity against 4T1 murine breast cancer cells cancer cells was assessed in vitro by seeding $1 \times 10^4$ cells/well in flat bottom culture plates, then treating with selected 1 μM or 5 μM concentrations of compounds for 18 hr after plating. Then 10 μL of Wst1 dye reagent, a tetrazolium dye indicator for cell death, was added/well and incubated approximately 2 hr before being assayed on the Biotek EL800 Universal microplate reader (450 nm, reference 630 nm).

Activity against PC3 human prostate cancer cells in vitro was assessed by a similar method. PC-3 prostate cancer cells were plated at $2 \times 10^4$ cells/well in 96 well flat bottom tissue culture plates, and incubated for approximately 20 hours with vehicle or test compounds at concentrations of 0.4, 0.5 or 2.5 μM as indicated for specific compounds in the right-hand column of Table 37. A $\frac{1}{10}^{th}$ volume of Wst1 dye was added/well and incubated for two hours in the cell culture incubator. Samples were analyzed in triplicate on an EL800 Universal Microplate Reader at 450 nm, reference wavelength 630 nm.

Numerical values in the Table 37 represent percent of cancer cell survival relative to vehicle treated cells at the indicated concentrations, with values under 100 indicating anticancer cytotoxic activity at the drugs concentrations tested.

TABLE 37

| Compound | 4T1 1 μM | 4T1 5μM | PC-3, [μM] | |
|---|---|---|---|---|
| Control | (100%) | (100%) | (100%) | 0 |
| CH | 45.2 | 27.2 | 102 | 0.4 μM |
| CI | 28.3 | 19.1 | 77.9 | 0.4 μM |
| CJ | 22.6 | 24.1 | 53.7 | 0.4 μM |
| CK | 62.5 | 45.3 | 51.4 | 0.5 μM |
| CL | 25.6 | 19.5 | 58.1 | 0.4 μM |
| AL | 16.6 | 18.3 | 61.6 | 0.4 μM |
| AM | 24.3 | 29.5 | 58.5 | 0.4 μM |
| EI | 95 | 45.8 | 31.2 | 2.5 μM |
| AG | | | 18.4 | 2.5 μM |

TABLE 37-continued

| Compound | 4T1 1 μM | 4T1 5μM | PC-3, [μM] | |
|---|---|---|---|---|
| CO | 28.4 | 55.6 | 77.1 | 0.4 μM |
| AR | 25.4 | 47 | 57 | 0.4 μM |
| AN | 26.6 | 50.3 | 75.9 | 0.4 μM |
| AD | 21.6 | 51.1 | 54.7 | 0.4 μM |
| CX | 25.1 | 20.7 | 45.9 | 0.4 μM |
| BH | 21 | 19.3 | 98.5 | 0.4 μM |
| CV | 25.7 | 16.9 | 73.8 | 0.5 μM |
| AZ | 52.2 | 29.1 | 95.4 | 0.4 μM |
| CW | 25.1 | 18.4 | 98.5 | 0.4 μM |
| BE | 23.1 | 18.7 | 99.1 | 0.4 μM |
| BF | 17.2 | 19 | 92.8 | 0.4 μM |
| BG | 17.4 | 17.8 | 99.1 | 0.4 μM |
| DA | 17.6 | 18.4 | 95.7 | 0.4 μM |
| BJ | 16.9 | 31.3 | 23.9 | 0.4 μM |
| BI | 30 | 17.3 | 110.9 | 0.4 μM |
| DB | 20.1 | 22.2 | 24.7 | 0.4 μM |
| BA | 71.7 | 219.6 | 42.4 | 1.5 μM |
| CY | 24.5 | 29.1 | 40.5 | 0.4 μM |
| CZ | 50.6 | 28.3 | 96.7 | 0.4 μM |
| CP | 82.6 | 38 | 35.6 | 2.5 μM |
| CQ | 71.9 | 57.9 | 95.8 | 2.5 μM |
| CR | 109.9 | 31.8 | 53.2 | 2.5 μM |
| CS | | | 41.3 | 2.5 μM |
| CT | | | 34.5 | 2.5 μM |
| CU | | | 37.6 | 2.5 μM |
| BR | 105.5 | 122.4 | | |
| CM | 104.5 | 221.4 | 37.8 | 5 μM |
| BB | 59.6 | 41.1 | 16.3 | 2.5 μM |
| BC | 96.9 | 47.2 | 26 | 2.5 μM |
| AJ | 22.4 | 21.1 | 18.5 | 0.4 μM |
| BD | 25.5 | 27.7 | 29.3 | 0.4 μM |
| BS | 104.8 | 117.4 | | |
| BT | 119.2 | 120.9 | | |
| DW | 102.4 | 193.9 | | |
| DX | 112.2 | 104.8 | | |
| AI | 16.2 | 17.9 | 36.4 | 0.4 μM |
| DY | 88.9 | 60.5 | 16.1 | 5 μM |
| DZ | 23.7 | 17.4 | 84.8 | 0.4 μM |
| EA | 31.1 | 36.8 | 108 | 0.4 μM |
| EE | 24 | 18.1 | 34 | 0.4 μM |
| EF | 15.6 | 23.7 | 16.7 | 0.4 μM |
| EG | 34.7 | 27.7 | 92.2 | 0.4 μM |
| EB | | | 94.4 | 2.5 μM |
| EC | | | 94.6 | 2.5 μM |
| DC | 110.3 | 96.7 | | |
| AO | 28.9 | 18.6 | 35 | 0.4 μM |
| DI | 107.5 | 126.1 | | |
| DK | 101.8 | 87.6 | | |
| DL | 70.9 | 21 | 43 | 2.5 μM |
| DN | 103.5 | 56.7 | 31.7 | 2.5 μM |
| DP | 72.5 | 25.4 | 37.5 | 2.5 μM |
| AP | 109.7 | 246.1 | | |
| DD | 97.4 | 104.1 | | |
| DE | 60.1 | 28.6 | 42 | 2.5 μM |
| DF | 27.1 | 20.8 | 101.9 | 0.4 μM |
| DJ | 89 | 66.9 | 85.9 | 2.5 μM |
| DM | 128.1 | 47.8 | 45.6 | 2.5 μM |
| DO | 116.2 | 35.2 | 59.2 | 2.5 μM |
| DR | 77.9 | 27.2 | 31.5 | 2.5 μM |
| DQ | 99.5 | 122.3 | | |
| AA | 69.1 | 31.2 | 82.6 | 1.5 μM |
| AC | 23.3 | 19.3 | 61.5 | 0.4 μM |
| DS | 35.6 | 25.5 | 70 | 0.4 μM |
| AF | 24.7 | 25.6 | 19.1 | 0.4 μM |
| BU | 17.6 | 21.4 | 24 | 0.4 μM |
| BV | 23.7 | 23.3 | 31.6 | 0.4 μM |
| BK | | | 29.2 | 0.4 μM |
| BL | | | 106.3 | 0.4 μM |
| DG | 105.2 | 94.7 | | |
| DH | 96.6 | 112.3 | | |
| AQ | 94.8 | 92.7 | | |
| BV | 115 | 100.6 | | |
| BW | 122.6 | 235.7 | | |
| BX | 116.3 | 116 | | |
| EH | 115.8 | 128 | | |
| BY | 107.4 | 209.4 | 96.6 | 2.5 μM |
| BZ | 122.2 | 259.8 | | |
| CA | 107.6 | 108.6 | | |

TABLE 37-continued

| Compound | 4T1 1 μM | 4T1 5μM | PC-3, [μM] | |
|---|---|---|---|---|
| FO | 106.2 | 145.9 | | |
| FP | 116.2 | 116.2 | | |
| FQ | 110 | 98 | | |
| AU | 93 | 23.2 | 32.4 | 2.5 μM |
| FV | 104.1 | 101.2 | | |
| EK | 116.4 | 114.2 | | |
| EL | 108 | 39.4 | 41.8 | 2.5 μM |
| FS | 121.5 | 107.3 | | |
| EM | 105.7 | 93 | | |
| FT | 112.8 | 27.6 | 41.1 | 2.5 μM |
| EW | 21.2 | 18.9 | 14.1 | 0.4 μM |
| FU | 118.3 | 105.5 | | |
| CB | 104.6 | 102.1 | | |
| CC | 109.5 | 99.5 | | |
| FW | | | 98.1 | 5 μM |
| FX | 111.6 | 96.6 | | |
| AS | 94.6 | 23.1 | 31.1 | 2.5 μM |
| FR | | 100.9 | | 2.5 μM |
| AV | 136.2 | 30 | 38.2 | 2.5 μM |
| AW | 44.2 | 18 | 38.2 | 0.4 μM |
| AX | 24.3 | 18 | 31.2 | 0.4 μM |
| EN | 93.3 | 89.8 | | |
| AY | 131.3 | 34.5 | 50.4 | 2.5 μM |
| CN | 32.5 | 18.8 | | 0.4 μM |
| FN | 92.9 | 79.4 | | |
| FM | | | | |
| AT | 31.7 | 18.7 | 34.6 | 0.4 μM |
| BO | 20.7 | 18.6 | 13.4 | 0.4 μM |
| FL | 27.7 | 21.4 | 41.2 | 0.4 μM |
| FD | 106.2 | 111.7 | 112.1 | 5 μM |
| FB | 92.7 | 90 | 97.7 | 2.5 μM |
| FC | 115.4 | 122.9 | | |
| FH | 100.9 | 102 | 89 | 5 μM |
| FF | 103.4 | 102.2 | 93 | 5 μM |
| FE | 107.5 | 31.7 | 34.2 | 5 μM |
| FY | 95.2 | 26.8 | 36 | 2.5 μM |
| BP | 33.6 | 23.3 | 50.5 | 0.5 μM |
| FG | 85.7 | 25.5 | 39.2 | 1.5 μM |
| FZ | 91.4 | 56.6 | 32.7 | 5 μM |
| GA | 97.1 | 35.5 | 41.3 | 1.5 μM |
| FI | 26.5 | 26.7 | 35.2 | 0.5 μM |
| GB | 97 | 22.6 | 36.4 | 1.5 μM |
| CD | | | 16.6 | 2.5 μM |
| CE | | | 16.2 | 2.5 μM |
| BQ | | | 21.4 | 2.5 μM |
| FJ | 38.1 | 24.5 | 38.6 | 0.5 μM |
| FK | 23.6 | 15.6 | 35.5 | 0.5 μM |
| GC | 84.8 | 21.1 | 19.8 | 2.5 μM |
| CF | 96.7 | 28.6 | 126.4 | 2.5 μM |
| GD | | | 24.3 | 2.5 μM |

Example T

Effects of Compounds of the Invention of Resistance of Human Prostate Cancer Cells to Cytotoxic Chemotherapy Agents In Vitro Cancer therapy is hindered by inherent or acquired resistance of tumor to single cytotoxic anticancer agents. One mechanism of cancer cell resistance to chemotherapy agents such as anthracylines, platinum compounds, vinca alkaloids, taxanes, and some tyrosine kinase inhibitors, is to sequester anticancer agents in lysosomes or related acidic vacuoles. Compounds of the invention were tested in vitro for their ability to increase sensitivity to several other classes of anticancer agents to which PC-3 prostate cancer cells are relatively resistant in vitro and in vivo.

PC-3 prostate cancer cells were plated at 2×10⁴ cells/well in 96 well flat bottom tissue culture plates, and incubated approximately 20 hours. Cells were treated with an anticipated suboptimal concentration of test compounds for cell killing as a single agent for approximately 30 minutes. Chemotherapeutic agents (doxorubicin, oxaliplatin, paclitaxel or vincristine at concentrations suboptimal for PC-3 cell killing) were added and PC-3 cells were incubated for an additional 72 hours before being assayed using Wst1 reagent. A $^{1}\!/_{10}{}^{th}$ volume of Wst1 dye was added/well and incubated for two hours in the cell culture incubator. Samples were analyzed in triplicate on an EL800 Universal Microplate Reader at 450 nm, reference wavelength 630 nm.

In Table 38, numerical values in the column headed "No Chemo" represent percent cell survival after exposure to the compounds of the invention at concentrations indicated to the left of that column. In the columns headed by the names of the four chemotherapeutic agents, values lower than the corresponding "No Chemo" values indicate better anticancer activity of the specific combination of the cytotoxic agent in combination with a compound of the invention than was obtained with either class of compound alone. At the concentrations indicated, the minimal activity of the chemotherapy agents alone during 72 hours of exposure was normalized to 100% for clarity in discerning synergistic or additive effects of compounds of the invention. The results indicate that, at the concentrations tested, a broad range of compounds of the invention increase sensitivity of cancer cells to one or more of the tested cytotoxic chemotherapy agents doxorubicin, oxaliplatin, paclitaxel or vincristine.

TABLE 38

Cytotoxicity of suboptimal concentrations of compounds of the invention alone and combined with cytotoxic chemotherapy agents

| Compound | [μM] | No Chemo | Doxorubicin 3.5 μM | Oxaliplatin 100 μM | Paclitaxel 50 μM | Vincristine 100 nM |
|---|---|---|---|---|---|---|
| Vehicle | | (100) | (100) | (100) | (100) | (100) |
| CH | 0.4 μM | 102 | 62.8 | 101.1 | 84.6 | 67.4 |
| CI | 0.4 μM | 77.9 | 67.6 | 21.8 | 48.7 | 33.8 |
| CJ | 0.4 μM | 53.7 | 18.9 | 19.7 | 51.7 | 16.9 |
| CK | 0.5 μM | 51.4 | 111.6 | 143 | 64.2 | 138.2 |
| CL | 0.4 μM | 58.1 | 22.6 | 23.2 | 50.3 | 27.1 |
| AL | 0.4 μM | 61.6 | 21.9 | 21.9 | 51.8 | 28.1 |
| AM | 0.4 μM | 58.5 | 24.7 | 25.4 | 54.8 | 26 |
| EI | 2.5 μM | 31.2 | 66.1 | 75.1 | 50.1 | 69.5 |
| AG | 2.5 μM | 18.4 | 21.1 | 27.1 | 21.8 | 17.1 |
| CO | 0.4 μM | 77.1 | 28.4 | 29.2 | 51.6 | 32.8 |
| AR | 0.4 μM | 57 | 22.4 | 24.1 | 54.1 | 24.2 |
| AN | 0.4 μM | 75.9 | 28.2 | 24.7 | 45.8 | 67.3 |
| AD | 0.4 μM | 54.7 | 23.9 | 23.1 | 46.1 | 46.7 |
| CX | 0.4 μM | 45.9 | 21.7 | 22.2 | 48.2 | 38.1 |
| BH | 0.4 μM | 98.5 | 35.7 | 30.6 | 61 | 71.6 |
| CV | 0.5 μM | 73.8 | 36.2 | 30.6 | 21.4 | 36.1 |
| AZ | 0.4 μM | 95.4 | 33.6 | 26.9 | 54.1 | 71.2 |
| CW | 0.4 μM | 98.5 | 31.9 | 26.6 | 55.9 | 69.4 |
| BE | 0.4 μM | 99.1 | 44.1 | 41.2 | 64 | 74.9 |
| BF | 0.4 μM | 92.8 | 40.9 | 37.2 | 57.1 | 74.1 |
| BG | 0.4 μM | 99.1 | 40.1 | 36.2 | 59.2 | 71.1 |
| DA | 0.4 μM | 95.7 | 82.8 | 91.3 | 100.8 | 19.1 |
| BJ | 0.4 μM | 23.9 | 56.8 | 64.1 | 50.2 | 50.8 |
| BI | 0.4 μM | 110.9 | 76.6 | 84.3 | 71.7 | 81.7 |
| DB | 0.4 μM | 24.7 | 56 | 62.3 | 40.3 | 29.6 |
| BA | 1.5 μM | 42.4 | 167.3 | 146.7 | 145.7 | 148.7 |
| CY | 0.4 μM | 40.5 | 76.6 | 84.3 | 71.7 | 81.7 |
| CZ | 0.4 μM | 96.7 | 89.1 | 91.1 | 101.9 | 90.3 |
| CP | 2.5 μM | 35.6 | 72.4 | 76.5 | 74.5 | 48.2 |
| CQ | 2.5 μM | 95.8 | 86.5 | 93.8 | 34.8 | 47.1 |
| CR | 2.5 μM | 53.2 | 87.6 | 89.3 | 93.4 | 86.9 |
| CS | 2.5 μM | 41.3 | 79 | 84.2 | 69.7 | 82.8 |
| CT | 2.5 μM | 34.5 | 63.2 | 71.9 | 46.3 | 46.3 |
| CU | 2.5 μM | 37.6 | 65 | 74.9 | 100.2 | 56.7 |
| CM | 5 μM | 37.8 | 72.6 | 78.1 | 74.8 | 81.3 |
| BB | 2.5 μM | 16.3 | 20.4 | 24.7 | 25 | 17.2 |
| BC | 2.5 μM | 26 | 32.6 | 32.3 | 29.8 | 28.9 |
| AJ | 0.4 μM | 18.5 | 33.1 | 22.5 | 20.8 | 20.1 |
| BD | 0.4 μM | 29.3 | 66.1 | 61.3 | 28.4 | 33.3 |

TABLE 38-continued

Cytotoxicity of suboptimal concentrations of compounds of the invention alone and combined with cytotoxic chemotherapy agents

| Compound | [μM] | No Chemo | Doxorubicin 3.5 μM | Oxaliplatin 100 μM | Paclitaxel 50 μM | Vincristine 100 nM |
|---|---|---|---|---|---|---|
| AI | 0.4 μM | 36.4 | 80.8 | 89 | 96.1 | 64.9 |
| DY | 5 μM | 16.1 | 21.2 | 20.6 | 23.3 | 18.3 |
| DZ | 0.4 μM | 84.8 | 85.6 | 86.7 | 71.8 | 89 |
| EA | 0.4 μM | 108 | 87.8 | 89 | 73.5 | 84.5 |
| EE | 0.4 μM | 34 | 66.4 | 70.8 | 45.3 | 47.1 |
| EF | 0.4 μM | 16.7 | 31.3 | 21.7 | 24.3 | 23.4 |
| EG | 0.4 μM | 92.2 | 91.3 | 96.2 | 95.3 | 88.5 |
| EB | 2.5 μM | 94.4 | 93.4 | 98.8 | 143.3 | 98.2 |
| EC | 2.5 μM | 94.6 | 82.8 | 100.4 | 136.8 | 91.6 |
| AO | 0.4 μM | 35 | 80.7 | 91 | 93.1 | 91.1 |
| DL | 2.5 μM | 43 | 193.5 | 172.6 | 164.8 | 164.9 |
| DN | 2.5 μM | 31.7 | 64.1 | 78 | 64.7 | 72.3 |
| DP | 2.5 μM | 37.5 | 65.3 | 77.4 | 64.6 | 74.1 |
| DE | 2.5 μM | 42 | 69.3 | 84.7 | 68.6 | 74 |
| DF | 0.4 μM | 101.9 | 88.7 | 96.5 | 89.4 | 95.4 |
| DJ | 2.5 μM | 85.9 | 116.2 | 137.1 | 137.1 | 115.3 |
| DM | 2.5 μM | 45.6 | 79.2 | 91.1 | 105.4 | 92.1 |
| DO | 2.5 μM | 59.2 | 79.9 | 89.9 | 93.4 | 90.1 |
| DR | 2.5 μM | 31.5 | 59.9 | 68.7 | 49.2 | 35.5 |
| AA | 1.5 μM | 82.6 | 38.6 | 31 | 22.2 | 43 |
| AC | 0.4 μM | 61.5 | 32.8 | 30 | 14 | 34.1 |
| DS | 0.4 μM | 70 | 86.4 | 97 | 97.1 | 98.6 |
| AF | 0.4 μM | 19.1 | 35 | 32.4 | 25.2 | 22.6 |
| BU | 0.4 μM | 24 | 48.1 | 57.2 | 31 | 26.7 |
| DV | 0.4 μM | 31.6 | 76.7 | 61.9 | 23.3 | 32.2 |
| BK | 0.4 μM | 29.2 | 32.1 | 27.3 | 20.6 | 28.3 |
| BL | 0.4 μM | 106.3 | 135.5 | 120 | 141.4 | 111.2 |
| BY | 2.5 μM | 96.6 | 98.4 | 101.1 | 99.9 | 94.1 |
| AU | 2.5 μM | 32.4 | 25.7 | 41.1 | 34.2 | 32 |
| EL | 2.5 μM | 41.8 | 73.7 | 99.4 | 86.1 | 70.8 |
| FT | 2.5 μM | 41.1 | 74.4 | 94.2 | 85.2 | 78.3 |
| EW | 0.4 μM | 14.1 | 20 | 16.6 | 21.9 | 14.8 |
| FW | 5 μM | 98.1 | 102.7 | 109.6 | 128.5 | 104.6 |
| AS | 2.5 μM | 31.1 | 51.1 | 55.5 | 36.8 | 30.8 |
| FR | 2.5 μM | 100.9 | 93.2 | 102.5 | 102.5 | 99.1 |
| AV | 2.5 μM | 38.2 | 62.6 | 59.3 | 34.4 | 37.2 |
| AW | 0.4 μM | 38.2 | 59.5 | 70 | 51.3 | 33.6 |
| AX | 0.4 μM | 31.2 | 57.9 | 49.5 | 26.7 | 31.5 |
| AY | 2.5 μM | 50.4 | 78.9 | 92 | 90.1 | 78.7 |
| AT | 0.4 μM | 34.6 | 65.4 | 76.8 | 57.4 | 32.9 |
| BO | 0.4 μM | 13.4 | 82.4 | 28.4 | 28.2 | 18.4 |
| FL | 0.4 μM | 41.2 | 81.3 | 87.9 | 92.8 | 69.7 |
| FD | 5 μM | 112.1 | 101 | 85.3 | 95.6 | 98.7 |
| FB | 2.5 μM | 97.7 | 89.1 | 95.5 | 93.2 | 98.6 |
| FH | 5 μM | 89 | 79.6 | 82.3 | 131.8 | 114.9 |
| FF | 5 μM | 93 | 90.7 | 95.2 | 136.1 | 110.1 |
| FE | 5 μM | 34.2 | 46.8 | 67.6 | 113.7 | 37.3 |
| FY | 2.5 μM | 36 | 74.6 | 91.5 | 91 | 80.1 |
| BP | 0.5 μM | 50.5 | 79.1 | 113.6 | 95.1 | 93 |
| FG | 1.5 μM | 39.2 | 65.7 | 85.5 | 47.2 | 41 |
| FZ | 5 μM | 32.7 | 39.6 | 67.7 | 114.8 | 38.5 |
| GA | 1.5 μM | 41.3 | 82.2 | 91.8 | 109.2 | 84.2 |
| FI | 0.5 μM | 35.2 | 79.8 | 91.4 | 84 | 73.7 |
| GB | 1.5 μM | 36.4 | 52.8 | 76.2 | 24 | 38.8 |
| CD | 2.5 μM | 16.6 | 19.5 | 20.1 | 23.2 | 17.1 |
| CE | 2.5 μM | 16.2 | 44.3 | 18.8 | 23.5 | 15.6 |
| BQ | 2.5 μM | 21.4 | 48.5 | 25.1 | 26.9 | 21.4 |
| FJ | 0.5 μM | 38.6 | 75.1 | 93 | 97.3 | 82.2 |
| FK | 0.5 μM | 35.5 | 47.4 | 62 | 18 | 39 |
| GC | 2.5 μM | 19.8 | 59.5 | 63.2 | 30.3 | 26.4 |
| CF | 2.5 μM | 126.4 | 68.8 | 83.5 | 70.3 | 75.3 |
| GD | 2.5 μM | 24.3 | 39.5 | 26.7 | 27 | 23.5 |

What is claimed is:

1. A compound represented by Formula IB1 or a pharmaceutically acceptable salt thereof

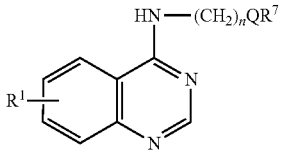

IB1 wherein n is 1;
Q is absent;
$R^1$ is hydrogen or halo; and
$R^7$ is phenyl substituted by alkoxy having from 6 to 10 carbon atoms or phenoxy.

2. The compound or salt of claim 1, wherein the compound is selected from the group consisting of:
N-[3-(Hexyloxy)benzyl]quinazolin-4-amine,
N-[3-(Decyloxy)benzyl]quinazolin-4-amine,
N-[4-(Decyloxy)benzyl]quinazolin-4-amine,
N-[4-(Hexyloxy)benzyl]quinazolin-4-amine.

3. A pharmaceutical composition comprising an effective amount of the compound or pharmaceutically acceptable salt of claim 1 and a pharmaceutically acceptable carrier.

4. The compound or salt of claim 1, wherein the compound is N-(3-Phenoxybenzyl)quinazolin-4-amine.

5. A pharmaceutical composition comprising an effective amount of the compound or pharmaceutically acceptable salt of claim 4 and a pharmaceutically acceptable carrier.

6. A method of inhibiting a fungus ex vivo, comprising contacting a surface or the fungus with the compound or pharmaceutically acceptable salt of claim 1.

7. A method of inhibiting a fungus ex vivo, comprising contacting a surface or the fungus with the compound or pharmaceutically acceptable salt of claim 4.

* * * * *